US007884107B2

(12) United States Patent
Ma et al.

(10) Patent No.: US 7,884,107 B2

(45) Date of Patent: Feb. 8, 2011

(54) SUBSTITUTED PIPERIDINES THAT INCREASE P53 ACTIVITY AND THE USES THEREOF

(75) Inventors: Yao Ma, Westwood, MA (US); Brian Robert Lahue, Millbury, MA (US); Gerald W. Shipps, Jr., Stoneham, MA (US); Yaolin Wang, Edison, NJ (US); Stephane L. Bogen, Somerset, NJ (US); Matthew Ernst Voss, Nassau, NY (US); Latha G. Nair, Edison, NJ (US); Yuan Tian, Newton, MA (US); Ronald J. Doll, Convent Station, NJ (US); Zhuyan Guo, Scotch Plains, NJ (US); Corey O. Strickland, Martinsville, NJ (US); Rumin Zhang, Edison, NJ (US); Mark A. McCoy, Acton, MA (US); Weidong Pan, Somerset, NJ (US); Elise M. Siegel, Jersey City, NJ (US); Craig R. Gibeau, Arlington, MA (US)

(73) Assignee: Merck, Kenilworth, NJ (US)

( * ) Notice: Subject to any disclaimer, the term of this patent is extended or adjusted under 35 U.S.C. 154(b) by 110 days.

(21) Appl. No.: 11/769,030

(22) Filed: Jun. 27, 2007

(65) Prior Publication Data

US 2008/0004287 A1 Jan. 3, 2008

Related U.S. Application Data

(60) Provisional application No. 60/817,753, filed on Jun. 30, 2006.

(51) Int. Cl.

| | |
|---|---|
| *A61K 31/54* | (2006.01) |
| *C07D 413/00* | (2006.01) |
| *C07D 403/00* | (2006.01) |
| *C07D 405/00* | (2006.01) |

(52) U.S. Cl. .................. 514/253.13; 544/130; 544/364; 514/225.5

(58) Field of Classification Search ....................... None
See application file for complete search history.

(56) References Cited

U.S. PATENT DOCUMENTS

| | | | | |
|---|---|---|---|---|
| 6,403,584 | B1 | 6/2002 | deLaszlo et al. | |
| 6,645,987 | B2 * | 11/2003 | Chackalamannil et al. | .. 514/337 |
| 2004/0259867 | A1 | 12/2004 | Fotouhi et al. | |
| 2004/0259884 | A1 | 12/2004 | Haley | |
| 2005/0037383 | A1 | 2/2005 | Taremi et al. | |

FOREIGN PATENT DOCUMENTS

| | | | |
|---|---|---|---|
| EP | 0 947 494 | A1 | 3/1999 |
| JP | 09 249566 | A | 9/1997 |
| WO | WO 00/15657 | A1 | 3/2000 |
| WO | WO 2004/080460 | A1 | 9/2004 |
| WO | WO 2007/070398 | A1 | 6/2007 |

OTHER PUBLICATIONS

Ding et al. Emerging cancer therapeutic opportunities target DNA-repair systems. TRENDS in Pharmacological Sciences, vol. 27, No. 6, Published online May 2006.*

Translation of JP 09-249566, Part 1.*

Translation of JP 09-249566, Part 2.*

Jordan, V.C. Nature Reviews: Drug Discovery, 2, 2003, p. 205.*

Dorwald F. Zaragoza. Side Reviews in Organic Synthesis: A guide to successful synthesis design, Weinheim: Wiley-Vch, Verlag, GMBH & Co. KGaA, 2005, Preface.*

Wolff et al. Burger's Medicinal Chemistry and Drug Discovery—Fifth Edition, New York: John Wiley & Songs, 1996, vol. 1, pp. 975-976.*

Vippagunta et al. Advanced Drug Delivery Reviews, 48, 2001, p. 18.*

Yang et al. Small molecular inhibitors of HDM2 ubiquitin ligase activity stabilize and activate p53 in cells. Cancer Cell. Jun. 2005.*

Schaefer et al. Failure is not an option: learning from unsuccessful proof-of-concept trials. Drug Discovery Today, 2006, 13(21/22): 913-916.*

Horig et al. Review: From bench to clinic and back: Perspective on the 1$^{st}$ IQPC Translational Research Conference. Journal of Translational Medicine, 2004, 2(44).*

J.G. Cannon. Chapter Nineteen in Bruger's Medicinal Chemistry and Drug Discovery, Fifth Edition, vol. I: Principles and Practice. Wiley-Interscience, 1995, pp. 783-802.*

Freedman et al., "Nuclear Export Is Required for Degradation of Endogenous p53 by MDM2 and Human Papillomavirus E6", *Molecular and Cellular Biology*, 18(12): 7288-7293 (Dec. 1988).

Galatin et al., "A Nonpeptidic Sulfonamide Inhibits the p53—mdm2 Interaction and Activates p53-Dependent Transcription in mdm2-Overexpressing Cells", 47(17): 4163-4165 (2004).

Grasberger et al., "Discovery and Cocrystal Structure of Benzodiazepinedione HDM2 Antagonists that Activate p53 in Cells", *J. Med. Chem.*, 48(4): 909-912 (2005).

Hainaut et al., "Database of p53 gene somatic mutations in human tumors and cell lines: updated compilation and future prospects", *Nucleic Acids Research*, 25(1): 151-157 (1997).

Hall et al., "Genetic Alterations of Cyclins, Cyclin-Dependent Kinases, and Cdk Inhibitors in Human Cancer", *Advances in Cancer Research*, 68: 67-108 (1996).

Honda et al., "Oncoprotein. MDM2 is a ubiquitin ligase E3 for tumor suppressor p53", *FEBS Letters*, 420: 25-27 (1997).

Honda et al., "Activity of MDM2, a ubiquitin ligase, toward p53 or itself is dependent on the RING finger domain of the ligase", *Oncogene*, 19: 1473-1476 (2000).

Ko et al. "p53: puzzle and paradigm", *Genes & Development*, 10: 1054-1072 (1996).

(Continued)

*Primary Examiner*—Brandon J Fetterolf
*Assistant Examiner*—Anna Pagonakis
(74) *Attorney, Agent, or Firm*—Krishna G. Banerjee

(57) ABSTRACT

In its many embodiments, the present invention discloses novel compounds, as inhibitors of HDM2 protein methods for preparing such compounds, pharmaceutical compositions including one or more such compounds, methods of treatment, prevention, inhibition, of one or more diseases associated with the HDM2 protein or P53 using such compounds or pharmaceutical compositions.

36 Claims, No Drawings

PUBLICATIONS

Kojima et al., "MDM2 antagonists induce p53-dependent apoptosis in AML: implications for leukemia therapy", *Blood*, 106(9): 3150-3159 (Nov. 1, 2005).
Kussie et al., "Structure of the MDM2 Oncoprotein Bound to the p53 Tumor Suppressor Transactivation Domain", *Science* 274: 948-953 (Nov. 8, 1996).
Levine, "p53, the Cellular Gatekeeper for Growth and Division", *Cell*, 88: 323-331 (Feb. 7, 1997).
Lu et al., "Discovery of a Nanomolar Inhibitor of the Human Murine Double Minute 2 (MDM2)—p53 Interaction through an Integrated, Virtual Database Screening Strategy", *Journal of Medicinal Chemistry*, 49(13): 3759-3762 (2006).
May et al., "Twenty years of p53 research: structural and functional aspects of the p53 protein", *Oncogene*, 18: 7621-7636 (1999).
Momand et al., "MDM2—master regulator of the p53 tumor suppressor protein", *Gene* 242 15-29 (2000).
Momand et al., "The mdm-2 Oncogene Product Forms a Complex with the p53 Protein and Inhibits p53—Mediated Transactivation", *Cell*, 69: 1237-1246 (Jun. 26, 1992).
Oliner et al., "Oncoprotein MDM2 conceals the activation domain of tumour suppressor p53", *Letters to Nature*, 362: 857-860 (Apr. 29, 1993).
Oren, "Decision making by p53: life, death and cancer", *Cell Death and Differentiation*, 10: 431-442 (2003).
Roth, "Nucleo-cytoplasmic shuttling of the hdm2 oncoprotein regulates the levels of the p53 protein via a pathway used by the human immunodeficiency virus rev protein", *The EMBO Journal*, 7(2): 554-564 (1998).
Sherr, "The Pezcoller Lecture: Cancer Cell Cycles Revisited", *Cancer Research*, 60: 3689-3695 (Jul. 15, 2000).
Stoll et al., "Chalcone Derivatives Antagonize Interactions between the Human Oncoprotein MDM2 and p53", *Biochemistry*, 40(2): 336-344 (2001).
Tao et al., "Nucleocytoplasmic shuttling of oncoprotein Hdm2 is required for Hdm2-mediated degradation of p53", *Proc. Natl. Acad. Sci. USA*, 96: 3077-3080 (Mar. 1999).
Vassilev, "p53 Activation by Small Molecules: Application in Oncology", *Journal of Medicinal Chemistry*, 48(14): 4491-4499 (Jul. 14, 2005).
Vassilev et al., In Vivo Activation of the p53 Pathway by Small-Molecule antagonists of "MDM2", *Science*, 303: 844-848 (Feb. 6, 2004).
Wu et al., "The p53-mdm-2 autoregulatory feedback loop", *Genes & Development*, 7: 1126-1132 (1993).
Zheleva et al., "The p53-Mdm2 Pathway: Targets for the Development of New Anticancer Therapeutics", *Mini Reviews in Medicinal Chemistry*, 3(3): 257-270 (2003).
International Search Report for corresponding PCT Application No. PCT/US2007/014958 dated Nov. 23, 2007.
Chemical Abstract No. 1998-035793 for Takeda Chemical Industries Ltd., "Piperidine-Containing Chemokine Receptor Antagonist" (1997) (which is attached to said abstract).
Patent Abstracts of Japan, Publication No. 09249566, Sep. 22, 1997.
Barak et al., "mdm2 expression is induced by wild type p53 activity", *The EMBO Journal*, 12(2): 461-468 (1993).
Blaydes et al., "Tolerance of high levels of wild-type p53 in transformed epithelial cells dependent on auto-regulation by mdm-2", *Oncogene*, 14: 1859-1868 (1997).
Bottger et al., "Identification of novel mdm2 binding peptides by phage display", *Oncogene*, 13: 2141-2147 (1996).
Chene, "Inhibition of the p53-MDM2 interaction: Targeting a protein-protein interface", *Molecular Cancer Research*, 2: 20-28 (Jan. 2004).
Chene, "Inhibiting the p53-MDM2 interaction: An Important target for cancer therapy", *Nature Reviews*, 3: 102-109 (Feb. 2003).
Ding et al., "Structure-Based Design of Potent Non-Peptide MDM2 Inhibitors", *J. Am. Chem. Soc.*, 127(29): 10130-10131 (2005).
Ding et al., "Structure-Based Design of Spiro-oxindoles as Potent, Specific Small-Molecule Inhibitors of the MDM2-p53 Interaction", *Journal of Medicinal Chemistry*, 49(12): 3432-3435 (2006).
Donehower et al., "Mice deficient for p53 are developmentally normal but susceptible to spontaneous tumours", *Nature*, 356: 215-221 (Mar. 19, 1992).
Duncan et al., "Isolation and Structure Elucidation of chlorofusin, a Novel p53-MDM2 Antagonist from a *Fusarium* sp.", *J. Am. Chem. Soc.*, 123(4): 554-560 (2001).
Fotouhi et al., "Small Molecule Inhibitors of p53/MDM2 Interaction", *Current Topics in Medicinal Chemistry*, 5(2): 159-165 (2005).

* cited by examiner

SUBSTITUTED PIPERIDINES THAT INCREASE P53 ACTIVITY AND THE USES THEREOF

The present application claims priority under 35 USC section 119(e) of U.S. Provisional application Ser. No. 60/817,753 filed Jun. 30, 2006, the complete text, claims and figures of which are incorporated by reference herein as if fully set forth.

FIELD OF THE INVENTION

The present invention relates to novel compounds useful as Human Double Minute 2 protein inhibitors, regulators or modulators, pharmaceutical compositions containing the compounds and methods of treatment using the compounds and compositions to treat diseases such as, for example, cancer, diseases involving abnormal cell proliferation, and diseases caused by inadequate P53 levels.

BACKGROUND OF THE INVENTION

The tumor suppressor protein P53 plays a central role in maintaining the integrity of the genome in a cell by regulating the expression of a diverse array of genes responsible for DNA repair, cell cycle and growth arrest, and apoptosis [May et at, *Oncogene* 18 (53) (1999) p. 7621-7636; Oren, *Cell Death Differ.* 10 (4) (2003) p. 431-442, Hall and Peters, *Adv. Cancer Res.,* 68: (1996) p. 67-108; Hainaut et al., *Nucleic Acid Res.,* 25: (1997) p. 151-157; Sherr, *Cancer Res.,* 60: (2000) p. 3689-95]. In response to oncogenic stress signals, the cell triggers the P53 transcription factor to activate genes implicated in the regulation cell cycle, which thereby initiates either apoptosis or cell cycle arrest. Apoptosis facilitates the elimination of damaged cells from the organism, while cell cycle arrest enables damaged cells to repair genetic damage [reviewed in Ko et al., *Genes & Devel.* 10: (1996) p. 1054-1072; Levine, *Cell* 88: (1997) p. 323-331]. The loss of the safeguard functions of P53 predisposes damaged cells to progress to a cancerous state. Inactivating P53 in mice consistently leads to an unusually high rate of tumors [Donehower et al., *Nature,* 356, (1992) p. 215-221].

The P53 transcription factor promotes the expression of a number of cell cycle regulatory genes, including its own negative regulator, the gene encoding the Mouse Double Minute 2 (Mdm2) protein [Chene, *Nature Reviews Cancer* 3: (2003) p. 102-109; Momand, *Gene* 242 (1-2): (2000) p. 15-29; Zheleva et al. *Mini. Rev. Med. Chem.* 3: (2003) p. 257-270]. The Mdm2 protein (designated HDM2 in humans) acts to down-regulate P53 activity in an auto-regulatory manner [Wu et al, *Genes Dev.,* 7: (1993) p. 1126-1132; Bairak et al., *EMBO J,* 12: (1993) p. 461-468]. In the absence of oncogenic stress signals, i.e., under normal cellular conditions, the Mdm2 protein serves to maintain P53 activity at low levels [Wu et al, *Genes Dev.,* 7: (1993) p. 1126-1132; Barak et al., *EMBO J,* 12: (1993) p. 461-468]. However, in response to cellular DNA damage or under cellular stress, P53 activity increases helping to prevent the propagation of permanently damaged clones of cells by induction of cell cycle and growth arrest or apoptosis.

The regulation of P53 function relies on an appropriate balance between the two components of this P53-Mdm2 auto-regulatory system. Indeed, this balance appears to be essential for cell survival. There are at least three ways that Mdm2 acts to down-regulate P53 activity. First, Mdm2 can bind to the N-terminal transcriptional activation domain of P53 to block expression of P53-responsive genes [Kussie et al., *Science,* 274: (1996) p. 948-953; Oliner et al., *Nature,* 362: (1993) p. 857-860; Momand et al, *Cell,* 69: (1992) p. 1237-1245]. Second, Mdm2 shuttles P53 from the nucleus to the cytoplasm to facilitate the proteolytic degradation of P53 [Roth et al., *EMBO J.* 17: (1998) p. 554-564; Freedman et al., *Mol Cell Biol,* 18: (1998) p. 7288-7293; Tao and Levine, *Proc. Natl. Acad. Sci.* 96: (1999) p. 3077-3080]. Finally, Mdm2 possesses an intrinsic E3 ligase activity for conjugating ubiquitin to P53 for degradation within the ubiquitin-dependent 26S proteosome pathway [Honda et al., *FEBS Lett,* 420: (1997) p. 25-27; Yasuda, *Oncogene* 19: (2000) p. 1473-1476]. Thus, Mdm2 impedes the ability of the P53 transcription factor to promote the expression of its target genes by binding P53 in the nucleus. Attenuating the P53-Mdm2 auto-regulatory system can have a critical effect on cell homeostasis. Consistently, a correlation between the overexpression of Mdm2 and tumor formation has been reported [Chene, *Nature* 3: (2003) p. 102-109]. Functional inactivation of wild type P53 is found in many types of human tumors. Restoring the function of P53 in tumor cells by anti-MDM2 therapy would result in slowing the tumor proliferation and instead stimulate apoptosis. Not surprisingly then, there is currently a substantial effort being made to identify new anticancer agents that hinder the ability of HDM2 to interact with P53 [Chene, *Nature* 3: (2003) p. 102-109]. Antibodies, peptides, and antisense oligonucleotides have been demonstrated to destroy the P53-Mdm2 interaction, which would release P53 from the negative control of Mdm2, leading to activation of the P53 pathway allowing the normal signals of growth arrest and/or apoptosis to function, which offers a potential therapeutic approach to treating cancer and other diseases characterized by abnormal cell proliferation. [See, e.g., Blaydes et al., *Oncogene* 14: (1997) p. 1859-1868; Bottger et al., *Oncogene* 13 (10: (1996) p. 2141-2147].

U.S. Pub. No. 2005/0037383 A1 describes modified soluble HDM2 protein, nucleic acids that code for this HDM2 protein, the crystals of this protein that are suitable for X-ray crystallization analysis, the use of the proteins and crystals to identify, select, or design compounds that may be used as anticancer agents, and some of the compounds themselves that bind to modified HDM2. (Schering-Plough Corp.).

Small molecules, said to antagonize the P53-Mdm2 interaction, have been described. WO 00/15657 (Zeneca Limited) describes piprizine-4-phenyl derivatives as inhibitors of the interaction between Mdm2 and P53. Grasberger et al. (*J. Med. Chem.,* 48 (2005) p. 909-912) (Johnson & Johnson Pharmaceutical Research & Development L.L. C.) describes discovery and cocrystal structure of benzodiazepinedione as HDM2 antagonists that activate P53 in cells. Galatin et al. (*J. Med. Chem.* 47 (2004) p. 4163-4165) describes a nonpeptidic sulfonamide inhibitor of the P53-Mdm2 interaction and activator of P53 dependent transcription in mdm2-overexpressing cells.

Vassilev (*J. Med. Chem.* (*Perspective*) Vol. 48 No. 14, (2005) p. 1-8) (Hoffmann-LaRoche Inc.) describes several small molecule P53 activators as an application in oncology, including the following formulas:

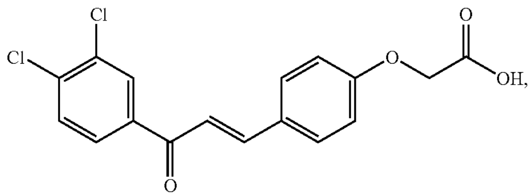
,

-continued

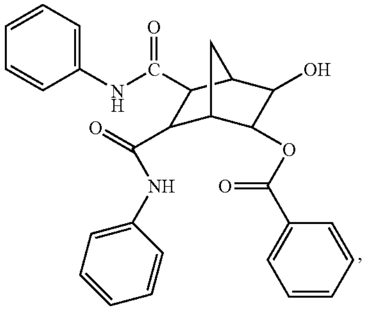
,

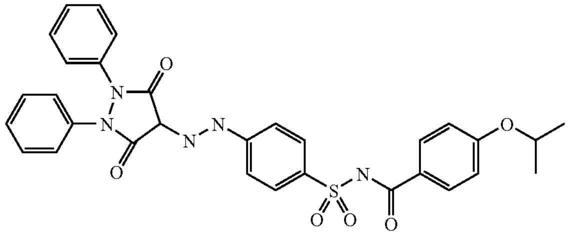

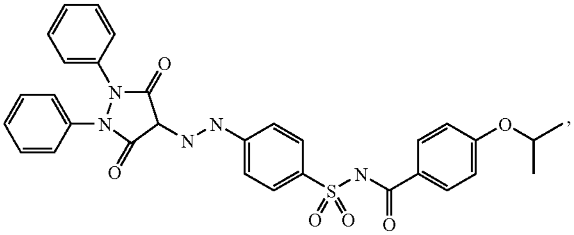
,

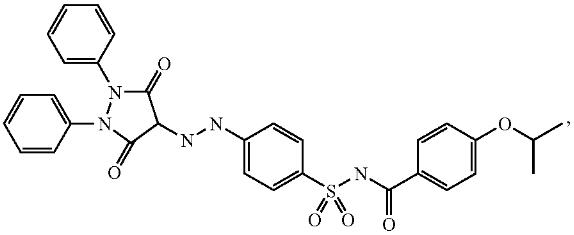
,

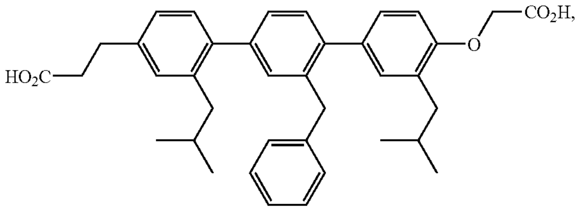
,

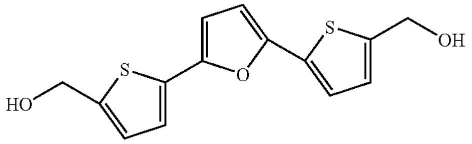

-continued

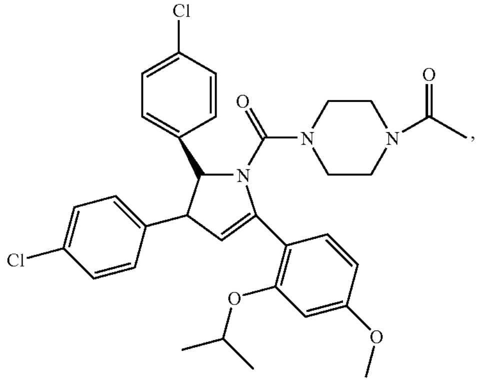
,

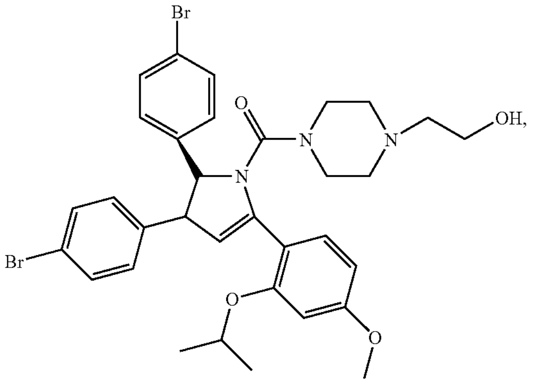
, and

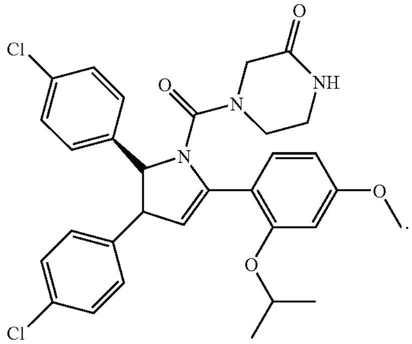
.

The first four compounds listed above were also described in Totouhi et al. (*Current Topics in Medicinal Chemistry* Vol. 3, No. 2 (2005) p. 159-166, at 161) (Hoffmann La Roche Inc.). The last three compounds listed above were also described in Vassilev et al. (*Science* Vol. 303 (2004): p. 844-848) (Hoffmann La Roche Inc.) and their implications on leukemia activity were investigated in Kojima et al. (*Blood*, Vol. 108 No. 9 (November 2005) p. 3150-3159).

Ding et. al. (*J. Am. Chem. Soc.* Vol. 127 (2005): 10130-10131) and (*J. Med. Chem.* Vol. 49 (2006): 3432-3435) describes several spiro-oxindole compounds as Mdm2-P53 inhibitors.

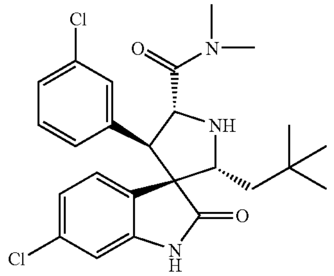

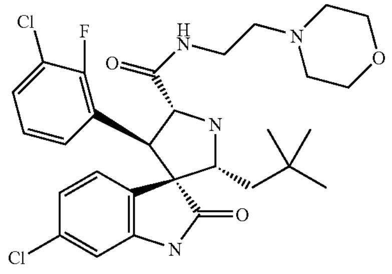

Lu, et. al. (*J. Med. Chem.* Vol. 49 (2006): 3759-3762) described 7-[anilino(phenyl)methyl]-2-methyl-8-quinolinol as a small molecule inhibitor of MDM2-P53 interaction.

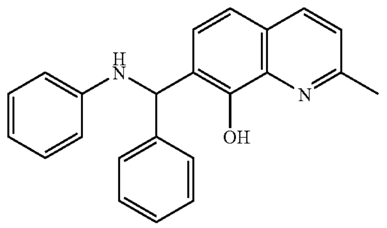

Chéne (*Molecular Cancer Research* Vol. 2: (January 2006) p. 20-28) describes inhibition of the P53-Mdm2 interaction by targeting the protein-protein interface. U.S. Pub. No. 2004/0259867 A1 and 2004/0259884 A1 describes Cis-imidazoles (Hoffmann La Roche Inc.) and WO2005/110996A1 and WO 03/051359 describes Cis-Imidazolines (Hoffmann La Roche Inc.) as compounds that inhibit the interaction of Mdm2 with P53-like peptides resulting in antiproliferation. WO 2004/080460 A1 describes substituted piperidine compounds as Mdm2-P53 inhibitors for treating cancer (Hoffmann La Roche Inc.). EP 0947494 A1 describes phenoxy acetic acid derivatives and phenoxy methyltetrazole that act as antagonists of Mdm2 and interfere with the protein-protein interaction between Mdm2 and P53, which results in anti-tumor properties (Hoffmann La Roche Inc.). Duncan et al., *J. Am. Chem. Soc.* 123 (4): (2001) p. 554-560 describes a p-53-Mdm2 antagonist, chlorofusin, from a *Fusarium* Sp. Stoll et al., *Biochemistry* 40 (2) (2001) p. 336-344 describes chalcone derivatives that antagonize interactions between the human oncoprotein Mdm2 and P53.

There is a need for effective inhibitors of the HDM2 or MDM2 protein in order to treat or prevent cancer, other disease states associated with cell proliferation, diseases associated with HDM2, or diseases caused by inadequate P53 activity. The present application discloses compounds that have potency in inhibiting or antagonizing the HDM2-P53 and Mdm2-P53 interaction and/or activating P53 proteins in cells. The HDM2-P53 and Mdm2-P53 inhibitory activity of such compounds have not been disclosed previously.

SUMMARY OF THE INVENTION

In its many embodiments, the present invention provides novel compounds having HDM2 or MDM2 antagonist activity, methods of preparing such compounds, pharmaceutical compositions comprising one or more of such compounds, methods of preparing pharmaceutical formulations comprising one or more of such compounds, methods of treatment or prevention of one or more diseases associated with HDM2, MDM2, P-53, or P-53 peptides by administering such compounds or pharmaceutical compositions.

In one aspect, compounds of the present invention have the general structure shown in Formula I:

Formula I

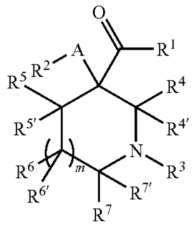

or a pharmaceutically acceptable salt, solvate, ester, or prodrug thereof, wherein: $R^1$ is heterocyclyl, heterocyclenyl, or heteroaryl wherein each of said heterocyclyl, heterocyclenyl, or heteroaryl contains independently 1-3 heteroatoms on the ring and further wherein each of said heterocyclyl or heterocyclenyl, or heteroaryl is attached by one of its heteroatoms to the carbonyl in Formula I and still further, wherein each of said heterocyclyl, heterocyclenyl, or heteroaryl can be unsubstituted or independently substituted with at least one moiety, which may be the same or different, selected from the group Z;

or $R^1$ is heteroalkyl or heteroalkenyl wherein each of said heteroalkyl or heteroalkenyl contains 1-3 heteroatoms and further wherein each of said heteroalkyl or heteroalkenyl is attached by one of its heteroatoms to the carbonyl in Formula I and still further, wherein each of said heteroalkyl or heteroalkenyl can be unsubstituted or independently substituted with at least one moiety, which may be the same or different, selected from the group Z;

wherein each Z, which can be the same or different, is independently selected from the group consisting of H, —$OR^9$, -alkyl$NR^{10}R^{11}$, -alkenyl$NR^{10}R^{11}$, —$CO_2R^9$, —$CONR^{10}R^{11}$, —$NR^{10}CONR^{10}R^{11}$, —$NR^{10}COR^9$, alkoxyalkyl, alkoxyalkenyl, cyano, halogen, trihaloalkyl, dihaloalkyl, monohaloalkyl, trihaloalkenyl, dihaloalkenyl, monohaloalkenyl, trihaloheteroalkyl, dihaloheteroalkyl, monohaloheteroalkyl, trihaloheteroalkenyl, dihaloheteroalkenyl, monohaloheteroalkenyl, alkyl, alkenyl, alkynyl, heteroalkyl, heteroalkenyl, aryl, arylalkyl, arylalkenyl, heteroaryl, hbteroarylalkyl, heteroarylalkenyl, haterocyclenyl, heterocyclenylalkyl, heterocyclenylalkenyl, heterocyclyl, heterocyclylalkyl, heterocyclylalkenyl, cycloalkyl, cycloalkylalkyl, cycloalkylalkenyl, cyclenyl, cyclenylalkyl, cyclenylalkenyl, —O-alkyl, —O-alkenyl, —O-alkynyl, —O-heteroalkyl, —O-heteroalkenyl, —O-aryl, O-arylalkyl, O-arylalkenyl, —O-heteroaryl, —O-heteroarylalkyl, —O-heteroarylalkenyl, —O-heterocyclenyl, —O-heterocyclenylalkyl, —O-heterocyclenylalkenyl, —O-heterocyclyl, —O-heterocyclylalkyl, —O-heterocyclylalkenyl, —O-cycloalkyl, —O-cycloalkylalkyl, —O-cycloalkylalkenyl, —O-cyclenyl, —O-cyclenylalkyl, —O-cyclanylalkenyl, —S-alkyl, —S-alkenyl, —S-alkynyl, —S-heteroalkyl, —S-heteroalkenyl, —S-aryl, —S-arylalkyl, —S-arylalkenyl, —S-heteroaryl, —S-heteroarylalkyl, —S-heteroarylalkenyl, —S-heterocyclenyl, —S-heterocyclenylalkyl, —S-heterocyclenylalkenyl, —S-heterocyclyl, —S-heterocyclylalkyl, —S-heterocyclylalkenyl, —S-cycloalkyl, —S-cycloalkylalkyl, —S-cycloalkylalkenyl, —S-cyclenyl, —S-cyclenylalkyl, —S-cyclenylalkenyl, -alkyl-SH, —NR$^{10}$-alkyl, —NR$^{10}$-alkenyl, —NR$^{10}$-alkynyl, —NR$^{10}$-heteroalkyl, —NR$^{10}$-heteroalkenyl, —NR$^{10}$-aryl, —NR$^{10}$-arylalkyl, —NR$^{10}$-arylalkenyl, —NR$^{10}$-heteroaryl, —NR$^{10}$-heteroarylalkyl, —NR$^{10}$-heteroarylalkenyl, —NR$^{10}$-heterocyclenyl, —NR$^{10}$-heterocyclenylalkyl, —NR$^{10}$-heterocyclenylalkenyl, —NR$^{10}$-heterocyclyl, —NR$^{10}$-heterocyclylalkyl, —NR$^{10}$-heterocyclylalkenyl, —NR$^{10}$-cycloalkyl, —NR$^{10}$-cycloalkylalkyl, —NR$^{10}$-cycloalkylalkenyl, —NR$^{10}$-cyclenyl, —NR$^{10}$-cyclenylalkyl, —NR$^{10}$-cyclenylalkenyl, —CO-alkyl, —CO-alkenyl, —CO-alkynyl, —CO-heteroalkyl, —CO-heteroalkenyl, —CO-aryl, —CO-arylalkyl, —CO-arylalkenyl, —CO-heteroaryl, —CO-heteroarylalkyl, —CO-heteroarylalkenyl, —CO-heterocyclenyl, —CO-heterocyclenylalkyl, —CO-heterocyclenylalkenyl, —CO-heterocyclyl, —CO-heterocyclylalkyl, —CO-heterocyclylalkenyl, —CO-cycloalkyl, —CO-cycloalkylalkyl, —CO-cycloalkylalkenyl, —CO-cyclenyl, —CO-cyclenylalkyl, —CO-cyclenylalkenyl, —SO$_2$-alkyl, —SO$_2$-alkenyl, —SO$_2$-alkynyl, —SO$_2$-heteroalkyl, —SO$_2$-heteroalkenyl, —SO$_2$-aryl, —SO$_2$-arylalkyl, —SO$_2$-arylalkenyl, —SO$_2$-heteroaryl, —SO$_2$-heteroarylalkyl, —SO$_2$-heteroarylalkenyl, —SO$_2$-heterocyclenyl, —SO$_2$-heterocyclenylalkyl, —SO$_2$-heterocyclenylalkenyl, —SO$_2$-heterocyclyl, —SO$_2$-heterocyclylalkyl, —SO$_2$-heterocyclylalkenyl, —SO$_2$-cycloalkyl, —SO$_2$-cycloalkylalkyl, —SO$_2$-cycloalkylalkenyl, —SO$_2$-cyclenyl, —SO$_2$-cyclenylalkyl, —SO$_2$-cyclenylalkenyl, spiroheteroaryl, spiroheterocyclenyl, spiroheterocyclyl, spirocycloalkyl, spirocyclenyl, spiroaryl, wherein each of said alkyl, alkenyl, alkynyl, heteroalkyl, heteroalkenyl, aryl, arylalkyl, arylalkenyl, heteroaryl, heteroarylalkyl, heteroarylalkenyl, heterocyclenyl, heterocyclenylalkyl, heterocyclenylalkenyl, heterocyclyl, heterocyclylalkyl, heterocyclylalkenyl, cycloalkyl, cycloalkylalkyl, cycloalkylalkenyl, cyclenyl, cyclenylalkyl, cyclenylalkenyl, —O-alkyl, —O-alkenyl, —O-alkynyl, —O-heteroalkyl, —O-heteroalkenyl, —O-aryl, O-arylalkyl, O-arylalkenyl, —O-heteroaryl, —O-heteroarylalkyl, —O-heteroarylalkenyl, —O-heterocyclenyl, —O-heterocyclenylalkyl, —O-heterocyclenylalkenyl, —O-heterocyclyl, —O-heterocyclylalkyl, —O-heterocyclylalkenyl, —O-cycloalkyl, —O-cycloalkylalkyl, —O-cycloalkylalkenyl, —O-cyclenyl, —O-cyclenylalkyl, —O-cyclenylalkenyl, —S-alkyl, —S-alkenyl, —S-alkynyl, —S-heteroalkyl, —S-heteroalkenyl, —S-aryl, —S-arylalkyl, —S-arylalkenyl, —S-heteroaryl, —S-heteroarylalkyl, —S-heteroarylalkenyl, —S-heterocyclenyl, —S-heterocyclenylalkyl, —S-heterocyclenylalkenyl, —S-heterocyclyl, —S-heterocyclylalkyl, —S-heterocyclylalkenyl, —S-cycloalkyl, —S-cycloalkylalkyl, —S-cycloalkylalkenyl, —S-cyclenyl, —S-cyclenylalkyl, —S-cyclenylalkenyl, -alkynyl, —NR$^{10}$-alkyl, —NR$^{10}$-alkenyl, —NR$^{10}$-alkynyl, —NR$^{10}$-heteroalkyl, —NR$^{10}$-heteroalkenyl, —NR$^{10}$-aryl, —NR$^{10}$-arylalkyl, —NR$^{10}$-arylalkenyl, —NR$^{10}$-heteroaryl, —NR$^{10}$-heteroarylalkyl, —NR$^{10}$-heteroarylalkenyl, —NR$^{10}$-heterocyclenyl, —NR$^{10}$-heterocyclenylalkyl, —NR$^{10}$-heterocyclenylalkenyl, —NR$^{10}$-heterocyclyl, —NR$^{10}$-heterocyclylalkyl, —NR$^{10}$-heterocyclylalkenyl, —NR$^{10}$-cycloalkyl, —NR$^{10}$-cycloalkylalkyl, —NR$^{10}$-cycloalkylalkenyl, —NR$^{10}$-cyclenyl, —NR$^{10}$-cyclenylalkyl, —NR$^{10}$-cyclenylalkenyl, —CO-alkyl, —CO-alkenyl, —CO-alkynyl, —CO-heteroalkyl, —CO-heteroalkenyl, —CO-aryl, —CO-arylalkyl, —CO-arylalkenyl, —CO-heteroaryl, —CO-heteroarylalkyl, —CO-heteroarylalkenyl, —CO-heterocyclenyl, —CO-heterocyclenylalkyl, —CO-heterocyclenylalkenyl, —CO-heterocyclyl, —CO-heterocyclylalkyl, —CO-heterocyclylalkenyl, —CO-cycloalkyl, —CO-cycloalkylalkyl, —CO-cycloalkylalkenyl, —CO-cyclenyl, —CO-cyclenylalkyl, —CO-cyclenylalkenyl, —SO$_2$-alkyl, —SO$_2$-alkenyl, —SO$_2$-alkynyl, —SO$_2$-heteroalkyl, —SO$_2$-heteroalkenyl, —SO$_2$-aryl, —SO$_2$-arylalkyl, —SO$_2$-arylalkenyl, —SO$_2$-heteroaryl, —SO$_2$-heteroarylalkyl, —SO$_2$-heteroarylalkenyl, —SO$_2$-heterocyclenyl, —SO$_2$-heterocyclenylalkyl, —SO$_2$-heterocyclenylalkenyl, —SO$_2$-heterocyclyl, —SO-heterocyclyalkyl, —SO$_2$-heterocyclylalkenyl, —SO$_2$-cycloalkyl, —SO$_2$-cycloalkylalkyl, —SO$_2$-cycloalkylalkenyl, —SO$_2$-cyclenyl, —SO$_2$-cyclenylalkyl, —SO$_2$-cyclenylalkenyl, spiroheteroaryl, spiroheterocyclenyl, spiroheterocyclyl, spirocycloalkyl, spirocyclenyl, spiroaryl, can be unsubstituted or substituted with one or more moieties, which may be the same or different, each moiety being independently selected from the group consisting of halogen, —CN, hydroxyalkyl, hydroxyalkenyl, alkyl, alkenyl, alkynyl, —O-alkyl, —O-alkenyl, —O-alkynyl, —S-alkyl, —S-alkenyl, —S-alkynyl, hydroxyl, carboxyl, —CO$_2$-alkyl, —CO—NR$^8$R$^9$, —NR$^8$COR$^9$, —NR$^8$SO$_2$R$^9$, —NR$^8$CONR$^8$R$^9$, —NR$^8$CO$_2$R$^9$, —OR$^9$, —SR$^9$, —SO$_2$R$^9$, —COR$^9$, -alkylNR$^8$R$^9$, -alkenylNR$^8$R$^9$, —NR$^8$R$^9$, -heteroalkyl heteroalkenyl, trihaloalkyl, dihaloalkyl, monohaloalkyl, trihaloalkenyl, dihaloalkenyl, monohaloalkenyl, -trihaloheteroalkyl, dihaloheteroalkyl, monohaloheteroalkyl, alkoxyalkyl, alkoxyalkoxy, alkoxy(alkoxy)$_b$alkoxyl, hydroxyalkoxyalkoxyl, hydroxyalkoxy(alkoxy)$_b$alkoxyl, —S-alkyl-S-alkyl, —S-alkyl-O-alkyl, —O-alkyl-S-alkyl, —S-alkyl-(S-alkyl)$_b$-S-alkyl, —S-alkyl-(O-alkyl)$_b$-S-alkyl, —O-alkyl-(S-alkyl)$_b$-O-alkyl, —S-alkyl-(S-alkyl)$_b$-O-alkyl, —O-alkyl-(S-alkyl)$_b$-S-alkyl, —S-alkyl-(S-alkyl-O-alkyl)$_b$-S-alkyl, —O-alkyl-(S-alkyl-O-alkyl)$_b$-O-alkyl, SH-alkoxyalkoxyl, —S-alkyl-S-alkyl-SH, —S-alkyl-(S-alkyl)$_b$-SH, —O-alkyl-S-alkyl-SH, —O-alkyl-(S-alkyl)$_b$-SH, heterocyclyl, heterocyclenyl, heteroaryl, cycloalkyl, cyclenyl, aryl, heterocyclylalkyl, heterocyclenylalkyl, heteroarylalkyl, cycloalkylalkyl, cyclenylalkyl, arylalkyl, —O-alkyl-NR$^{10}$-alkyl, —NR$^{10}$-alkyl-O-alkyl, and —NR$^{10}$-alkyl-NR$^{10}$-alkyl, —NR$^{10}$-alkyl-S-alkyl, —S-alkyl-NR$^{10}$-alkyl, —NR$^{10}$-alkyl-(NR$^{10}$-alkyl)$_b$-NR$^{10}$-alkyl, further wherein, R$^8$ and R$^9$ are independently selected from the group consisting of hydrogen, hydroxyl, —NH$_2$, —N(alkyl)$_2$, —N(alkenyl)$_2$, —NHalkyl, —NHalkenyl, —NH-alkyl-O-alkyl, —NH-alkenyl-O-alkyl, -alkyl-S-alkyl, -alkyl-O-alkyl, -alkenyl-O-alkenyl, -alkyl-O-alkenyl, -alkenyl-S-alkyl, -alkenyl-S-alkenyl, trifluoroalkyl, difluroalkyl, monofluoroalkyl, alkoxy, —S-alkyl, -alkyl-S-alkyl, alkoxyalkyl, alkyl, alkenyl, alkynyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, heteroalkyl, heteroalkenyl, -alkylN(alkyl)$_2$, -alkylNHalkyl, -alkyl- $NH_2$, -alkenyl-N(alkyl)$_2$, -alkyl-N(alkenyl)$_2$, -alkyl-Nalkyl(alkenyl), -alkenyl-$NH_2$, hydroxyalkyl, hydroxyalkenyl, -alkyl-SH, -alkenyl-SH, -alkyl$CO_2$H, -alkyl$CO_2$alkyl, -alkylCONHalkyl, -alkylCON$H_2$, -alkyl-CON(alkyl)$_2$, -alkylCON(alkenyl)$_2$, wherein each of said cycloalkyl, cyclenyl, aryl, heterocyclyl, heterocyclenyl, heteroaryl, cycloalkylalkyl, cyclenylalkyl arylalkyl, heterocyclylalkyl, heterocyclenylalkyl, heteroarylalkyl, heteroalkyl, heteroalkenyl can be unsubstituted or substituted with one or more moieties, which can be the same or different, independently selected from the group consisting of alkyl, heteroalkyl, heteroalkenyl, alkenyl, alkynyl, alkoxyalkoxy, —S-alkyl-S-alkyl, hydroxyalkyl, -alkylSH, hydroxyalkenyl, -alkyl-$NH_2$, -alkyl-N(alkyl)$_2$, and -alkyl-NHalkyl, b is 0-3;

$R^{10}$ and $R^{11}$, which can be the same or different, are independently selected from the group consisting of hydrogen, alkyl, alkenyl, alkynyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, alkoxyalkyl, alkenoxyalkyl, alkynoxyalkyl, cycloalkoxyalkyl, cycloalkenoxyalkyl, aryloxyalkyl, heterocycloalkoxyalkyl, heterocycloalkenoxyalkyl, heteroaryloxyalkyl, cycloalkylalkoxyalkyl, cyclenylalkoxyalkyl, arylalkoxyalkyl, heterocyclylalkoxyalkyl, heterocyclenylalkoxyalkyl, heteroarylalkoxyalkyl, -alkyl-S-alkyl, -alkyl-S-alkenyl, -alkyl-S-alkynyl, -alkyl-S-cycloalkyl, -alkyl-S-cyclenyl, -alkyl-S-aryl, -alkyl-S-heterocyclyl, -alkyl-S-heterocyclenyl, -alkyl-S-heteroaryl, -alkyl-S-cycloalkylalkyl, -alkyl-S-cyclenylalkyl, -alkyl-S-arylalkyl, -alkyl-S-heterocyclylalkyl, -alkyl-S-heterocyclenylalkyl, -alkyl-S-heteroarylalkyl, hydroxyalkyl, hydroxyalkenyl, -alkyl-SH, -alkenyl-SH, -alkyl$NH_2$, -alkenyl$NH_2$, —COR$^9$, —$CO_2$alkyl, —$CO_2$alkenyl, -alkylN(alkoxy)$_2$, -alkylNHalkoxy, —CONH$SO_2$alkyl, —CONH$SO_2$alkenyl, —CONalkyl$SO_2$alkyl, —CONHalkyl, —CONHalkenyl, -alkyl$CO_2$alkyl, -alkylCONHalkyl, -alkylCON$H_2$, -alkylCON(alkyl)$_2$, -alkylCON(alkenyl)$_2$, -alkyl$CO_2$H, -alkylN(alkyl)$_2$, -alkylNHalkyl, -alkyl-$NH_2$, -alkenyl-N(alkyl)$_2$, -alkyl-N(alkenyl)$_2$, -alkyl-Nalkyl(alkenyl), -alkenyl-$NH_2$, wherein each of said cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, cycloalkoxyalkyl, cycloalkenoxyalkyl, aryloxyalkyl, heterocycloalkoxyalkyl, heterocycloalkenoxyalkyl, heteroaryloxyalkyl, cycloalkylalkoxyalkyl, cyclenylalkoxyalkyl, arylalkoxyalkyl, heterocyclylalkoxyalkyl, heterocyclenylalkoxyalkyl, heteroarylalkoxyalkyl, can be unsubstituted or substituted with one or more moieties, which may be the same or different, each moiety being independently selected from the group consisting of alkyl, alkenyl, alkynyl, —ON, hydroxyl, —SH, —$NH_2$, —N(alkyl)$_2$, —N(alkenyl)$_2$, —N(alkoxyalkyl)$_2$, trifluoroalkyl, difluoroalkyl, monofluoroalkyl, alkoxy, —S-alkyl, halogen, hydroxyalkyl, hydroxyalkenyl, -alkylSH, —COR$^9$, —$SO_2R^9$, heteroalkyl, alkoxyalkoxy, —S-alkyl-S-alkyl, -alkyl$NH_2$, -alkyl-N(alkyl)$_2$, and -alkylNHalkyl, further wherein, in any —$NR^{10}R^{11}$ in Formula I, said $R^{10}$ and $R^{11}$ can optionally be joined together with the N of said —$NR^{10}R^{11}$ to form a cyclic ring, A is O, $CR^8R^9$, S, $SO_2$, $NR^{10}$, or CO;

m is 0-2;

$R^2$ is aryl, heteroaryl, cyclyl, heterocyclyl, cyclenyl, or heterocyclenyl wherein each of said aryl, heteroaryl, cyclyl, heterocyclyl, cyclenyl, or heterocyclenyl can be unsubstituted or substituted with one or more moieties, which may be the same or different, each moiety being independently selected from the group consisting of trihaloalkyl, dihaloalkyl, monohaloalkyl, trihaloalkenyl, dihaloalkenyl, monohaloalkenyl, halogen, CN, hydroxyl, thiohydroxyl, amine, alkoxy, alkenoxy, aryloxy, cyclenyloxy, cycloalkyloxy, heteroaryloxy, heterocyclenyloxy, heterocyclyloxy, alkyl, alkenyl, trifluoroalkoxy, difluoroalkoxy, monofluoroalkoxy, heteroalkyl, heteroalkenyl, carboxyl, —CON$R^{10}R^{11}$, —COOR$^9$, —OCOR$^9$, —$NR^{10}$COR$^9$, cycloalkyl, heterocyclyl, —$NR^{10}R^{11}$, —S-alkyl, —S-alkenyl, —S-cycloalkyl, —S-cyclenyl, —S-aryl, —S-heterocyclyl, —S-heterocyclenyl, —S-heteroaryl, —S-trifluoroalkyl, —S-difluoroalkyl, —S-monofluoroalkyl, S-trifluoroalkenyl, —S-difluoroalkenyl, —S-monofluoroalkenyl cyclenyl, heterocyclenyl, aryl, heteroaryl, and alkynyl;

$R^3$ is 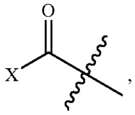 , 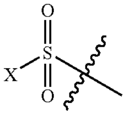 ,

—O—X, —$NR^{10}$—X, —S—X, aryl, heteroaryl, cycloalkyl, heterocyclyl, cyclenyl, or heterocyclenyl, wherein X is selected from the group consisting of aryl, heteroaryl, cycloalkyl, cyclenyl, heterocyclyl, heterocyclenyl, arylalkyl, heteroarylalkyl, cycloalkylalkyl, heterocyclylalkyl, cyclenylalkyl, heterocyclenylalkyl, alkyl, trihaloalkyl, dihaloalkyl, monohaloalkyl, trihaloalkenyl, dihaloalkenyl, monohaloalkenyl, alkenyl, or alkynyl, further wherein, each of said X, aryl, heteroaryl, cycloalkyl, heterocyclyl, cyclenyl, or heterocyclenyl can be unsubstituted or substituted with one or more moieties, which can be the same or different, each moiety being independently selected from the group consisting of trihaloalkyl, dihaloalkyl, monohaloalkyl, trihaloalkenyl, dihaloalkenyl, monohaloalkenyl, halogen, CN, hydroxyl, thiohydroxyl, amine, alkoxy, alkenoxy, aryloxy, cyclenyloxy, cycloalkyloxy, heteroaryloxy, heterocyclenyloxy, heterocyclyloxy, alkyl, alkenyl, trifluoroalkoxy, difluoroalkoxy, monofluroalkoxy, heteroalkyl, heteroalkenyl, carboxyl, —CON$R^{10}R^{11}$, —COOR$^9$, —OCOR$^9$, —$NR^{10}$COR$^9$, cycloalkyl, heterocyclyl, —$NR^{10}R^{11}$, —S-alkyl, —S-alkenyl, —S-cycloalkyl, —S-cyclenyl, —S-aryl, —S-heterocyclyl, —S-heterocyclenyl, —S-heteroaryl, —S-trifluoroalkyl, —S-difluoroalkyl, —S-monofluoroalkyl, cyclenyl, heterocyclenyl, aryl, heteroaryl, and alkynyl;

$R^4$ or $R^{4'}$, which may be the same or different, are independently selected from the group consisting of hydrogen, alkyl, alkenyl, alkynyl, heteroalkyl, heteroalkenyl, hydroxyalkyl, -alkyl$CO_2R^9$, alkylOCOR$^9$, -alkyl$NR^{10}$COR$^9$, hydroxyalkenyl, alkoxyalkyl, alkoxyalkenyl, aminoalkyl, aminoalkenyl, alkyl$NR^{10}R^{11}$, alkenyl$NR^{10}R^{11}$, cycloalkylalkyl, cycloalkylalkenyl, cyclenylalkyl, cyclenylalkenyl, cycloalkylalkynyl, cyclenylalkynyl, heterocyclylalkyl, heterocyclylalkenyl, heterocylenylalkyl, heterocyclenylalkenyl, arylalkyl, arylalkenyl, heteroarylalkyl, and heteroarylalkenyl, wherein each of said alkyl, alkenyl, alkynyl, heteroalkyl, heteroalkenyl, hydroxyalkyl, -alkyl$CO_2R^9$, alkylOCOR$^9$, -alkyl$NR^{10}$COR$^9$, hydroxyalkyl, hydroxyalkenyl, alkoxyalkyl, alkoxyalkenyl, aminoalkyl, aminoalkenyl, alkyl$NR^{10}R^{11}$, alkenyl$NR^{10}R^{11}$, cycloalkylalkyl, cycloalkylalkenyl, cyclenylalkyl, cyclenylalkenyl, cycloalkylalkynyl, cyclenylalkynyl, heterocyclylalkyl, heterocyclylalkenyl, heterocylenylalkyl, heterocyclenylalkenyl, arylalkyl, arylalkenyl, heteroarylalkyl, and heteroarylalkenyl can be unsubstituted or substituted with one or more moieties, which can be the same or different, independently selected from the group consisting of trihaloalkyl, dihaloalkyl, monohaloalkyl, trihaloalkenyl, dihaloalkenyl, monohaloalkenyl, halogen, CN, hydroxyl, thiohydroxyl, amine, alkoxy, alkenoxy, aryloxy, cyclenyloxy, cycloalkyloxy, heteroaryloxy, heterocyclenyloxy, heterocyclyloxy, alkyl, alkenyl, trifluoroalkoxy, difluroalkoxy, monofluoroalkoxy, heteroalkyl, heteroalkenyl, carboxyl, —CONR$^{10}$R$^{11}$, —COOR$^{9}$, —OCOR$^{9}$, —NR$^{10}$COR$^{9}$, cycloalkyl, heterocyclyl, —NR$^{10}$R$^{11}$, —S-alkyl, —S-alkenyl, —S-cycloalkyl, —S-cyclenyl, —S-aryl, —S-heterocyclyl, —S-heterocyclenyl, —S-heteroaryl, —S-trifluroalkyl, —S-difluoroalkyl, —S-monofluoroalkyl, cyclenyl, heterocyclenyl, aryl, heteroaryl, and alkynyl;

or wherein R$^4$ and R$^{4'}$ or R$^5$ and R$^{5'}$ or R$^6$ and R$^{6'}$ or R$^7$ and R$^{7'}$, together with the carbon to which each is attached, independently form a spirocyclic group, wherein said spirocyclic group can be unsubstituted or substituted with one or more moieties, which can be the same or different, independently selected from the group consisting of trihaloalkyl, dihaloalkyl, monohaloalkyl, trihaloalkenyl, dihaloalkenyl, monohaloalkenyl, halogen, CN, hydroxyl, thiohydroxyl, amine, alkoxy, alkyl, alkenyl, trifluoroalkoxy, difluoroalkoxy, monofluoroalkoxy, heteroalkyl, heteroalkenyl, carboxyl, —CONR$^{10}$R$^{11}$, —COOR$^{9}$, —OCOR$^{9}$, —NR$^{10}$COR$^{9}$, cycloalkyl, heterocyclyl, —NR$^{10}$R$^{11}$, alkylthio, trifluoroalkylthio, difluoroalkylthio, monofluoroalkylthio, cyclenyl, heterocyclenyl, aryl, heteroaryl, and alkynyl;

R$^4$ and R$^1$ together with the atoms to which each is attached, can cyclicize to form, together with the parent ring, a fused heterocyclyl or fused heterocyclenyl, wherein each of said fused heterocyclyl or fused heterocyclenyl can be unsubstituted or independently substituted with one or more moieties, each moiety being independently selected from the group Z;

R$^5$, R$^{5'}$, R$^7$ or R$^{7'}$, which may be the same or different, are independently selected from the group consisting of hydrogen, alkyl, alkenyl, alkynyl, alkoxyl, —S-alkyl, heteroalkyl, hydroxyalkyl, alkoxyalkyl, aminoalkyl, alkylNR$^{10}$R$^{11}$, trihaloalkyl, dihaloalkyl, monohaloalkyl, aryl, heteroaryl, cycloalkyl, cyclenyl, heterocyclyl, heterocyclenyl, arylalkyl, heteroarylalkyl, cycloalkylalkyl, cyclenylalkyl, heterocyclylalkyl, or heterocyclenylalkyl, wherein each of said aryl, heteroaryl, cycloalkyl, cyclenyl, heterocyclyl, heterocyclenyl, arylalkyl, heteroarylalkyl, cycloalkylalkyl, cyclenylalkyl, heterocyclylalkyl, heterocyclenylalkyl can be unsubstituted or substituted with one or more moieties, which can be the same or different, independently selected from the group consisting of alkyl, alkenyl, hydroxyl, —SH, —NH2, halogen, trifluoroalkyl, difluoroalkyl, and monofluoroalkyl;

R$^6$ or R$^{6'}$, which may be the same or different, are independently selected from the group consisting of hydrogen, alkyl, alkenyl, alkoxyl, trihaloalkyl, dihaloalkyl, and monohaloalky;

R$^6$ and R$^7$ or R$^5$ and R$^6$ or R$^5$ and R$^7$ together with the carbon to which each is attached, can independently cyclicize to form a fused cycloalkyl, cyclenyl, heterocyclyl, or heterocyclenyl together with the parent ring;

provided that the following compounds, which are identified as Group A Compounds herein, are excluded from Formula I:

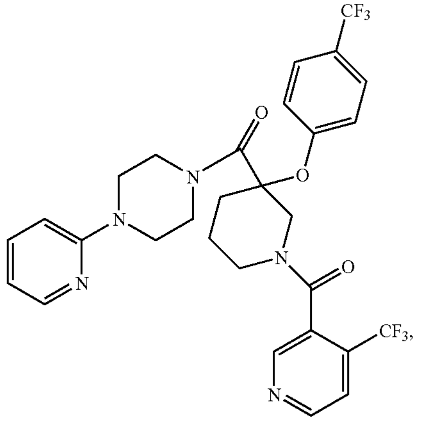

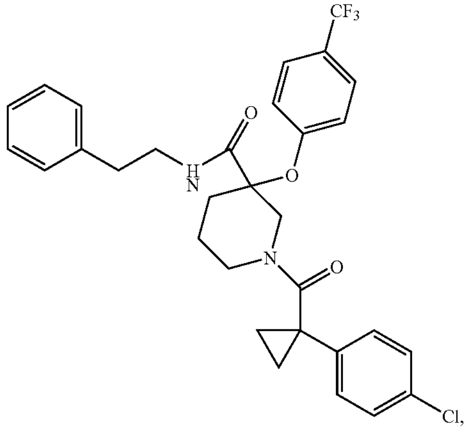

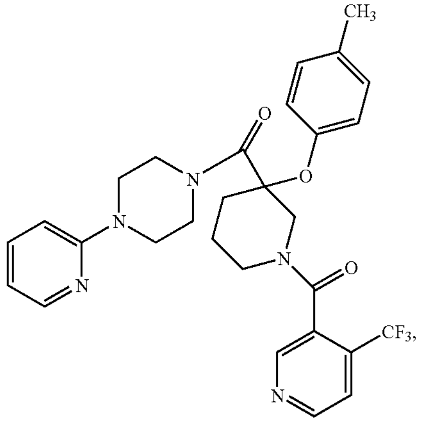

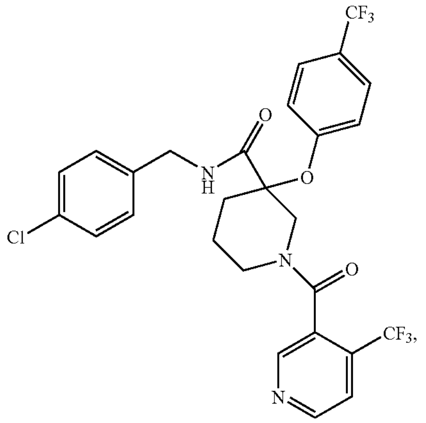

-continued
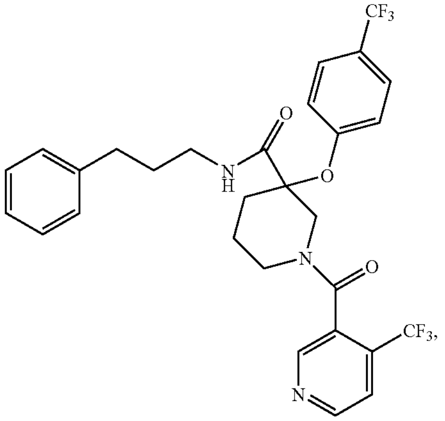
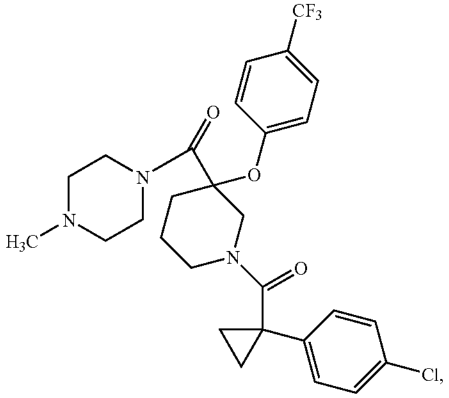
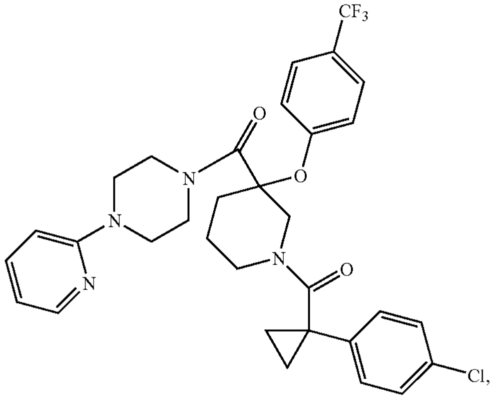
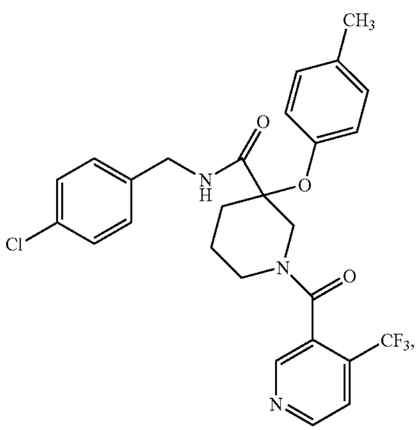
-continued
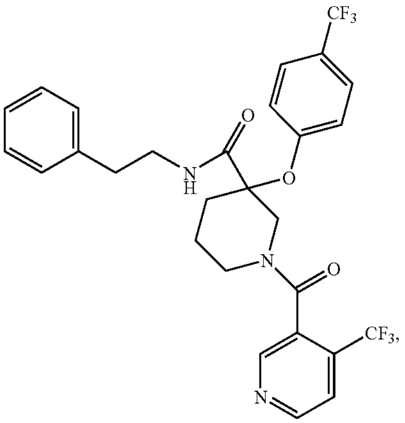
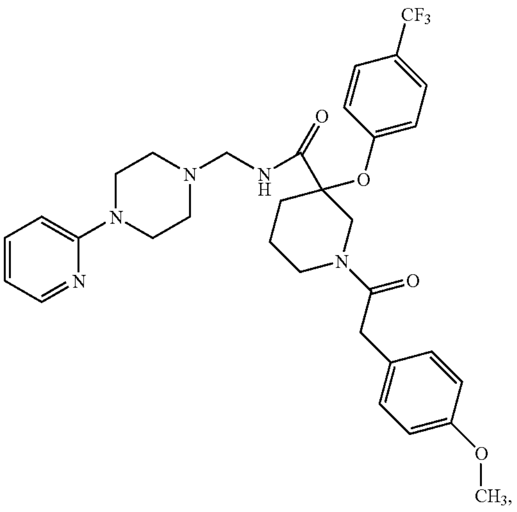
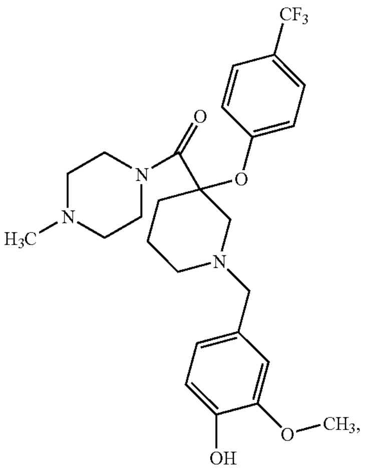

-continued
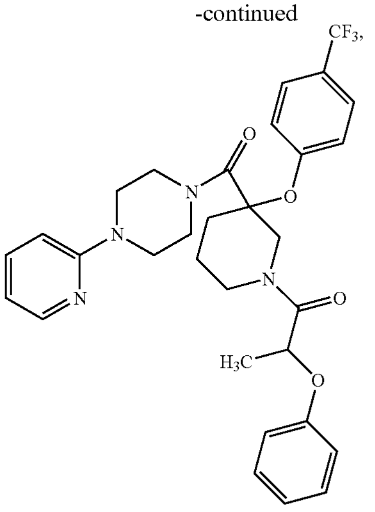
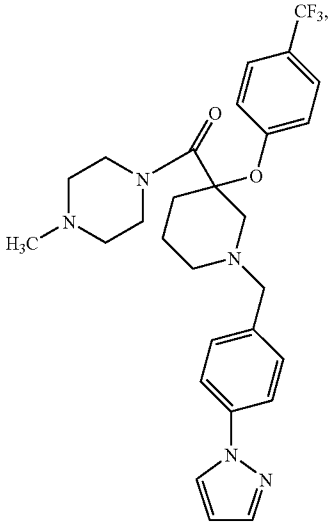
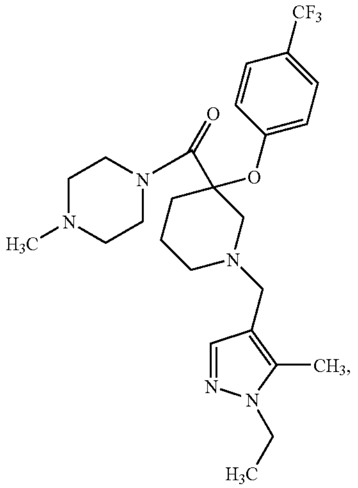
-continued
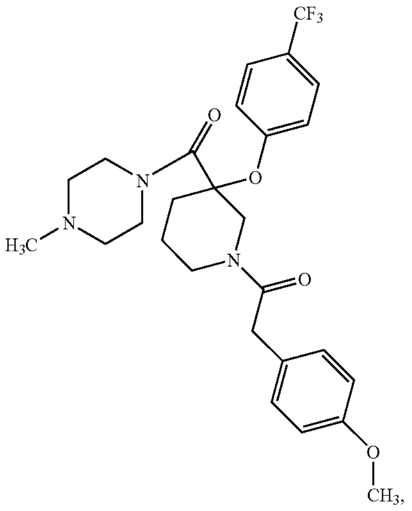
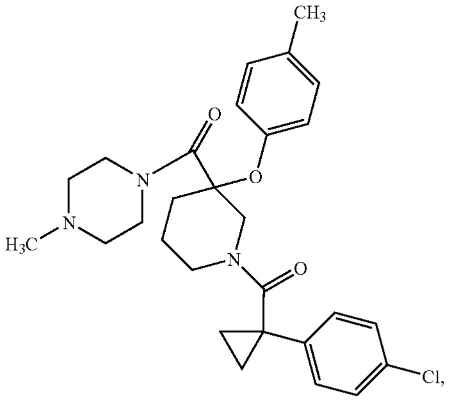
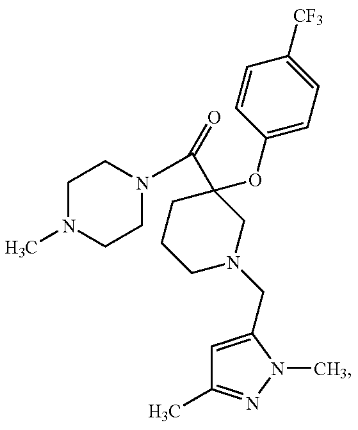

-continued
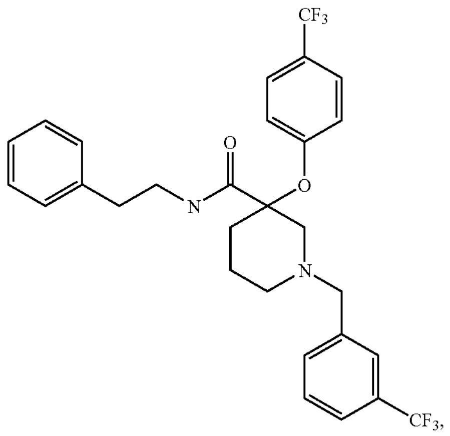
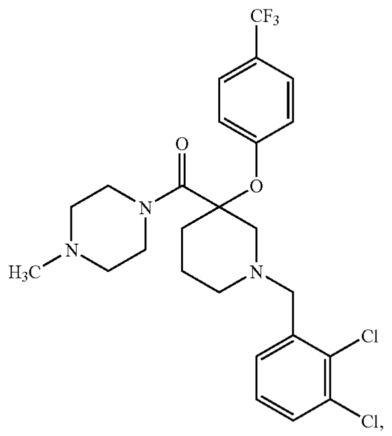
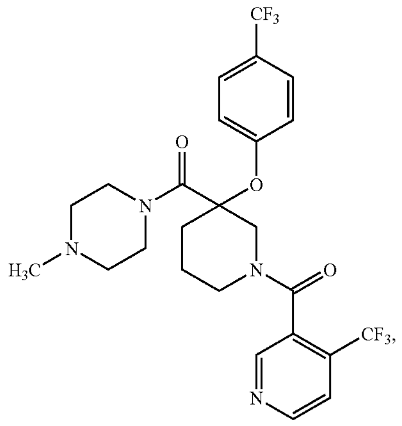
-continued
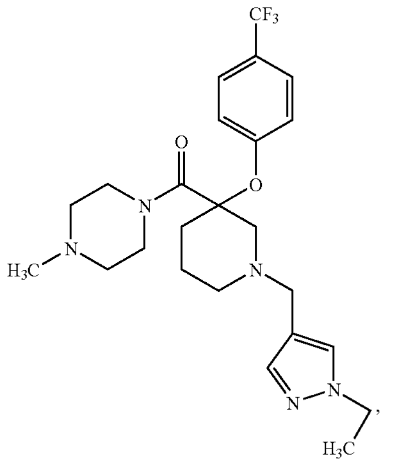
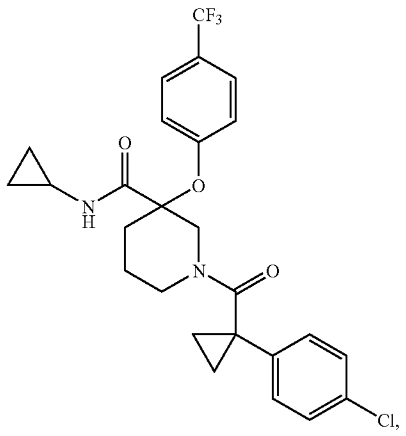
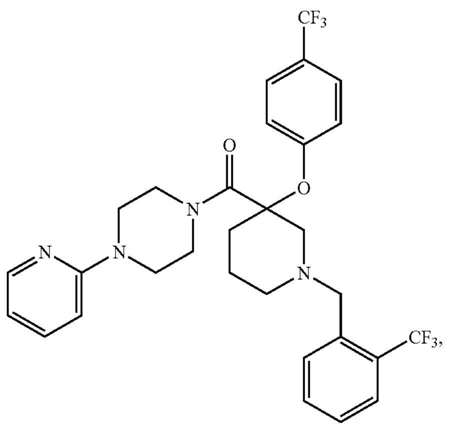

-continued

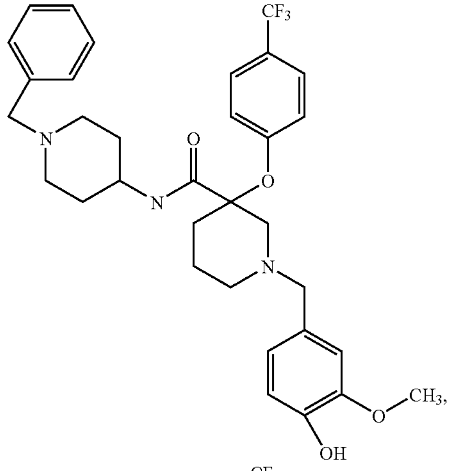

and

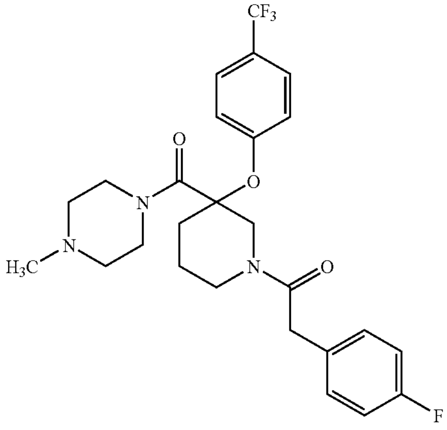

or a pharmaceutically acceptable salt, solvate, ester, or prodrug thereof.

The compounds of Formula I can be useful as HDM2 or MDM2 inhibitors and can be useful in the treatment and prevention of proliferative diseases.

DETAILED DESCRIPTION OF THE INVENTION

In an embodiment, the present invention provides compounds illustrated as Formula (I), excluding Group A compounds, as described above, or pharmaceutically acceptable salts, solvates, esters, or prodrugs thereof, wherein the various moieties are as described above.

In another embodiment, compounds of the present invention have the general structure shown the Formula II:

Formula II

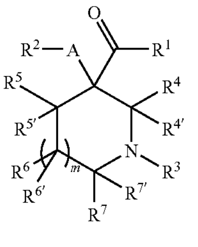

or a pharmaceutically acceptable salt, solvate, ester, or prodrug thereof, wherein:

$R^1$ is heterocyclyl or heterocyclenyl wherein each of said heterocyclyl or heterocyclenyl contains independently 1-3 heteroatoms on the ring and further wherein each of said heterocyclyl or heterocyclenyl is attached by one of its heteroatoms to the carbonyl in Formula II and still further, wherein each of said heterocyclyl or heterocyclenyl can be unsubstituted or independently substituted with at least one Z;

or $R^1$ is heteroalkyl or heteroalkenyl wherein each of said heteroalkyl or heteroalkenyl contains 1-3 heteroatoms and further wherein each of said heteroalkyl or heteroalkenyl is attached by one of its heteroatoms to the carbonyl in Formula II and still further, wherein each of said heteroalkyl or heteroalkenyl can be unsubstituted or independently substituted with at least one Z;

wherein each Z, which can be the same or different, is independently selected from the group consisting of H, amide, amine, ester, cyano, halogen, carboxyl, trihaloalkyl, dihaloalkyl, haloalkyl, alkyl, alkenyl, alkynyl, heteroalkyl, heteroalkenyl, aryl, heteroaryl, heterocyclenyl, heterocyclyl, cycloalkyl, cycloalkenyl, —O-alkyl, —O-alkenyl, —O-alkynyl, —O-heteroalkyl, —O-heteroalkenyl, —O-aryl, —O-heteroaryl, —O-heterocyclenyl, —O-heterocyclyl, —O-cycloalkyl, —O-cycloalkenyl, alkylthio, —S-alkenyl, —S-alkynyl, —S-heteroalkyl, —S-heteroalkenyl, —S-aryl, —S-heteroaryl, —S-heterocyclenyl, —S-heterocyclyl, —S-cycloalkyl, —S-cycloalkenyl, —NH-alkyl, —NH-alkenyl, —NH-alkynyl, —NH-heteroalkyl, —NH-heteroalkenyl, —NH-aryl, —NH-heteroaryl, —NH-heterocyclenyl, —NH-heterocyclyl, —NH-cycloalkyl, —NH-cycloalkenyl, spiroheteroaryl, spiroheterocyclenyl, spiroheterocyclyl, spirocycloalkyl, spirocyclenyl, spiroaryl, wherein each of said alkyl, alkenyl, alkynyl, heteroalkyl, heteroalkenyl, aryl, heteroaryl, heterocyclenyl, heterocyclyl, cycloalkyl, cycloalkenyl, —O-alkyl, —O-alkenyl, —O-alkynyl, —O-heteroalkyl, —O-heteroalkenyl, —O-aryl, —O-heteroaryl, —O-heterocyclenyl, —O-heterocyclyl, —O-cycloalkyl, —O-cycloalkenyl, alkylthio, —S-alkenyl, —S-alkynyl, —S-heteroalkyl, —S-heteroalkenyl, —S-aryl, —S-heteroaryl, —S-heterocyclenyl, —S-heterocyclyl, —S-cycloalkyl, —S-cycloalkenyl, —NH-alkyl, —NH-alkenyl, —NH-alkynyl, —NH-heteroalkyl, —NH-heteroalkenyl, —NH-aryl, —NH-heteroaryl, —NH-heterocyclenyl, —NH-heterocyclyl, —NH-cycloalkyl, —NH-cycloalkenyl, spiroheterocyclenyl, spiroheterocyclyl, spirocycloalkyl, or spirocyclenyl, can be unsubstituted or substituted with one or more moieties each moiety being independently selected from the group consisting of halogen, alkyl, ether, thioether, hydroxyl, carboxyl, ester, amide, amine, -heteroalkyl, -heteroalkyltrihaloalkyl, trihaloalkyl, dihaloalkyl, haloalkyl, —CN, hydroxyalkyl sulfonamide, urea, carbamate, —$NCO_2$alkenyl, —$NCO_2$alkyl, —$NCO_2$alkynyl, —NH—$SO_2CH_2CF_3$, —NH—$SO_2CH_3$, alkoxyalkoxy, alkylthioalkylthio, alkoxyalkylthio, alkylthioalkoxy, —O-alkyl-NH-alkyl, —NH-alkyl-O-alkyl, and —NH-alkyl-NH-alkyl;

A is O, $CH_2$, S, $SO_2$, NH, or CO;

m is 0-2;

$R^2$ is aryl, heteroaryl, cyclyl, heterocyclyl, cyclenyl, or heterocyclenyl wherein each of said aryl, heteroaryl, cyclyl, heterocyclyl, cyclenyl, or heterocyclenyl can be unsubstituted or substituted with one or more moieties, each moiety being independently selected from the group consisting of hydrogen, trihaloalkyl, dihaloalkyl, haloalkyl, trihaloheteroalkyl, dihaloheteroalkyl, haloheteroalkyl, trihaloalkenyl, dihaloalkenyl, haloalkenyl, trihaloheteroalkenyl, dihaloheteroalkenyl, haloheteroalkenyl, halogen, CN, hydroxyl, thiohydroxyl, amine, alkoxy, alkyl, heteroalkyl, carboxyl, amide, amine, ester, alkenyl, heteroalkenyl, cycloalkyl, heterocyclyl, —NH-alkyl, alkylthio, cycloalkenyl, heterocyclenyl, aryl, heteroaryl, and alkynyl;

$R^3$ is aryl, heteroaryl, cycloalkyl, heterocyclyl, cycloalkenyl, heterocyclenyl, arylalkyl, heteroarylalkyl, cycloalkyl, heterocyclylalkyl, cycloalkenylalkyl, heterocyclenylalkyl,

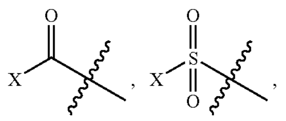

—O—X, or —N—X wherein X is aryl, heteroaryl, cycloalkyl, cycloalkenyl, heterocyclyl, heterocyclenyl, arylalkyl, heteroarylalkyl, cycloalkylalkyl, heterocyclylalkyl, cycloalkenylalkyl, heterocyclenylalkyl, alkyl, trihaloalkyl, dihaloalkyl, haloalkyl, trihaloalkenyl, dihaloalkenyl, haloalkenyl, alkenyl, or alkynyl, wherein each of said aryl, heteroaryl, cycloalkyl, heterocyclyl, cycloalkenyl, heterocyclenyl, arylalkyl, heteroarylalkyl, cycloalkylalkyl, heterocyclylalkyl, cycloalkenylalkyl, heterocyclenylalkyl and X can be unsubstituted or substituted with one or more moieties each moiety being independently selected from the group consisting of hydrogen, trihaloalkyl, dihaloalkyl, haloalkyl, trihaloalkenyl, dihaloalkenyl, haloalkenyl, halogen, CN, hydroxyl, thiohydroxyl, amine, alkoxy, alkyl, alkenyl, alkynyl, heteroalkyl, carboxyl, amide, amine, ester, heteroalkenyl, cycloalkyl, heterocyclyl, —NH-alkyl, alkylthio, —NH-alkenyl, —SH-alkenyl, cycloalkenyl, heterocyclenyl, aryl, heteroaryl, alkynyl, or heteroakynyl;

$R^4$ or $R^{4'}$, which may be the same or different, are independently hydrogen, alkyl, alkenyl, alkynyl, heteroalkyl, heteroalkenyl, hydroxyalkyl, -alkylalkylester, ether, alkoxyalkoxy, alkoxyalkyl, trihaloalkyl, dihaloalkyl, haloalkyl, cycloalkyl, cycloalkenyl, heterocyclyl, heterocyclenyl, aryl, heteroaryl, amine, hydroxyl, carboxyl, CN, ester, or amide, wherein said alkyl, alkenyl, alkynyl, heteroalkyl, heteroalkenyl, hydroxyalkyl, -alkylalkylester, alkoxy, alkoxyalkoxy, alkoxyalkyl, trihaloalkyl, dihaloalkyl, haloalkyl, cycloalkyl, cycloalkenyl, heterocyclyl, heterocyclenyl, aryl, or heteroaryl can be unsubstituted or independently substituted with one or more moieties, each moiety being independently selected from the group consisting of hydrogen, trihaloalkyl, dihaloalkyl, haloalkyl, trihaloalkenyl, dihaloalkenyl, haloalkenyl, halogen, CN, hydroxyl, thiohydroxyl, amine, alkoxy, alkyl, alkenyl, alkynyl, heteroalkyl, carboxyl, amide, amine, ester, heteroalkenyl, cycloalkyl, heterocyclyl, —NH-alkyl, alkylthio, —NH-alkenyl, —SH-alkenyl, cycloalkenyl, heterocyclenyl, aryl, heteroaryl, alkynyl, or heteroakynyl;

or $R^4$ and $R^{4'}$ together with the carbon to which it is attached, can cyclicize to form a spirocyclic, spiroheterocyclic, spirocyclenyl, or spiroheterocyclenyl;

$R^5$, $R^{5'}$, $R^6$, $R^{6'}$, $R^7$, or $R^{7'}$ are each independently H;

provided that the compounds identified as Group A Compounds herein, are excluded from Formula II:

In another embodiment, in Formulas I or II, $R^1$ is heterocyclenyl, wherein said heterocyclenyl is unsubstituted or substituted with aryl.

In another embodiment, in Formula I, $R^1$ is

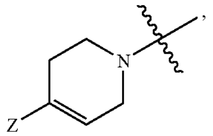

wherein Z is phenyl.

In another embodiment, in Formula I, $R^1$ is

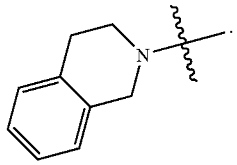

In another embodiment, in Formula I, $R^1$ is

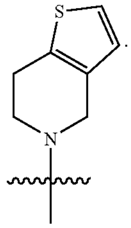

In another embodiment, in Formula I, $R^1$ is

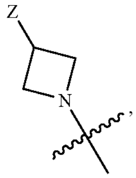

wherein Z is —O-phenyl.

In another embodiment, in Formulas I or II, $R^1$ is heterocyclyl substituted with Z, wherein Z is phenyl, further wherein said phenyl can be unsubstituted or substituted with at least one moiety, which may be the same or different, independently selected from the group consisting of halogen, —S-heterorraryl, heterocyclyl, —O-heterocyclyl, alkoxyalkoxyl, hydroxyalkoxyl, alkoxy(alkoxy)$_b$alkoxyl, hydroxyalkoxyalkoxyl, heterocyclylalkyl, —NHCONHalkyl-COOalkyl, —O-alkylCONR$^8$R$^9$, —O-alkylNR$^8$R$^9$, —O-alkylCONSO$_2$R$^9$, —NCOalkylcarboxyl, —CON-Halkyl-O-alkyl, —O-heterocyclylalkyl, wherein said heterocyclylalkyl is unsubstituted or substituted with hydroxyalkyl, and still further wherein R$^8$ and R$^9$ are independently selected from the group consisting of hydrogen, alkyl, alkoxyalkyl, and cycloalkyl, b is 1.

In another embodiment, in Formulas I or II, R$^1$ is piperazinyl, piperidinyl, or pyrrolidinyl substituted with Z, wherein Z is phenyl, wherein said phenyl can be unsubstituted or substituted with at least one moiety, which may be the same or different, independently selected from the group consisting of halogen, —S-heterorarayl, heterocyclyl, —O-heterocyclyl, alkoxyalkoxyl, hydroxyalkoxyl, alkoxy(alkoxy)$_b$alkoxyl, hydroxyalkoxyalkoxyl, heterocyclylalkyl, —NHCON-HalkylCOOalkyl, —O-alkylCONR$^8$R$^9$, —O-alkylNR$^8$R$^9$, —O-alkylCONSO$_2$R$^9$, —NCOalkylcarboxyl, —CON-Halkyl-O-alkyl, —O-heterocyclylalkyl, wherein said heterocyclylalkyl is unsubstituted or substituted with hydroxyalkyl, further wherein R$^8$ and R$^9$ are independently selected from the group consisting of hydrogen, alkyl, alkoxyalkyl, and cycloalkyl, and still further wherein b is 1.

In another embodiment, in Formulas I or II, R$^1$ is heterocyclyl substituted with Z, wherein Z is,

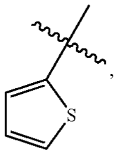, 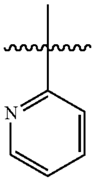, 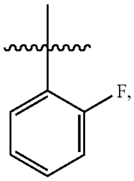

or —O-pyridinyl, wherein said —O— pyridinyl can be unsubstituted or substituted with —CONH$_2$.

In another embodiment, in Formulas I or II, R$^1$ is

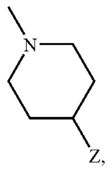

wherein Z is

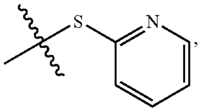, 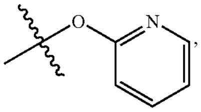, 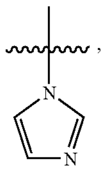,

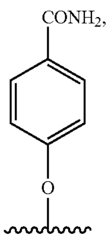 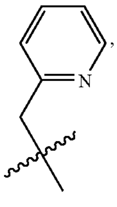, 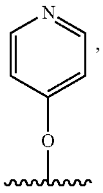, 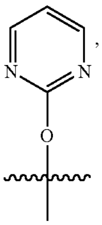,

-continued

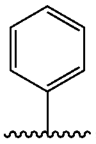, 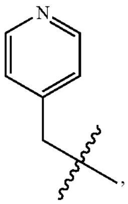, 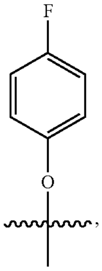,

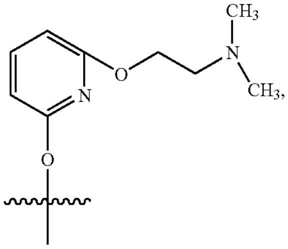 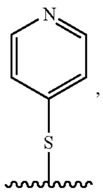, ,

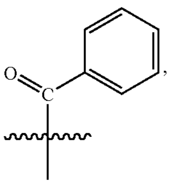, . 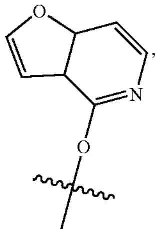, 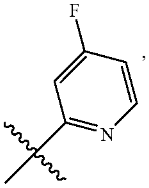,

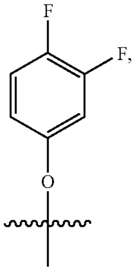 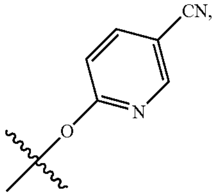

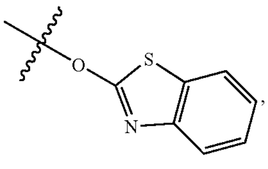, or 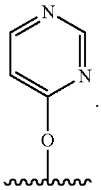.

In another embodiment, in Formulas I or II, R$^1$ is

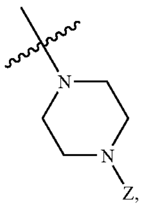

wherein Z is
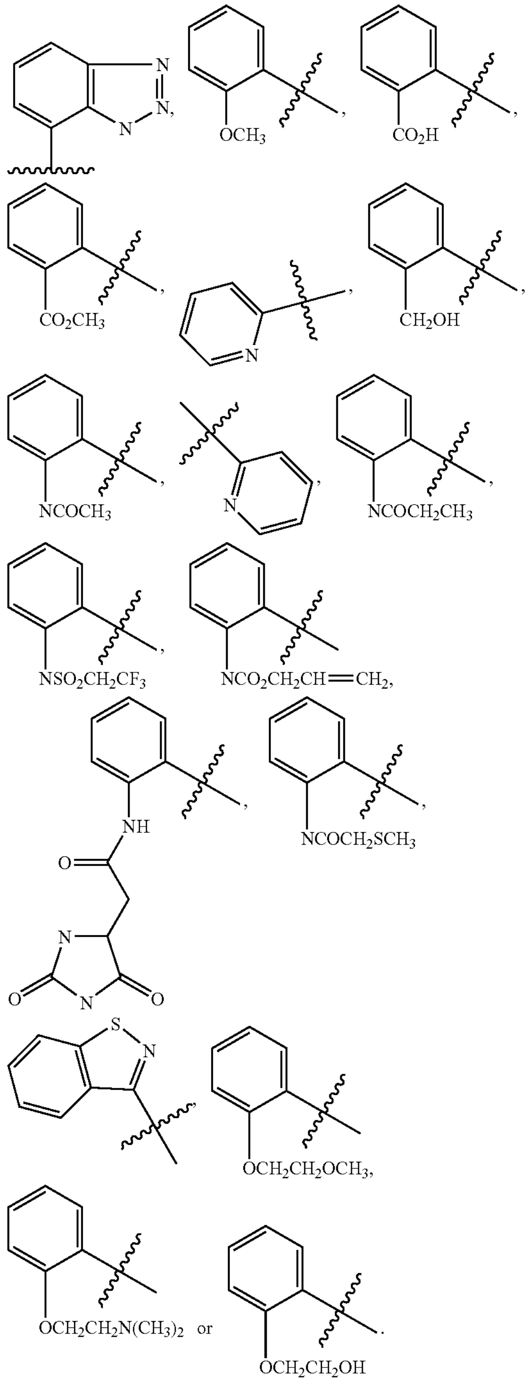
In another embodiment, in Formulas I or II, $R^1$ is
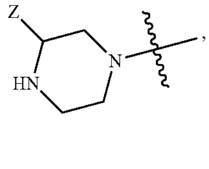
wherein Z is $—CO_2CH_3$.
In another embodiment, in Formulas I or II, $R^1$ is
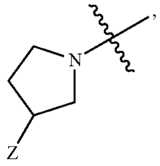
wherein Z is
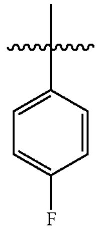
or
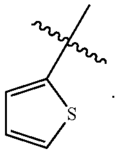
In another embodiment, in Formulas I or II, $R^1$ is
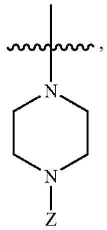
wherein Z is
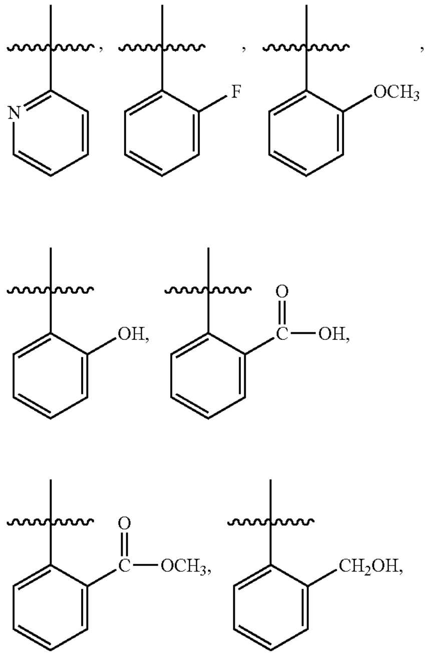

-continued
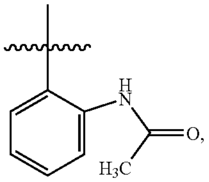
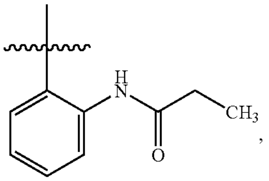
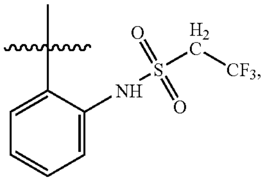
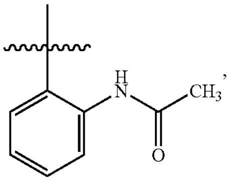
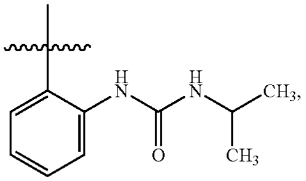
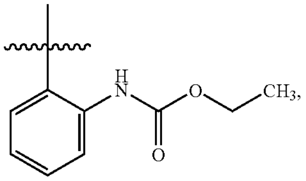
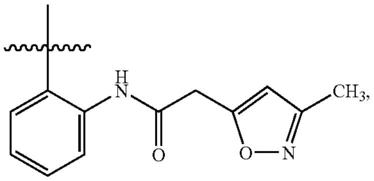
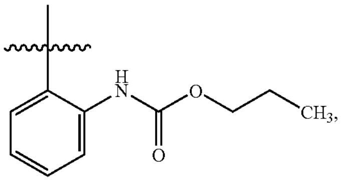
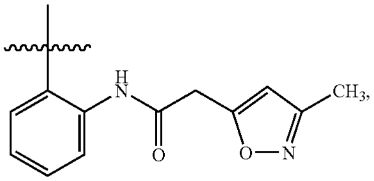
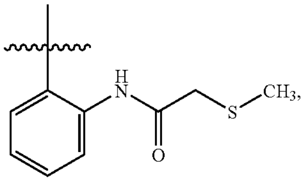
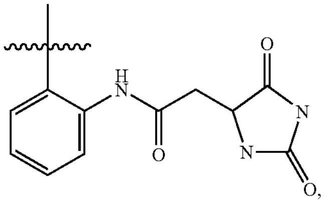
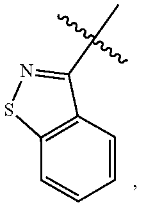
-continued
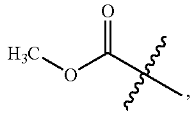
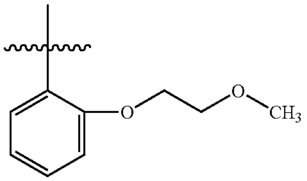
or
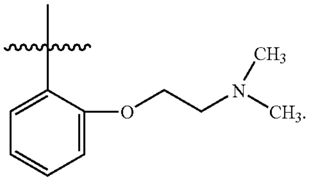
In another embodiment, in Formulas I or II, $R^1$ is
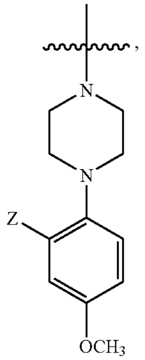
wherein Z is
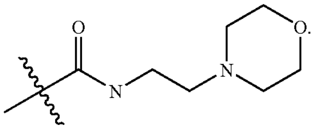
In another embodiment, in Formulas I or II, $R^1$ is
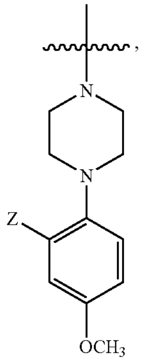

wherein Z is
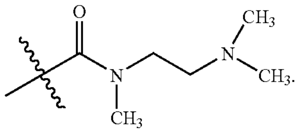
In another embodiment, in Formulas I or II, $R^1$ is
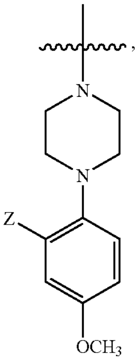
wherein Z is
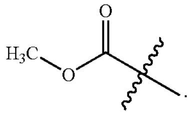
In another embodiment, in Formulas I or II, $R^1$ is
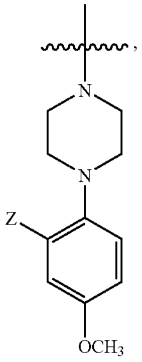
wherein Z is
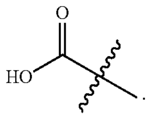
In another embodiment, in Formulas I or II, $R^1$ is
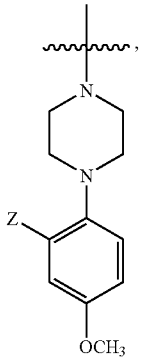
wherein Z is
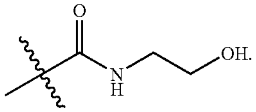
In another embodiment, in Formulas I or II, $R^1$ is
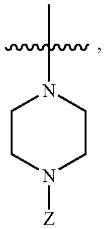
wherein Z is
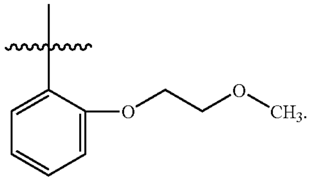
In another embodiment, in Formulas I or II, $R^1$ is
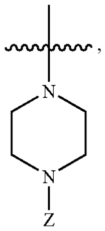

wherein Z is

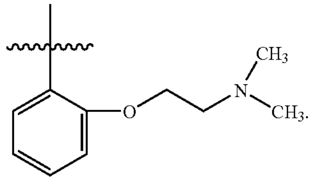

In another embodiment, in Formulas I or II, $R^1$ is

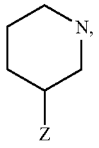

wherein Z is

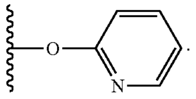

In another embodiment, in Formulas I or II, $R^1$ is

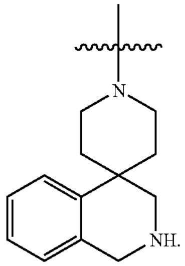

In another embodiment, in Formulas I or II, $R^1$ is

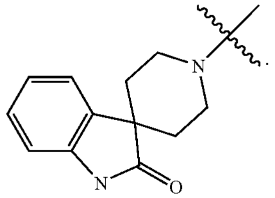

In another embodiment, in Formulas I or II, $R^1$ is

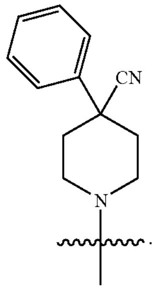

In another embodiment, in Formulas I or II, $R^1$ is

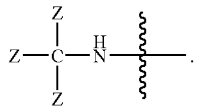

In another embodiment, in Formulas I or II, $R^1$ is

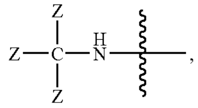

wherein each Z is different and independently selected from the group consisting of hydrogen, methylester, and phenyl substituted in its para position with chloro.

In another embodiment, in Formulas I or II, $R^1$ is

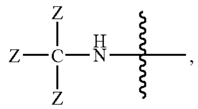

wherein each Z is different and independently selected from the group consisting of hydrogen, alkyl, phenyl substituted in its para position with hydroxyl.

In another embodiment, in Formulas I or II, $R^1$ is

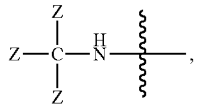

wherein each Z is different and independently selected from the group consisting of hydrogen, methyl, phenyl substituted in its para position with hydroxyl.

In another embodiment, in Formulas I or II, $R^1$ is

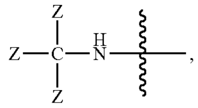

wherein each Z is different and independently selected from the group consisting of hydrogen and unsubstituted aryl.

In another embodiment, in Formulas I or II, $R^1$ is

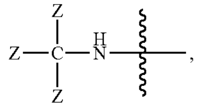

wherein each Z is different and independently selected from the group consisting of hydrogen,

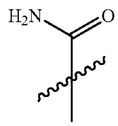

and phenyl.

In another embodiment, in Formulas I or II, A is O.

In another embodiment, in Formulas I or II, $R^2$ is heteroaryl or aryl, wherein said heteroaryl or aryl, can be unsubstituted or substituted with at least one moiety, which can be the same or different, independently selected from the group consisting of trifluroalkyl, difluoroalkyl, —O-trifluroalkyl, —S-trifluoroalkyl, —O-difluroalkyl, alkyl, and halogen.

In another embodiment, in Formulas I or II, $R^2$ is thiophene, phenyl, or 4-H-pyrazole wherein said thiophene, 4-H-pyrazole, or phenyl can be unsubstituted or substituted with at least one moiety, which can be the same or different, independently selected from the group consisting of trifluoromethyl, difluoromethyl, —O-trifluoromethyl, —S-trifluoromethyl, —O-difluoromethyl, methyl, F, Br, Cl, and I.

In another embodiment, in Formulas I or II, $R^3$ is CO—X or —$SO_2$—X wherein X is heteroaryl, arylalkyl, aryl, alkyl, or trifluoroalkyl, wherein said heteroaryl or arylalkyl, can be unsubstituted or substituted, with at least one moiety, independently selected from the group consisting of trifluoroalkyl, halogen and cycloalkyl.

In another embodiment, in Formulas I or II, $R^3$ is —CO—X or —SO—X, wherein X is pyridinyl, oxazolyl, thiophene, pyrimidinyl, phenylmethyl, phenyl, 2,2-dimethylpropyl, ethyl, or trifluoroethyl, wherein each of said pyridinyl, oxazolyl, thiophene, pyrimidinyl or phenylmethyl can be unsubstituted or substituted, with at least one moiety, independently selected from the group consisting of trifluoromethyl, methyl, chloro and cyclopropyl.

In another embodiment, in Formulas I or II, $R^3$ is —CO—X, wherein X is

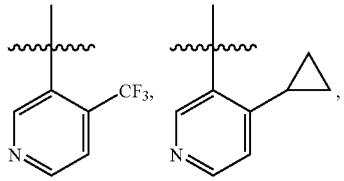

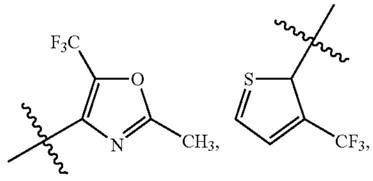

or

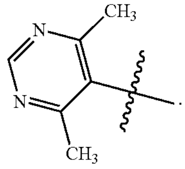

In another embodiment, in Formulas I or II, $R^2$ is

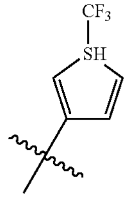

or

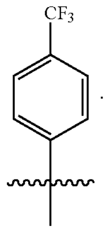

In another embodiment, in Formulas I or II, $R^3$ is —$SO_2$—X, wherein X is ethyl or trifluoroethyl.

In another embodiment, in Formulas I or II, $R^3$ is

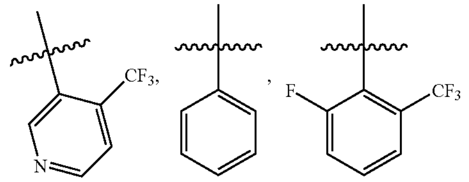

or

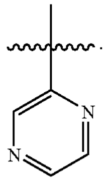

In another embodiment, in Formulas I or II, $R^4$ or $R^{4'}$ are independently selected from the group consisting of hydrogen, alkyl, alkenyl, heterocyclylalkyl, -alkyl$NR^{10}R^{11}$, hydroxyalkyl, cycloalkylalkyl, alkylesteralkyl, and alkoxyalkyl, wherein each of said heterocyclylalkyl, hydroxyalkyl or alkyl can be unsubstituted or substituted with a moiety selected from the group consisting of alkoxyl, alkoxyalkyl, hydroxyalkyl, and hydroxyl, further wherein said $R^{10}$ and $R^{11}$, which may be the same or different, are independently selected from the group consisting of hydrogen and alkyl;

or $R^4$ and $R^{4'}$, together with the carbon to which they are attached, form a cyclopropyl.

In another embodiment, in Formulas I or II, $R^4$ or $R^{4'}$ are independently selected from the group consisting of hydrogen, propyl, propenyl, butenyl, aminoalkyl, cycloalkylalkyl, methylesterethyl,

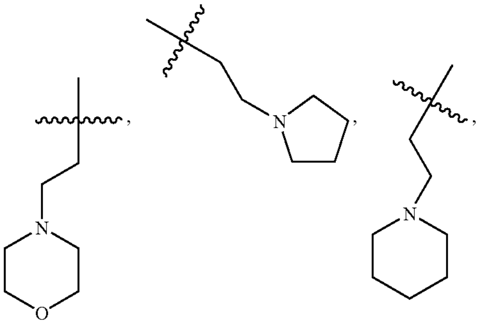

-continued

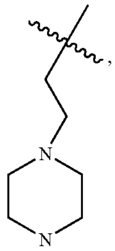,
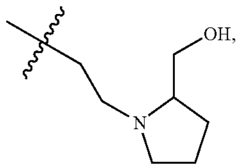

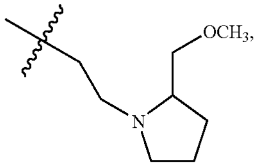, $—CH_2CH_2N(ethyl)_2$, $—CH_2CH_2N(methyl)_2$, $—CH_2CH_2—OH$,

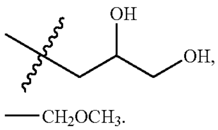, 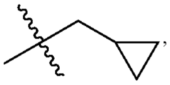, and $—CH_2OCH_3$.

In another embodiment, in Formulas I or II, $R^4$ and the nitrogen of $R^1$ attached to the carbonyl attached to the parent ring, together with the carbon to which they are attached, form a fused piperidin-2-one ring.

In another embodiment, in Formulas I or II, $R^5$, $R^{5'}$, $R^6$, $R^{6'}$, $R^7$, and $R^{7'}$ are each independently hydrogen.

In another embodiment, in Formula I, $R^7$ or $R^{7'}$ is phenyl; or $R^6$ and $R^7$ together with the carbons to which they are attached, form a fused cyclopropyl ring.

In another embodiment, in Formulas I or II, m is 1.

In another embodiment, this invention discloses a compound of the Formula:

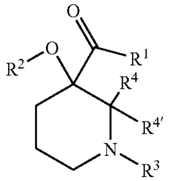

or a pharmaceutically acceptable salt, solvate, ester, or prodrug thereof, wherein $R^1$ is

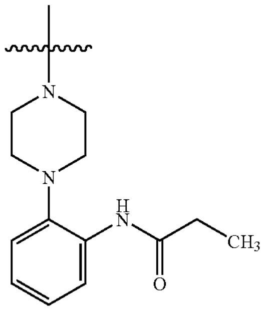 or 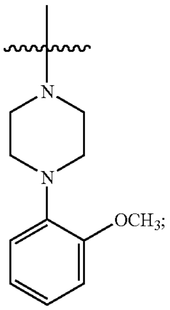;

$R^2$ is phenyl substituted with trifluoromethyl in the para position of said phenyl;

$R^3$ is phenyl;

$R^4$ and $R^{4'}$ are each H; provided that the compounds identified as Group A compounds herein, are excluded from said Formula.

In another embodiment, this invention discloses a compound of the Formula:

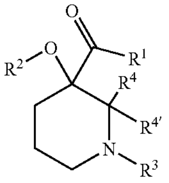

or a pharmaceutically acceptable salt, solvate, ester, or prodrug thereof, wherein $R^1$ is

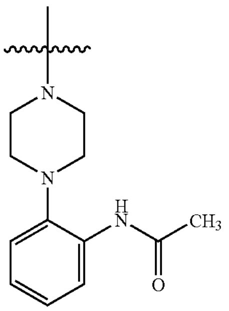 or 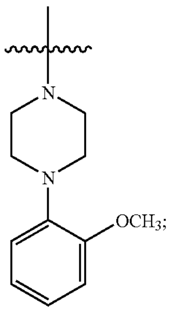;

$R^2$ is phenyl substituted with trifluoromethyl in the para position of said phenyl;

$R^3$ is 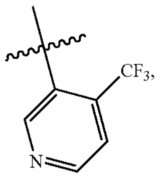, 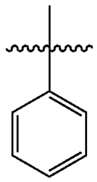,

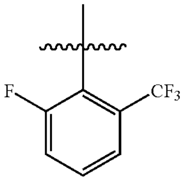 or 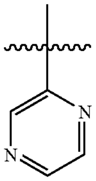

$R^4$ and $R^{4'}$ are each H; provided that the compounds identified as Group A compounds herein, are excluded from said Formula.

In another embodiment, this invention discloses a compound of the Formula:

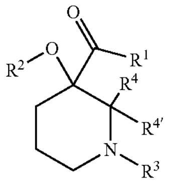

or a pharmaceutically acceptable salt, solvate, ester, or prodrug thereof, wherein $R^1$ is

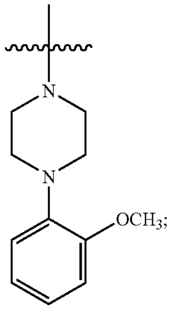

$R^2$ is phenyl substituted with trifluoromethyl in the para position of said phenyl;

$R^3$ is pyrazin-2-yl;

$R^4$ and $R^{4'}$ are each H; provided that the compounds identified as Group A compounds herein, are excluded from said Formula.

In another embodiment, this invention discloses a compound of the Formula:

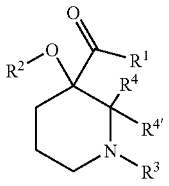

or a pharmaceutically acceptable salt, solvate, ester, or prodrug thereof, wherein $R^1$ is

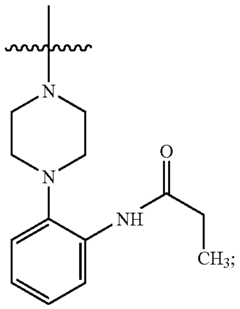

$R^2$ is phenyl substituted with trifluoromethyl in the para position of said phenyl;

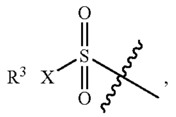

wherein X is $CH_2CF_3$ or $—CH_2CH_3$;

$R^4$ and $R^{4'}$ are each H; provided that the compounds identified as Group A compounds herein, are excluded from said Formula.

In yet another embodiment, this invention discloses a compound of the Formula:

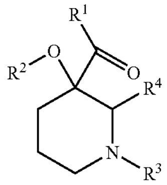

or a pharmaceutically acceptable salt, solvate or ester thereof, wherein $R^1$ is

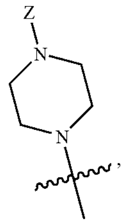

further wherein Z is phenyl, still further wherein said phenyl can be unsubstituted or substituted with at least one moiety, which may be the same or different, independently selected from the group consisting of halogen, —S-heterorаryl, heterocyclyl, —O-heterocyclyl, alkoxyalkoxyl, hydroxyalkoxyl, alkoxy(alkoxy)$_b$alkoxyl, hydroxyalkoxyalkoxyl, heterocyclylalkyl, —NHCONHalkylCOOalkyl, —O-alkylCONR$^{10}$R$^{11}$, —O-alkylNR$^{10}$R$^{11}$, —O-alkylCONSO$_2$R$^9$, —NCOalkylcarboxyl, —CONHalkyl-O-alkyl, —O-heterocyclylalkyl, wherein said heterocyclylalkyl is unsubstituted or substituted with hydroxyalkyl, and still further wherein $R^{10}$ and $R^{11}$ are independently selected from the group consisting of hydrogen, alkyl, alkoxyalkyl, and cycloalkyl, b is 1;

$R^2$ is 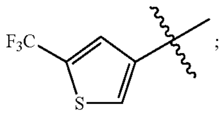 ; $R^3$ is 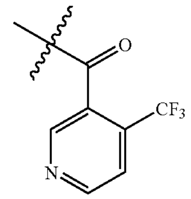

$R^4$ is hydrogen, propyl, propenyl, butenyl, aminoalkyl, cycloalkylalkyl, methylesterethyl,

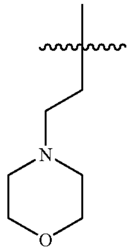, 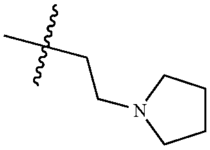, 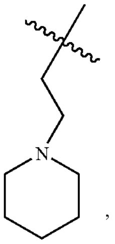, 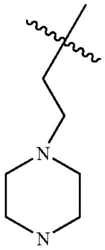, 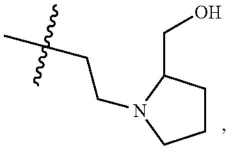, 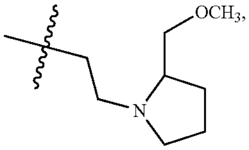

$CH_2CH_2N(ethyl)_2$, $—CH_2CH_2N(methyl)_2$, $—CH_2CH_2—OH$,

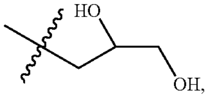 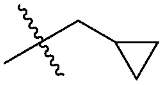, and $—CH_2OCH_3$; provided that the compounds identified as Group A compounds herein, are excluded from said Formula.

In yet another embodiment, this invention discloses a compound of the Formula:

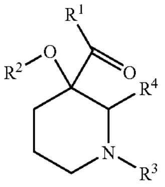

or a pharmaceutically acceptable salt, solvate or ester thereof, wherein $R^1$ is

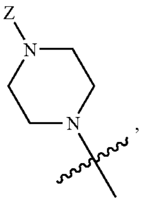, further wherein Z is phenyl, still further wherein said phenyl is substituted with $—O—(CH_2)_3COOH$, $—OCH_2COOH$ or —NCOalkylcarboxyl;

$R^2$ is 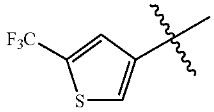; $R^3$ is 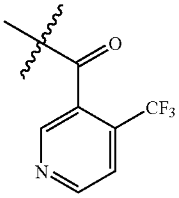

$R^4$ is propyl; provided that the compounds identified as Group A compounds herein, are excluded from said Formula.

In yet another embodiment, this invention discloses a compound of the Formula:

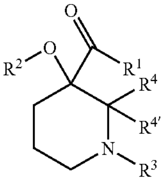

or a pharmaceutically acceptable salt, solvate or ester thereof, wherein $R^1$ is

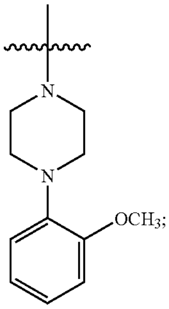

$R^2$ is phenyl substituted with trifluoromethyl in the para position of said phenyl;

$R^3$ is

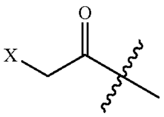, wherein X is

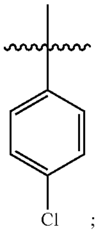 ;

$R^4$ and $R^{4'}$ are each H; provided that the compounds identified as Group A compounds herein, are excluded from said Formula.

In yet another embodiment, this invention discloses a compound of the Formula:

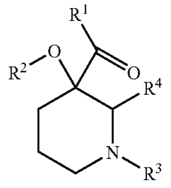

or a pharmaceutically acceptable salt, solvate or ester thereof, wherein $R^1$ is

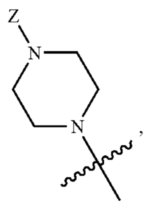

further wherein Z is phenyl, still further wherein said phenyl is substituted with $—O—CH_2CONH_2$, $—O—CH_2CONHCH_3$, or $—O—CH_2CON(CH_3)_2$;

$R^2$ is 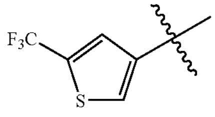 ; $R^3$ is 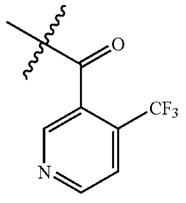

$R^4$ is propyl; provided that the compounds identified as Group A compounds herein, are excluded from said Formula.

In still another embodiment, this invention discloses a compound of the Formula:

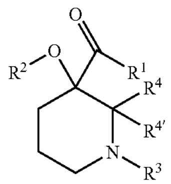

or a pharmaceutically acceptable salt, solvate or ester thereof, wherein $R^1$ is

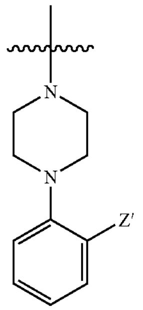

wherein Z' is —F, $—OCH_3$, —H, —COOH, $—COOCH_3$, $—CH_2OH$, $—NCOCH_3$, $—NCOCH_2CH_3$, 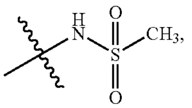

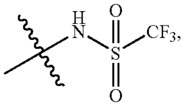 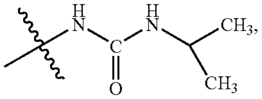

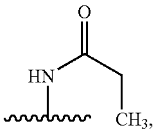 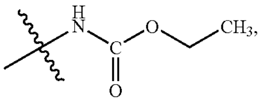

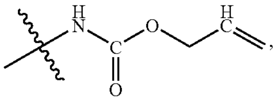

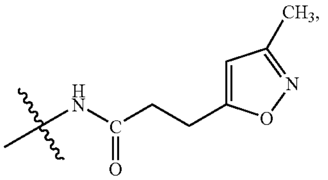

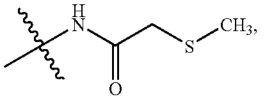 or

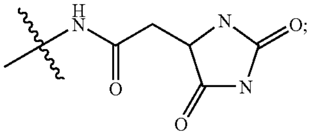

$R^2$ is phenyl substituted with one or more moieties each moiety being independently selected from the group consisting of trifluoromethyl and halogen, wherein said phenyl is substituted in the meta position, para position, or both meta and para positions;

$R^3$ is 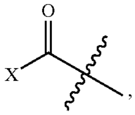, wherein X is

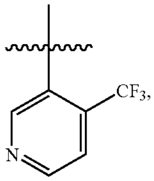, 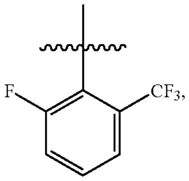, or 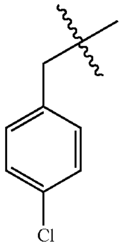;

$R^4$ and $R^{4'}$ are each H; provided that the compounds identified as Group A compounds herein, are excluded from said Formula.

In yet another embodiment, this invention discloses a compound of the Formula:

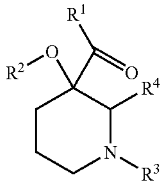

or a pharmaceutically acceptable salt, solvate or ester thereof, wherein $R^1$ is

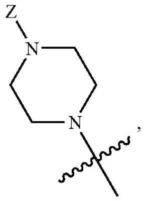, further wherein Z is phenyl, still further wherein said phenyl is substituted with methoxyl, hydroxyethoxyl, methoxyethoxyl, methoxyethoxyexthoxyl, or hydroxyethoxyethoxyl;

$R^2$ is 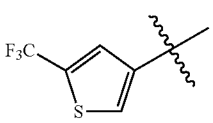; $R^3$ is 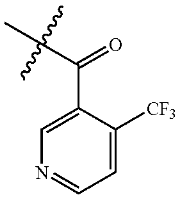

-continued $R^4$ is 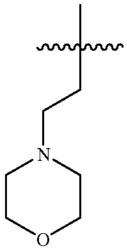, 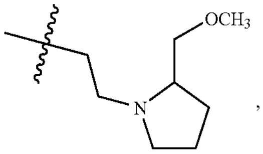,

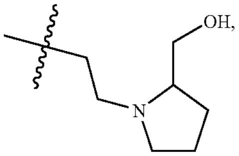, 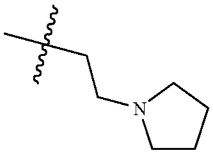,

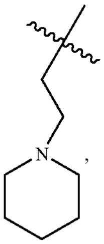, $-CH_2CH_2N(ethyl)_2$, $-CH_2CH_2N(methyl)_2$, propyl, propenyl,

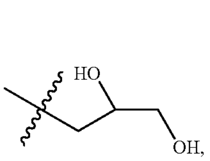 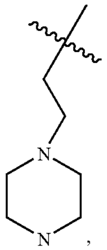, hydroxyethyl, cyclopropylmethyl, or methoxymethyl; provided that the compounds identified as Group A compounds herein, are excluded from said Formula.

In another embodiment, this invention discloses a compound of the Formula:

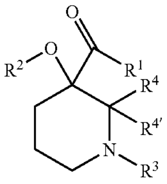

or a pharmaceutically acceptable salt, solvate or ester thereof, wherein $R^1$ is

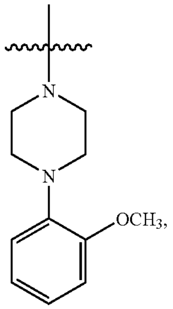

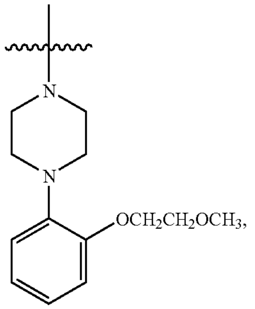

or

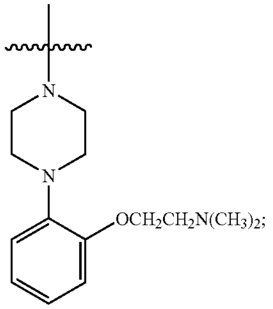

$R^2$ is phenyl substituted with one or more moieties each moiety being independently selected from the group consisting of trifluoromethyl and halogen, wherein said phenyl is substituted in the meta position, para position, or both meta and para positions;

$R^3$ is 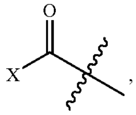 , wherein X is

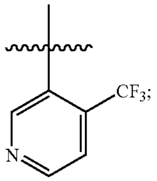

$R^4$ or $R^{4'}$, which can be the same or different are independently selected from the group consisting of hydrogen, alkyl, alkenyl, alkynyl, hydroxyalkyl, and -alkylCOOalkyl;

or $R^4$ and $R^{4'}$ together with the carbon atom to which it is attached, can cyclize to form spiro ring forms; provided that the compounds identified as Group A compounds herein, are excluded from said Formula.

In another embodiment, this invention discloses a compound of the Formula:

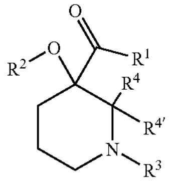

or a pharmaceutically acceptable salt, solvate or ester thereof, wherein $R^1$ is

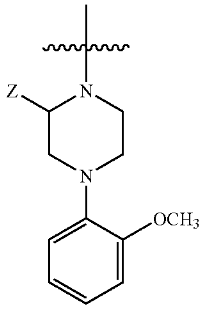

wherein Z is selected from the group consisting of hydrogen, —$COOCH_3$,

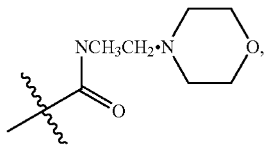

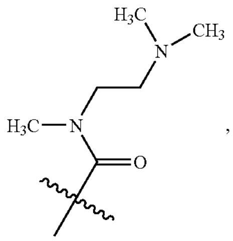

,

—COOH, and —$CONCH_2CH_2OH$;

$R^2$ is phenyl substituted with one or more moieties each moiety being independently selected from the group consisting of trifluoromethyl and halogen, wherein said phenyl is substituted in the meta position, para position, or both meta and para positions;

$R^3$ is

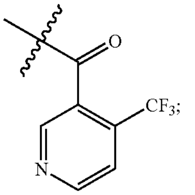

$R^4$ and $R^{4'}$ are each H; provided that the compounds identified as Group A compounds herein, are excluded from said Formula.

In another embodiment, this invention discloses a compound of the Formula:

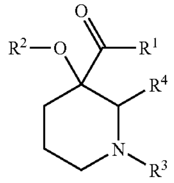

or a pharmaceutically acceptable salt, solvate or ester thereof, wherein $R^1$ is

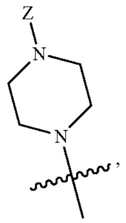

further wherein Z is phenyl, still further wherein said phenyl can be unsubstituted or substituted with at least one moiety, which may be the same or different, independently selected from the group consisting of halogen, S-heterorаryl, heterocyclyl, —O-heterocyclyl, alkoxyalkoxyl, hydroxyalkoxyl, alkoxy(alkoxy)$_b$alkoxyl, hydroxyalkoxyalkoxyl, heterocyclylalkyl, —NHCONHalkylCOOalkyl, —O-alkylCONR$^{10}$R$^{11}$, —O-alkylNR$^{10}$R$^{11}$, —O-alkylCONSO$_2$R$^9$, —NCOalkylcarboxyl, —CONHalkyl-O-alkyl, —O-heterocyclylalkyl, wherein said heterocyclylalkyl is unsubstituted or substituted with hydroxyalkyl, and still further wherein $R^{10}$ and $R^{11}$ are independently selected from the group consisting of hydrogen, alkyl, alkoxyalkyl, and cycloalkyl, b is 1;

$R^2$ is phenyl substituted with trifluoromethyl or halogen in the para position;

$R^3$ is 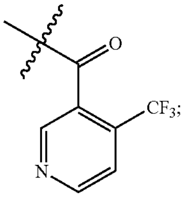

$R^4$ is hydrogen, propyl, propenyl, butenyl, aminoalkyl, cycloalkylalkyl, methylesterethyl,

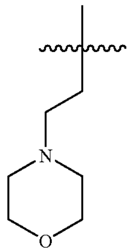 , 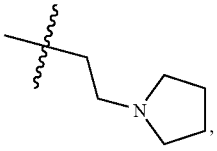 , 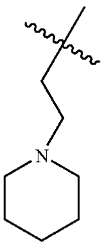 ,

-continued

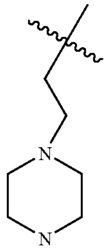 , 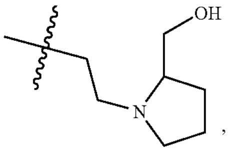 ,

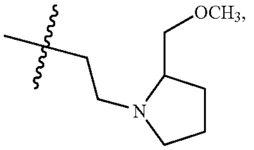

$CH_2CH_2N$ (ethyl)$_2$, —$CH_2CH_2N$(methyl)$_2$, —$CH_2CH_2$—OH,

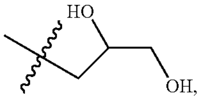 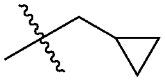 , and —$CH_2OCH_3$; provided that the compounds identified as Group A compounds herein, are excluded from said Formula.

In another embodiment, this invention discloses a compound of the Formula:

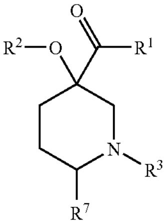

or a pharmaceutically acceptable salt, solvate or ester thereof, wherein $R^1$ is

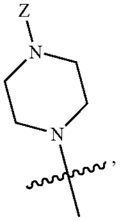

further wherein Z is phenyl, still further wherein said phenyl is substituted with methoxyl group in the ortho position;

$R^2$ is phenyl substituted with trifluoromethyl or halogen in the para position;

$R^3$ is

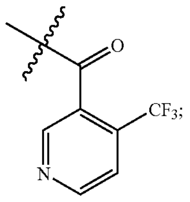

$R^7$ is phenyl; provided that the compounds identified as Group A compounds herein, are excluded from said Formula.

In another embodiment, this invention discloses a compound of the Formula:

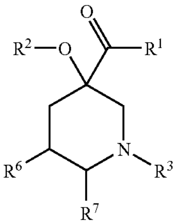

or a pharmaceutically acceptable salt, solvate or ester thereof, wherein $R^1$ is

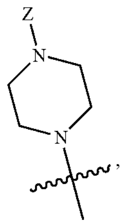

further wherein Z is phenyl, still further wherein said phenyl is substituted with methoxyl group in the ortho position;

$R^2$ is phenyl substituted with trifluoromethyl or halogen in the para position;

$R^3$ is

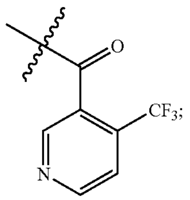

$R^6$ and $R^7$ together with the carbons to which each is attached form a fused cyclopropyl group against the parent ring; provided that the compounds identified as Group A compounds herein, are excluded from said Formula.

In another embodiment, this invention discloses a compound of the Formula:

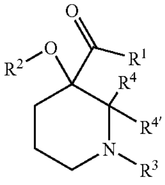

or a pharmaceutically acceptable salt, solvate or ester thereof, wherein $R^1$ is

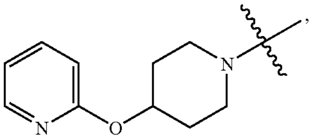

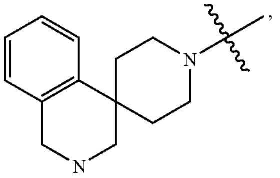

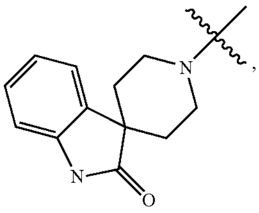

, or

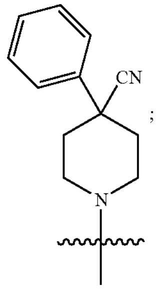

$R^2$ is phenyl substituted in the para position with trifluoromethyl;

$R^3$ is

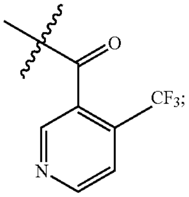

$R^4$ and $R^{4'}$ are each H; provided that the compounds identified as Group A compounds herein, are excluded from said Formula.

In another embodiment, this invention discloses a compound of the Formula:

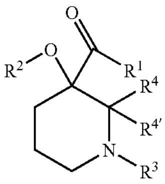

or a pharmaceutically acceptable salt, solvate or ester thereof, wherein $R^1$ is

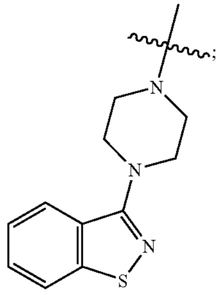

$R^2$ is phenyl substituted in the para position with trifluoromethyl;

$R^3$ is

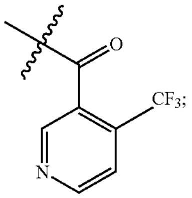

$R^4$ and $R^{4'}$ are each H; provided that the compounds identified as Group A compounds herein, are excluded from said Formula.

In yet another embodiment, this invention discloses a compound of the Formula:

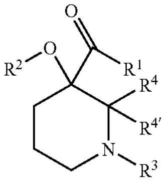

or a pharmaceutically acceptable salt, solvate or ester thereof, wherein $R^1$ is

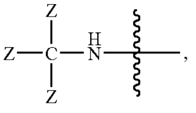

wherein each Z, which can be the same or different, is independently selected from the group consisting of hydrogen,

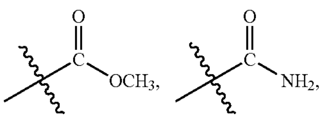

—$CH_3$, unsubstituted phenyl or phenyl substituted with Chloro or Hydroxyl in the para position of said phenyl;

$R^2$ is phenyl substituted in the para position with trifluoromethyl;

$R^3$ is

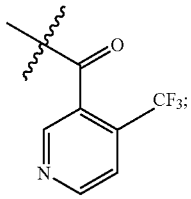

$R^4$ and $R^{4'}$ are H; provided that the compounds identified as Group A compounds herein, are excluded from said Formula.

In still another embodiment, this invention discloses a compound of the Formula:

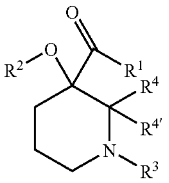

or a pharmaceutically acceptable salt, solvate or ester thereof, wherein $R^1$ is

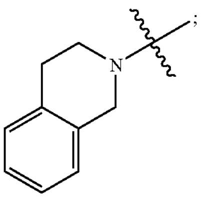

$R^2$ is phenyl substituted in the para position with trifluoromethyl;

$R^3$ is

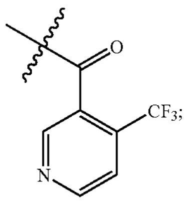

$R^4$ and $R^{4'}$ are H; provided that the compounds identified as Group A compounds herein, are excluded from said Formula.

In another embodiment, this invention discloses a compound of the Formula:

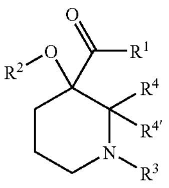

or a pharmaceutically acceptable salt, solvate or ester thereof, wherein $R^1$ is

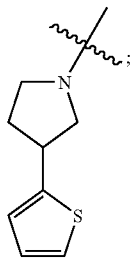

$R^2$ is phenyl substituted in the para position with trifluoromethyl;

$R^3$ is

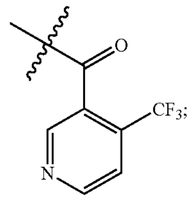

$R^4$ and $R^{4'}$ are H; provided that the compounds identified as Group A compounds herein, are excluded from said Formula.

In another embodiment, this invention discloses a compound of the Formula:

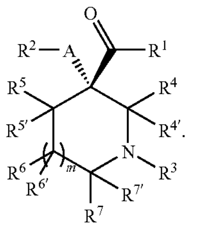

Non-limiting examples of compounds of Formulas I and II include:

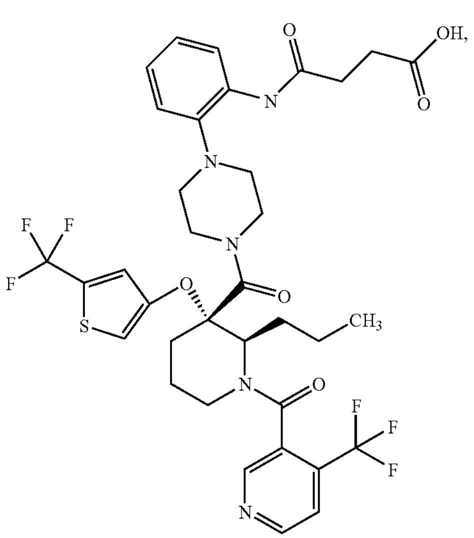

-continued

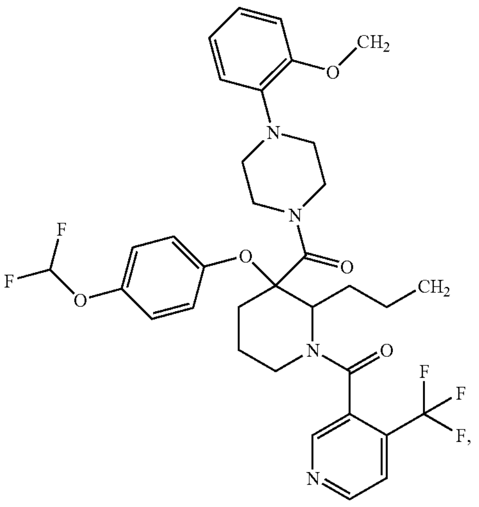

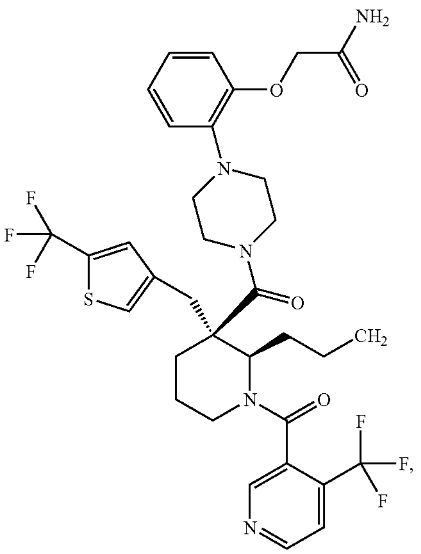

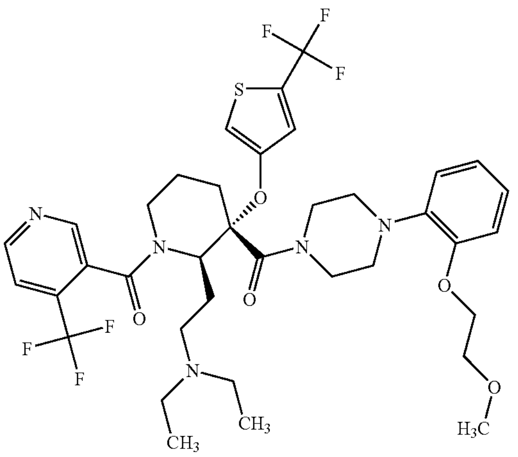

-continued
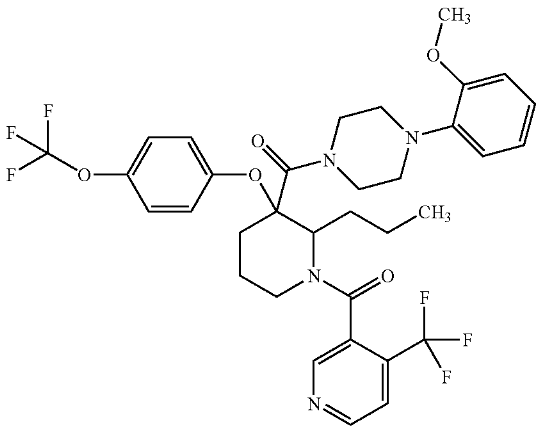
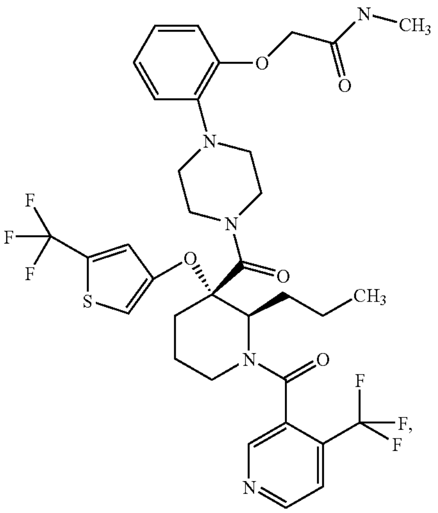
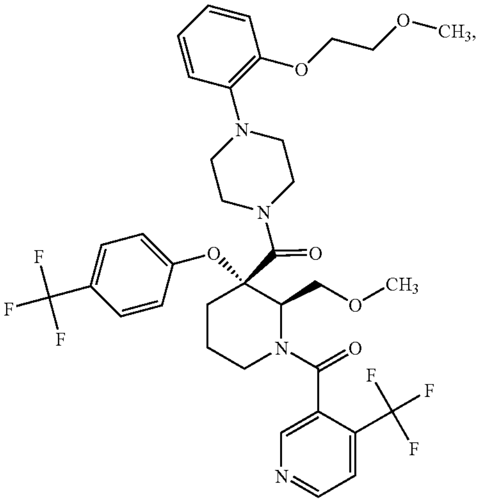
-continued
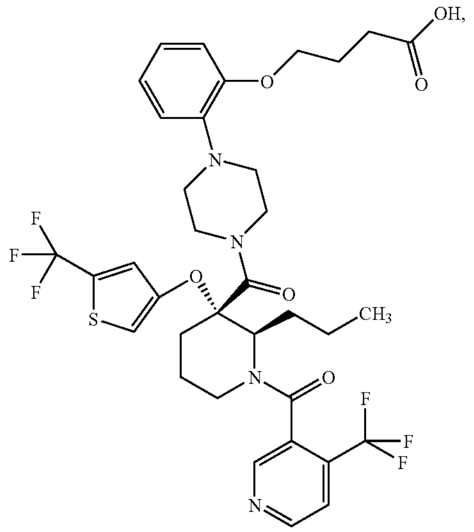
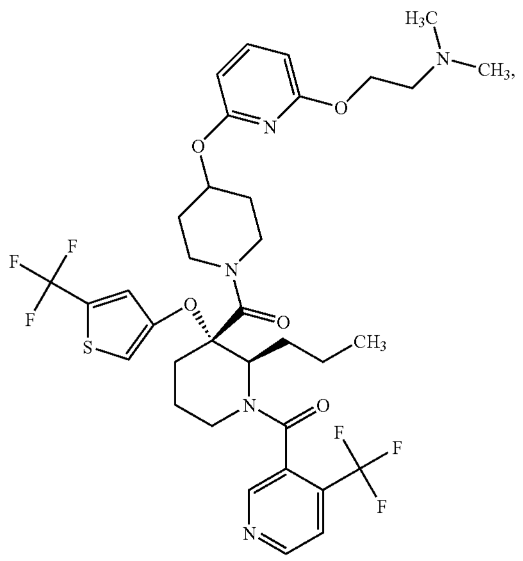
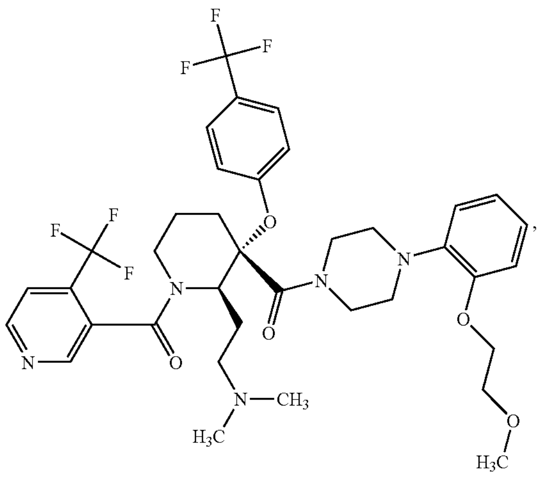

-continued
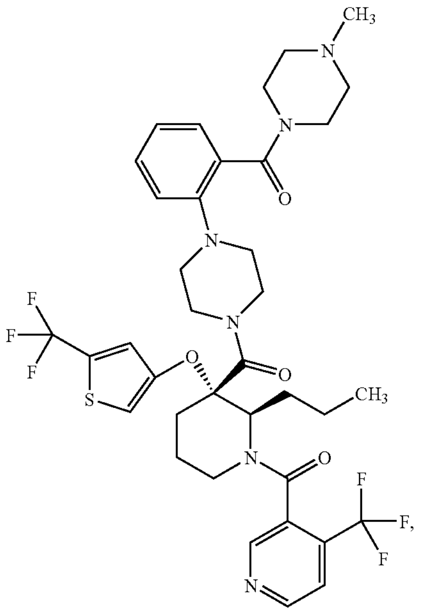
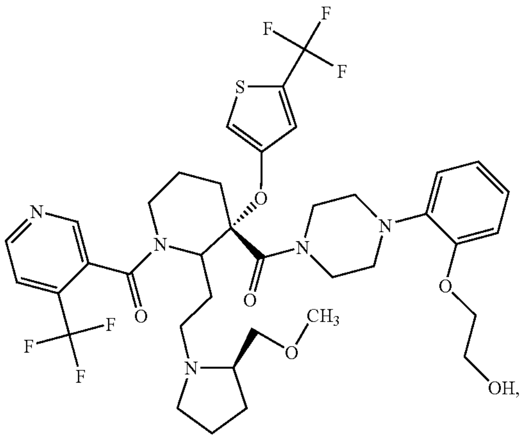
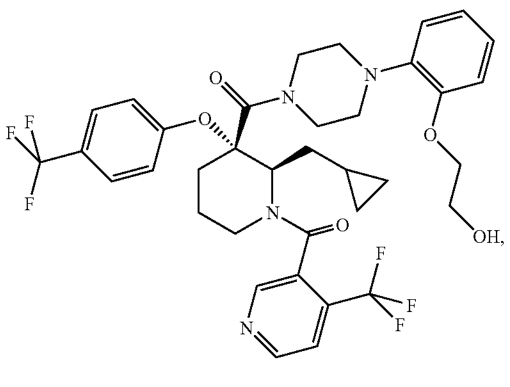
-continued
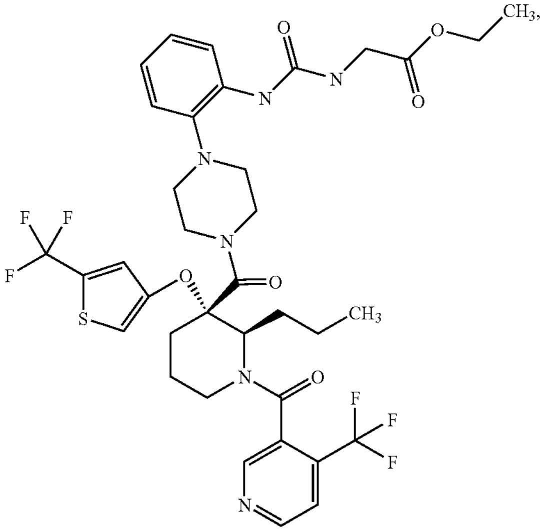
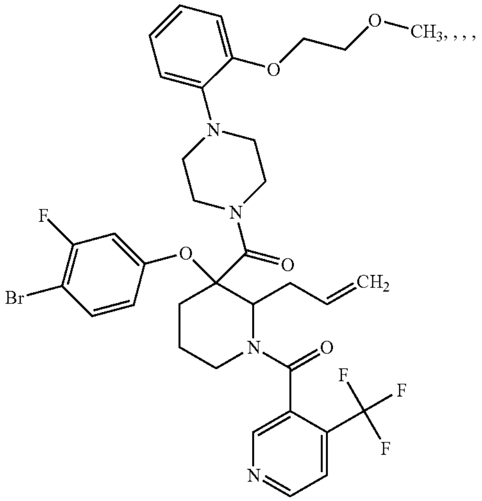
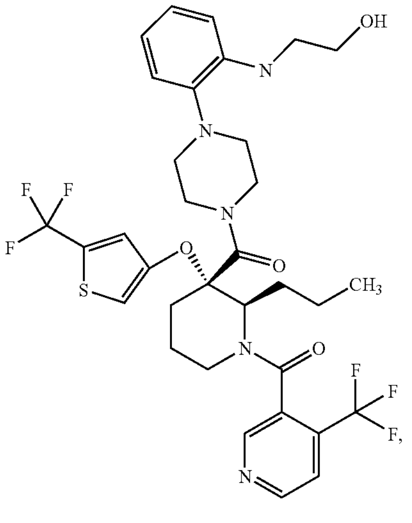

-continued
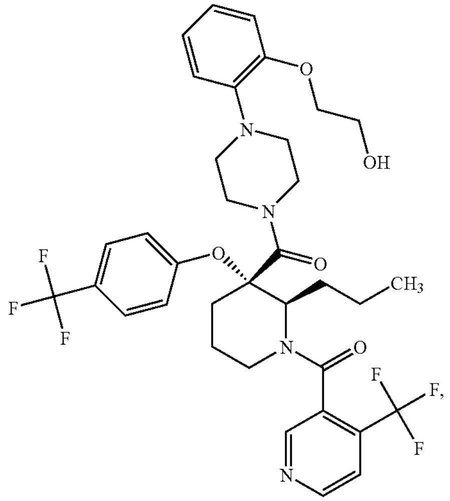
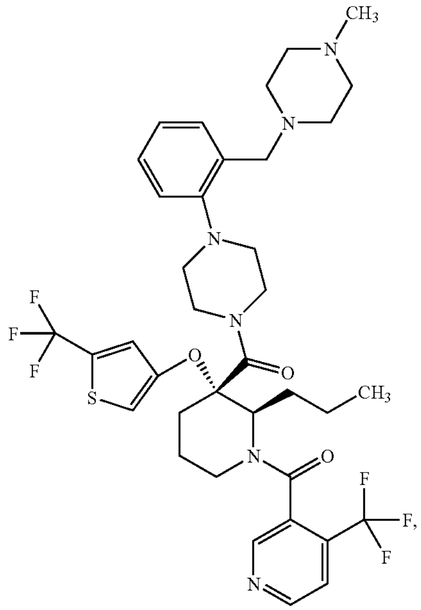
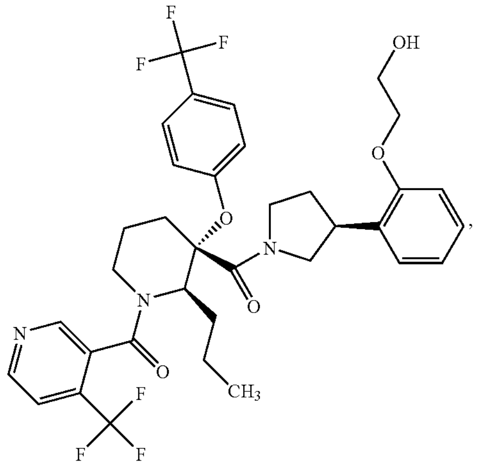
-continued
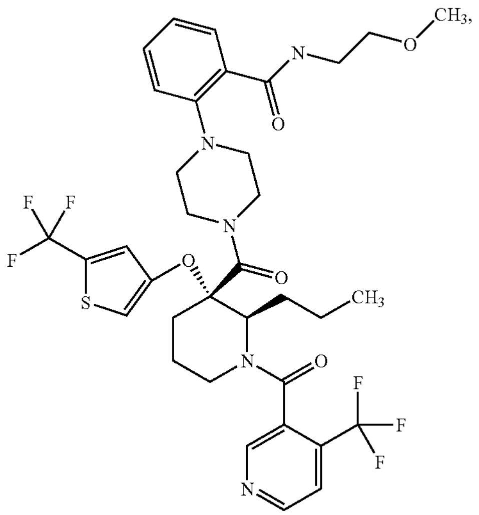
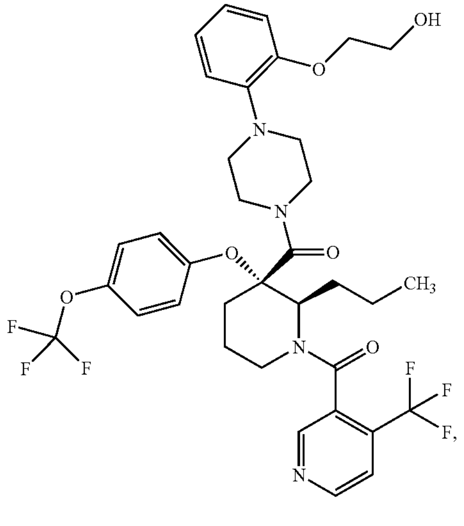
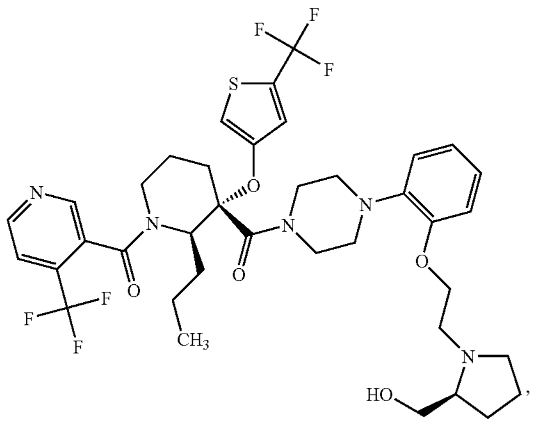

-continued
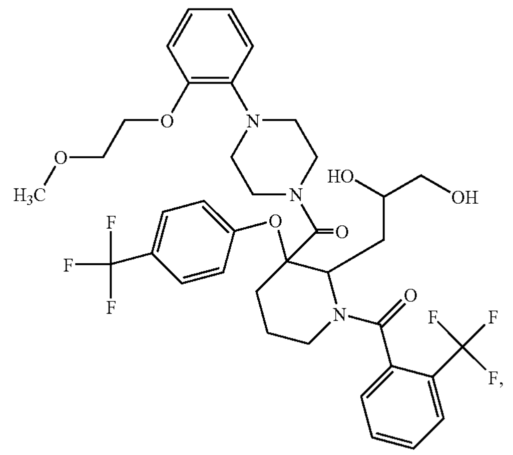
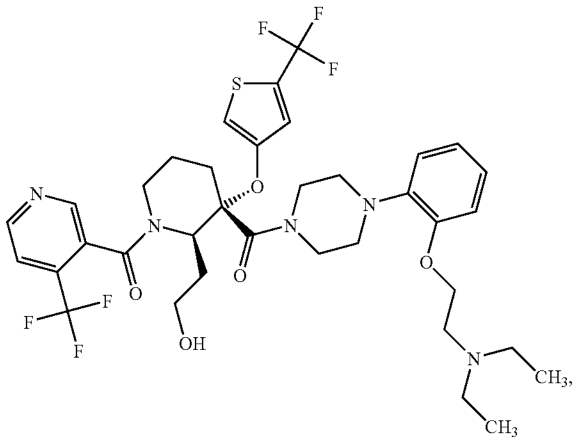
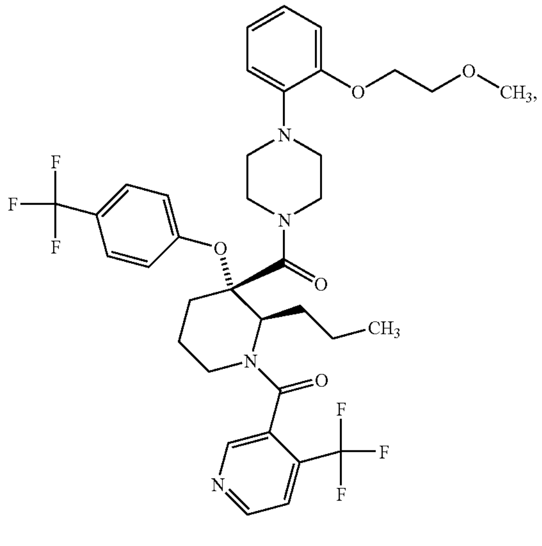
-continued
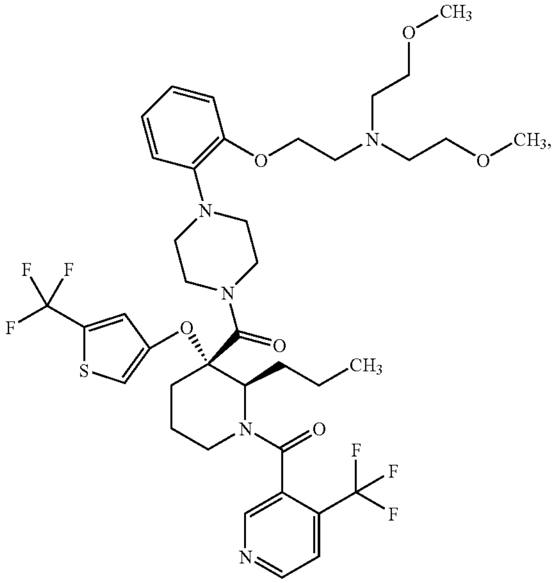
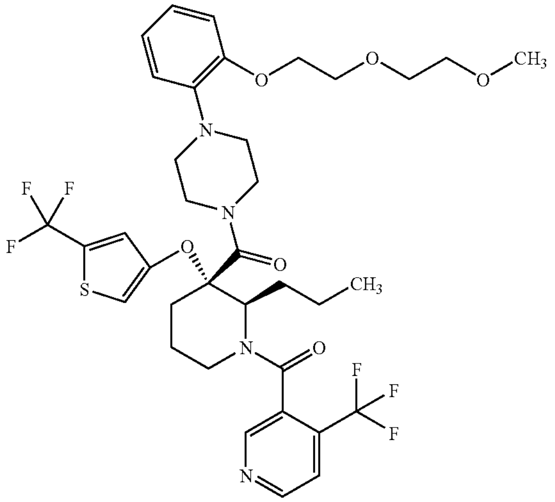
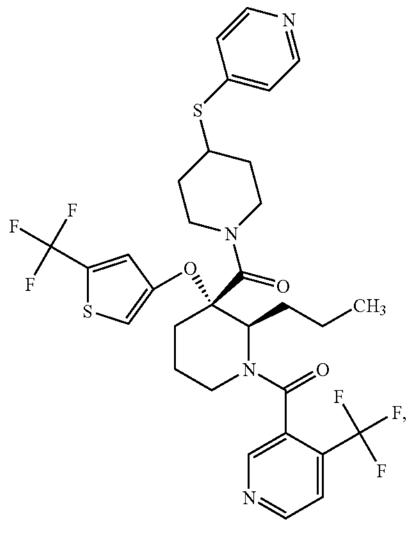

-continued
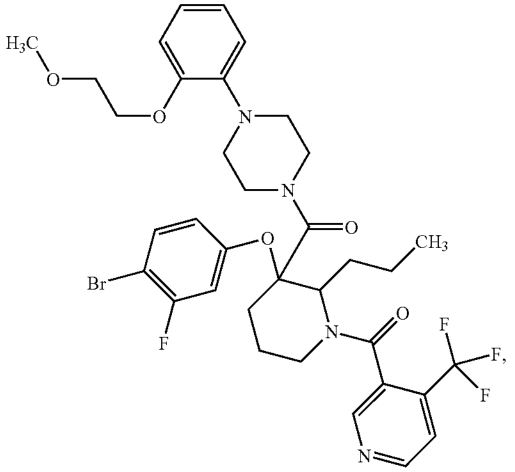
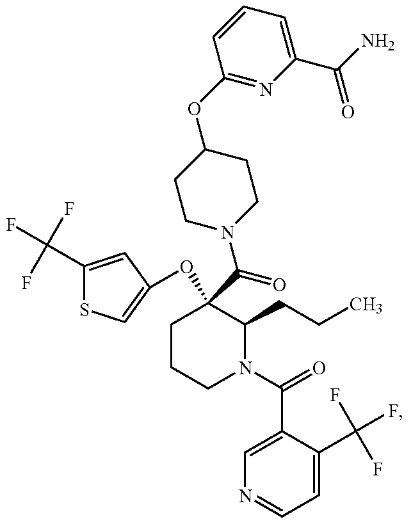
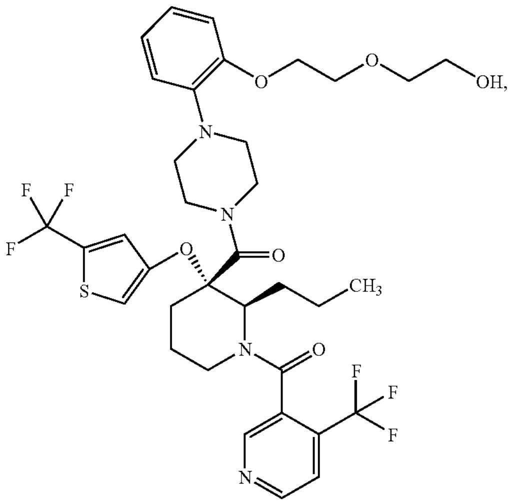
-continued
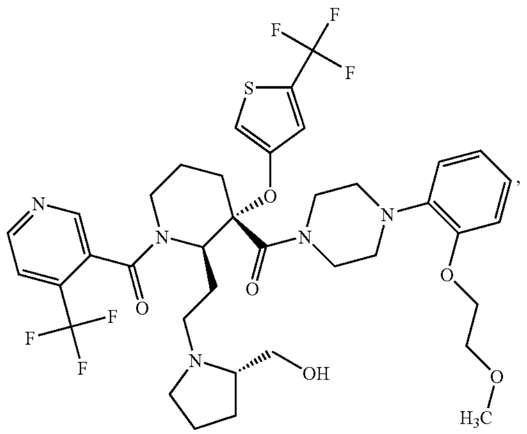
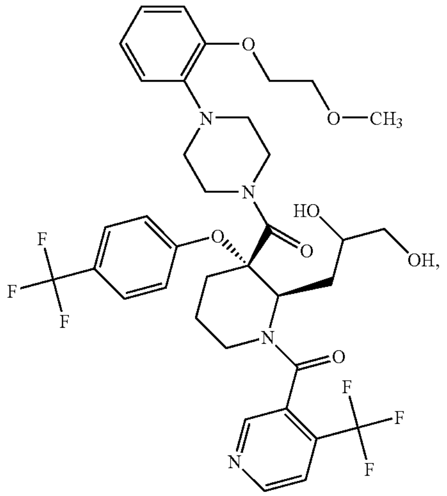
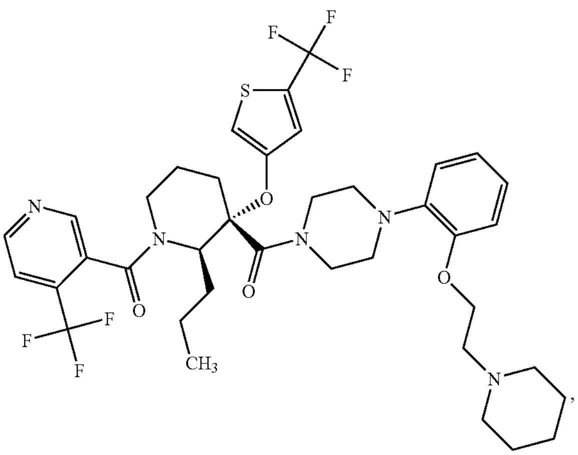

-continued
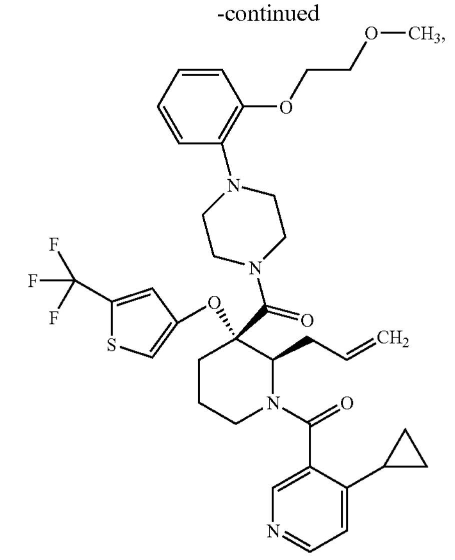
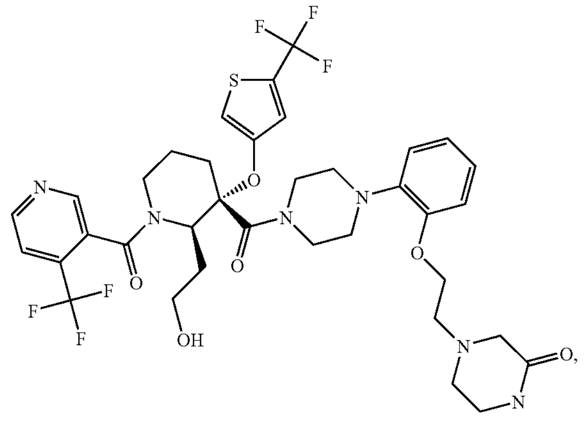
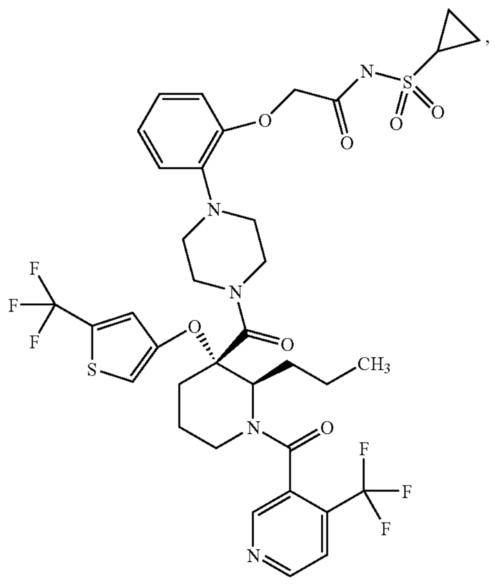
-continued
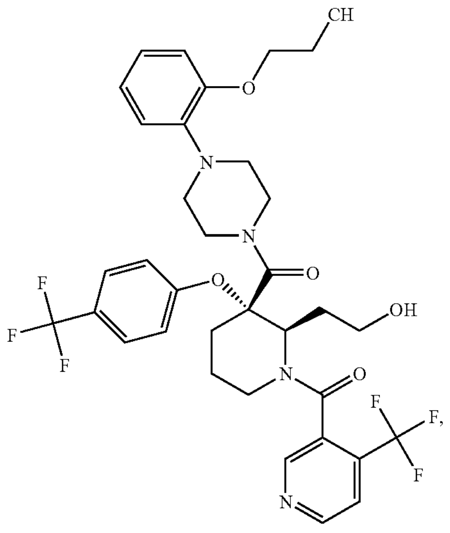
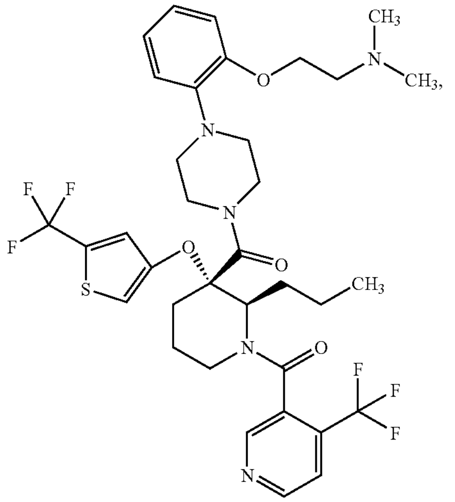
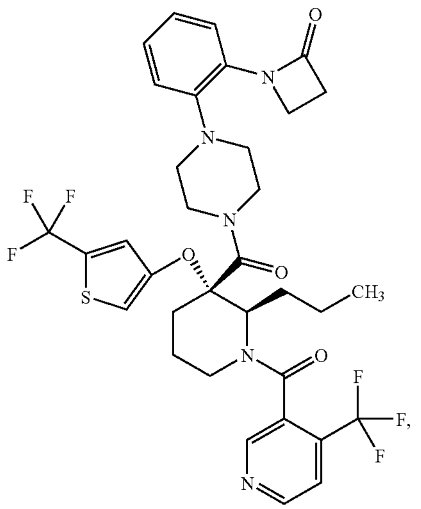

-continued
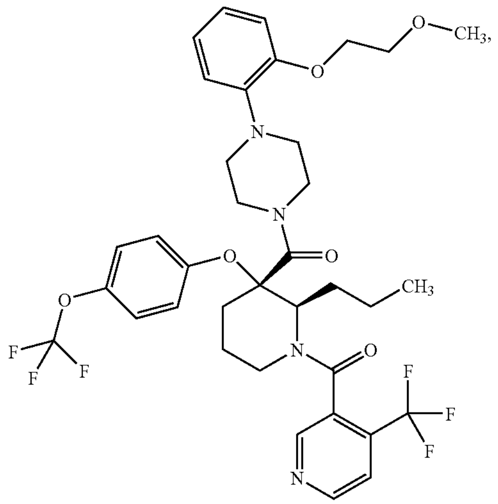
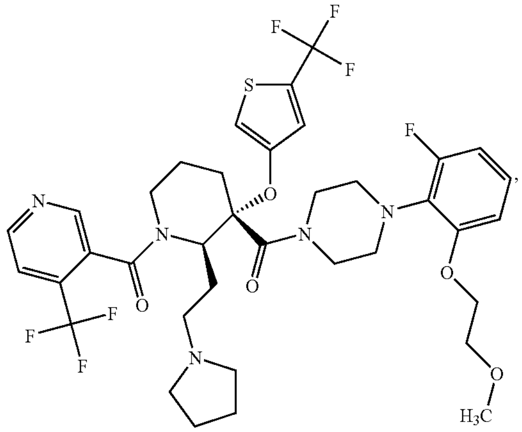
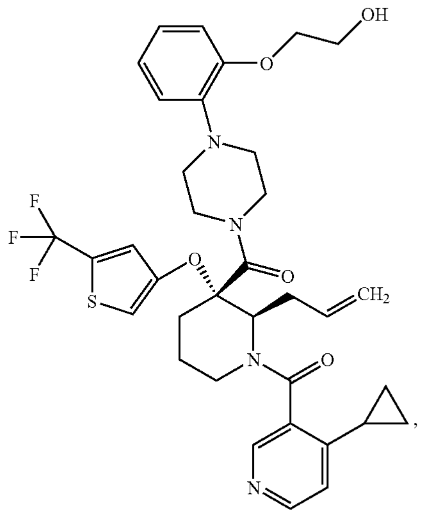
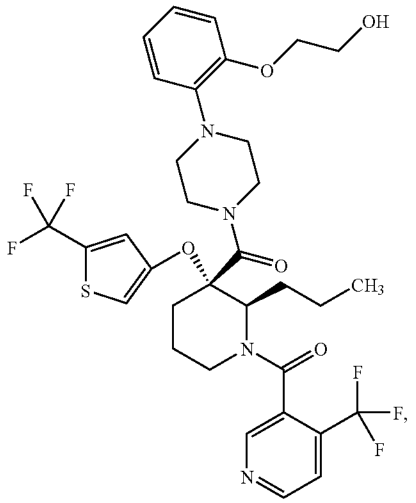
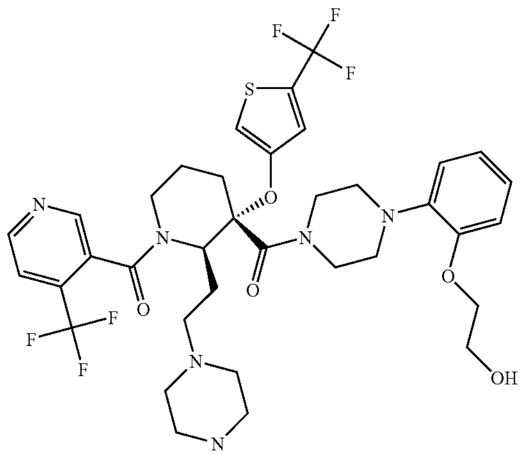
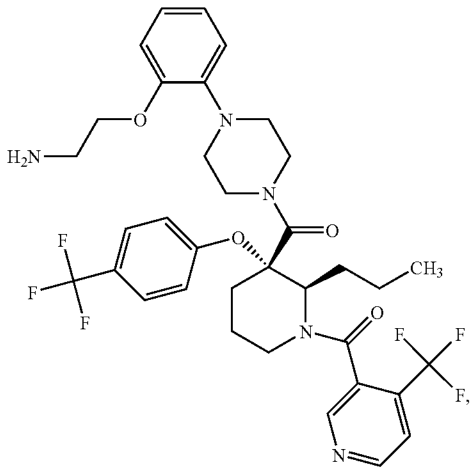

-continued

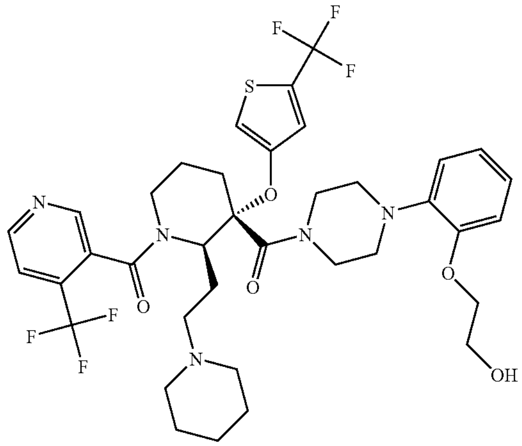

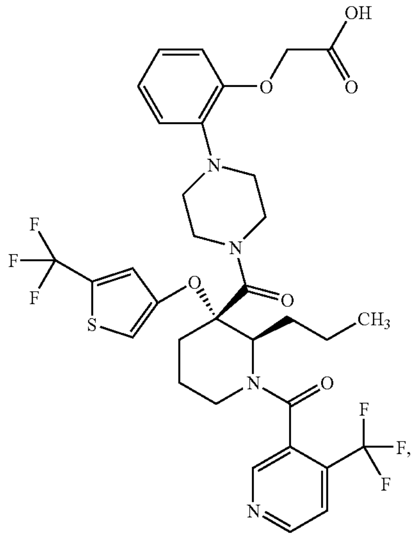

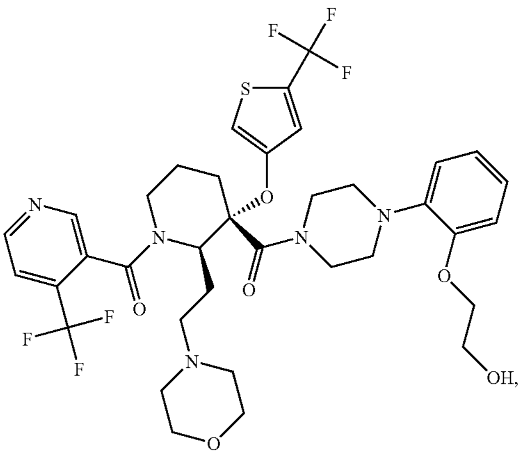

or

-continued

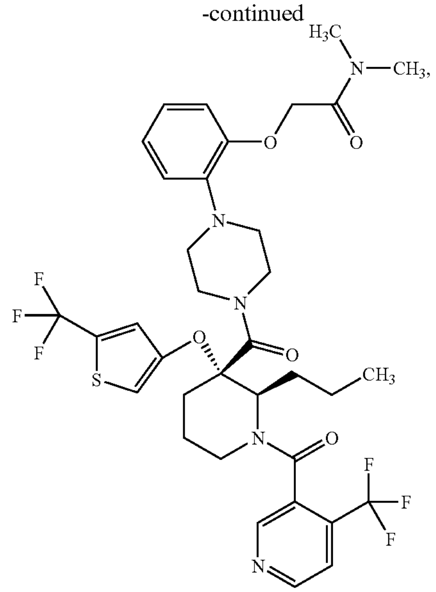

or a pharmaceutically acceptable salt, solvate or ester thereof.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkoxyalkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, carbazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above, Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $-C(=N-CN)-NH_2$, $-C(=NH)-NH_2$, $-C(=NH)-NH(alkyl)$, $Y_1Y_2N-$, $Y_1Y_2N$-alkyl-, $Y_1Y_2NC(O)-$, $Y_1Y_2NSO_2-$ and $-SO_2NY_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, $-C(CH_3)_2-$ and the like which form moieties such as, for example:

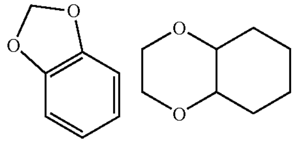

and

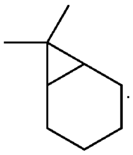

.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heteroalkyl" is a saturated or unsaturated chain (unsaturated chain may also be interchangeably referred to as heteroalkenyl) containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of suitable bicyclic heterocyclyl rings include decahydro-isoquinoline, decahydro-[2,6]naphthyridine, and the like. "Heterocyclyl" may also mean a single moiety (e.g., carbonyl) which simultaneously replaces two available hydrogens on the same carbon atom on a ring system. Example of such moiety is pyrrolidone:

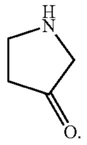

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 15 ring atoms, preferably about 5 to about 14 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 13 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or SS-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 1,2,3,4-tetrahydro-isoquinolinyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

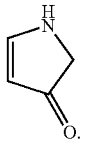

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

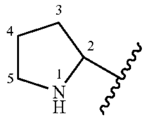

there is no —OH attached directly to carbons marked 2 and 5.

It should also be noted that tautomeric forms such as, for example, the moieties:

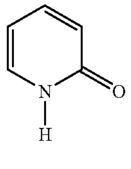 and 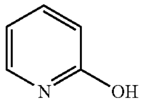

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Spiro ring systems" have two or more rings linked by one common atom. Preferred spiro ring systems include spiroheteroaryl, spiroheterocyclenyl, spiroheterocyclyl, spirocycloalkyl, spirocyclenyl, and spiroaryl. The Spiro ring systems can be optionally substituted by one or more ring system substituents, wherein "ring system substituent" is as defined above. Non-limiting examples of suitable spiro ring systems include

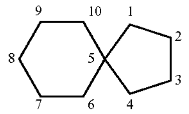

spiro[4.5]decane,

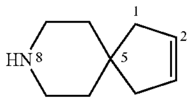

8-azaspiro[4,5]dec-2-ene, and

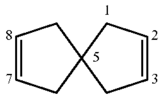

spiro[4,4]nona-2,7-diene.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen. An alkoxy linked directly to another alkoxy is an "alkoxyalkoxy".

"Aryloxy" means an aryl-O— group in which the aryl group is as previously described Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" or "thioalkoxy" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formulas I or II, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood, A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl, carboxy($C_1$-$C_6$)alkyl, amino ($C_1$-$C_4$)alkyl or mono-N— or di-N,N—($C_1$-$C_6$)alkylaminoalkyl, —C($Y^4$)$Y^5$ wherein $Y^4$ is H or methyl and $Y^5$ is mono-N or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.,* 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.,* 5(1), article 12 (2004); and A. L. Bingham et al, *Chem. Commun.,* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formulas I or II can form salts which are also within the scope of this invention. Reference to a compound of Formulas I or II herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formulas I or II contains both a basic moiety, such as, but not limited to a pyridine or imidazole, and an acidic moiety, such as, but not limited to a carboxylic acid, zwitterions ('inner salts') may be formed and are included within the term "salt(s)" as used herein. Pharmaceutically acceptable (i.e., non-toxic, physiologically acceptable) salts are preferred, although other salts are also useful. Salts of the compounds of the Formulas I or II may be formed, for example, by reacting a compound of Formulas I or II with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66 (1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl), (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formulas I or II, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formulas I or II, and of the salts, solvates, esters and prodrugs of the compounds of Formulas I or II, are intended to be included in the present invention.

HDM2, Hdm2, hDM2, and hdm2 are all equivalent representations of the Human Double Minute 2 protein. Likewise, MDM2, Mdm2, mDM2, and mdm2 are all equivalent representations mouse Double Minute 2 protein.

The compounds of Formulas I or II can be inhibitors or antagonists of the Human or Mouse Double Minute 2 protein interaction with P-53 protein and it can be activators of the P-53 protein in cells. Furthermore, the pharmacological properties of the compounds of Formula (I) can be used to treat or prevent cancer, treat or prevent other disease states associated with abnormal cell proliferation, and treat or prevent diseases resulting from inadequate levels of P53 protein in cells.

Those skilled in the art will realize that the term "cancer" to be the name for diseases in which the body's cells become abnormal and divide without control. The compounds of Formula (I) can be useful to the treatment of a variety of cancers, including, but not limited to: carcinoma, including, but not limited to, of the bladder, breast, colon, rectum, endometrium, kidney, liver, lung, head and neck, esophagus, gall bladder, cervix, pancreas, prostrate, larynx, ovaries, stomach, uterus, sarcoma and thyroid cancer;

hematopoietic tumors of the lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoetic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma, and schwannomas; and other tumors, including melanoma, skin (non-melanomal) cancer, mesothelioma (cells), seminoma, teratocarcinoma, osteosarcoma, xenoderoma pigmentosum, keratoctanthoma, thyroid follicular cancer and Kaposi's sarcoma.

Due to the key role of P53 in the regulation of cellular apoptosis (cell death), the compounds of Formulas I or II could act as agent to induce cell death which may be useful in the treatment of any disease process which features abnormal cellular proliferation eg, cancers of various origin and tissue types, inflammation, immunological disorders.

Due to the key role of HDM2 and P53 in the regulation of cellular proliferation, the compounds of Formulas I or II could act as reversible cytostatic agents which may be useful in the treatment of any disease process which features abnormal cellular proliferation, inhibitors could act as reversible cytostatic agents which may be useful in the treatment of any disease process which features abnormal cell proliferation, e.g., benign prostrate hyperplasia, familial adenomatosis polyposis, neuro-fibromatosis, atherosclerosis, pulmonary fibrosis, arthritis, psoriasis, glomerulonephritis, restenosis following angioplasty, or vascular surgery, hypertrophic scar formation, inflammatory bowel disease, transplantation rejection, endotoxic shock, and fungal infections.

Compounds of Formulas I or II may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formulas I or II may also be useful in inhibiting tumor angiogenesis and metastasis.

Another aspect of this invention is a method of treating a mammal (e.g., human) having a disease or condition associated with HDM2 by administering a therapeutically effective amount of at least one compound of Formulas I or II, or a pharmaceutically acceptable salt, solvate, ester or prodrug of said compound to the mammal.

A preferred dosage is about 0.001 to 500 mg/kg of body weight/day of the compound of Formulas I or II. An especially preferred dosage is about 0.01 to 25 mg/kg of body weight/day of a compound of Formulas I or II, or a pharmaceutically acceptable salt, solvate, ester or prodrug of said compound.

The compounds of this invention may also be useful in combination (administered together or sequentially) with one or more of anti-cancer treatments such as radiation therapy, and/or one or more anti-cancer agents different from compound of Formulas I or II. The compounds of the present invention can be present in the same dosage unit as the anticancer agent or in separate dosage units.

Another aspect of the present invention is a method of treating one or more diseases associated with HDM2, comprising administering to a mammal in need of such treatment an amount of a first compound, which is a compound of the present invention, or a pharmaceutically acceptable salt, solvate, ester or prodrug thereof; and an amount of at least one second compound, the second compound being an anti-cancer agent different from the compounds of the present invention, wherein the amounts of the first compound and the second compound result in a therapeutic effect.

Non-limiting examples of suitable anti-cancer agents include cytostatic agents, cytotoxic agents, targeted therapeutic agents (small molecules, biologics, siRNA and microRNA) against cancer and neoplastic diseases, 1) anti-metabolites (such as methoxtrexate, 5-fluorouracil, gemcitabine, fludarabine, capecitabine);
2) alkylating agents, such as temozolomide, cyclophosphamide,
3) DNA interactive and DNA damaging agents, such as cisplatin, oxaliplatin, doxorubicin,
4) Ionizing irradiation, such as radiation therapy,
5) topoisomerase II inhibitors, such as etoposide, doxorubicin,
6) topoisomerase I inhibitors, such as irinotecan, topotecan,
7) tubulin interacting agents, such as paclitaxel, docetaxel, Abraxane, epothilones,
8) kinesin spindle protein inhibitors,
9) spindle checkpoint inhibitors,
10) Poly(ADP-ribose) polymerase (PARP) inhibitors
11) Matrix metalloprotease (MMP) inhibitors
12) Protease inhibitors, such as cathepsin D and cathepsin K inhibitors
13) Proteosome or ubiquitination inhibitors, such as bortezomib,
14) Activator of mutant P53 to restore its wild-type P53 activity
15) Adenoviral-P53

16) Bcl-2 inhibitors, such as ABT-263
17) Heat shock protein (HSP) modulators, such as geldanamycin and 17-AAG
18) Histone deacetylase (HDAC) inhibitors, such as vorinostat (SAHA),
19) sex hormone modulating agents,
   a. anti-estrogens, such as tamoxifen, fulvestrant,
   b. selective estrogen receptor modulators (SERM), such as raloxifene,
   c. anti-androgens, such as bicalutamide, flutamide
   d. LHRH agonists, such as leuprolide,
   e. 5α-reductase inhibitors, such as finasteride,
   f. Cytochrome P450 C17 lysase (CYP450c17) inhibitors, such as Abiraterone
   g. aromatase inhibitors, such as letrozole, anastrozole, exemestane,
20) EGFR kinase inhibitors, such as geftinib, erlotinib, laptinib
21) dual erbB1 and erbB2 inhibitors, such as Lapatinib
22) multi-targeted kinases (serine/threonine and/or tyrosine kinase) inhibitors,
   a. ABL kinase inhibitors, imatinib and nilotinib, dasatinib
   b. VEGFR-1, VEGFR-2, PDGFR, KDR, FLT, c-Kit, Tie2, Raf, MEK and ERK inhibitors, such as sunitinib, sorafenib, Vandetanib, pazopanib, Axitinib, PTK787,
   c. Polo-like kinase inhibitors,
   d. Aurora kinase inhibitors,
   e. JAK inhibitor
   f. c-MET kinase inhibitors
   g. Cyclin-dependent kinase inhibitors, such as CDK1 and CDK2 inhibitor SCH 727965
   h. PI3K inhibitors
   i. mTOR inhibitors, such as Rapamycin, Temsirolimus, and RAD001
23) and other anti-cancer (also know as anti-neoplastic) agents include but are not limited to ara-C, adriamycin, cytoxan, Carboplatin, Uracil mustard, Clormethine, Ifosfsmide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Vinorelbine, Navelbine, Bleomycin, Dactinomycin, Daunorubicin, Doxorubicin, Epirubicin, teniposide, cytarabine, pemetrexed, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Flutamide Medroxyprogesteroneacetate, Toremifene, goserelin, Carboplatin, Hydroxyurea, Amsacrine, Procarbazine, Mitotane, Mitoxantrone, Levamisole, Drolloxafine, Hexamethylmelamine, Bexxar, Zevalin, Trisenox, Profimer, Thiotepa, Altretamine, Doxil, Ontak, Depocyt, Aranesp, Neupogen, Neulasta, Kepivance.
24) Farnesyl protein transferase inhibitors, such as, SARASAR™(4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-piperidinecarboxamide, tipifarnib
25) interferons, such as Intron A, Peg-Intron, 26) anti-erbB1 antibodies, such as cetuximab, panitumumab,
27) anti-erbB2 antibodies, such as trastuzumab,
28) anti-CD52 antibodies, such as Alemtuzumab,
29) anti-CD20 antibodies, such as Rituximab
30) anti-CD33 antibodies, such as Gemtuzumab ozogamicin
31) anti-VEGF antibodies, such as Avastin,
32) TRIAL ligands, such as Lexatumumab, mapatumumab, and AMG-655
33) antibodies against CTLA-4, CTA1, CEA, CD5, CD19, CD22, CD30, CD44, CD44V6, CD55, CD56, EpCAM, FAP, MHCII, HGF, IL-6, MUC1, PSMA, TAL6, TAG-72, TRAILR, VEGFR, IGF-2, FGF,
34) anti-IGF-1R antibodies, such as SCH 717454.

If formulated as a fixed dose such combination products employ the compounds of this invention within the dosage range described herein and the other pharmaceutically active agent or treatment within its dosage range. Compounds of Formulas I or II may also be administered sequentially with known anticancer or cytotoxic agents when a combination formulation is inappropriate. The invention is not limited in the sequence of administration; compounds of Formulas I or II may be administered either concurrent with, prior to or after administration of the known anticancer or cytotoxic agent. Such techniques are within the skills of the persons skilled in the art as well as attending physicians.

Accordingly, in an aspect, this invention includes combinations comprising an amount of at least one compound of Formulas I or II, or a pharmaceutically acceptable salt, solvate, ester or prodrug thereof, and an amount of one or more anti-cancer treatments and anti-cancer agents listed above wherein the amounts of the compounds/treatments result in desired therapeutic effect.

Another aspect of the invention is a method of protecting normal, healthy cells of a mammal from cytotoxic induced side-effects comprising administering at least one compound of the invention or a pharmaceutically acceptable salt, solvate, ester or prodrug thereof to a cancer patient, in particular those carrying mutated P53, prior to administration of anti-cancer agents other than the compounds of the invention) such as paclitaxel.

A method of inhibiting one or more HDM2 proteins in a patient in need thereof, comprising administering to the patient a therapeutically effective amount of at least one compound of claim 1 or a pharmaceutically acceptable salt, solvate, ester or prodrug thereof.

Another aspect of the present invention is a method of treating, or slowing the progression of a disease associated with one or more HDM2 proteins in a patient, comprising administering to a patient in need thereof, a therapeutically effective amount of at least one compound of the present invention or a pharmaceutically acceptable salt, solvate, ester or prodrug thereof.

Another aspect of the present invention is a method of treating, or slowing the progression of a disease associated with inadequate P53 levels in a patient, comprising administering to a patient in need thereof, a therapeutically effective amount of at least one compound of the present invention or a pharmaceutically acceptable salt, solvate, ester or prodrug thereof.

Yet another aspect of the present invention is a method of treating one or more diseases associated with HDM2, comprising administering to a mammal in need of such treatment an amount of a first compound, which is a compound of the present invention, or a pharmaceutically acceptable salt, solvate, ester or prodrug thereof; and an amount of at least one second compound, the second compound being an anti-cancer agent, wherein the amounts of the first compound and the second compound result in a therapeutic effect.

Another aspect of the present invention is a method of treating one or more diseases associated with inadequate P53 levels, comprising administering to a mammal in need of such treatment an amount of a first compound, which is a compound of the present invention, or a pharmaceutically acceptable salt, solvate, ester or prodrug thereof; and an amount of at least one second compound, the second compound being an anti-cancer agent, wherein the amounts of the first compound and the second compound result in a therapeutic effect.

Another aspect of the present invention is a method of treating, or slowing the progression of, a disease associated with a HDM2 protein comprising administering to a patient in need thereof, a therapeutically effective amount of a pharmaceutical composition comprising in combination at least one pharmaceutically acceptable carrier and at least one compound according to the present invention, or a pharmaceutically acceptable salt, solvate, ester or prodrug thereof.

Another aspect of the present invention is a method of treating, or slowing the progression of, a disease associated with inadequate P53 levels in a patient, comprising administering to a patient in need thereof, a therapeutically effective amount of a pharmaceutical composition comprising in combination at least one pharmaceutically acceptable carrier and at least one compound according to the present invention, or a pharmaceutically acceptable salt, solvate, ester or prodrug thereof.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Another embodiment of the invention discloses a method of making the substituted compounds disclosed above. The compounds may be prepared by several processes well known in the art. In one method, the starting material, 1-benzyl-3-(4-trifluoromethyl-phenoxy)-piperidine-3-carboxylic acid is converted to its diisopropylethyl ammonium salt of the dicarboxylic acid ester. This ester is combined with 1-(2-methoxy-phenyl)-piperazine forming the HCL salt of 4-(2-methoxy-phenyl)-piprazinl-yl]-[3-(4-trifluormethylphenoxy)-piperidin-3-yl]-methanone, which combined with 4-trifluoromethyl-nicotinic acid to form the target compound. Other substituted compounds of this invention can be made.

Isolation of the compound at various stages of the reaction may be achieved by standard techniques such as, for example, filtration, evaporation of solvent and the like. Purification of the product, intermediate and the like, may also be performed by standard techniques such as recrystallization, distillation, sublimation, chromatography, conversion to a suitable derivative, which may be recrystallized and converted back to the starting compound, and the like. Such techniques are well known to those skilled in the art.

The following compounds are identified as Group A compounds and are excluded from the compounds of the invention:

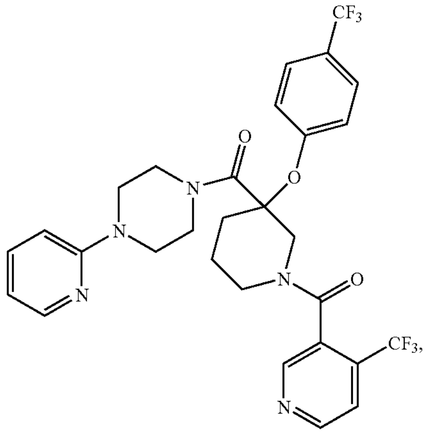

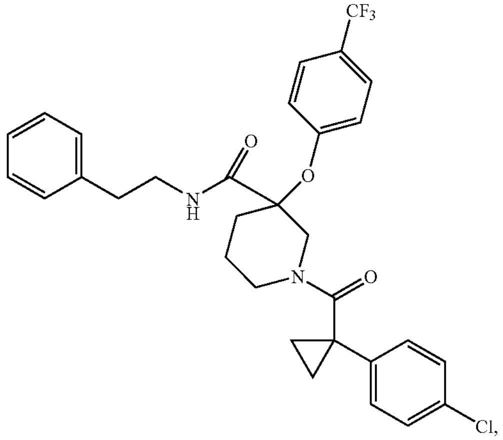

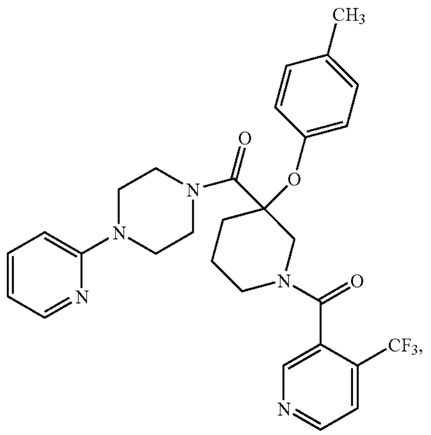

-continued
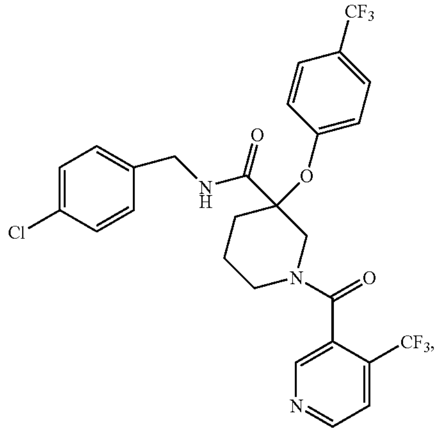
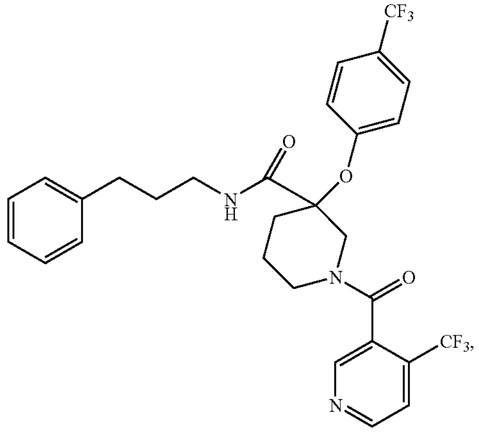
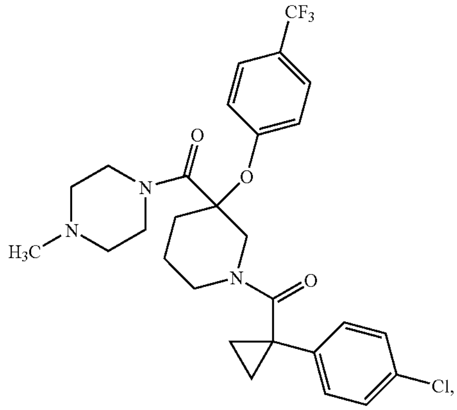
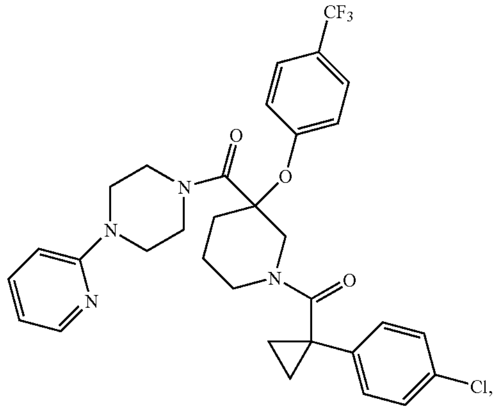
-continued
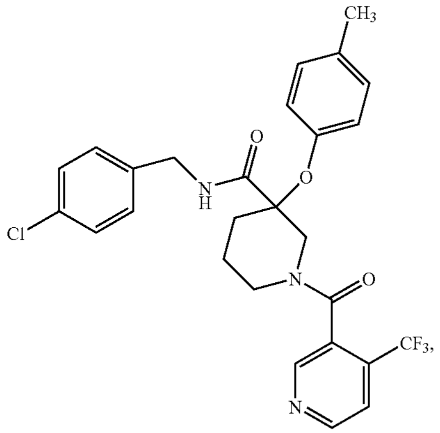
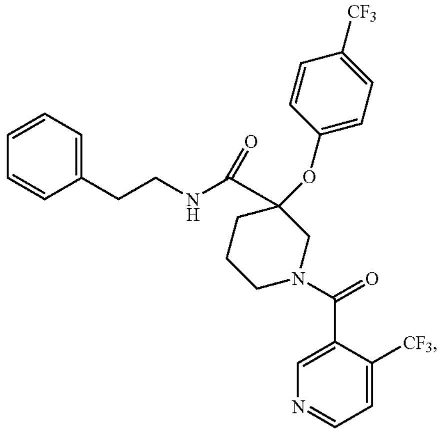
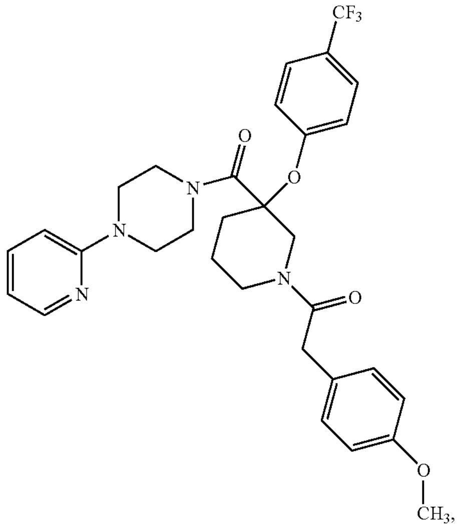

-continued
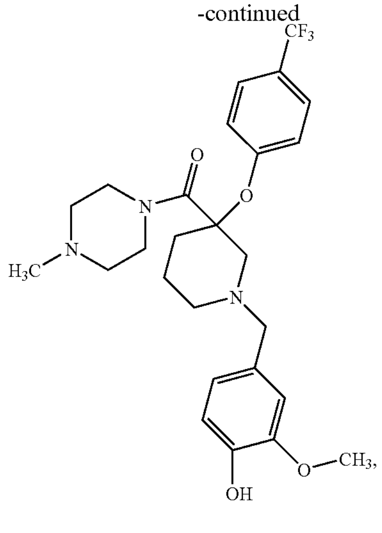
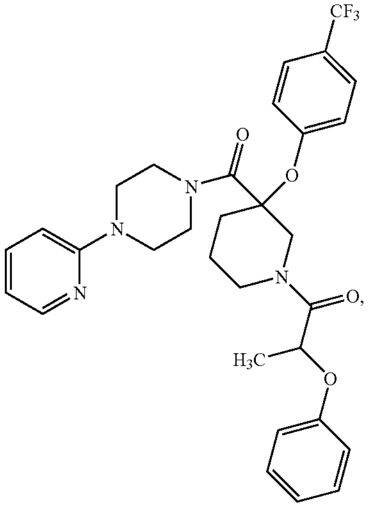
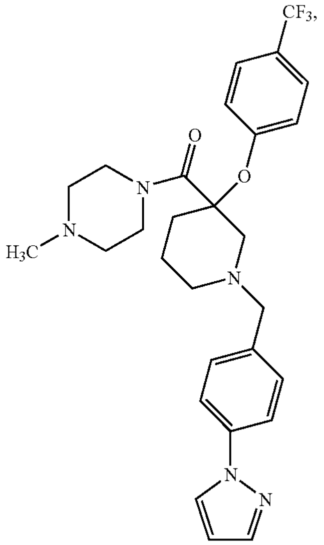
-continued
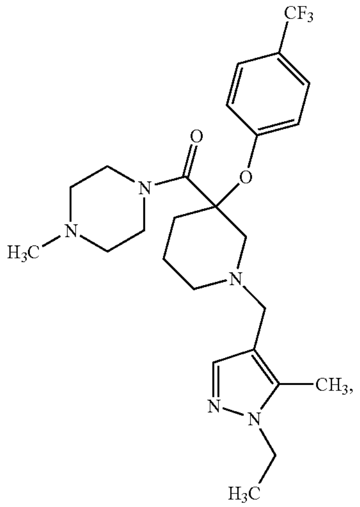
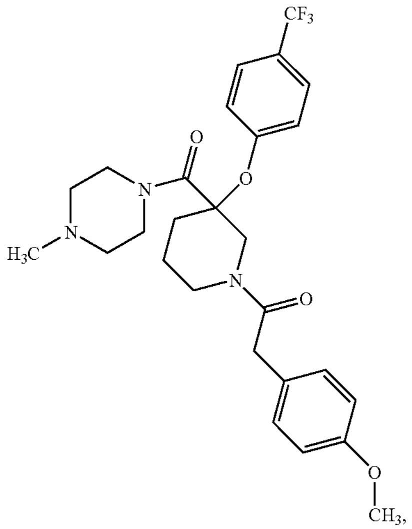
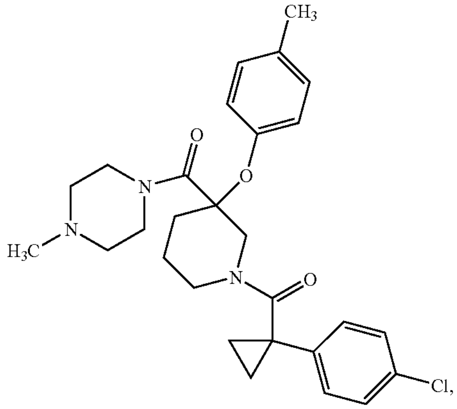

-continued
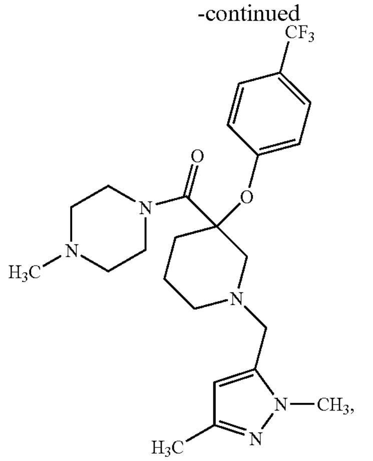
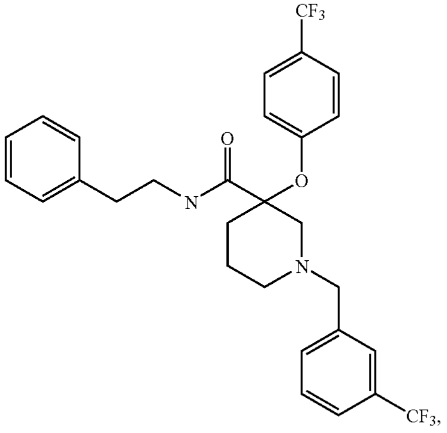
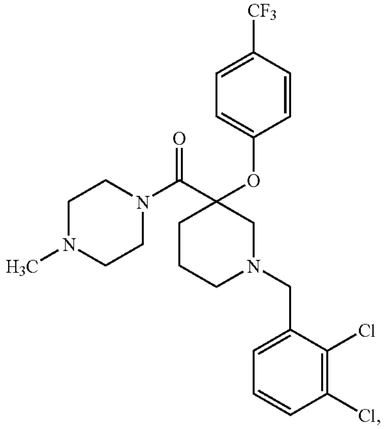
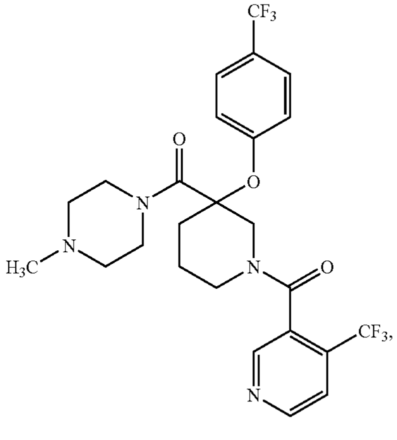
-continued
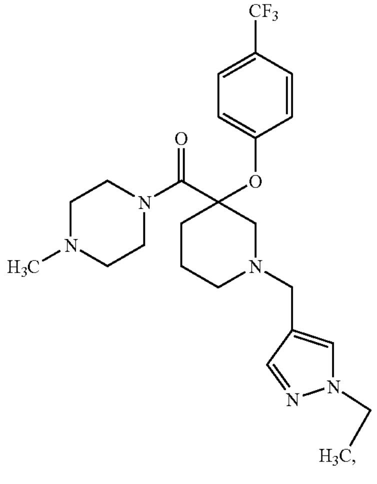
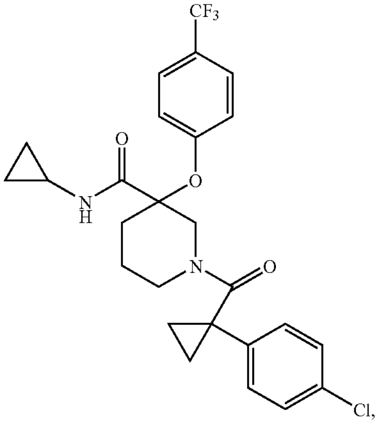
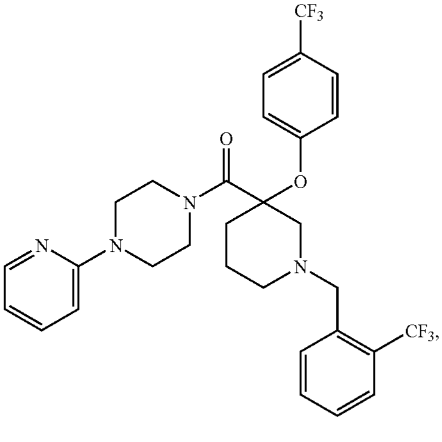

-continued

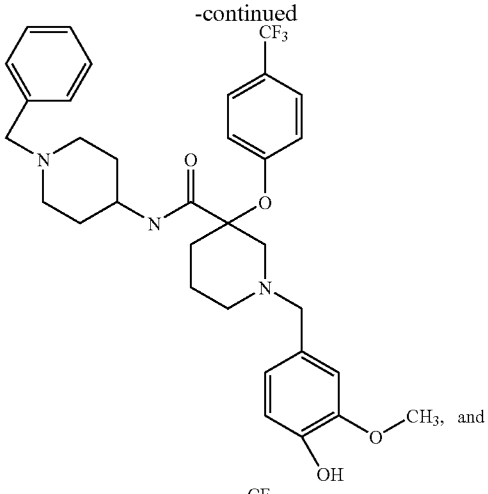

and

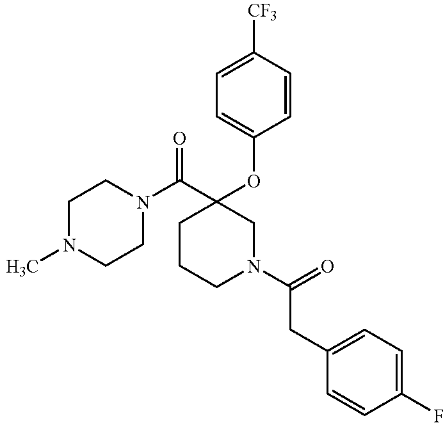

The compounds of this invention may be analyzed for their composition and purity as well as characterized by standard analytical techniques such as, for example, elemental analysis, NMR, mass spectroscopy, and IR spectra.

In another embodiment, this invention provides pharmaceutical compositions comprising the above-described inventive substituted compounds as an active ingredient. The pharmaceutical compositions generally additionally comprise a pharmaceutically acceptable carrier diluent, excipient or carrier (collectively referred to herein as carrier materials). Because of their HDM2 or Mdm2 antagonist activity, such pharmaceutical compositions possess utility in treating cancer, abnormal cell proliferation, and the like diseases.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Lubricants in these dosage forms include boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. anti-cell proliferation activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. For example, water or water-propylene glycol solutions may be included for parenteral injections or sweeteners and pacifiers may be added for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool to solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

Generally, the human oral dosage form containing the active ingredients can be administered 1 or 2 times per day. The amount and frequency of the administration will be regulated according to the judgment of the attending clinician, A generally recommended daily dosage regimen for oral administration may range from about 1.0 milligram to about 1,000 milligrams per day, in single or divided doses.

Another aspect of this invention is a kit comprising a therapeutically effective amount of at least one compound of Formulas I or II, or a pharmaceutically acceptable salt, solvate, ester or prodrug of said compound and a pharmaceutically acceptable carrier, vehicle or diluent.

Yet another aspect of this invention is a kit comprising an amount of at least one compound of Formulas I or II, or a pharmaceutically acceptable salt, solvate, ester or prodrug of said compound and an amount of at least one anticancer therapy and/or anti-cancer agent listed above, wherein the amounts of the two or more ingredients result in desired therapeutic effect.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refer to the active ingredients dispersed or solubilized in a hydrophillic semi-solid matrix.

Powders for constitution refer to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The invention disclosed herein is exemplified by the following preparations and examples which should not be construed to limit the scope of the disclosure. Alternative mechanistic pathways and analogous structures will be apparent to those skilled in the art.

The following abbreviations have the following meanings unless defined otherwise:

| | |
|---|---|
| ACN | Acetonitrile |
| AcOH | Acetic acid |
| DAST | (diethylamino)sulfur trifluoride |
| DCC | Dicyclohexylcarbodiimide |
| DCU | Dicyclohexylurea |
| DCM | Dichloromethane |
| DI | Deionized water |

-continued

| | |
|---|---|
| DIAD | Diisopropylazodicarboxylate |
| DIEA | Diisopropylethylamine |
| DMAP | 4-Dimethylaminopyridine |
| DME | Dimethoxyethane |
| DMF | Dimethylformamide |
| DMFDMA | N,N-Dimethylformamide dimethylacetal |
| DMSO | Dimethyl sulfoxide |
| DTT | Dithiothreitol |
| EDCl | 1-(3-dimethylamino-propyl)-3-ethylcarbodiimide hydrochloride |
| EtOAc | Ethyl acetate |
| EtOH | Ethanol |
| HATU | N,N,N',N'-Tetramethyl-O-(7-Azabenzotriazol-1-yl)Uronium hexafluorophosphate |
| Hex | hexanes |
| HOBt | 1-Hydroxylbenzotriazole |
| HPLC | High pressure liquid chromatography |
| LCMS | Liquid chromatography mass spectrometry |
| LDA | Lithium diisopropylamide |
| mCPBA | meta-Chloroperoxybenzoic acid |
| MeOH | Methanol |
| MTT | (3-[4,5-dimethyl-thiazol-2-yl]-2,5-diphenyltetrazolium bromide, Thiazolyl blue) |
| NMR | Nuclear magnetic resonance |
| PFP | Pentafluorophenol |
| PMB | p-methoxybenzyl |
| Pyr | Pyridine |
| Rb | Round bottom flask |
| Rbt | Round bottom flask |
| RT | Room temperature |
| SEMCl | 2-(Trimethylsily)ethoxy methyl chloride |
| TBTU | O-(Benzotriazol-1-yl)-N,N,N',N'-tetramethyluronium tetrafluoroborate |
| TEA | Triethylamine |
| Tr | Triphenyl methane |
| Trt | Triphenyl methane |
| TrCl | Triphenyl methane chloride |
| TFA | Trifluoroacetic acid |
| THF | Tetrahydrofuran |
| TLC | Thin layer chromatography |
| TMS | Trimethylsilyl |

General Synthetic Schemes

Scheme 1

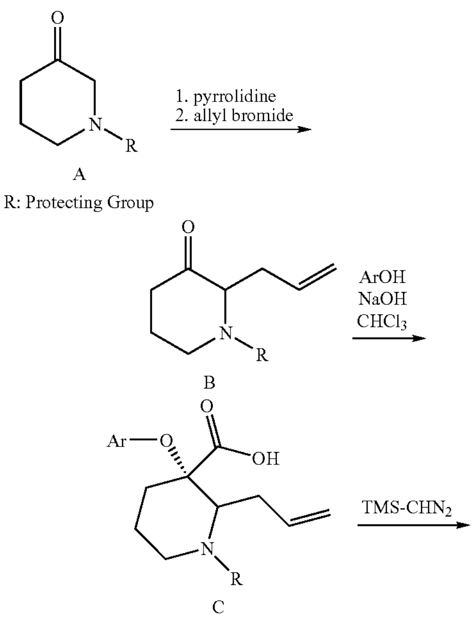

-continued

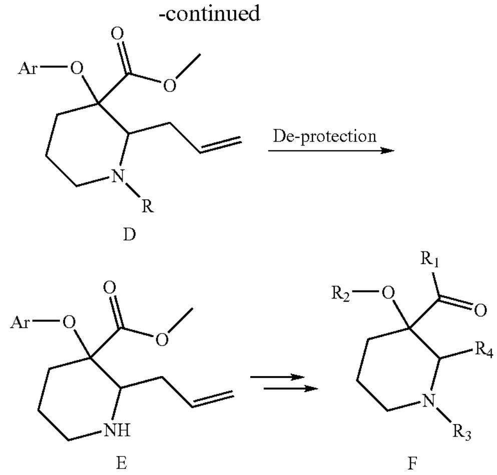

N-protected 3-piperidone (A) underwent alkylation to yield B. Subsequent reaction of B in the presence of substituted aryl or heteroaryl phenols, NaOH and chloroform produced C as a mixture of stereoisomers. Similar reactions were carried out with various N-substituents, including but not limited to N-methyl carbamate, N-benzyl, and N-Boc. The reaction temperature varied from 0° C. to 50° C.; depending upon the nature of the other substituents. References for this type of transformation include I. Lalezari et al., *J. Med. Chem.* 1989, 32, 2352; A. M. Youssef et al. *J. Med. Chem.* 2002, 45, 1184; and P. K. Sen et al., *Tetrahedron Lett.* 2005, 46, 8741. Note: ArOH represents substituted aryl or heteroaryl phenols as well as corresponding keto-tautomers that may exist under the reaction conditions.

For example:

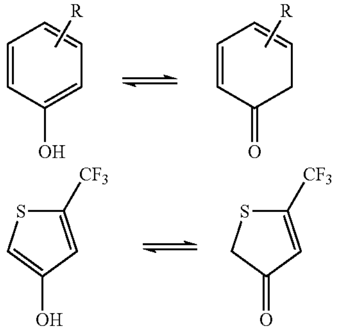

Treatment of intermediate C with trimethylsilyl diazomethane gave the corresponding methyl ester D. Deprotection of the piperidine nitrogen afforded compounds of type E, which were further elaborated on the piperidine nitrogen, alkene, and methyl ester yielding final products of type F. Additional modifications on the piperidine substituents may also have been performed; including amide formation, ester hydrolysis, and coupling reactions to form C—N, C—O, and C—C bonds.

Compounds of this invention are exemplified in the following examples, which should not be constructed as limiting the scope of the disclosure. Alternative mechanistic pathways and analogous structures within the scope of the invention may be apparent to those skilled in the art.

Separation of racemates: Racemic intermediates and/or final compounds were separated (resolved) to yield optically enriched compounds using chiral HPLC. This separation could be performed at different stages of the synthesis or with the final products. Upon testing in biochemical or biophysical assays the more active isomer typically exhibited twice the potency (one-half of the racemic $IC_{50}$ and/or Ki) of the racemic mixture. Representative separation conditions include: Chiral HPLC Column: ChiralPak AD-5 cm 20μ; Mobile phase: Hexane/Isopropanol or Hexane/Ethanol; Conditions: 25 mL/min, 25° C. Please refer following compounds 27 and 30 for some examples. The chirality of the active isomer was determined by X-ray crystallography. NMR experiments also supported the stereochemical assignments.

Scheme 2: General protocol to prepare 4-ArO substituted piperidines

Route 1:

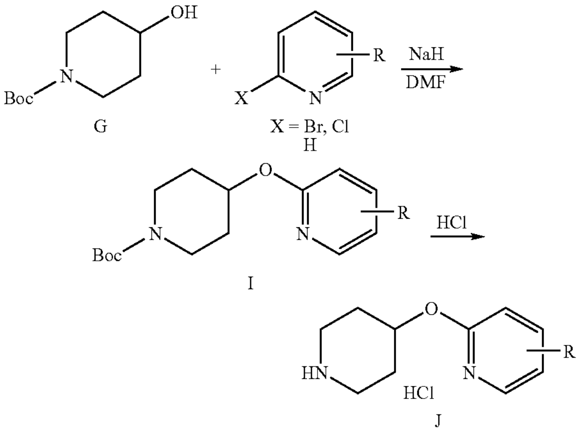

Route 2:

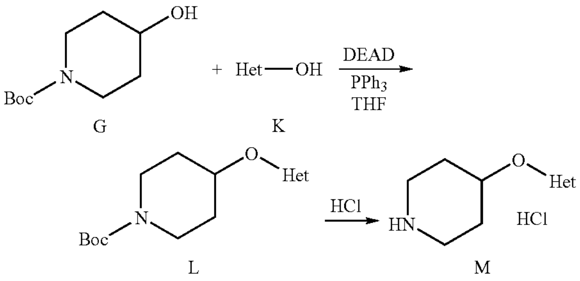

Route 1:

To a solution of 1.0 eq of alcohol G in DMF, 1.2 eq of sodium hydride was added. The reaction solution is stirred at room temperature for 15 mins and then 1.0 eq of Halo-pyridine H was added. The reaction mixture was stirred at room temperature overnight and then $H_2O$ was added to quench the reaction. After standard aqueous work up and purification, the desired ether I was obtained.

To a solution of 1.0 eq of ether I in MeOH, 5 eq of 4M HCl in dioxane was added. The reaction solution is stirred at room temperature for 2 hours. Removal of solution gave the desired piperidine HCl salt J.

Route 2:

At 0° C., to a solution of 1.0 eq of alcohol G, 1.0 eq of hydroxyl-heterocycle K and 1.3 eq of $PPh_3$ in dry THF, 1.3 eq of DEAD was added dropwise. The reaction solution was stirred at room temperature overnight. After standard aqueous work up and purification using silica gel chromatography, the desired ether L was obtained.

To a solution of 1.0 eq of ether L in MeOH, 5 eq of 4M HCl in dioxane was added. The reaction solution is stirred at room temperature for 2 hours. Removal of solution gave the desired piperidine HCl salt of M.

Scheme 2: General Protocol to Prepare Substituted N-aryl-piperazines

Aryl Amination Route

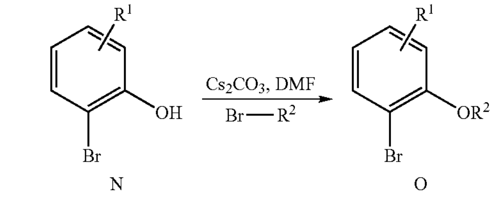

To a stirring solution of N (1.0 eq) and $Cs_2CO_3$ (3.0 eq) in DMF (0.1 M) was added Br—$R^2$ (1.1 eq) and the reaction stirred at room temperature 16 h. The salts were removed by filtration, the reaction mixture concentrated in vacuo, and purified by flash silica gel chromatography to give O.

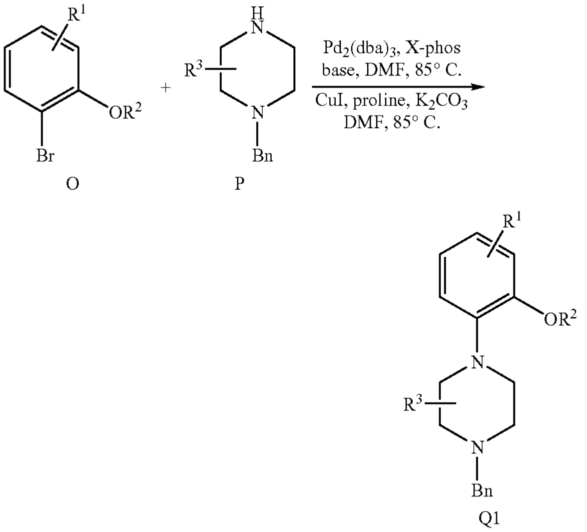

Method 1: To $Pd_2(dba)_3$ (0.05 eq), X-phos (0.25 eq), and base (typically $K_3PO_4$, $Cs_2CO_3$, or NaOtBu) (2 eq)) under argon was added a solution of O (1.5 eq) and P (1.0 eq) in DMF (0.1 M) and the reaction mixture heated to 85° C. for 16 h. The reaction mixture was cooled to room temperature, filtered through celite, concentrated in vacuo, and purified by flash silica gel chromatography to give Q1.

Method 2: To CuI (0.10 eq), proline, (0.40 eq), and $K_2CO_3$ (2 eq)) under argon was added a solution of O (1.0 eq) and P (1.5 eq) in DMF (0.1 M) and the reaction mixture heated to 90° C. for 16 h. The reaction mixture was cooled to room temperature, filtered through celite, concentrated in vacuo, and purified by flash silica gel chromatography to give Q1.

Hydroxylphenylpiperazine Route

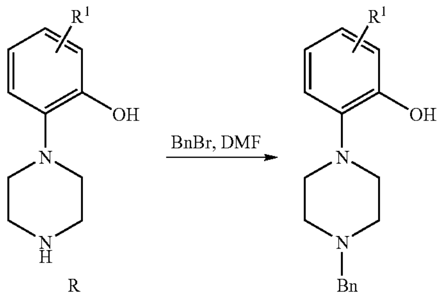

R S

To a stirring solution of R (1.0 eq) in DMF (0.1 M) was added BnBr (1.0 eq) and the reaction mixture stirred at room temperature 16 h. The mixture was concentrated in vacuo and used without further purification.

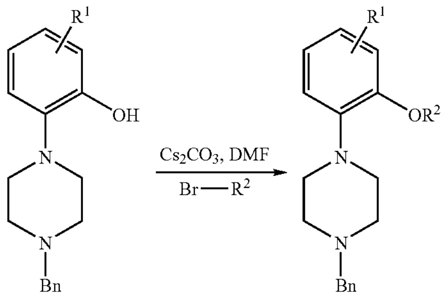

S Q2

To a stirring solution of S (1.0 eq) and $Cs_2CO_3$ (3.0 eq) in DMF (0.1 M) was added Br—$R^2$ (1.1 eq) and the reaction stirred at room temperature or heated to 55° C. 16 h. The salts were removed by filtration, the reaction mixture concentrated in vacuo, and purified by flash silica gel chromatography to give $O_2$.

Piperazine Cyclization Route

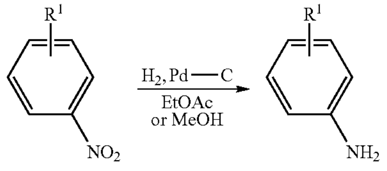

T U

To a stirring solution of T (10 eq) in ethyl acetate (0.1 M) was added 5% palladium on carbon (20 wt %), the reaction vessel was purged with hydrogen, and stirred under balloon-pressure hydrogen for 2 h. The reaction mixture was filtered through celite, concentrated in vacuo, and used without further purification

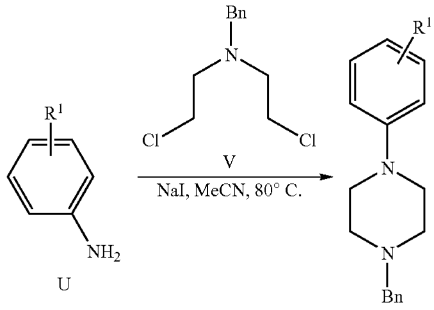

U Q3

To a stirring solution of U (1.0) and V (1.1) in acetonitrile (0.1 M) was added sodium iodide (0.2 eq) and the reaction mixture heated to 80° C. 16 h. The mixture was concentrated in vacuo and purified by flash silica gel chromatography to give Q3.

General Deprotection of 1-benzyl-4-arylpiperazines

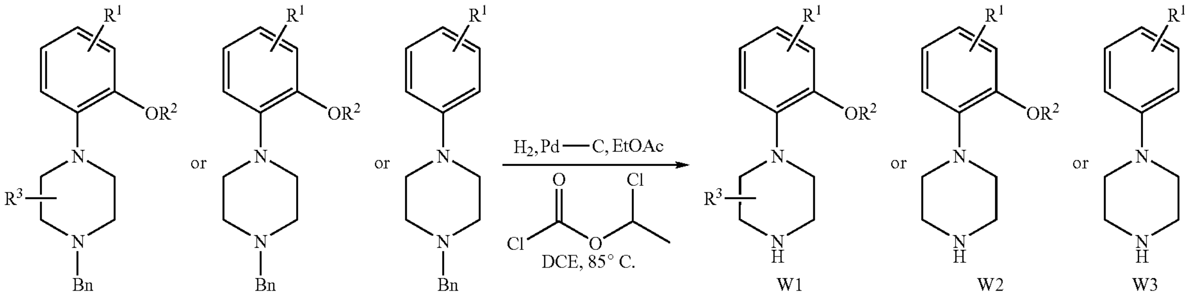

Q1 or Q2 or Q3 W1 or W2 or W3

Method 1: To a stirring solution of Q (1.0 eq) in ethyl acetate (0.1 M) was added 5% palladium on carbon (40 wt %), the reaction vessel was purged with hydrogen, and stirred under balloon-pressure hydrogen for 16 h. The reaction mixture was filtered through celite, and concentrated in vacuo, to give W which used without further purification Method 2: To a stirring solution of r (1.0 eq) in 1,2-dichloroethane (0.1 M) at room temperature was added 1-chloroethyl chloroformate (4 eq) and the reaction mixture heated to 85° C. 16 h. The mixture was concentrated in vacuo, redissolved in ethanol (0.1 M), and heated to 85° C. 1 h. The mixture was concentrated in vacuo, diluted with ethyl acetate washed with 10% NaOH, dried ($Na_2SO_4$), the solvent evaporated to give W which was used without further purification.

Scheme 3: Preparation of aryl boronic acid examples AA, AB, AE and AF

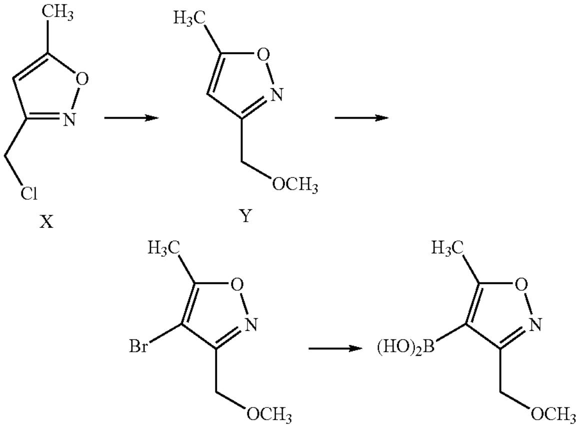

X Y Z AA

3-Methoxymethyl-5-methylisoxazole (Y): Sodium methoxide (30% in methanol, 7.46 mmol) was added to 3-chloromethyl-5-methyisoxazole (491 mg, 3.73 mmol) in methanol (4 mL) at room temperature under nitrogen. The reaction mixture was stirred for 15 h at room temperature then heated to reflux for 3 h. After cooling to room temperature the reaction was diluted with ether (75 mL) and washed with saturated aqueous ammonium chloride (15 mL), water (15 mL), and brine (15 mL). The organic layer was dried over magnesium sulfate, filtered, and evaporated to provide 362 mg (76% yield) of 3-methoxymethyl-5-methyl isoxazole as a clear liquid which was used in the next step without further purification: $^1$H NMR (300 MHz, $CDCl_3$) δ ppm 6.02 (s, 1H), 4.48 (s, 2H), 3.38 (s, 3H), 2.42 (d, J=0.6 Hz, 3H).

4-Bromo-3-methoxymethyl-5-methylisoxazole (Z): N-bromosuccinimide (590 mg, 3.31 mmol) was added to 3-methoxymethyl-5-methyisoxazole (351 mg, 2.76 mmol) in DMF (3.5 mL) at room temperature under nitrogen. The reaction was heated at 60° C. for 15 h then allowed to cool to room temperature. Ether (50 mL) was added to the reaction mixture, then washed with water (3×10 mL), saturated aqueous sodium hydrogen carbonate (10 mL), and brine (10 mL). The organic layer was dried over magnesium sulfate, filtered, and evaporated to provide 526 mg (92% yield) of 4-bromo-3-methoxymethyl-5-methylisoxazole as a clear liquid which was used in the next step without further purification: $^1$H NMR (300 MHz, $CDCl_3$) δ ppm 4.50 (s, 2H), 3.41 (s, 3H), 2.43 (s, 3H).

3-methoxymethyl-5-methylisoxazole-4-boronic acid (AA): n-Butyl lithium (2.5 M in hexanes, 2.20 mmol) was added dropwise to 4-bromo-3-methoxymethyl-5-methyl isoxazole (412 mg, 2.00 mmol) in THF (8 mL) at −78° C. under nitrogen. After stirring at −78° C. for 30 min triisopropylborate (564 mg, 3.00 mmol) was added dropwise. The temperature was maintained at −78° C. for 2 h then the reaction was allowed to warm to room temperature and stirred for 15 h. The reaction mixture was poured into a mixture of 1N hydrochloric acid and water (1:1, 100 mL) and stirred rapidly for 1 h. The organic layer was separated and the aqueous layer was extracted with ether (3×25 mL). The combined organic layers were washed with brine (25 mL), dried over magnesium sulfate, filtered and evaporated to dryness. The residue was triturated with hexanes (30 mL) then dried under high vacuum to provide 89 mg (29% yield) of 3-methoxymethyl-5-methyl isoxazole-4-boronic acid as a waxy tan solid which was immediately carried forward to the next reaction: $^1$H NMR (300 MHz, $CDCl_3$) δ ppm 4.74 (s, 2H), 3.37 (s, 3H), 2.74 (s, 3H), 2.60 (s, 2H).

AB

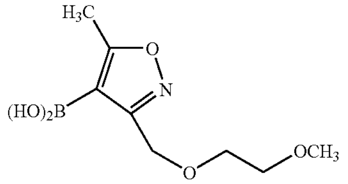

3-((2-methoxyethoxy)methyl)-5-methylisoxazol-4-boronic acid (AB): Example AB was prepared in a similar manner to example AA beginning with X and the sodium salt of 2-methoxy ethanol.

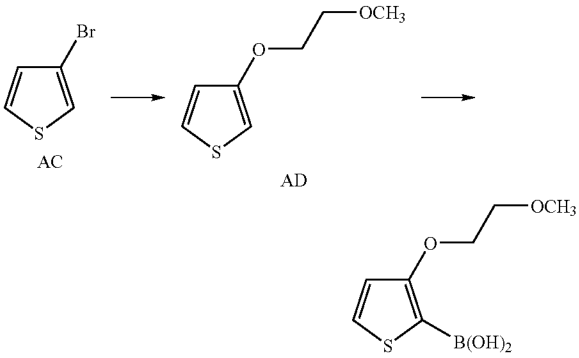

AC AD AE 3-(2-methoxyethoxy)thiophene (AD): Sodium metal (1.05 g, 45.8 mmol) cut into small pieces was added to 2-methoxyethanol (12 mL) at room temperature under nitrogen. The reaction was heated at 75° C. until all the sodium metal dissolved (about 45 min). 3-Bromothiophene (2.49 g, 15.3 mmol) and copper(1) bromide (0.22 g, 1.53 mmol) were added to the reaction mixture and the heat was increased to 118° C. for 1.5 h. The reaction was allowed to cool to room temperature and the mixture was poured into a mixture of brine and ether (1:1, 100 mL). Vigorous stirring caused an emulsion which was removed by filtration through celite washing the filter cake with ether (40 mL). The organic layer was separated and the aqueous layer extracted with ether (3×30 mL). The combined organic layers were washed with brine, dried over magnesium sulfate, filtered and evaporated to dryness. The residue was purified by silica gel chromatography to afford 1.83 g of 3-(2-methoxyethoxy)thiophene (76% yield) as a clear liquid. $^1$H NMR (300 MHz, $CDCl_3$) δ ppm 7.17 (dd, J=5.3, 3.2 Hz, 1H), 6.80 (dd, J=5.1, 1.5 Hz, 1H), 6.26 (dd, J=3, 1.5 Hz, 1H), 4.14-4.08 (m, 2H), 3.77-3.70 (m, 2H), 3.44 (s, 3H).

3-(2-methoxyethoxy)thiophene-2-boronic acid (AE): n-Butyl lithium (2.5 M in hexanes, 3.95 mmol) was added dropwise to 7 (568 mg, 3.59 mmol) in anhydrous THF (10 mL) at −78° C. The reaction mixture was stirred at −78° for 30 min, 0° C. for 30 min, and room temperature for 1 h, then recooled to −78° C. and triisopropylborate (0.81 g, 4.31 mmol) was added dropwise. After stirring for 1 h at −78° C. the reaction was allowed to come to room temperature and stirred for 4 h. The reaction was then poured into a mixture of 1 N hydrochloric acid and ether (1:1, 50 mL) and stirred vigorously for 0.5 h. The organic layer was separated and the aqueous layer was extracted with ether (3×25 mL). The combined organic layers were washed with brine (25 mL), dried over magnesium sulfate, filtered and evaporated to dryness. The oily residue was triturated in a mixture of ether and hexanes (1:10, 55 ml) then dried under high vacuum to provide 170 mg (23% yield) of 3-(2-methoxyethoxy)thiophene-2-boronic acid as an oily brown solid which was carried immediately forward to the next reaction: $^1$H NMR (300 MHz, $CDCl_3$) δ ppm 7.61 (d, J=1.2 Hz, 1H), 6.78 (d, J=1.2 Hz, 1H), 4.25-4.05 (m, 2H), 3.85-3.65 (m, 2H), 3.55-3.35 (m, 3H).

AF

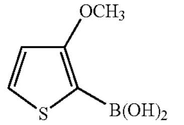

3-methoxythiophen-2-boronic acid (AF); Example AF was prepared by metalation of commercially available 3-methoxythiophene as demonstrated in example AE.

Scheme 4 Synthesis of pyrrolidine building block example AI

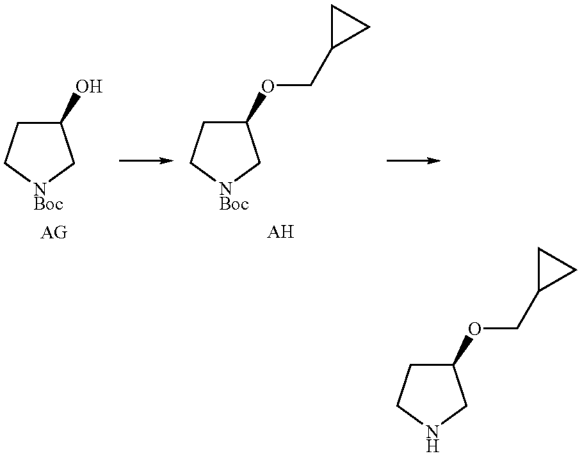

AG AH AI (R)-t-Butyl 3-(cyclopropylmethoxy)pyrrolidine-1-carboxylate (AH): Sodium hydride (60% in mineral oil, 128 mg, 3.20 mmol) was added in one portion to pyrrolidine AG (500 mg, 2.67 mmol) in anhydrous DMF (4 mL) at room temperature under nitrogen. Gas evolution was noted and the reaction mixture was stirred vigorously for 0.5 h. Bromomethylcyclopropane (721 mg, 5.34 mmol) was added dropwise and the mixture stirred for 60 h. Excess sodium hydride was quenched by the addition of saturated aqueous ammonium chloride (4 mL) and the mixture poured into water and ether (1:1, 30 mL). The organic layer was separated and the aqueous layer extracted with ether (3×15 mL). The combined organic layers were washed with water (3×15 mL) and brine (25 mL), dried over magnesium sulfate, filtered and evaporated to dryness. The residue was purified by silica gel chromatography to afford 352 mg of (R)-t-butyl 3-(cyclopropylmethoxy)pyrrolidine-1-carboxylate (AH): (76% yield) as a clear oil: $^1$H NMR (300 MHz, $CDCl_3$) δ ppm 4.02 (t, J=3.9 Hz, 1H), 3.50-3.20 (m, 4H) 3.24 (d, J=6.6 Hz, 2H), 2.10-1.80 (m, 2H), 1.42 (s, 9H), 1.10-0.90 (m, 1H), 0.51 (dd, J=7.2, 5.4 Hz, 2H), 0.17 (dd, J=10.2, 4.8 Hz, 2H).

(R)-3-(cyclopropylmethoxy)pyrrolidine (AI): Anhydrous hydrochloric acid (4 M in 1,4-dioxane, 2 mL) was added to pyrrolidine AH (352 mg, 1.46 mmol) in DCM (2 mL) at room temperature. After 1 h the reaction was evaporated to dryness and the residual HCl was removed by suspending the white solid in chloroform and evaporating the solvent in vacuo (repeated 4 times). The white solid was dried under vacuum to provide 264 mg of (R)-3-(cyclopropylmethoxy)pyrrolidine AI (quantitative yield): $^1$H NMR (300 MHz, $CDCl_3$) δ ppm 9.98 (s, 1H) 9.66 (s, 1H), 4.24 (s 1H), 3.55-3.20 (m, 4H) 3.28 (dd, J=6.9, 1.5 Hz, 2H), 2.25-1.90 (m, 2H), 1.12-0.95 (m, 1H), 0.54 (d, J=7.8 Hz, 2H), 0.32-0.11 (m, 2H).

Example 1

Compound 1

1-Benzyl-3-(4-trifluoromethyl-phenoxy)-piperidine-3-carboxylic acid

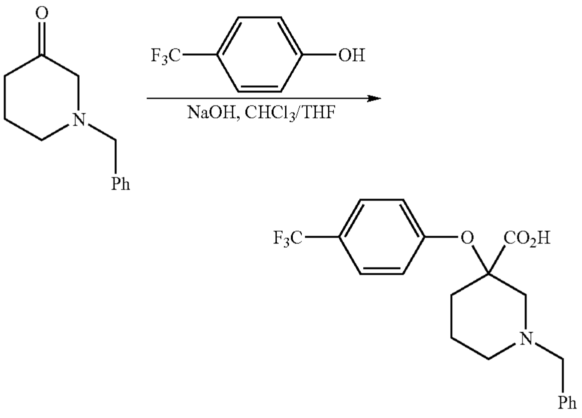

1

1-Benzyl-3-piperidone HCl salt hydrate (33 g, 0.135 mol) was suspended in methylene chloride (200 mL), and triethylamine (21 mL, 0.15 mol) was added to the suspension; which was stirred for three hours. The resultant mixture was washed with $H_2O$ (200 mL×2) and 300 mL of brine, then dried over magnesium sulfate, filtered, and the methylene chloride was removed to give 1-Benzyl-3-piperidone.

Sodium hydroxide (12.1 g, 0.302 mol) was added to stirred solution of 4-hydroxybenzotri-fluoride (5.5 g, 0.034 mol) in anhydrous tetrahydrofuran (165 mL). After 3 h, 1-benzyl-3-piperidone (25.6 g, 0.135 mol) was added to the mixture, the mixture was cooled to 0° C. and anhydrous chloroform (16.5 mL, 0.21 mol) was added dropwise. The reaction mixture was maintained at 0° C. for one hour, allowed to warm to 40° C. for 2~3 h, then stirred overnight at room temperature. Tetrahydrofuran was removed under reduced pressure. The residue was suspended in water (150 mL) and washed with diethyl ether (150 mL). The aqueous layer was acidified with 6 N hydrochloric acid to pH 7, filtered and washed with methylene chloride to give compound 1 as the desired material. (observed $[M+H]^+$: 380.2).

Compound 6

[4-(2-Methoxy-phenyl)-piperazin-1-yl]-[3-(4-trifluoromethyl-phenoxy)-1-(4-trifluoromethyl-pyridine-3-carbonyl)-piperidin-3-yl]-methanone

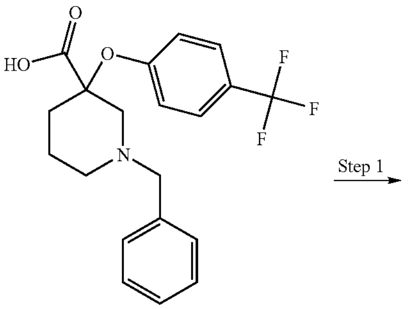

1

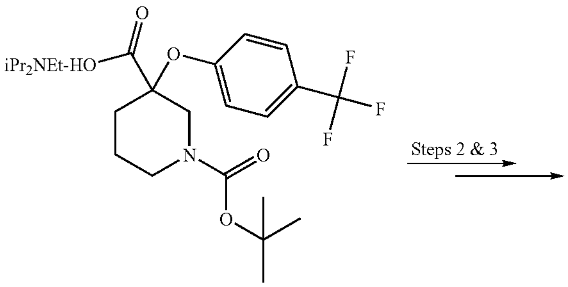

2

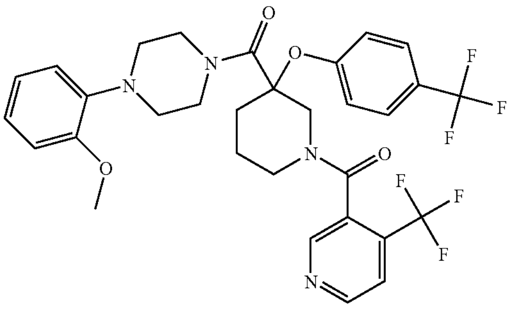

6

Step 1:

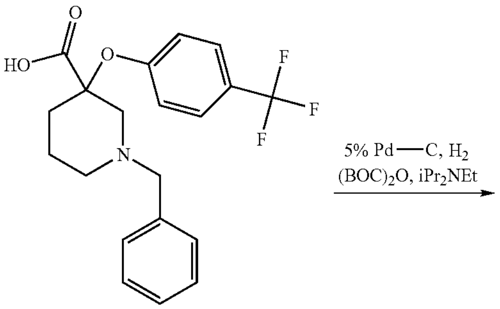

1

-continued

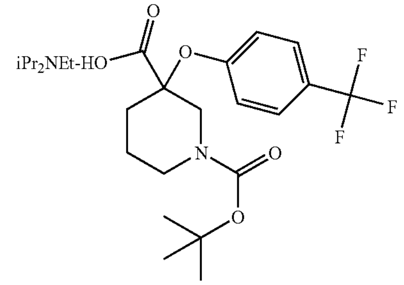

2

To 1 (1 eq, 18 mmol, 6.9 g) and N,N-diisopropylethylamine (5 eq, 91 mmol, 15.8 mL) completely dissolved in 25% ethanol/75% ethyl acetate (400 mL) was added a solution of di-tertbutyl dicarbonate (1 eq, 18 mmol, 4.0 g) in ethyl acetate (50 mL) followed by 5% palladium on carbon (30 wt %, 2.0 g) at room temperature. The reaction vessel was sealed with a septum, purged with argon, and hydrogen gas was bubbled through the solvent for 2 minutes. The reaction mixture was stirred under a hydrogen gas atmosphere at room temperature for 15 hours, then filtered through celite and concentrated in vacuo to give 2 as an off-white solid in the form of the corresponding diisopropylethylammonium salt which was used without further purification.

Step 2:

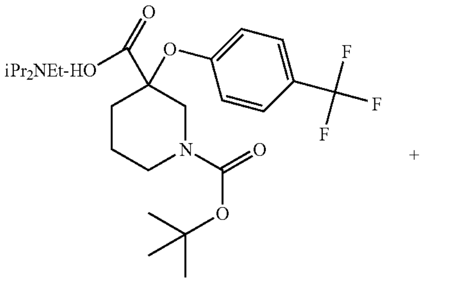

2

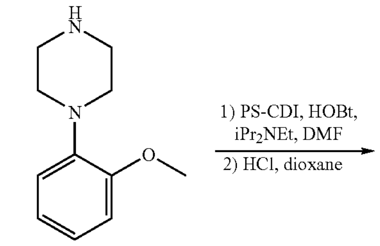

3

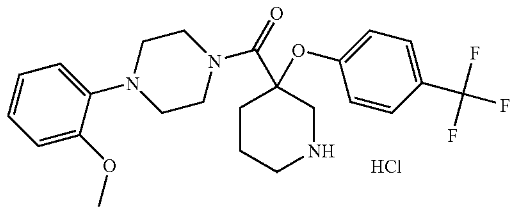

4

To 2, the product of step 1, (0.1 mmol) in N,N-dimethylformamide (0.67 mL) and N,N-diisopropylethylamine (3.0 eq, 0.3 mmol, 52 µL) was added 1-hydroxybenzotriazole (1.0 eq, 0.1 mmol, 14 mg), 3 (1.5 eq, 0.15 mmol, 29 mg), and polystyrene-bound carbodiimide resin, loading: 1.3 mmol/g (3.0 eq, 0.3 mmol, 231 mg). The mixture was shaken overnight at room temperature and scavenged with MP-trisamine and MP-isocyanate resins (excess) in tetrahydrofuran (3 mL) for 2 h. The resins were removed by filtration and the solvent removed in vacuo. The crude reaction mixture was dissolved in 4N hydrochloric acid in 1,4-dioxane (3 mL) and shaken at room temperature for 2 hours followed by evaporation in vacuo. The crude residue was used without further purification.

Step 3:

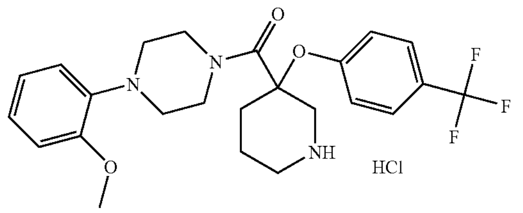

4

+

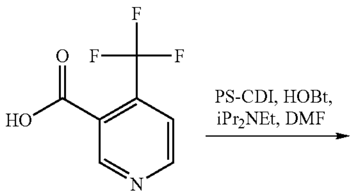

5

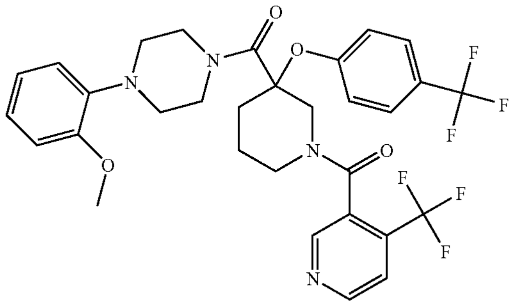

6

To 4, the product of step 2, (1.0 eq, 0.2 mmol, 100 mg), 5 (1.5 eq, 0.3 mmol, 58 mg), and 1-hydroxybenzotriazole (1.0 eq, 0.2 mmol, 27 mg) in N,N-dimethylformamide (6.7 mL) and N,N-diisopropylethylamine (4.0 eq, 0.8 mmol, 140 μL) was added polystyrene-bound carbodiimide resin, loading: 1.3 mmol/g (3.0 eq, 0.6 mmol, 462 mg) and shaken overnight at room temperature. The resin was removed by filtration, the solvent removed in vacuo, and the crude residue was purified by HPLC-MS to give the target compound 6, of preparation 1 as the TFA-salt. The solid was dissolved in an acetonitrile/$H_2O$ solution (1:1, 1.0 mL total) and 1.0 N hydrochloric acid (200 mL) and lyophilized to give the target compound of preparation 1 in the form of the corresponding hydrochloric acid-salt (observed $[M+H]^+$, 637.2)

Compound 13

(1,3,4,9-Tetrahydro-b-carbolin-2-yl)-[3-(4-trifluoromethyl-phenoxy)-1-(4-trifluoromethyl-pyridine-3-carbonyl)-piperidin-3-yl]-methanone

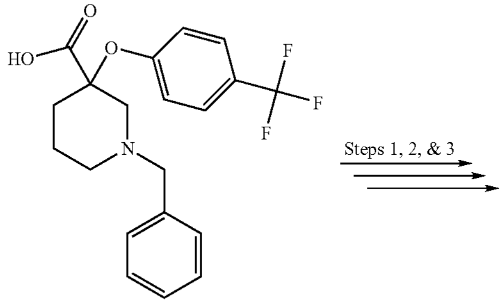

1

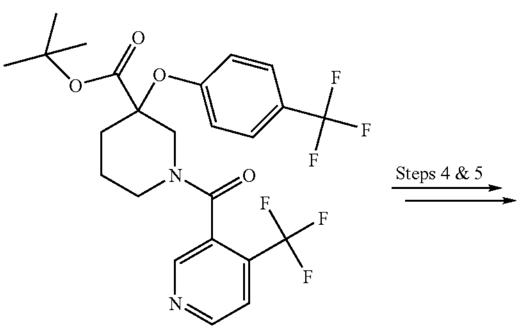

10

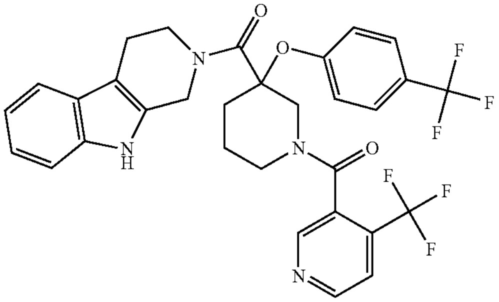

13

Step 1:

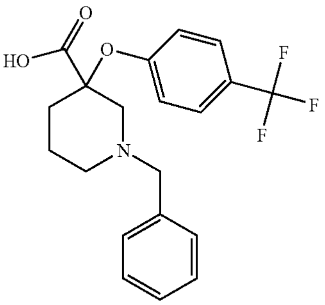

+

1

-continued

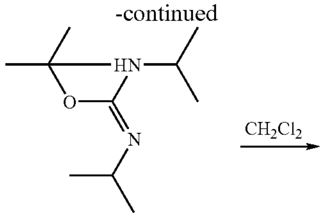

7

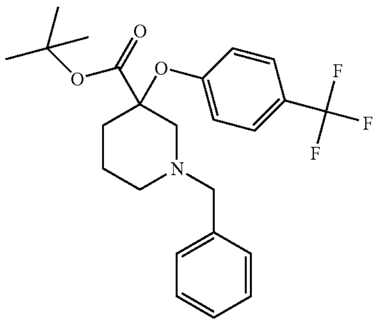

8

To 1 (1.0 eq, 18 mmol, 7.0 g) suspended in methylene chloride (100 mL) was added 7 [reference: Mathias, L. J. *Synthesis* 1979, 561-579] (1.35 eq, 25 mmol, 5.0 g) in methylene chloride (20 mL), the reaction mixture stirred at room temperature for one hour, then heated to reflux for three hours. Upon cooling to room temperature, additional 7 was added as necessary to push the reaction to completion with stirring overnight at room temperature. The precipitate was removed by filtration through celite and the solvent removed in vacuo. The filtrate F was further purified by silica gel flash column chromatography (100% $CH_2Cl_2$) and gave 8 as a colorless oil (5.76 g).

Step 2:

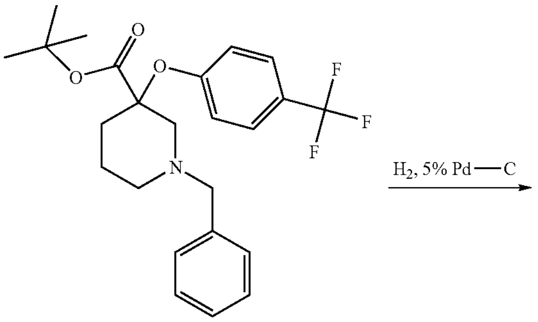

8

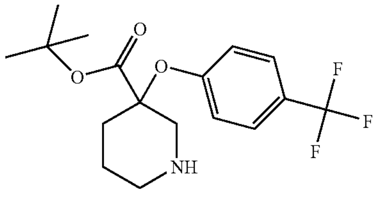

9

To 8 (1.0 eq, 9.4 mmol, 4.1 g) in ethylacetate (47 mL) added 5% palladium on carbon, purged the flask with argon, then purged with hydrogen gas. The reaction mixture was stirred under a hydrogen gas atmosphere (at balloon pressure) overnight, then filtered through celite, and the solvent removed in vacuo to give 9 as a brown oil which was used without further purification.

Step 3:

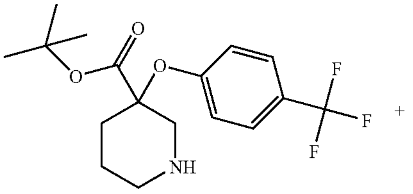

9

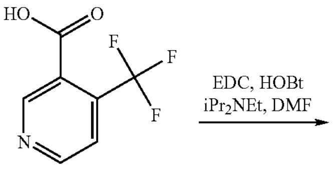

5

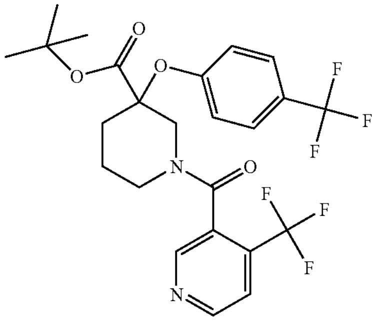

10

To 9 (1.0 eq, 2.5 mmol, 860 mg), 1-hydroxybenzotriazole (0.5 eq, 1.25 mmol, 168 mg), and 5 (1.1 eq, 2.74 mmol, 523 mg) in N,N-dimethylformamide (25 mL) and N,N-diisopropylethylamine (3 eq, 7.5 mmol, 1.3 mL) was added 1-(3-dimethylaminopropyl)-3-ethylcarbodiimide hydrochloride (1.3 eq, 3.2 mmol, 621 mg) and the reaction mixture stirred at room temperature overnight. The solvent was removed in vacuo and the residue was further purified by silica gel flash column chromatography in a methylene chloride/ethylacetate solution (20:1) and gave 10 as a light brown oil (988 mg)

Step 4:

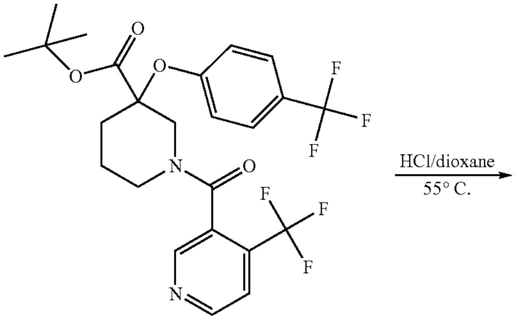

10

-continued

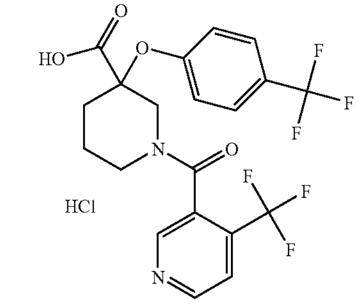

11

To 10 (1.0 eq, 1.9 mmol, 987 mg) was added 4N hydrochloric acid in 1,4-dioxane (10 mL) and the reaction mixture was stirred and heated to 55° C. for 2 hours. The solvent was removed in vacuo to give 11, which was used without further purification.

Step 5:

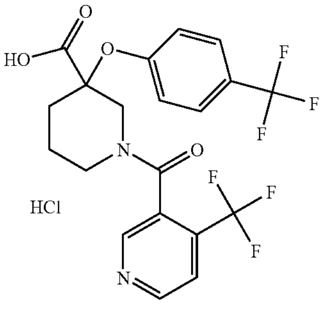

11

+

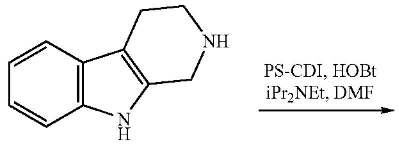

12

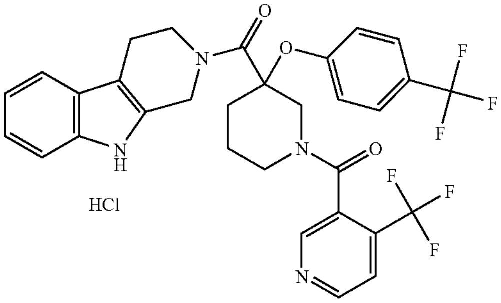

13

To polystyrene-bound carbodiimide resin, loading: 1.3 mmol/g (3.0 eq, 0.09 mmol, 69 mg) was added 11 (1.0 eq, 0.03 mmol, 15 mg), 12 (1.3 eq, 0.04 mmol, 7 mg), and 1-hydroxybenzotriazole (1.0 eq, 0.03 mmol, 4 mg) in N,N-dimethylformamide (1 mL) and N,N-diisopropylethylamine (5.0 eq, 0.15 mmol, 26 μL) was added and shaken overnight at room temperature. The resin was removed by filtration, the solvent removed in vacuo, and the crude residue was purified by HPLC-MS to give target compound of preparation 2 as the TFA-salt. The solid was dissolved in acetonitrile/$H_2O$ (1:1, 1.0 mL total) and 1.0 N hydrochloric acid (200 μL) and lyophilized to give target compound 13 of preparation 2 in the form of the corresponding hydrochloric acid-salt (observed $[M+H]^+$: 617).

Example 2

Alternative Reaction Route to Compound 19, which is Similar to Compound II Above

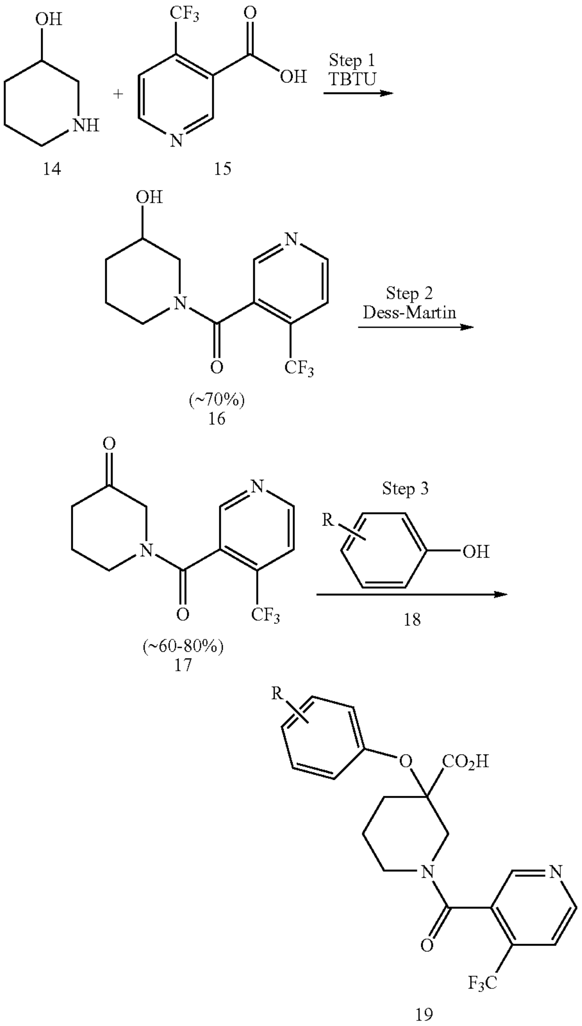

R = at least one Br, Cl, F, CN, t-Bu

Step 1:

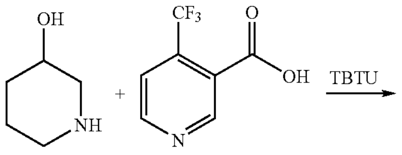

14 15

-continued

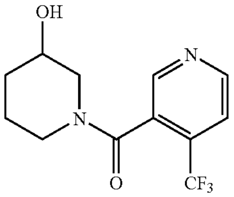

(~70%)
16

4-(Trifluoromethyl)nicotinic acid 15 was dissolved in 20 mL of dimethyl formamide, followed by the addition of O-(Benzotriazol-1-yl)-N,N,N',N'-tetramethyluronium tetrafluoroborate (TBTU) (3.3 mmol, 1.06 g) and triethylamine (TEA) (3-3 mmol, 460 μL). The mixture was cooled to 0° C., and then 3-Hydroxypiperidine 14 was added. The cooled mixture was stirred at room temperature for 20 hours. The solvent was removed under vacuum. The resulting residue was dissolved in 100 mL of ethyl acetate, and it was washed with saturated sodium bicarbonate and brine successively. The solution was then dried over magnesium sulfate. Removal of the solvent gave a crude product 16 which was purified through a silica gel column chromatography (EtOAc/Hexane=11) (yield, 0.58 g)

Step 2:

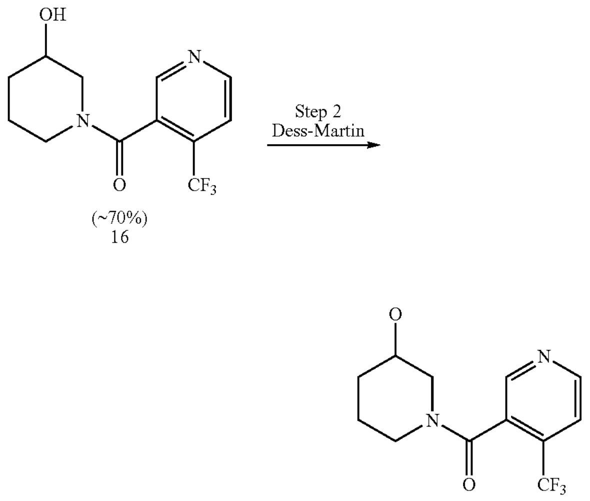

(~70%)
16

(~60-80%)
17

To compound 16 (0.58 g) in dichloromethane (20 mL) at 0° C. was added Dess-Martin periodinane slowly (3 mmol, 1.27 g). The mixture was stirred at room temperature overnight. The reaction was diluted with 30 mL of dichloromethane followed by the addition of 30 mL of saturated sodium bicarbonate with stirring. The mixture was filtered through celite and the solution was extracted with ethyl acetate twice (2×50 mL). The organic phases were combined and dried over magnesium sulfate. The solvent was evaporated to yield crude 17 which was purified through a silica gel column chromatography in an ethylacetate/hexane 1:1 mixture.

Step 3:

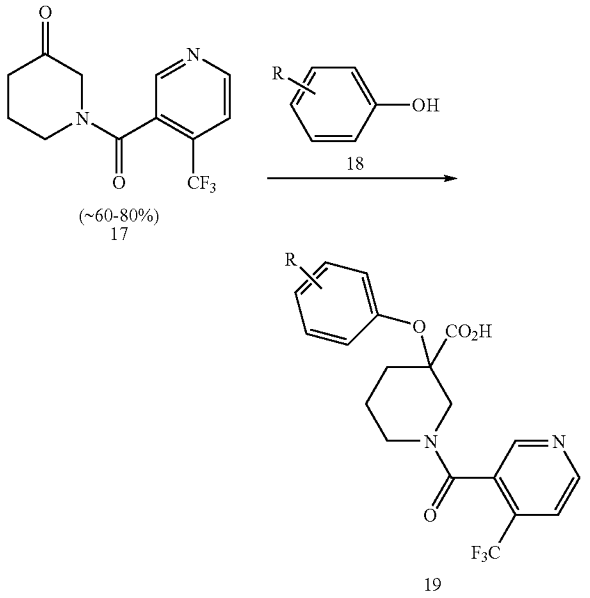

(~60-80%)
17
18
19

R = at least one Br, Cl, F, CN, t-Bu

Sodium hydroxide (40 mg, 1 mmol) was added to stirred solution of phenol (0.2 mmol) in 1 mL anhydrous tetrahydrofuran. After 0.5 h, compound 17 (0.2 mmol) was added, the mixture was cooled to 0° C. and anhydrous chloroform (82 μL, 1 mmol) was added dropwise. The reaction mixture was maintained at 0° C. for 1 h and then allowed to warm up to 40° C. for 2~3 h, the mixture was then stirred overnight at room temperature. Tetrahydrofuran was removed from the mixture under reduced pressure leaving a residue. The residue was suspended in water (2 mL) and washed with diethyl ether (2×3 mL). The aqueous layer was acidified with 6N hydrochloric acid to pH 7, and extracted with ethyl acetate 3 times. The organic phases were combined and dried over magnesium sulfate. The solvent was evaporated to yield crude 19 which was directly used for the next step of amide formation as discussed above.

Piperidine Ring Modification

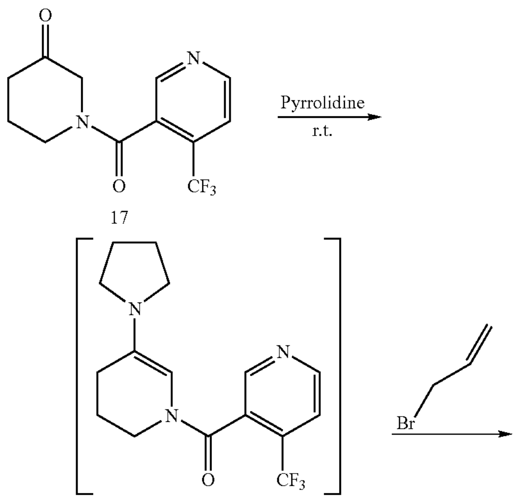

17
20

-continued

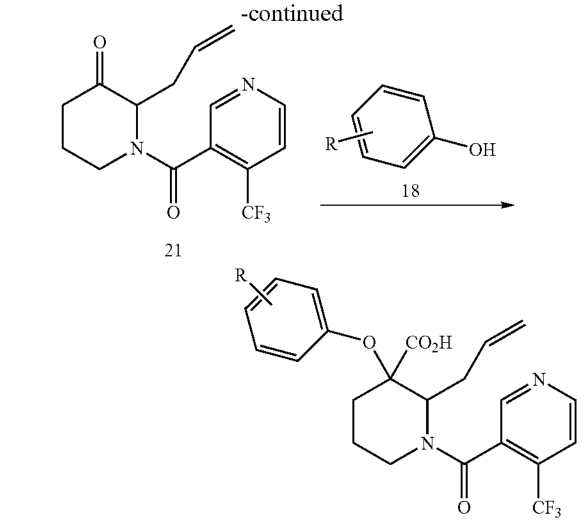

21

22

R is a single or disubstitution of Br, Cl, F, CN, or t-Bu

Preparation of Compound 21:

To 17 (1.7 g, 6.25 mmol) in benzene (25 mL) was added pyrrolidine. The mixture was stirred at room temperature for 2 h. It was then heated and 15 mL of solvent was distilled. To the remaining solution allyl bromide in acetonitrile (10 mL) was added and the reaction was heated at 70° C. for 16 h. Solvent was evaporated, and the resulting residue was suspended in 30 mL of dilute sodium bicarbonate solution and stirred at 80° C. for 1 h. The mixture was cooled to r.t. and extracted with ethyl acetate 3 times. Combined organic phases were dried over MgSO4. Evaporation of solvent to yield crude 21 which was purified by column chromatography (ethyl acetate/hexane=1:2) (yield, 800 mg, ~40%).

General Procedure for Preparation of Target Compound 22

Similar procedure as described above in the alternative route to compound 19, where compound 18 was added to 17.

Example 3

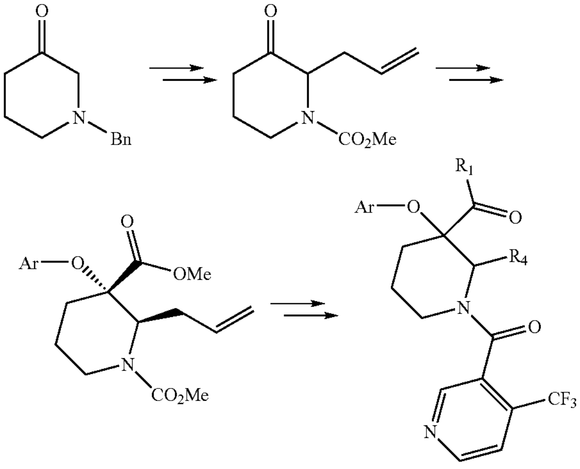

Step 1:

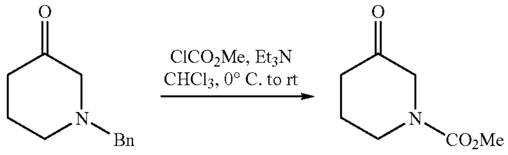

23

To 1-benzyl-3-piperidone HCl salt hydrate (1 eq, 0.111 mol, 25 g) completely dissolved in chloroform (100 mL) and triethylamine (1.1 eq, 0.122 mol, 17 mL) was added methyl chloroformate (1.1 eq, 0.122 mol, 9.4 mL) dropwise at 0° C. After the dropwise addition was complete, additional methyl chloroformate (0.7 eq, 0.078 mol, 6 mL) was added, the reaction mixture warmed to room temperature, and stirred 1 h. The volatiles were removed in vacuo and the resulting residue was taken up in 1N HCl (100 mL) and washed with hexanes (3×70 mL). The aqueous layer was then extracted with ethyl acetate (3×100 mL), the combined ethyl acetate layers washed with brine (1×50 mL), dried ($Na_2SO_4$), and concentrated in vacuo to give 23 as an orange oil (10 g), which was used without further purification. Note: If the aqueous layer retains some product, it can be completely extracted using 10% isopropyl alcohol in chloroform.

Step 2:

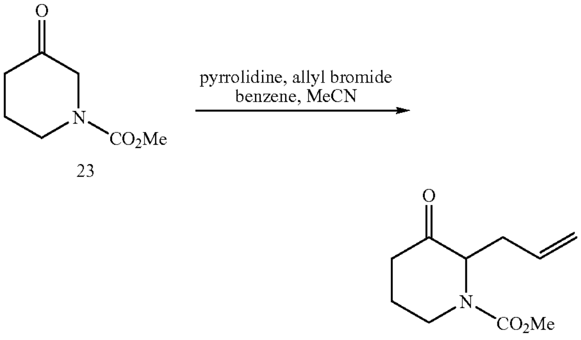

23

24

To 23 (75.1 mmol, 11.8 g) in benzene (170 mL) was added pyrrolidine (1.2 eq, 90.1 mmol, 7.5 mL) under Ar and the reaction stirred at room temperature 1.5 h. The reaction flask was then fitted with a Dean-Stark trap and heated to reflux to remove ~1.3 mL of water and ~85 mL of benzene. Upon cooling to room temperature, a solution of allyl bromide (1.3 eq, 97.6 mmol, 8.4 mL) in acetonitrile (70 mL) was added and the mixture was stirred at 70° C. overnight. The solvent was removed in vacuo and the crude residue was suspended in dilute (~5%) aqueous sodium bicarbonate solution (75 mL) and stirred for 1 h at 80° C. Upon cooling to room temperature, the aqueous solution was extracted with ethyl acetate (3×75 mL), dried ($Na_2SO_4$), and concentrated in vacuo. Purification by flash silica gel chromatography (3:1 hexanes/ethyl acetate, visualized with PMA stain) gave 24 as a light brown oil (10.1 g).

Step 3a

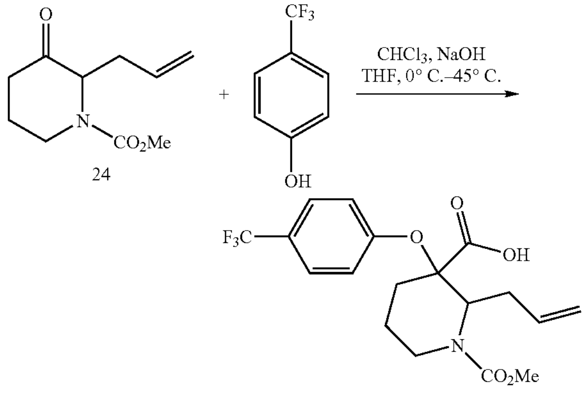

24

25

Dry NaOH (5 eq, 0.2 mol, 8 g) under Ar was added to 4-trifluoromethylphenol (1 eq, 40 mmol, 6.5 g) in extra dry THF (80 mL) and the reaction mixture was stirred at room temperature for 2 h. A solution of 24 (1.25 eq, 50 mmol, 10 g) in extra dry THF (20 mL) was added with stirring for 20 min at room temperature. The reaction mixture was then cooled to 0° C., and extra dry chloroform (4.5 eq, 0.18 mol, 15 mL) was added dropwise. The reaction mixture was warmed to room temperature for 2 h and heated to 45° C. overnight. The solvent was removed in vacuo and the residue redissolved in 200 mL of 3N NaOH and washed with diethyl ether (2×100 mL). The pH was adjusted to pH 1 with concentrated HCl, then the aqueous solution extracted with ethyl acetate (3×200 mL). The combined extracts were dried over $MgSO_4$, filtered and evaporated. The resulting residue 25 was used without further purification.

Step 3b

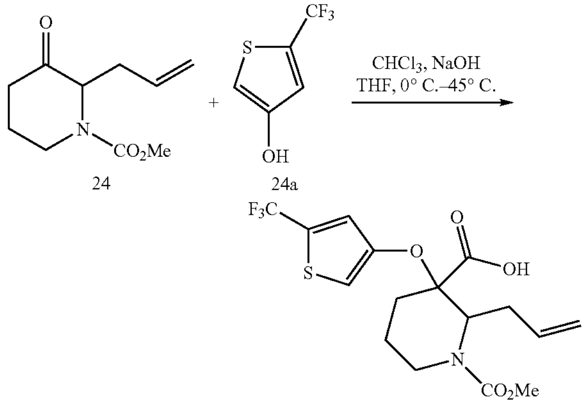

24

24a

26

26 was prepared from 24 using a similar protocol described in Step 3a

To dry NaOH (5 eq, 14.6 mmol, 0.58 g) in extra dry THF (6 mL) under Ar was added 5-trifluoromethylthiophen-3-ol (24a, 1.25 eq, 3.65 mmol, 0.61 g) in extra dry THF (2 mL) and the reaction mixture stirred at room temperature for 1 h. The solution was cooled to 0° C. and a solution of 24 (1.0 eq, 2.92 mmol, 0.58 g) in extra dry THF (2 mL) was added with stirring for 20 min. Extra dry chloroform (4.5 eq, 13.12 mmol, 1.1 mL) was added dropwise via addition funnel over ~30 min and stirred an additional 2.5 hours at 0° C. The reaction mixture was warmed to room temperature for 2 h, then heated to 45° C. overnight. The solvent was removed in vacuo and the residue redissolved in ~20 mL of 3N NaOH and washed with diethyl ether (2×30 mL). The pH was adjusted to pH 1 with concentrated HCl, then the aqueous solution extracted with ethyl acetate (3×30 mL). The combined extracts were dried over Na2SO4, filtered and evaporated. The resulting residue 26 was used without further purification.

Step 4a

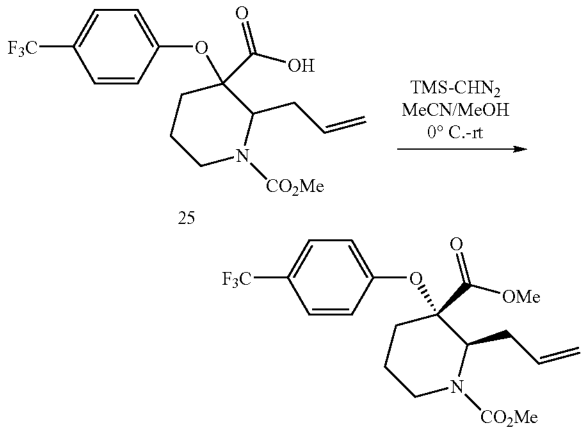

25

27

To 25 (Crude, 1.0 eq, 11.6 mmol, 4.5 g) in 1:1 acetonitrile and methanol (58 mL) at 0° C. was added a solution of trimethylsilyl diazomethane (5 eq, 58 mmol, 29 mL), the reaction mixture was warmed to room temperature, and stirred overnight. The solvent was removed in vacuo, and the crude residue purified by flash silica gel chromatography (5:1→3:1 hexane/ethyl acetate) to give 27 as a racemic mixture of enantiomers in the form of a pale yellow oil (~2.0 g). The enantiomers were separated by chiral HPLC to give the active enantiomer (drawn) of 27 (later-eluting peak, 540 mg). Chiral HPLC:Column: ChiralPak AD-5 cm 20μ; Mobile phase: 90/10 hexane/isopropyl alcohol; Conditions: 40 mL/min, 25° C.

Step 4b

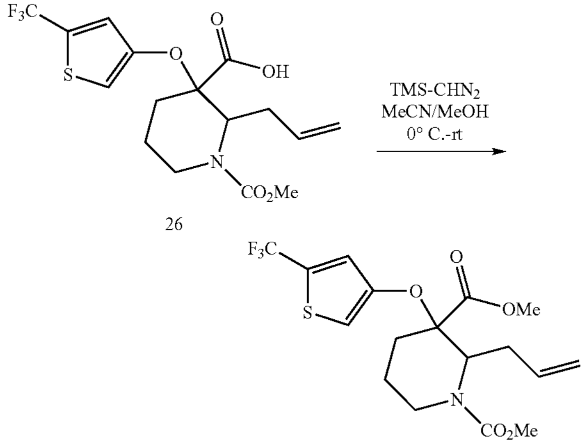

26

28

28 (Mixture of stereoisomers) was prepared from 26 using a similar protocol described in Step 4a To 26 (Crude, 1.0 eq, ~1.69 mmol, ~0.7 g) in 1:1 acetonitrile and methanol (8 mL) at 0° C. was added a solution of trimethylsilyl diazomethane (4 eq, 6.78 mmol, 3.4 mL), the reaction mixture was warmed to room temperature, and stirred 3 h. The solvent was removed in vacuo, and the crude residue purified by flash silica gel chromatography (5:1 to 3:1 hexane/ethyl acetate) to give 28 as a racemic mixture of enantiomers in the form of a pale yellow oil (0.6 g).

Step 5a

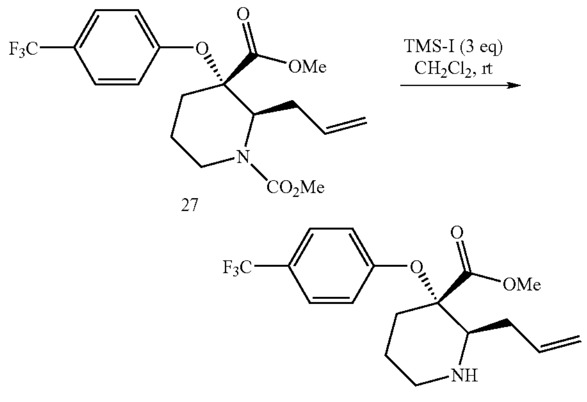

27

29

To 27 (1.0 eq, 0.287 mmol, 115 mg) in anhydrous $CH_2Cl_2$ (2 mL) at room temperature was added a solution of iodotrimethylsilane (3 eq, 0.86 mmol, 122 uL) in $CH_2Cl_2$ (1 mL) and the reaction mixture stirred at room temperature 2 h. The solvent was removed in vacuo, and the crude residue used directly in the following reaction step.

Step 5b

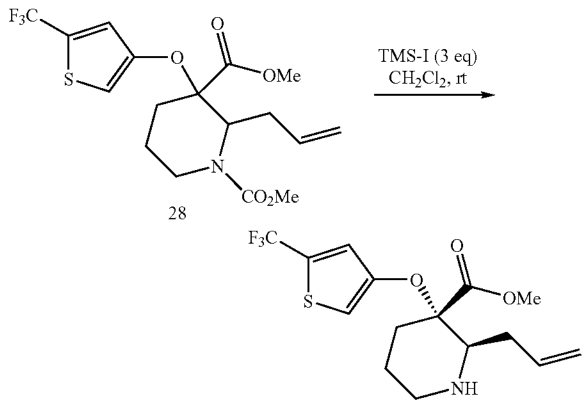

28

30

30 (Active isomers) was prepared from 28 using a similar protocol described in Step 5a, followed by chiral HPLC separation.

To 28 (1.0 eq, 1.24 mmol, 0.5 g) in anhydrous $CH_2Cl_2$ (6 mL) at room temperature was added iodotrimethylsilane (3 eq, 3.7 mmol, 0.52 mL) dropwise (30 sec) and the reaction mixture stirred at room temperature 2 h. The solvent was removed in vacuo, the crude residue dissolved in EtOAc (20 mL) and 1N NaOH (15 mL), extracted with EtOAc (3×20 mL), dried ($Na_2SO_4$), and the solvent was removed in vacuo to give racemic 30 (0.44 g). The racemic material was then separated using chiral HPLC to give the active enantiomer (drawn) of 30 as the earlier-eluting peak (a 0.2 g). Note: the chirality of the active isomer was determined using X-ray crystallography, Chiral HPLC: Column: ChiralPak AD-5 cm 20μ; Mobile phase: 90/10 hexane/isopropyl alcohol; Conditions: 25 mL/min, 25° C.

Step 6:

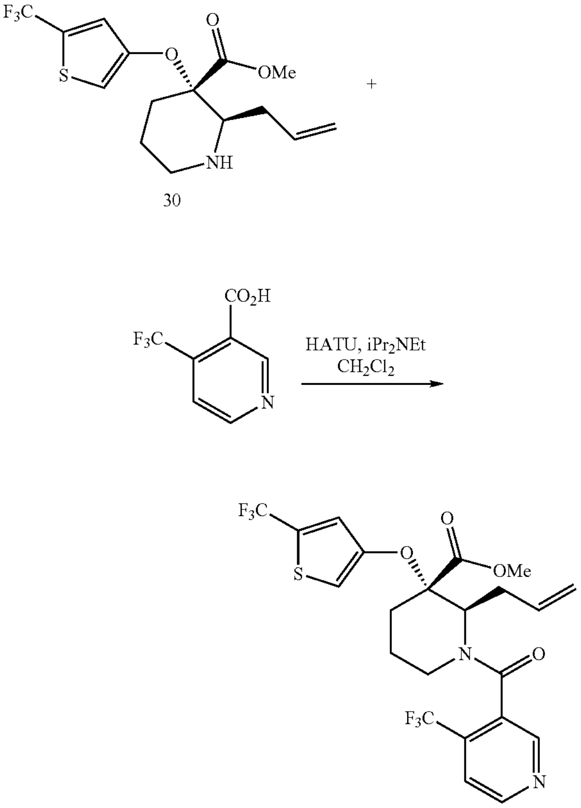

30

31

To a stirring solution of 30 (1.0 eq, 1.97 mmol, 0.68 g) and 4-trifluoromethyl nicotinic acid (1.2 eq, 2.35 mmol, 0.45 g) in $CH_2Cl_2$ (20 mL) at 0° C. was added HATU (1.2 eq, 2.35 mmol, 0.9 g) followed by diisopropylethylamine (5 eq, 9.8 mmol, 1.7 mL). The reaction was warmed to room temperature then heated to 45° C. overnight. The solvent was removed in vacuo and the crude residue purified by flash silica gel chromatography (1:1 hexane/EtOAc) to give 31 as an orange oil (Rf=0.4, 0.9 g).

Step 7:

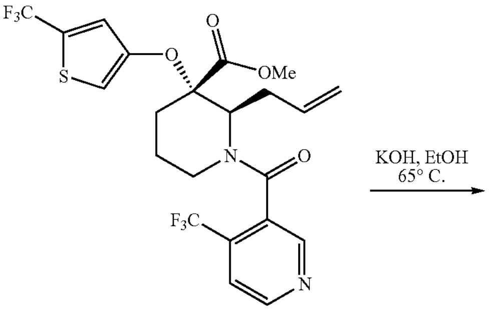

31

-continued

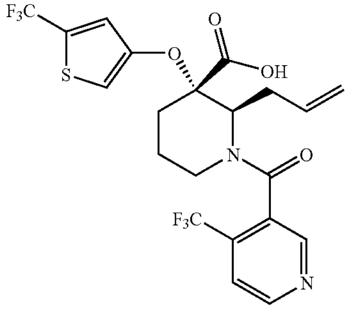

32

To a stirring solution of 31 (1.0 eq, 1.03 mmol, 0.54 g) in ethanol (10 mL) was added KOH pellets (5 eq, 5.15 mmol, 0.29 g) and the mixture heated to 65° C. for 2.5 h. The solvent was removed in vacuo, the crude residue dissolved in water (10 mL) which was acidified to pH 5 with 6N HCl, then extracted with EtOAc (3×20 mL), dried (sodium sulfate), and concentrated in vacuo to give 32 as a pale red solid (0.50 g).

Step 8:

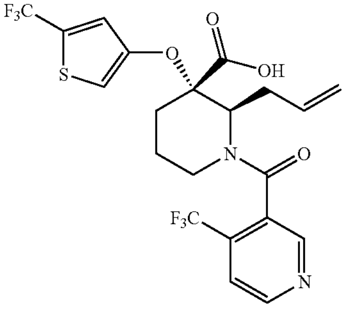

32

+

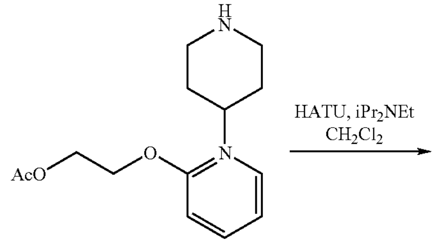

33

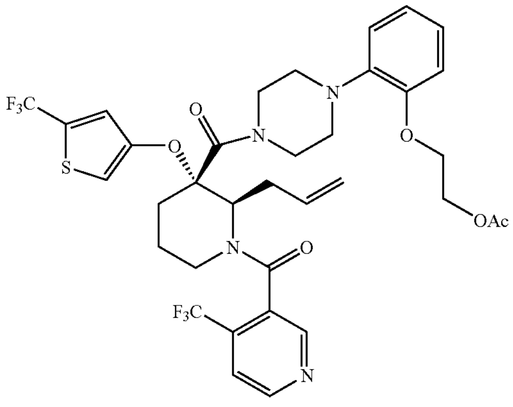

34

To a stirring solution of 32 (1.0 eq, 0.99 mmol, 0.5 g) and 33 (1.2 eq, 1.18 mmol, 0.23 g) in $CH_2Cl_2$ (10 mL) at room temperature was added HATU (1.2 eq, 1.18 mmol, 0.45 g) followed by diisopropylethylamine (5 eq, 4.93 mmol, 0.85 mL). The reaction was heated to 45° C. overnight. The solvent was removed in vacuo and the crude residue purified by flash silica gel chromatography (1:1 hexane/EtOAc) to give 34 (Rf=0.4, 2.96 g).

Note: various amines were used for similar amidation reactions.

Step 9: Alkene Oxidation

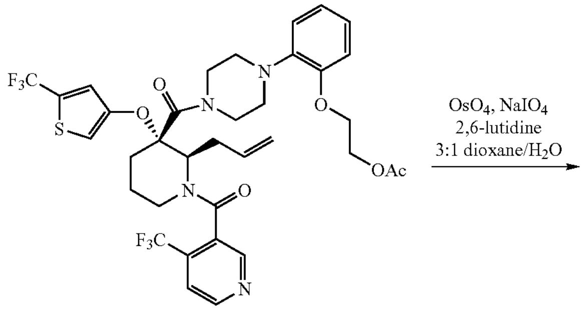

34

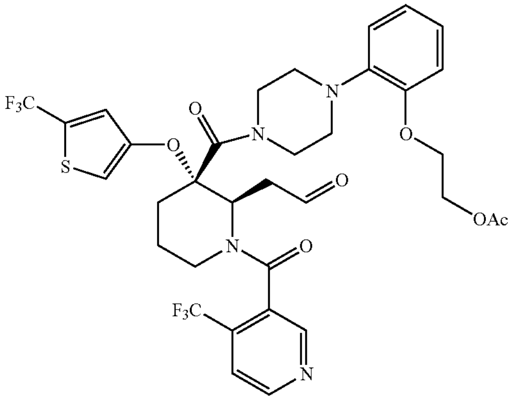

35

To a stirring solution of 34 (1.0 eq, 0.93 mmol, 0.7 g) in 3:1 dioxane/water (10 mL) was added 2,6-lutidine (2 eq, 1.85 mmol, 0.2 mL), Osmium tetroxide solution (0.1 eq, 0.09 mmol, 1.17 mL), then $NaIO_4$ (5 eq, 4.65 mmol, 1.0 g). The reaction mixture was allowed to stir at room temperature 2.5 h then it was diluted with water (15 mL) and extracted with $CH_2Cl_2$ (3×30 mL). The crude material was used without further purification.

Alternatively an ozonolysis-based procedure may also be employed, although the yields were usually lower.

Step 10: Example Reductive Amination

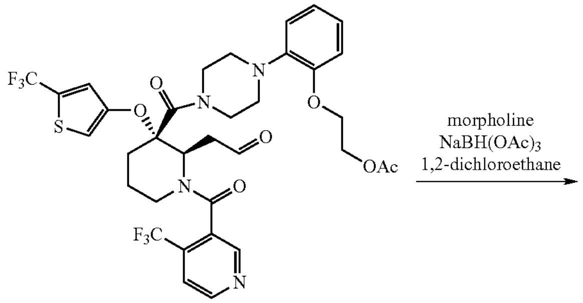

35

-continued

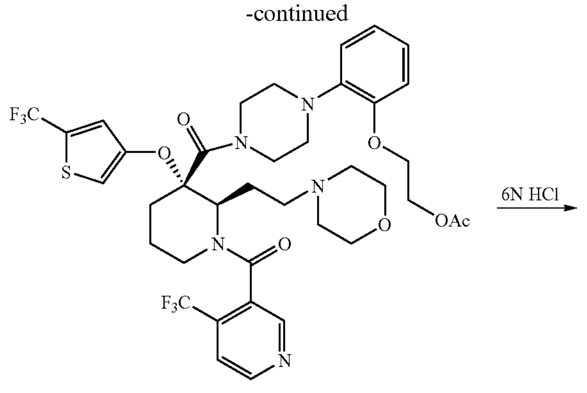

36

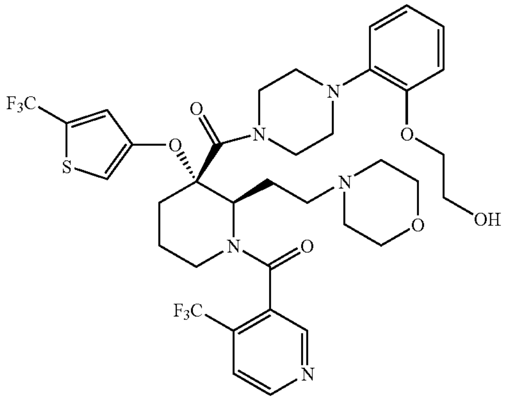

37

To a stirring solution of 35 (1.0 eq, 0.026 mmol, 20 mg) and morpholine (5 eq, 0.132 mmol, 11.5 mg) in 1,2-dichloroethane (1.3 mL) was added $NaBH(OAc)_3$ (5 eq, 0.132 mmol, 28 mg) and the reaction mixture stirred at room temperature overnight. The solvent was removed in vacuo and the crude residue was treated with 6N HCl at 55° C. for 1 h to convert the —OAc to —OH and/or purified by HPLC-MS.

Step 11: Exemplary Route to Arylpiperazine Alkyl Amines

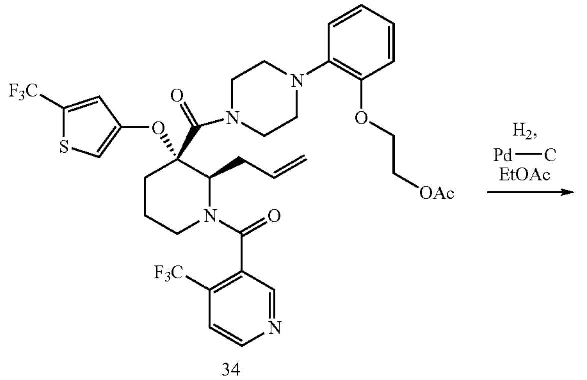

34

-continued

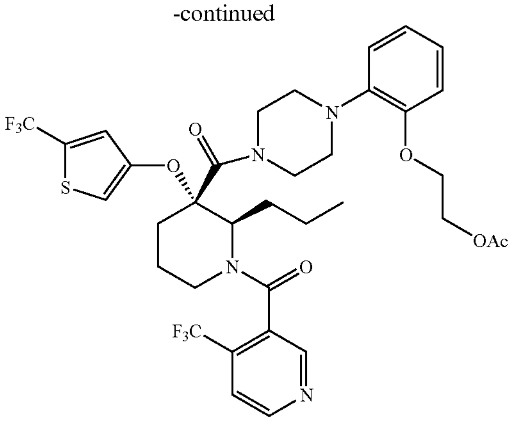

38

To a stirring solution of 34 (1.0 eq, 0.321 mmol, 240 mg) in EtOAc (3 mL) was added Pd—C (10 wt %, 24 mg) and the reaction mixture purged with $H_2$. After stirring at room temperature 2 h, the mixture was filtered through celite and concentrated in vacuo to give 38 (210 mg) which was used without further purification.

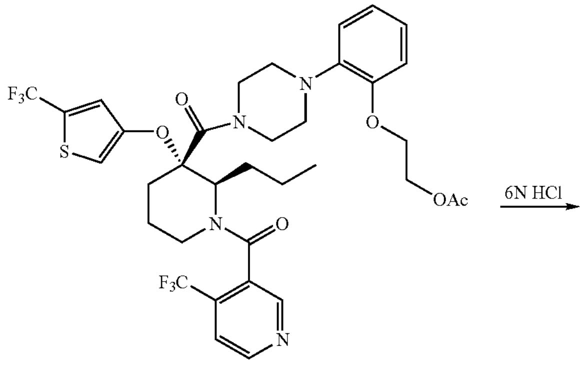

38

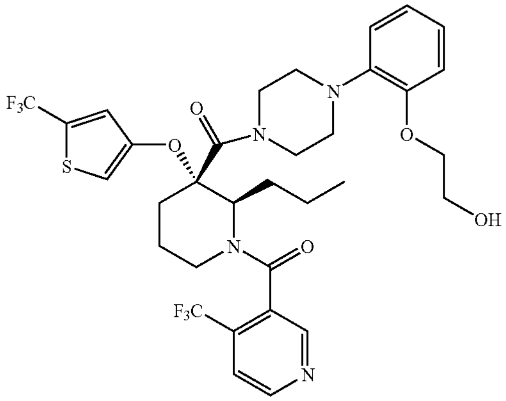

39

A stirring solution of 38 (1.0 eq, 0.159 mmol, 120 mg) in 6N HCl (2 mL) was heated to 90° C. for 1 h then concentrated in vacuo to give crude 39. To the residue in $CH_2Cl_2$ (10 mL) was added solid $K_2CO_3$ (~50 mg) and the mixture sonicated for 5 min. The salts were removed by filtration and the filtrate concentrated in vacuo to give 39 as a pale yellow oil (108 mg). (observed $[M+H]^+$: 715.28)

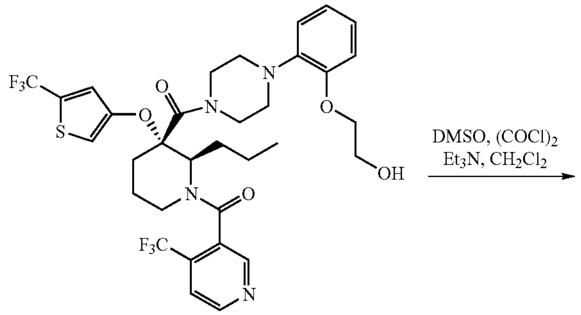

39

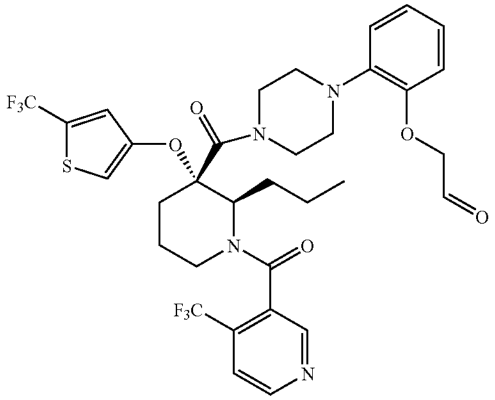

40

To a stirring solution of $(COCl)_2$ (2 eq, 0.302 mmol, 26 uL) in $CH_2Cl_2$ (3 mL) at −78° C. was added DMSO (4 eq, 0.6 mmol, 43 uL) dropwise (~30 sec) and the solution stirred 10 min. A solution of 39 (1 eq, 0.15 mmol, 108 mg) in $CH_2Cl_2$ (3 mL) was then added dropwise (1 min) followed by stirring at 78° C. for 30 min. Then $Et_3N$ (4 eq, 060 mmol, 84 uL) was added, the reaction mixture warmed to 0° C., and stirred an additional 30 min. The reaction mixture was concentrate in vacuo and used without further purification.

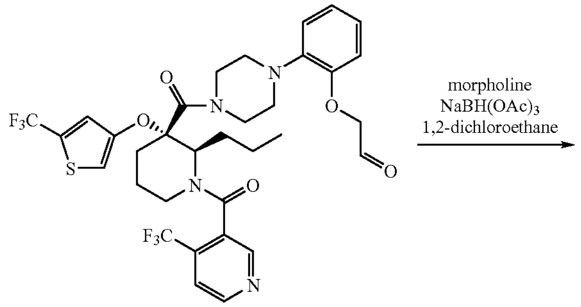

40

-continued

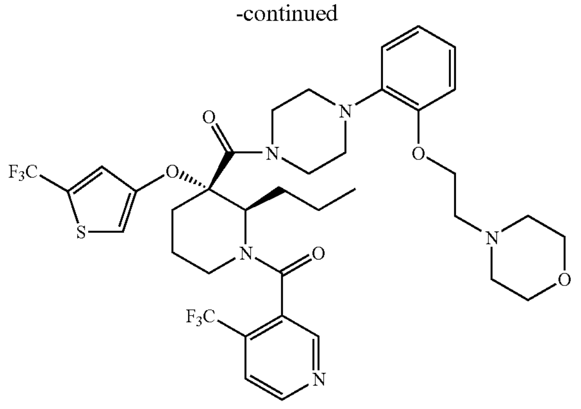

41

To a stirring solution of 40 (1.0 eq, 0.014 mmol, 10 mg) and morpholine (4 eq, 0.056 mmol, 5 mg) in 1,2-dichloroethane/acetic acid (1 mL/1 drop) was added $NaBH(OAc)_3$ (4 eq, 0.056 mmol, 12 mg) and the reaction mixture stirred at room temperature overnight. The solvent was removed in vacuo and the crude residue purified by HPLC-MS to give 41. (observed $[M+H]^+$: 784.46)

Example 4

General Scheme to Prepare ortho-N-Acyl arylpiperazine Related Target Compounds

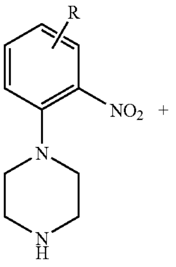

42

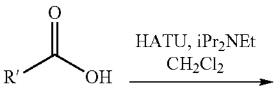

43

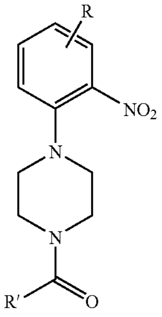

44

To a stirring solution of 42 (1.2) and 43 (1.0 eq) in $CH_2Cl_2$ (0.1 M) and $iPr_2NEt$ (5 eq) was added HATU and the reaction mixture stirred 2-16 h. The mixture was concentrated in vacuo and purified by flash silica gel chromatography to give 44.

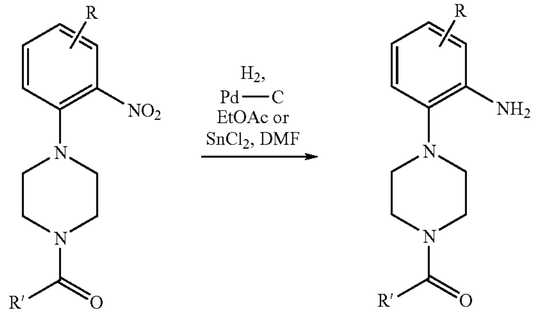

44 45

Method 1: To a stirring solution of 44 (1.0 eq) in ethyl acetate (0.1 M) was added 5% palladium on carbon (20 wt %), the reaction vessel was purged with hydrogen, and stirred under balloon-pressure hydrogen for 2 h. The reaction mixture was filtered through celite and concentrated in vacuo to give 45 which was used without further purification Method 2: To a stirring solution of 44 (1.0 eq) in DMF (0.1 M) was tin (II) chloride (2 eq) and the reaction mixture stirred at room temperature 16. The solvent was removed in vacuo and the crude residue purified by flash silica gel chromatography to give 45.

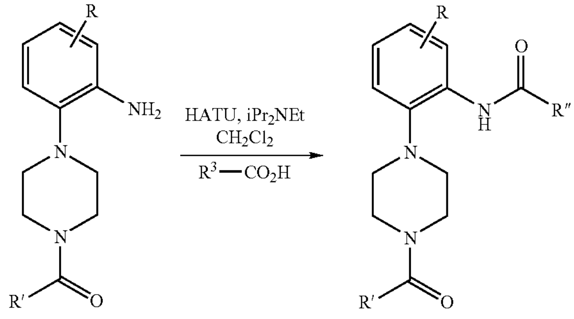

45 46

To a stirring solution of 45 (1.0) and R"-$CO_2H$ (1.0 eq) in $CH_2Cl_2$ (0.1 M) and $iPr_2NEt$ (5 eq) was added HATU and the reaction mixture stirred 2-16 h. The mixture was concentrated in vacuo and purified by flash silica gel chromatography or HPLC-MS to give 46.

Example 5

General Procedures for Preparation Example 54

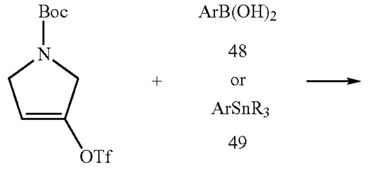

47

-continued

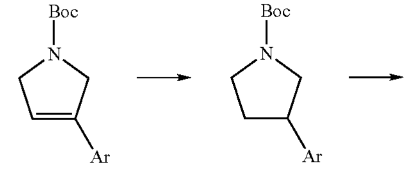

50 51

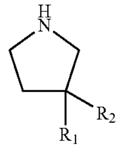

52a, $R_1$ = Ar, $R_2$ = H
52b
52c

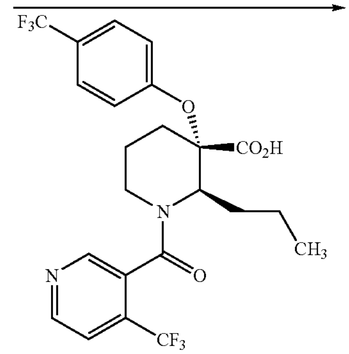

53

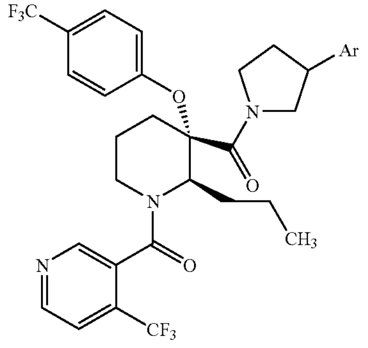

54

1) Suzuki Coupling for Preparation of 3-aryldihydropyrrole (50):

A pyrex tube or a round bottom flask charged with powdered $K_3PO_4$ (2.5 equiv) and $PdCl_2(dppf)$ (0.05 equiv) was evacuated then backfilled with nitrogen (repeated twice). A solution containing triflate 47 (1.0 equiv) and either a commercially available or synthesized boronic acid (or ester) 48 (1.05 equiv) in 5% aqueous 1,4-dioxane (3 mL) was added under nitrogen. The resulting mixture was heated at 55° C. until complete. The reaction was followed by TLC and completion times were typically 1-24 hours. The reaction mixture was allowed to cool to room temperature and the solvent removed in vacuo. The crude residue was diluted with EtOAc (5 mL) then washed with saturated aqueous $NH_4Cl$ (5 mL), saturated aqueous $NaHCO_3$ (5 mL) and brine (5 mL). The organic layer was dried over $MgSO_4$, filtered and the solvent removed in vacuo. The crude product was purified by Combi-flash or flash chromatography (silica gel, hexanes/ethyl acetate) to afford 3-aryldihydropyrrole 50.

2) Stille Coupling for Preparation of 3-Aryldihydropyrrole (50):

A pyrex tube or a round bottom flask charged with KF (3.0 equiv), $PdCl_2(dppf)$ (0.10 equiv) and triflate 47 (1.0 equiv) was evacuated then backfilled with nitrogen (repeated twice). 1,4-Dioxane (4 mL) was added, followed by stannane 49 (2.0 equiv) and the resulting mixture heated at 85° C. until complete. The reaction was followed by TLC and completion times were typically 3-18 hours. The reaction mixture was allowed to cool to room temperature and the solvent was removed in vacuo. The crude residue was diluted with EtOAc (10 mL) and washed with water (5 mL), 10% aqueous citric acid (5 mL), saturated aqueous $NaHCO_3$ (5 mL) and brine (5 mL). The organic layer was dried over $MgSO_4$, filtered and the solvent removed in vacuo. The crude product was purified by Combi-flash or flash chromatography (silica gel, hexanes/ethyl acetate) to afford 3-aryidihydropyrrole 50.

General Procedure for Hydrogenation of 50 to 3-Arylpyrollidine (51):

Compound 50 was taken up in solvent, typically methanol or a mixture of methanol and acetic acid (2:1) then sparged with nitrogen. Then under a bed of nitrogen the catalyst chosen from 5% Pd/C, 10% Pd/C or $PtO_2$ was added in one portion. The atmosphere over the reaction was evacuated and then backfilled with hydrogen (repeated 3 times). This could be accomplished with either a hydrogen balloon or at 50 psi in a Parr shaker. When the reaction was complete the catalyst was removed by filtration and the solvent removed in vacuo to afford 3-arylpyrollidine 51 which was carried forward without further purification or, if needed, purified by Combi-flash or flash chromatography (silica gel, hexanes/ethyl acetate).

General Procedure for Deprotection of 51 to Pyrrolidine (52):

A solution of 51 in DCM (0.5 mL) was cooled to 0° C. and a mixture of TFA/DCM (1:1, 1.0 mL) or 4 M HCl in 1,4-dioxane (0.5 mL) was added. The reaction mixture was allowed to warm to room temperature then stirred for 30 to 60 min. The solvent was removed in vacuo and the residue dissolved in DCM or toluene (5 mL) and the solvent removed in vacuo (repeated 2-3 times) to afford pyrrolidine 52 which was carried forward without further purification.

General Procedure for Coupling of Acid 53 to Pyrrolidine 52 Providing Example 54:

4-Methylmorpholine (5.0 equiv) was added to carboxylic acid 53 (1.0 equiv), HATU (1.2 equiv) and either 3-arylpyrrolidine 52a, a commercially available pyrrolidine building block 52b, or a synthesized pyrrolidine building block 52c (1.0-2.0 equiv) and in DMF (0.4-0.6 mL). The resulting solution was stirred overnight at room temperature under $N_2$. The solvent was removed in vacuo. The residue was dissolved in EtOAc (5 mL) and washed with saturated aqueous $NH_4Cl$ (5 mL), saturated aqueous $NaHCO_3$ (5 mL) and brine (5 mL). The organic layer was dried over $MgSO_4$, filtered, and the solvent removed in vacuo. The crude product was purified by C18 preparative HPLC and freeze-dried from water/acetonitrile (1:1, 2 mL) and 2N HCl (0.2 mL) to afford 54.

Modification on Example 55

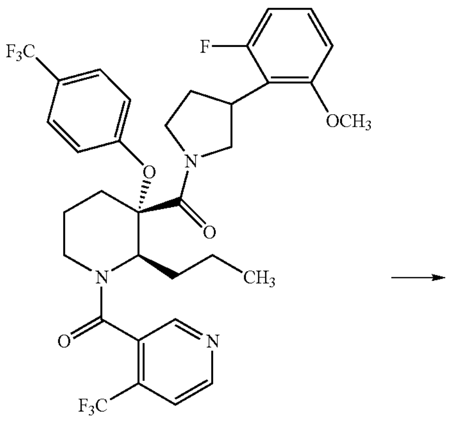

55

-continued

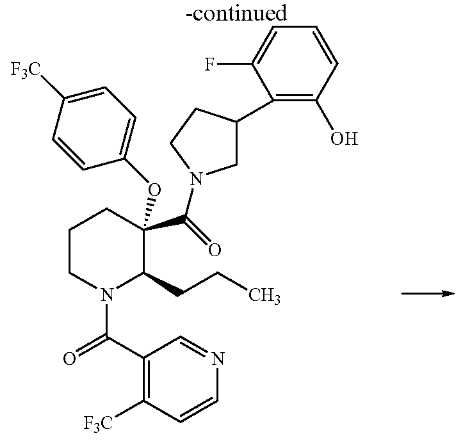

56

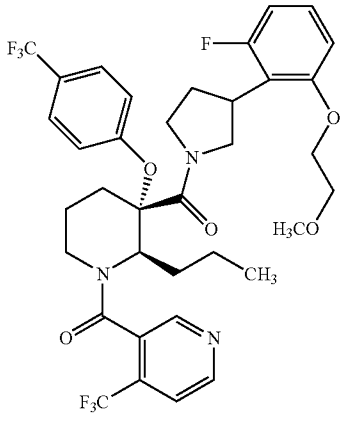

57

Preparation of compound 56: Sodiumthioethoxide (165 mg, 1.96 mmol) was added in one portion to 55 (134 mg, 0.20 mmol) in DMF (4.0 mL) and the resulting suspension was heated at reflux. After 3.5 h the reaction mixture was allowed to cool to room temperature, additional sodiumthioethoxide (99 mg, 1.18 mmol) was added and the reaction mixture was heated at reflux again. After 1 h the reaction mixture was allowed to cool to room temperature, poured into saturated aqueous $NH_4Cl$ (20 mL) and extracted with ethyl acetate (3×20 mL). The combined organic layers were washed with brine (20 mL) then dried over $Na_2SO_4$, filtered and evaporated to dryness. The crude residue was purified by C18 preparative HPLC and freeze-dried from water/acetonitrile (1:1, 2.0 mL) and 2N HCl (0.2 mL) to afford 48 mg (37% yield) of 56 as an off-white solid: MS (ESI) m/z 668 $[C_{33}H_{32}F_7N_3O_4+H]^+$.

Preparation of compound 57: To a suspension of 56 (16 mg, 0.024 mmol) and $Cs_2CO_3$ (12 mg, 0.037 mmol) in DMF (0.4 mL) was added 2-bromoethyl methyl ether. The reaction mixture was stirred at room temperature overnight then poured into saturated aqueous $NH_4Cl$ (10 mL) and extracted with ethyl acetate (3x5 mL). The combined organic layers were washed with brine (10 mL) dried over $Na_2SO_4$, filtered and evaporated to dryness. The crude residue was purified by C18 preparative HPLC and freeze-dried from water/acetonitrile (1:1, 2.0 mL) and 2N HCl (0.2 mL) to afford 8 mg (47% yield) of 57 as a white solid.

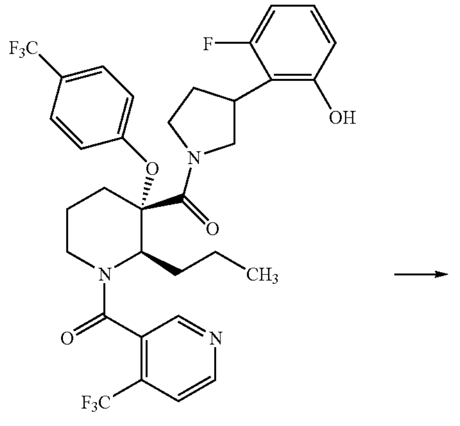

56

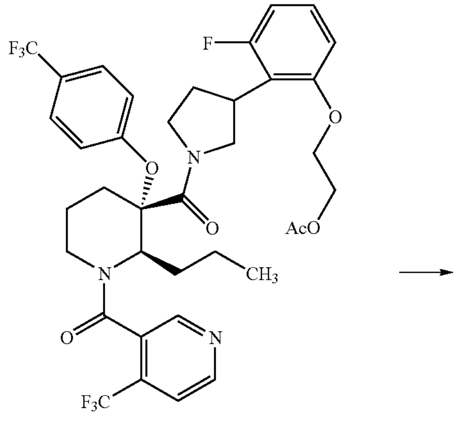

58

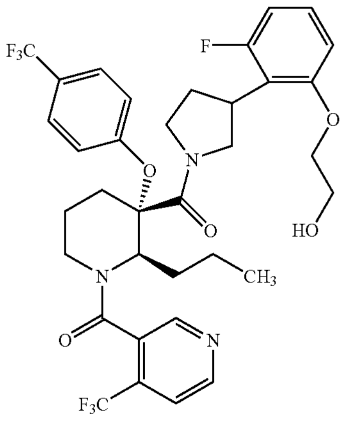

59

Preparation of compound 58: To a suspension of 56 (48 mg, 0.072 mmol) and $Cs_2CO_3$ (35 mg, 0.107 mmol) in DMF (1.0 mL) was added 2-bromoethyl acetate and the reaction mixture was stirred at room temperature under nitrogen. After 4 h the reaction mixture was poured into saturated aqueous $NH_4Cl$ (20 mL) and extracted with ethyl acetate (3×15 mL). The combined organic layers were washed with brine (20 mL) and dried over $Na_2SO_4$, filtered and evaporated to dryness. The crude residue was purified by C18 preparative HPLC and freeze-dried from water/acetonitrile (1:1, 2.0 mL) and 2N HCl (0.2 mL) to afford 32 my (59% yield) of 58 as a white solid: MS (ESI) m/z 754 $[C_{37}H_{38}F_7N_3O_6+H]^+$.

Preparation of Compound 59:

59 was prepared from 58 in a similar manner as described in the EXAMPLE 3, where 39 was made from 38.

Example 6

Compound Example 60

60

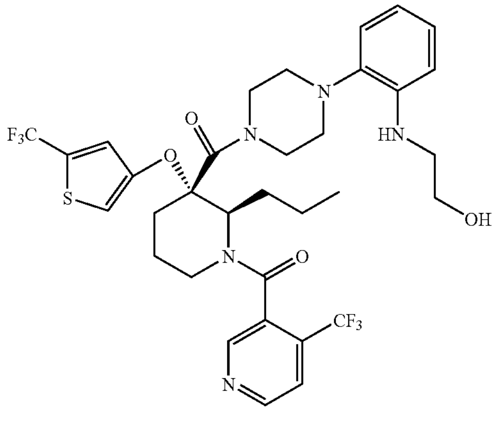

Step 1:

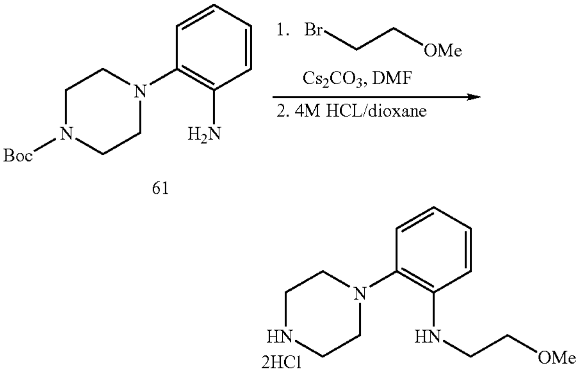

61

62

To the amine 61 (163 mg, 1 equiv.) dissolved in DMF (3 ml) added the cesium carbonate (3 equiv.) and the bromoethyl methyl ether (1.2 equiv.) and heated at 65° C. overnight. If starting material remained, additional bromide and tetra n-butyl ammonium iodide were added and the reaction mixture refluxed (2 days). The mixture was diluted with water, extracted with ethyl acetate, washed with brine (50 mL×3), dried over sodium sulfate, and concentrated in vacuo. The crude product was purified via flash column chromatography (Analogyx, 10-80% ethyl acetate-hexane) to afford the Boc-protected precursor of 62 as a pale yellow oil (30 mg, 16%) with 68% of starting material recovered. The Boc-protected compound was dissolved in 4M HCL/Dioxane (5 mL) and stirred for 30 min at room temperature. The solvent was removed in vacuo to give 62 which was used without further purification.

Step 2:

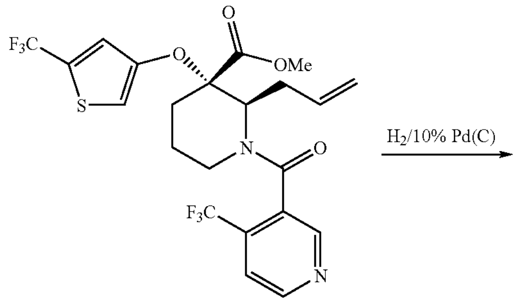

31

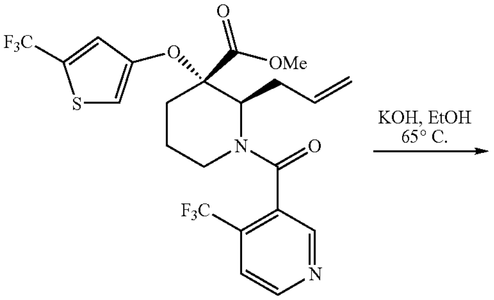

63

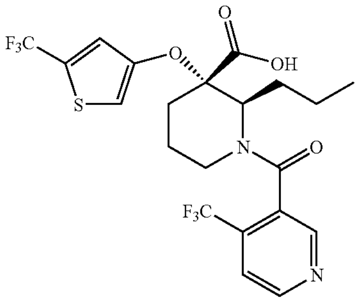

64

Acid 64 was prepared through hydrogenation of 31, followed by the hydrolysis of methyl ester 63. Similar reaction conditions have been used as described in the EXAMPLE 3, where 38 was prepared from 34 and 32 was prepared from 31 respectively.

65

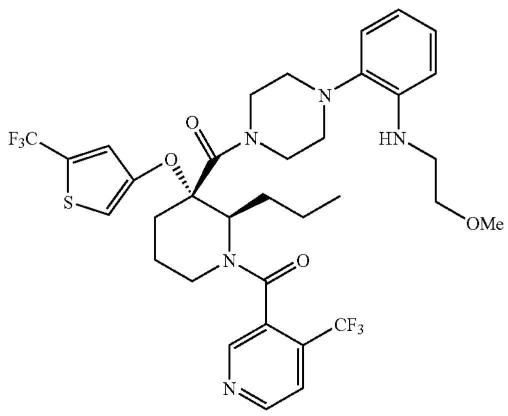

-continued

60

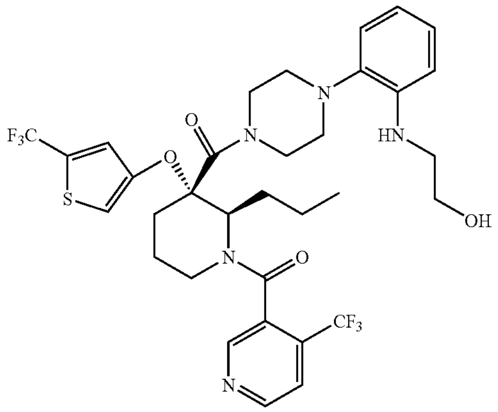

Compound 62 was used in a coupling reaction with intermediate 64 to yield compound 65. Compound 60 was generated from compound 65 according the general procedure used in the present invention.

Compound Example 66

66

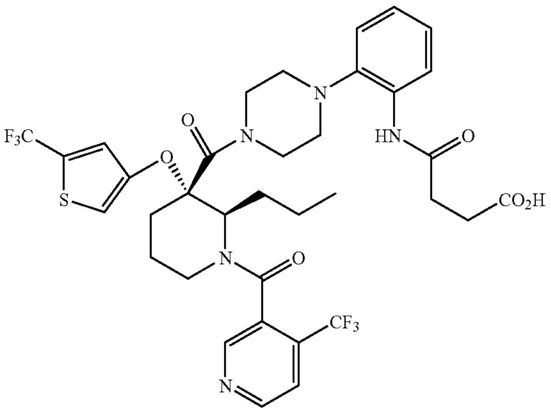

Step 1:

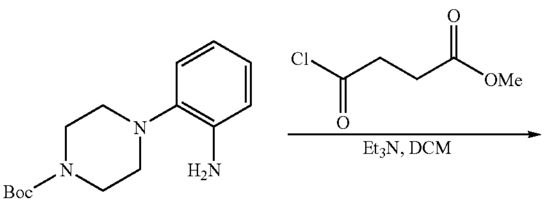

61

-continued

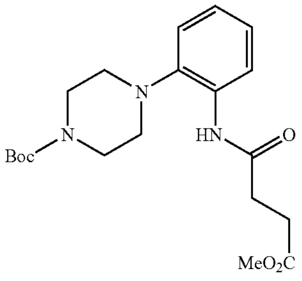

67

To the amine 61 (250 mg, 1 equiv.) was added the acid chloride, (2 equiv, 0.220 ml) and Et3N, (3 equiv, 0.476 ml) in 10 mL DCM and the reaction mixture stirred overnight. The mixture was diluted with ethyl acetate, washed with brine, dried over sodium sulfate, and concentrated in vacuo. The crude product was purified via flash column chromatography (10-40% ethyl acetate-hexane) to afford 300 mg of 67 (85%) as a yellow oil.

68

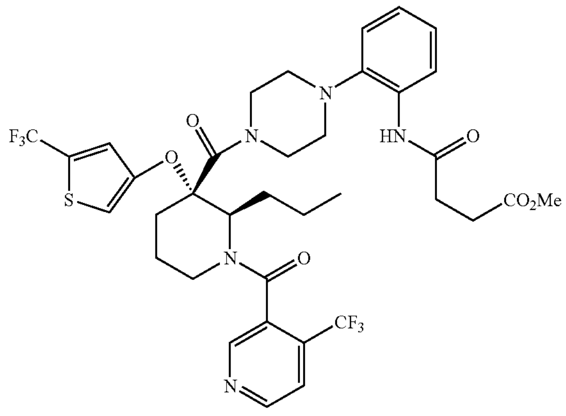

66

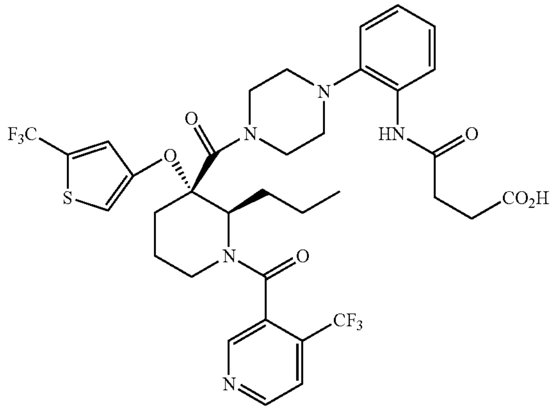

To compound 67 (50 mg, 1 equiv.) was added a solution of HCl in dioxane (4.0 M, 5 ml) at room temperature with stirring. After 30 minutes the reaction mixture was concentrated to dryness to give the deprotected form of piperazine 67. The crude product (white solid) was used as it is for the coupling with intermediate 64 to yield compound 68. Compound 66 was generated from compound 68 according the general procedure used in the present invention.

Compound Example 69

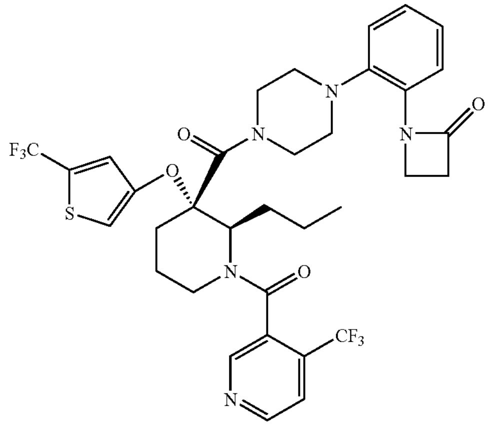

69

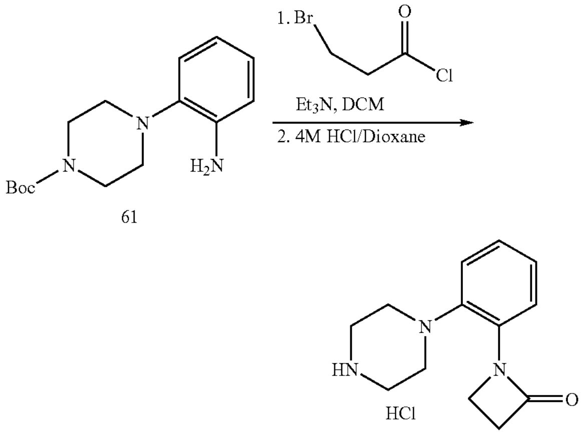

61

70

Intermediate 70, used in the preparation of inhibitors 69 was synthesized according the procedure described for the preparation of 67. The crude product (white solid) was used as it is for the coupling with intermediate 64 to yield compound 69.

Compound Examples 71, 72

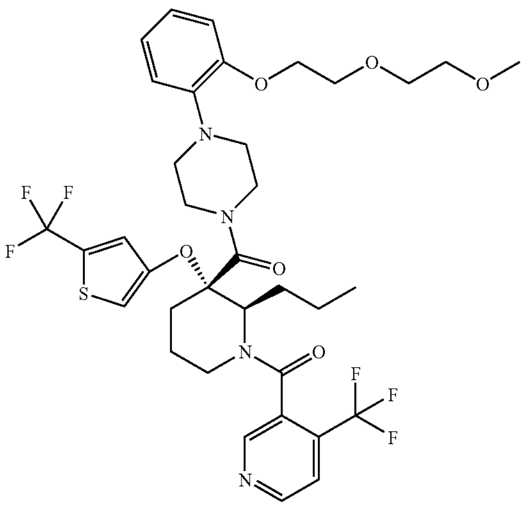

71

-continued

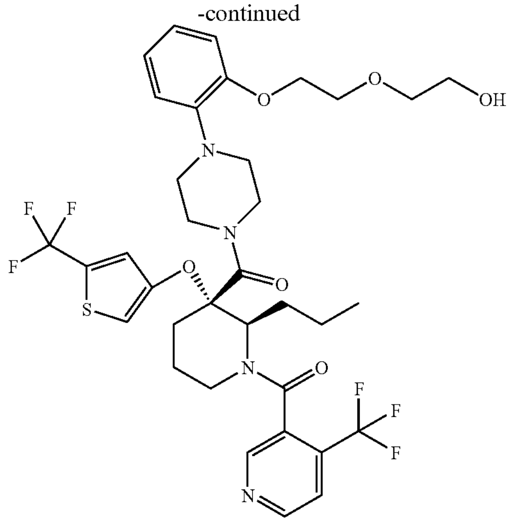

72

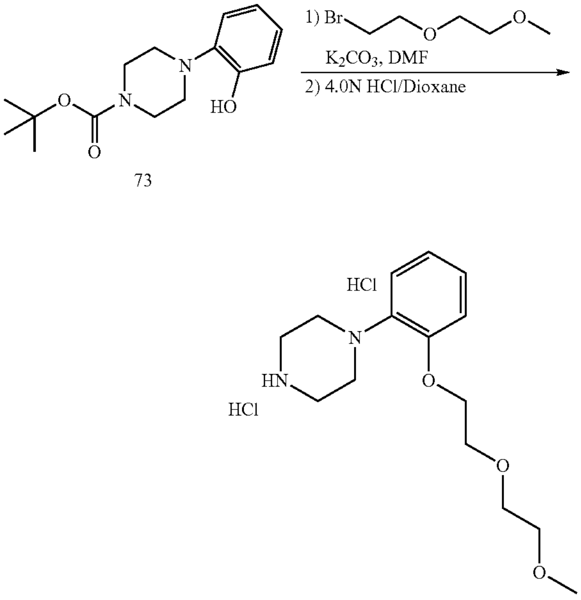

73

74

Step 1:

To a solution of commercially available Boc-piperazine 73 (10 mmol, 2.8 g) in DMF (40 mL) at room temperature was added $K_2CO_3$ (2 equiv, 20 mmol, 2.8 g), followed by 1.5 equiv of Bromo-2-(2-methoxyethoxy)ethane (15 mmol, 2.75 g). Reaction was stirred at 85° C. for 3 days. Reaction was diluted with ethyl acetate and washed with water and brine. Organic layer was dried over $MgSO_4$, filtered and concentrated down.

Step 2:

HCl in dioxane (4.0N, 100 mL) was added to the above residue and reaction mixture was stirred for 2 hours before it was concentrated to dryness to provide 74 as a light yellow solid. Compound 74 was used in a coupling reaction with intermediate 64 to yield compound 71. Compound 72 was generated from compound 71 according the general procedure used in the present invention.

Compound Example 75

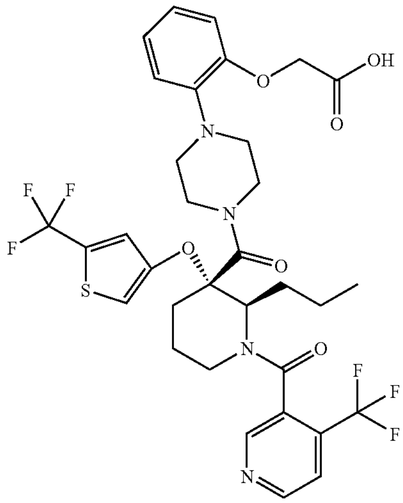

75

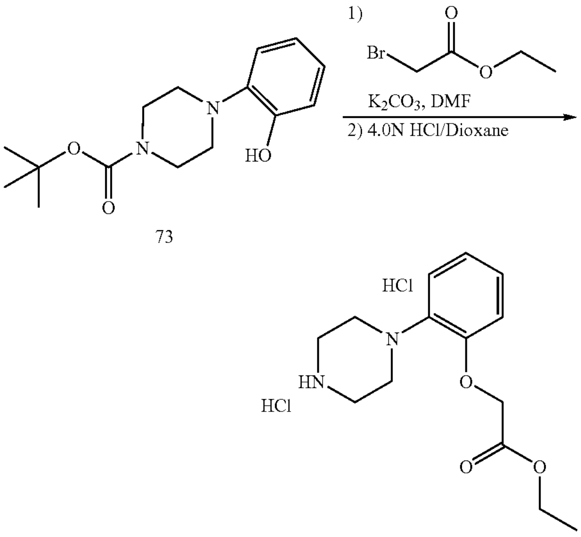

73

76

Step 1:

Intermediate 76 was prepared following the same procedure as describe in Compound example 71, replacing in step 1, Bromo-2-(2-methoxyethoxy)ethane with ethyl bromoacetate.

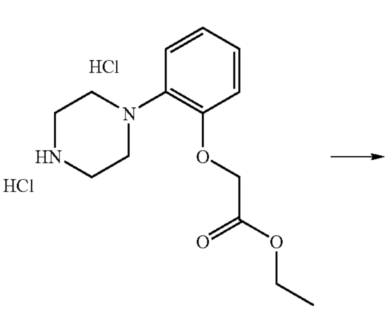

76

-continued

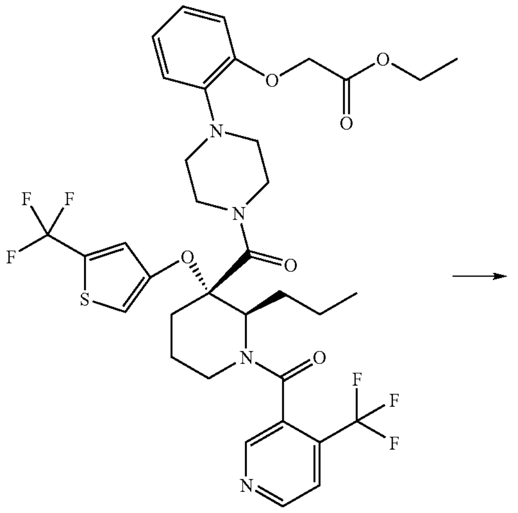

77

75

-continued

79

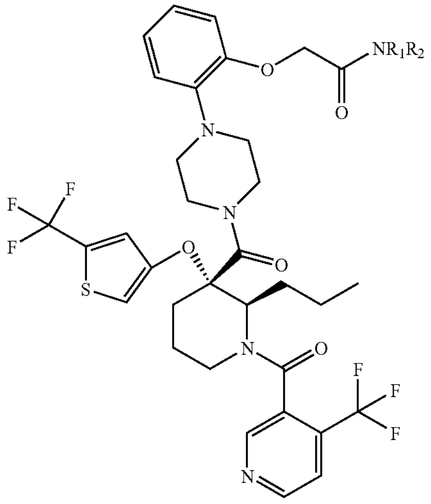

Step 2:

Compound 76 was used in a coupling reaction with intermediate 64 to yield compound 77 according the general procedure used in the present invention. To 77 (49 mg, 0.065 mmol) in 1 mL of THF was added 1M LiOH (0.19 mL, 0.19 nm mmol, 3 equiv) at 0° C. The reaction was stirred at room temperature for 18 hours then concentrated to dryness and diluted with water. The aqueous solution was washed with Et2O, acidified using 1M HCl to pH~4, and extracted it with 20 mL of EtOAc×2. The combined organic layers were washed with 20 mL of brine dried over $MgSO_4$ filtered and concentrated in vacuo to give 75 (47 mg, 100%).

Compound Examples 78, 79

78

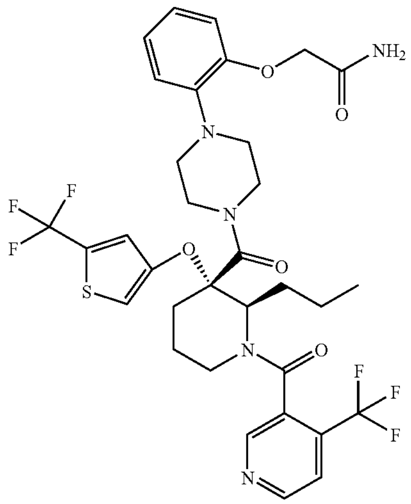

To compound 75 (22 mg, 0.028 mmol) in DCM/DMF was added $NH_4Cl$ (12 mg, 0.22 mmol, 8 eq.), HATU (13 mg, 0.034 mmol, 1.2 eq.) and DIPEA (0.036 mL, 0.22 mmol, 8 eq.) at RT. The mixture was stirred at room temperature for 18 hours then diluted with EtOAc and washed with sat. NH4Cl, sat. $NaHCO_3$ and brine. Organic layers was dried over MgSO4, filtered and concentrated in vacuo. The residue was purified by reverse phase HPLC to give 78 (15 mg, 68%).

The compounds 79 were prepared in a similar manner by replacing NH4Cl with various substituted amines during the coupling step.

Compound Example 80

80

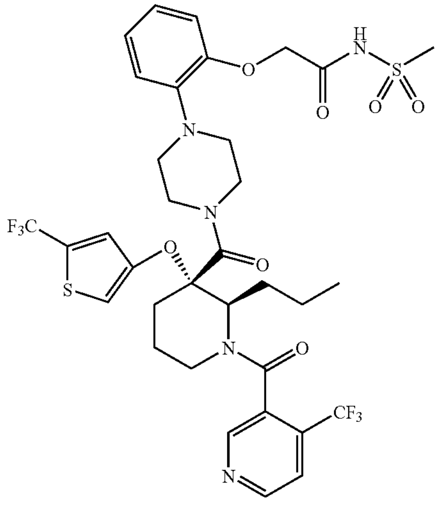

Step 1:

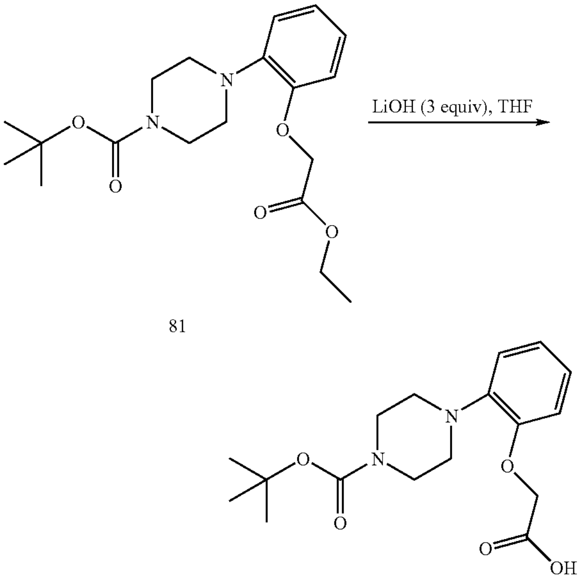

81

82

To a solution of ester 81 (precursor of 76, 0.8 g, 2.2 mmol) in THF (5 mL) was added LiOH (1.0M, 3 equiv, 6.6 mL) at r.t. Reaction was stirred a r.t. until completion (MS analysis, 2 hours). The pH was adjusted to 4.5 with 1.0N HCl and reaction mixture was extracted with EtOAc. Organic layer was dried over MgSO4, filtered and concentrated to dryness to provide 0.6 g of acid 82.

Step 2:

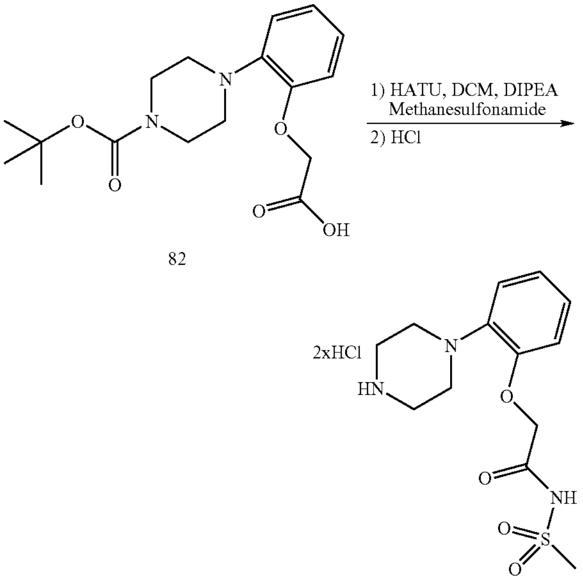

82

83

To a DCM solution of acid 82 (150 mg, 0.44 mmol) was added HATU (1.1 equiv, 0.5 mmol, 190 mg) and methanesulfonamide (1.1 equiv, 0.5 mmol, 50 mg). Reaction was stirred at r.t. overnight then diluted with EtOAc and washed with NaHCO3, NH4Cl and brine. Organic layer was dried over MgSO4, filtered and concentrated to dryness. The crude material was purified by HPFC using 5% MeOH in DCM to provide the desired acylsulfonamide in 75% isolated yield.

Step 3:

To the acyclsulfonamide was added 5 mL of 4.0N HCl in dioxane. The reaction mixture was stirred for 2 hours at RT before it was concentrated in vacuo to provide 83 (127 mg) as a light yellow solid. Compound 83 was used in a coupling reaction with intermediate 64 to yield compound 80 according the general procedure used in the present invention.

Other substituted acylsulfonamides were prepared following the same procedure by replacing methanesulfonamide in step 2 with other substituted sulfonamides.

Compound Example 84

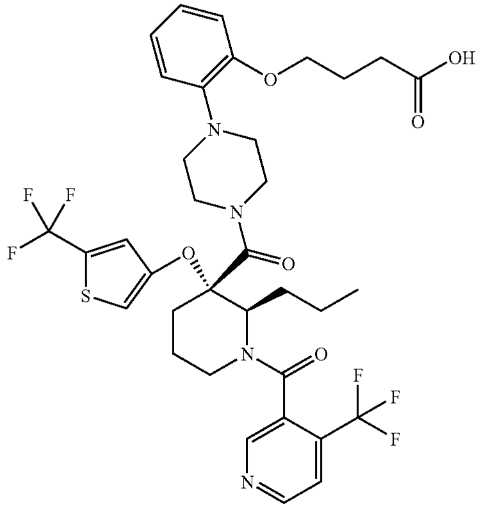

84

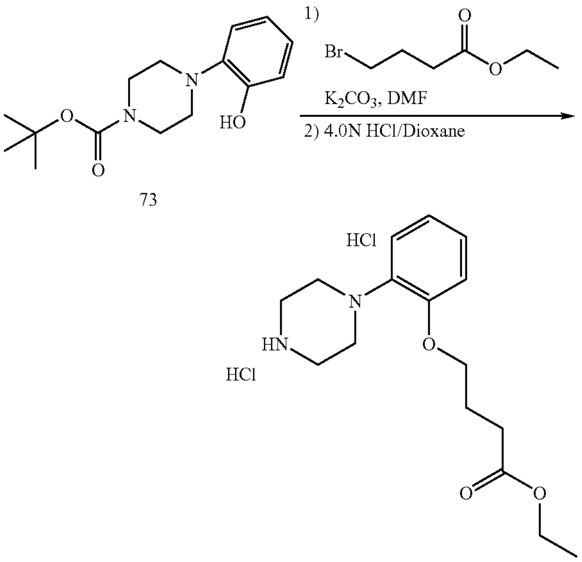

73

85

Step 1:

Intermediate 85 was prepared following the same procedure as described in Compound example 75, by replacing ethyl bromoacetate in step 1, with ethyl bromopropionate.

Step 2:

Compound 84 was prepared following the same procedure as described in Compound example 75, by replacing intermediate 76 in step 2, with intermediate 85.

Compound Examples 86, 87

86

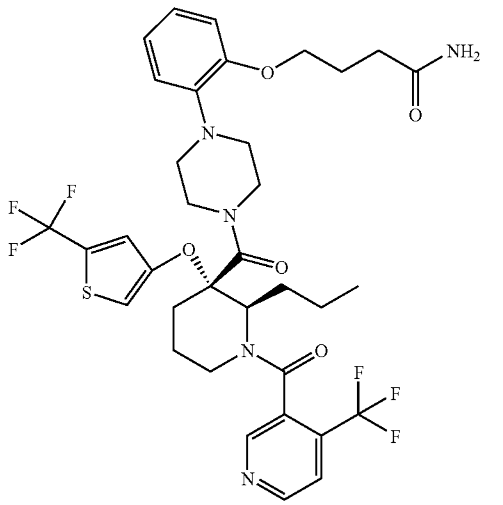

87

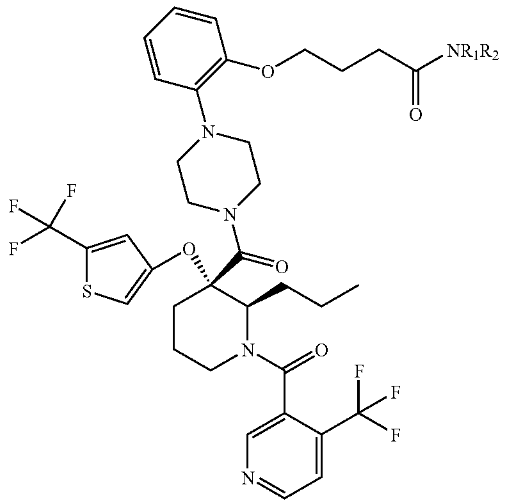

Compounds 86, 87 were prepared following the similar reaction procedures as described in Compound examples 78, 79.

Compound Example 88

88

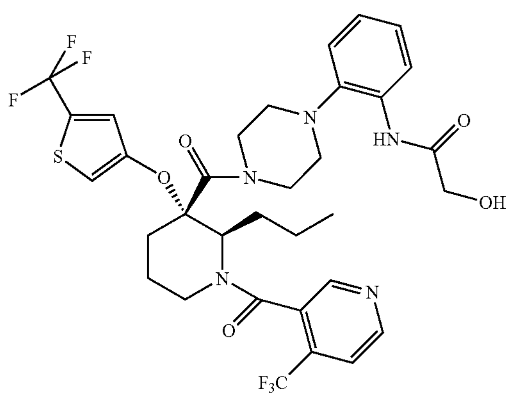

Step 1:

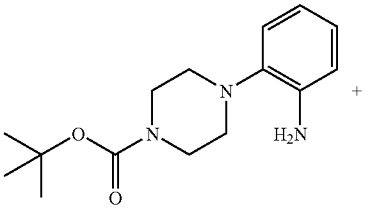

61

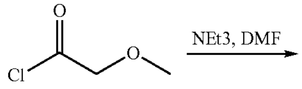

89

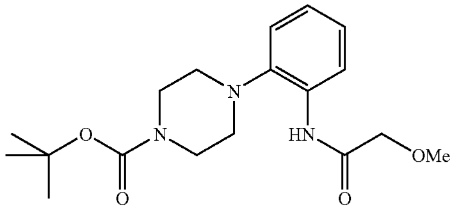

90

To 4-Boc-1-(2-aniline)-piperazine 61 (1 eq., 100 mg, 0.36 mmol) in DMF (7 mL) at 0° C. was added methoxyacetyl chloride 89 (1.5 eq., 58 mg, 0.54 mmol) and triethylamine (3 eq., 153 uL, 1.08 mmol). The reaction mixture was allowed to warm to room temperature and then heated to 36 C overnight. The reaction mixture was diluted with ethyl acetate and water. The phases were separated and the organic phase was washed 3 times with water, twice with saturated sodium bicarbonate solution, and once with brine. The organic phase was then dried over sodium sulfate and concentrated in vacuo to a yellow oil (190 mg). The product was then purified using an RS-4 silica gel column with a gradient of ethyl acetate/hexane from 0-50%. The compound eluted at approximately 20% ethyl acetate/hexane. The product 90 was a clear oil (86 mg, 0.25 mmol, 68%).

Step 2:

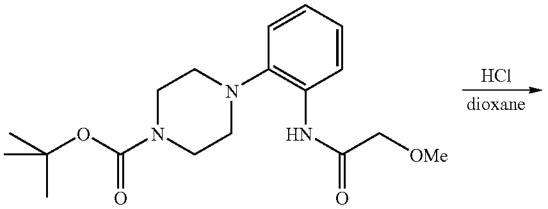

90

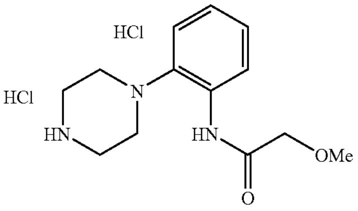

91

To compound 90, (1 eq., 86 mg, 0.25 mmol), was added a solution of HCl in dioxane (4.0 M, 6 mL, 24 mmol) at room temperature with stirring. After 30 minutes the reaction mixture was concentrated to dryness. The product 91 was a yellow solid (80 mg, 100% crude yield).

Step 3:
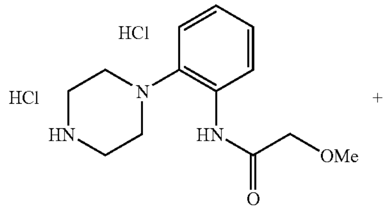
91
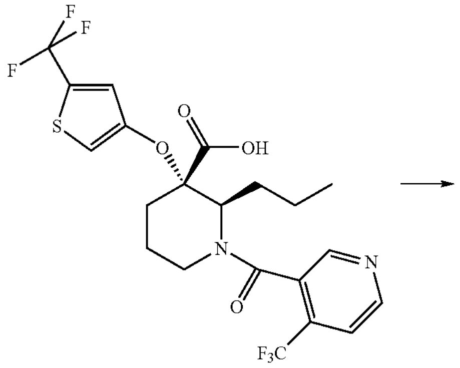
64
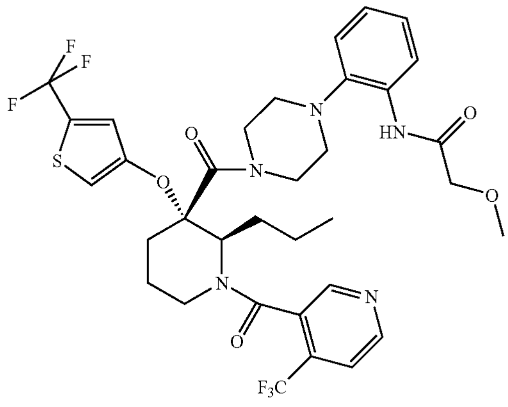
92
Compound 92 was prepared according to the general amide formation conditions as described in this invention (LCMS: M+H$^+$: 742.4, retention time: 5.12 min).
Step 4:
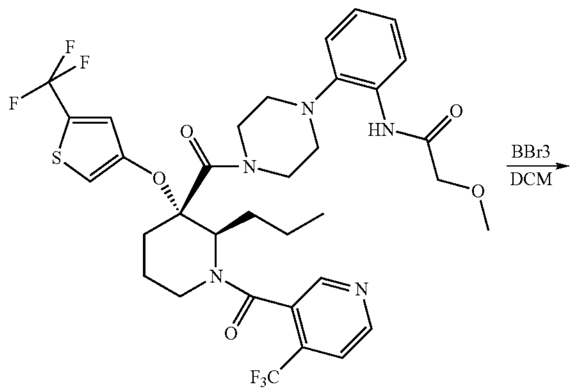
92
-continued
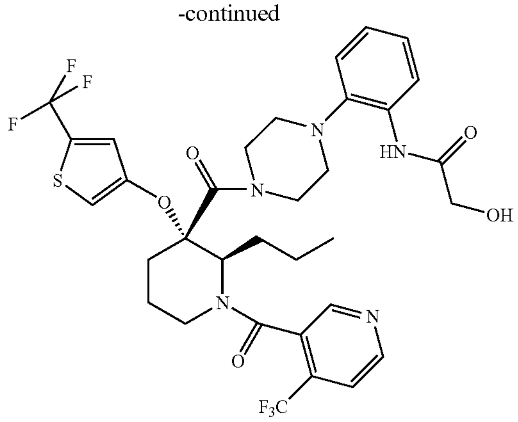
88
Compound 88 was prepared by the treatment of 92 with BBr3 (LCMS: M+H$^+$: 728.4, retention time: 4.65 min).
Compound Examples 93, 94
93
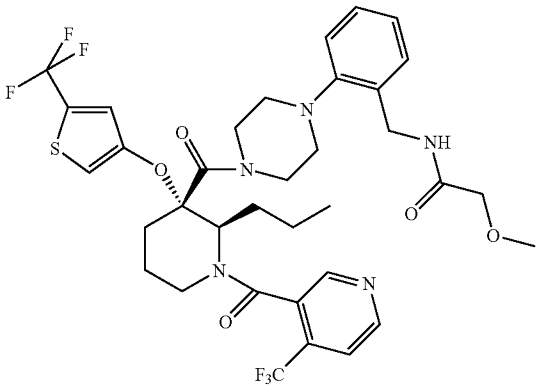
94
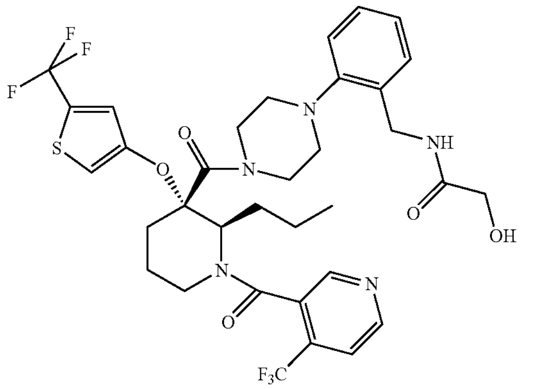

Compound 93, 94 were prepared in a similar manner where compounds 90 and 88 were synthesized (93, LCMS: $M+H^+$: 756.4, retention time: 4.66 min; 94, LCMS $M+H^+$: 742.4, retention time: 4.25 min).

Compound Example 95

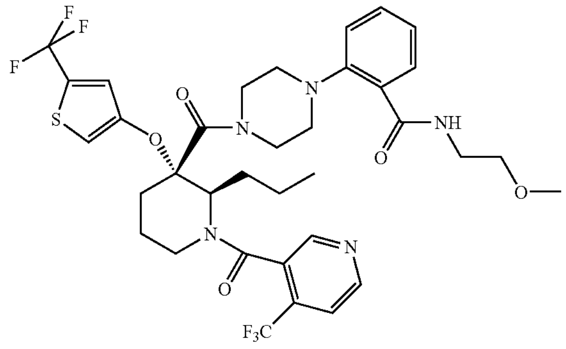

95

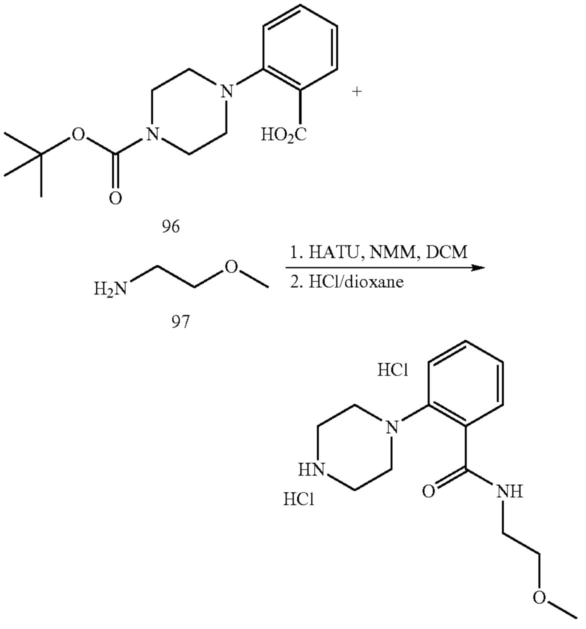

96

97

98

To 4-Boc-1-(2-benzoic acid)-piperazine 96 (1 eq., 100 mg, 0.33 mmol), in DCM (5 mL) was added methoxyethylamine 97 (1.5 eq., 43 uL, 0.50 mmol), HATU, (1.5 eq., 190 mg, 0.50 mmol), and N-methylmorpholine (5 eq., 1.66 mmol, 180 uL). The reaction was stirred overnight under nitrogen and was then diluted with ethyl acetate and water. The organic phase was extracted and washed with saturated sodium bicarbonate solution and brine. The product was dried over sodium sulfate and concentrated. The product was then purified using an RS-12 silica gel column with a gradient of ethyl acetate/hexane from 0-50%. The compound was then treated with a solution of HCl in dioxane as described in the step 2 of Compound example 88 to give compound 98.

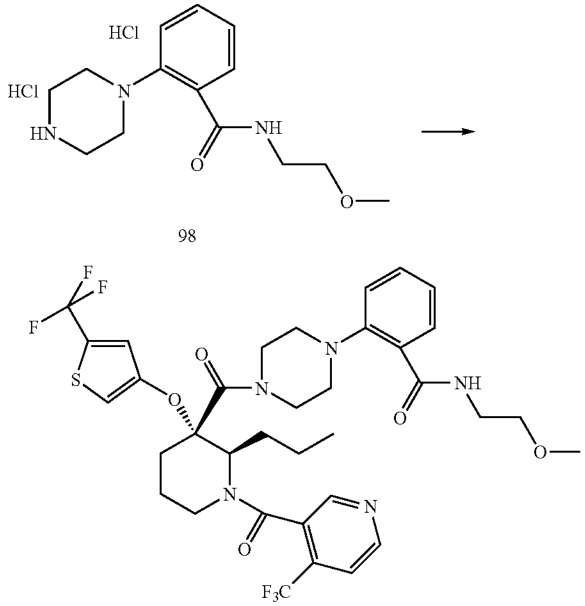

98

95

Compound 95 was prepared according to the general amide formation conditions as described in this invention (LCMS: $M+H^+$: 756.4, retention time: 4.78 min).

Compound Example 99

99

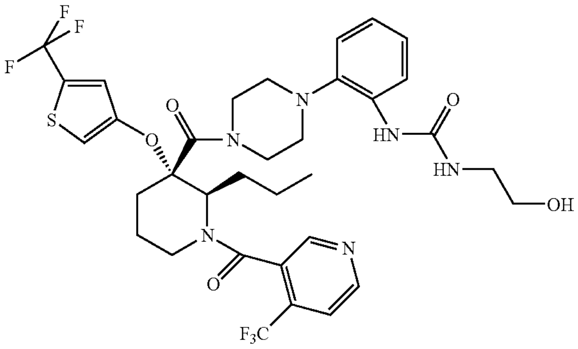

Step 1:

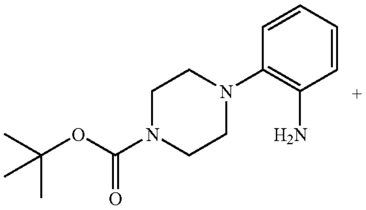

61

-continued

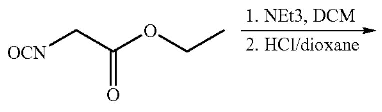

100

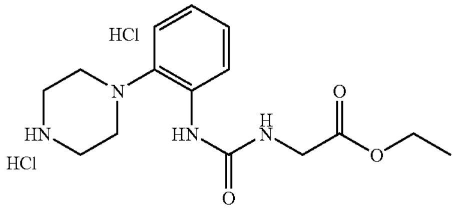

101

To 4-Boc-1-(2-aniline)-piperazine 61 (1 eq., 200 mg, 0.72 mmol) in DCM (5 mL) was added ethyl isocyanatoacetate 100 (1.5 eq., 1.08 mmol, 123 uL) and triethylamine (6 eq., 4.32 mmol, 470 uL). The reaction was allowed to stir at room temperature under nitrogen overnight and was then diluted with ethyl acetate and saturated sodium bicarbonate solution. The organic phase was washed with brine, dried over sodium sulfate and concentrated. The product was purified using an RS-12 silica gel column and a gradient of ethyl acetate/hexanes from 0-40%. The product was then treated with a solution of HCl in dioxane as described previously in step 2 of Compound example 88 to give 101.

Step 2:

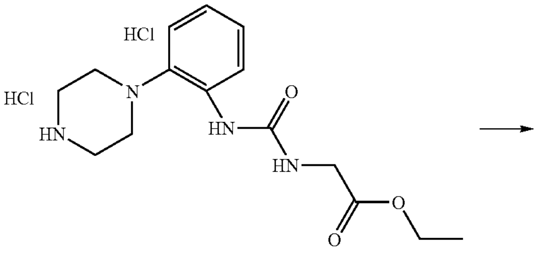

101

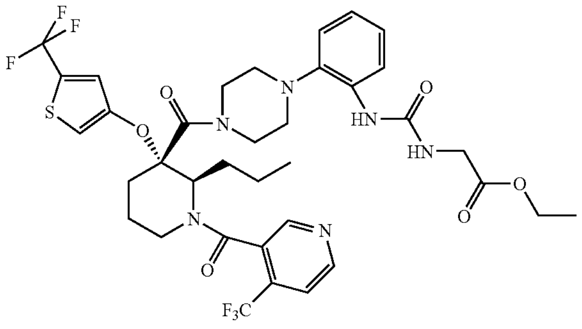

102

Compound 102 was prepared according to the general amide formation conditions as described in this invention (LCMS; M+H$^+$: 799.4, retention time: 4.88 min).

Step 3:

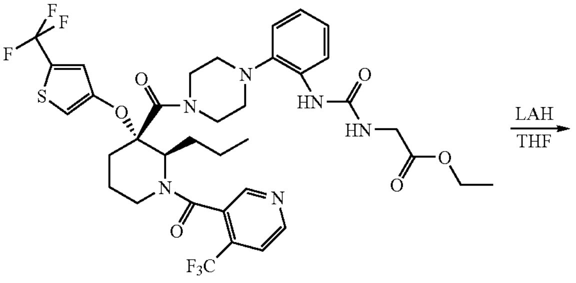

102

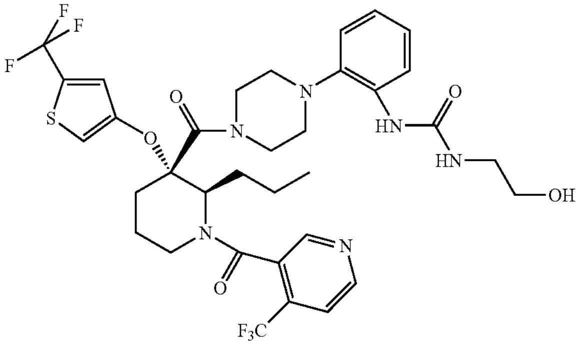

99

The crude product 102 (~10 mg, 0.02 mmol, 1 eq.) was dissolved in anhydrous THF (2 mL) with stirring under nitrogen. This solution was cooled to −78° C. A solution of lithium aluminum hydride in THF (6 eq. 0.12 mmol, 120 uL THF) was then added to the reaction mixture. The reaction mixture was allowed to warm to room temperature for 30 minutes. The reaction was then cooled back to −78° C. and quenched dropwise with saturated ammonium chloride solution. The reaction was diluted with ethyl acetate and the product was extracted. The product was then purified using a Sunfire C18 semiprep column and a gradient of acetonitrile/water from 20-100%. The product was extracted with ethyl acetate, dried over sodium sulfate, and concentrated to give 99 as a white solid (1.0 mg, LCMS: M+H$^+$: 757.4, retention time: 4.28 mint)

Compound Example 103

103

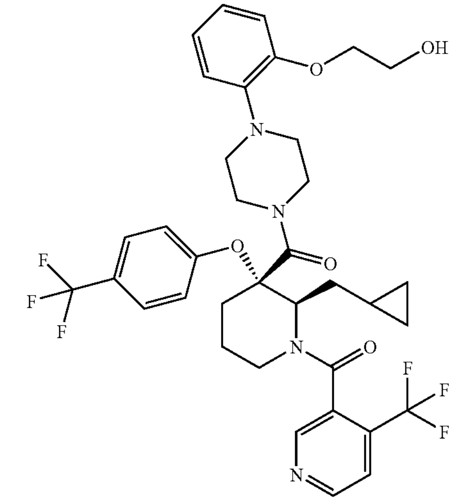

Step 1:

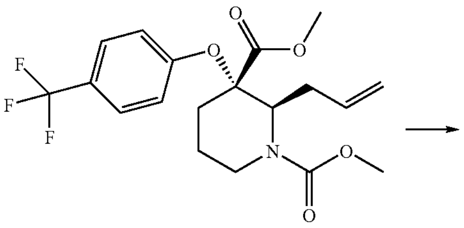

27

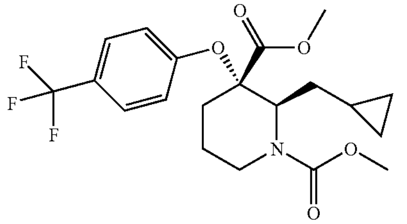

104

To a 0° C. solution of $(Et)_2Zn$ (15.8 mL, 15.8 mmol, 3 eq.) in dry DCM was added TFA (1.2 mL, 15.8 mmol) very slowly. Upon stirring for 20 min, $CH_2I_2$ (1.27 mL, 15.8 mmol, 3 eq.) was added slowly. After additional 20 min at 0° C., olefin 27 (2.11 g, 5.26 mmol) in 5 mL of DCM was added. The ice-bath was removed, the mixture was stirred at r.t. for 48 hrs. The reaction was quenched with sat. NH4Cl solution, the organic layer was washed with sat. NaHCO3 and brine and dried over MgSO4. Solvent was removed in vacuo and residue was purified by HPFC using 5~20% EtOAc in hexane to give 104 (2.185 g, Yield 100%).

Step 2:

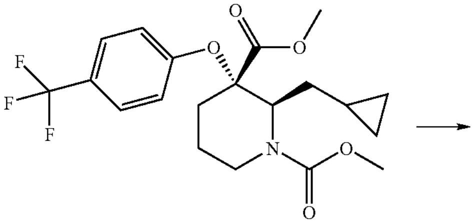

104

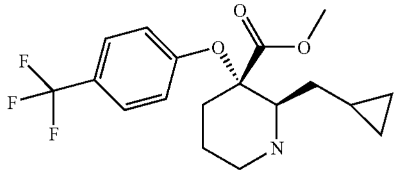

105

To 104 (1.2 g, 2.89 mmol) in anhydrous DCM was added TMS-I (1.18 mL, 8.67 mmol, 3 eq.) in 20 mL of DCM at RT. The mixture was stirred at RT for 3 hrs, then it was concentrated to dryness to give 1.47 g of crude product 105.

Step 3:

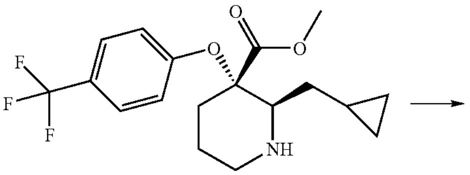

105

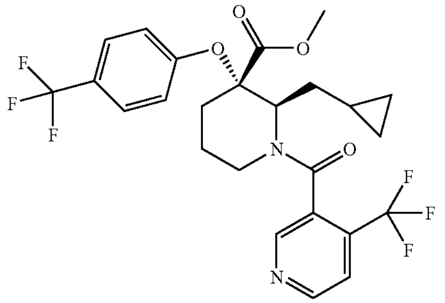

106

To crude 105 (2.89 mmol) in DCM/DMF (5/5 mL) was added 4-(trifluoromethyl)nicotinic acid (663 mg, 3.47 mmol, 1.2 eq.), HATU (1.65 g, 4.34 mmol, 1.5 eq.) and DIPEA (2.39 mL, 14.45 mmol, 6 eq.). The mixture was stirred at room temperature for 18 hours. Reaction was diluted with EtOAc and washed with water, NaHCO3 and NH4Cl and brine. Organic layer was dried over MgSO4, filtered and concentrated in vacuo. The residue was purified by HPFC using 20~85% EtOAc in hexane to give 106 (1.146 g, 75%).

Step 4:

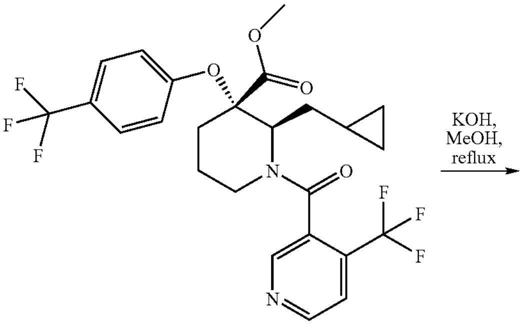

106

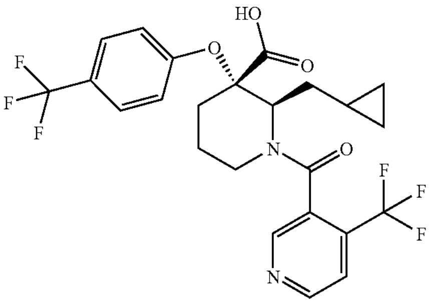

107

Compound 106 (1.140, 2.15 mmol) in aqueous KOH (9.2 mL, 32.2 mmol, 15 equiv) and 13.8 mL of MeOH was stirred at 63° C. for 18 hours. TLC and MS analysis indicated the reaction completed. Reaction mixture was concentrated in vacuo to remove MeOH. Residue was diluted with ~10 mL H2O, the aqueous layer acidified with 3N HCl and 10% citric acid at RT to PH~3.5, and extracted with EtOAc. The combined extracts were dried over MgSO4 and concentrated to dryness to give 107 (1.05 g, 95%).

Intermediate 107, was used in the preparation of inhibitors 103 according the procedure described in the preparation of 39 in Example 3.

Example 7

Compound Example 108

108

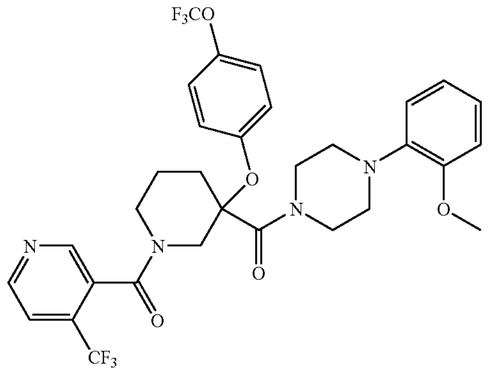

Step 1:

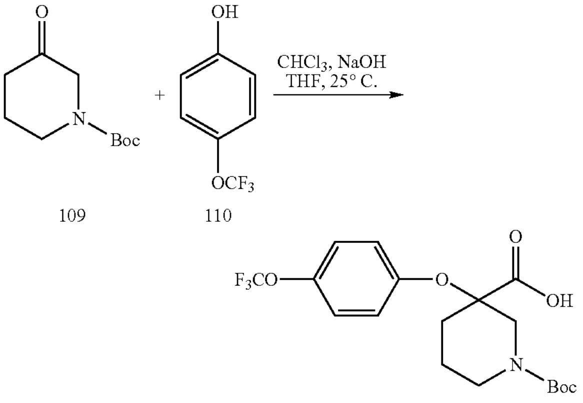

109 110

111

To the trifluoromethoxy phenol 110 (500 mg, 1 eq, 2.8 mmol) in a flash dried round bottom flask under nitrogen atmosphere dissolved in anhydrous THF (10 mL) was added sodium hydroxide (10 eq, 28 mmol, 1.12 g) and the reaction mixture stirred at room temperature for 1 hr. Boc piperidone 109 (1.5 eq, 4.2 mmol, 836 mg) was added followed by chloroform (1 equiv, 2.8 mmol) in 5 mL of THF dropwise over 20 min (using a syringe pump). The reaction mixture was stirred overnight at room temperature then concentrated in vacuo. The crude residue was redissolved in water, washed with ether, then diluted with ethyl acetate (200 mL), and acidified with 1N HCl to pH ~3. The combined the organic layers and washed with brine, dried over anhydrous sodium sulfate, filtered and concentrated in vacuo to give crude acid 111 (780 mg) which was used without further purification.

Step 2:

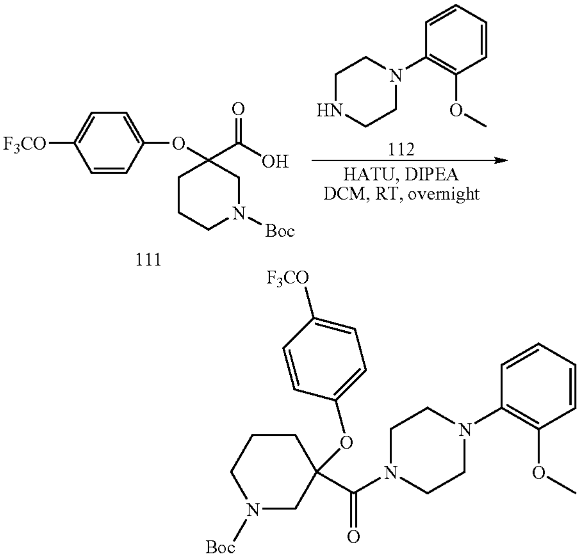

111

113

Intermediate 113 was prepared according to the general amide formation procedure as described in this invention.

Step 3:

Conversion of intermediate 113 to compound 108 was achieved using the deprotection of 113 Boc group, followed by the general amide formation procedure as described in this invention.

Compound Example 114

114

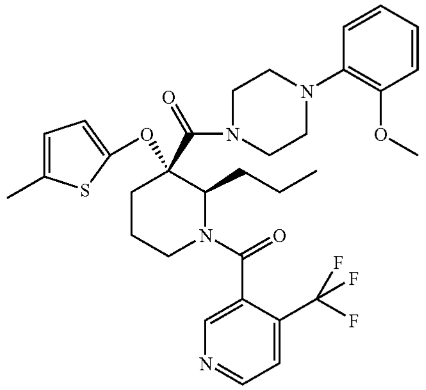

Step 1:

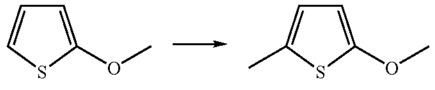

115 116

To 2-methoxythiophene 115 (1 g, 8.6 mmol, 1 eq.) in THF was added nBuLi (5.6 mL, 9.0 mmol, 1.05 eq.) dropwise at −78° C. After 10 min, MeI (0.54 mL, 8.6 mmol, 1 eq.) was added dropwise at −78° C. The mixture was stirred at −78° C. for 30 min. As crude NMR showed the reaction almost completed, it was quenched with brine, diluted with ether, washed with brine, and the organic layer dried over MgSO4. The solvents were removed in vacuo and the crude product used without further purification for step 2.

Step 2:

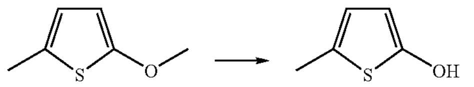

116 117

To 116 (1.1 g, 8.6 mmol) in dry DCM was added BBr3 (13.8 mL, 13.8 mmol, 1.5 eq.) dropwise at 0° C. The mixture was stirred at 0° C. for 18 hrs then another 1.5 eq. BBr3 was added and the reaction stirred at 0° C. for 3 days. 10 mL of ether was added and sat. NaHCO3 was added slowly at 0° C. The reaction mixture was then diluted with DCM, the organic layer was dried over MgSO4, and concentrated in vacuo to give 1.0 g of crude product 117. The crude product used without further purification for step 3.

Step 3:

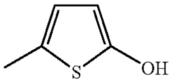

117

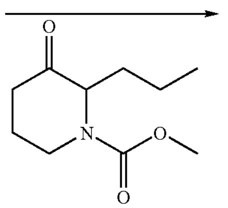

118

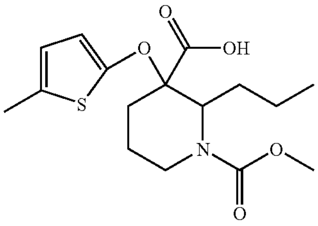

119

To a mixture of NaOH (0.993 g, 24.8 mmol, 6 eq.) in 25 mL of THF was added 117 (0.47 g, 4.14 mmol, 1 eq.) and the mixture was stirred at RT for 3.0 hrs under N2. Ketone 118 (From hydrogenation of 24, 1.0 g, 4.14 mmol, 1 eq.) in 5 mL of THF was added. After 20 min, the reaction mixture was cooled to 0° C., then CHCl3 (1.7 mL, 20.7 mmol, 5 eq.) was added drop wise. The mixture was warmed up to room temperature for 2 h, then heated to 40~42° C. for 48 hours. The mixture was cooled to RT, diluted with 20 mL of 1N NaOH, and stirred for 10 min. The pH of aqueous layer was adjusted to ~4 with 3N HCl. The aqueous layer was extracted with EtOAc×2 and the combined organic extracts were dried over MgSO4, filtered and concentrated to dryness to give 119 (1.48 g). The crude product used without further purification for step 4.

Step 4:

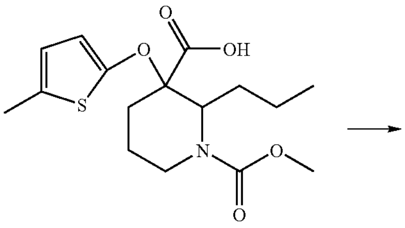

119

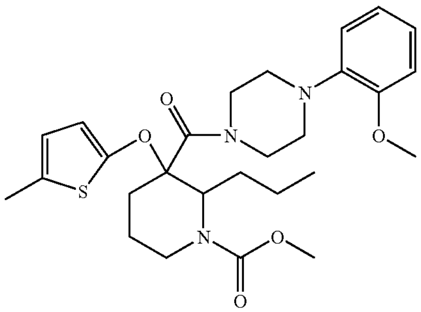

120

To 119 (705 mg, 2.07 mmol) in DCM/DMF at RT was added 1-(2-Methoxyphenyl)piperazine HCl salt (473 mg, 2.07 mmol, 1 eq.), HATU (787 mg, 2.07 mmol, 1 eq.) and DIPEA (1.7 mL, 10.7 mmol, 5 eq.). The mixture was stirred at RT for 18 hours, then diluted with EtOAc, washed with sat. NH4Cl, then sat. NaHCO3, and brine. The organic layer was dried over MgSO4 and concentrated to dryness. Purification HPFC Biotage, using 10% to 40% EtOAc in hexane gave 83 mg of 120.

Step 5:

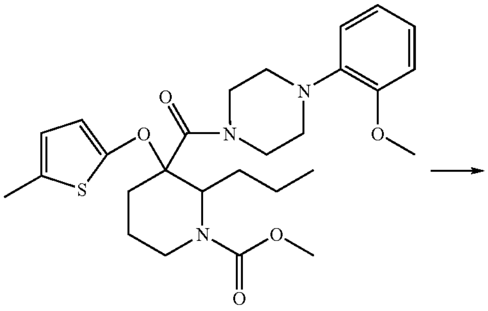

120

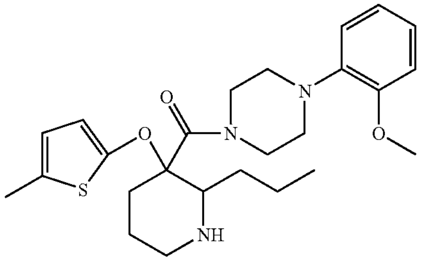

121

To 120 (83 mg, 0.16 mmol) in anhydrous $CH_2Cl_2$ was added TMS-I (0.066 mL, 0.48 mmol, 3 eq.) slowly at RT. The mixture was stirred at RT for 3 hrs then reaction was concentrated to dryness to give 121 (62 mg, 85% yield).

Step 6:

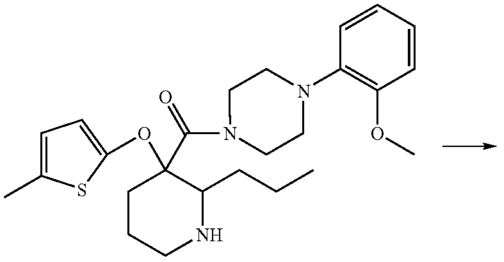

121

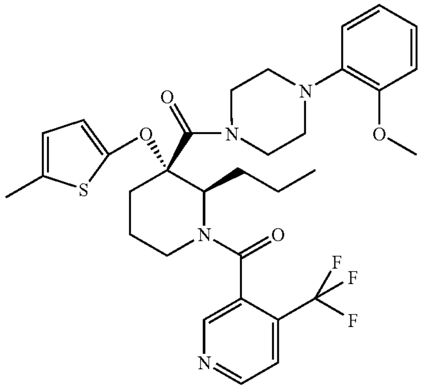

114

To 121 (31 mg, 0.068 mmol) in DCM/DMF was added 4-(trifluoromethyl)nicotinic acid (13 mg, 0.068 mmol, 1.5 eq.), HATU (31 mg, 0.082 mmol, 1.2 eq.) and DIPEA (0.11 mL, 0.68 mmol, 10 eq.) at RT. The mixture was stirred at 45° C. overnight, then diluted with EtOAc, washed with sat. NH4Cl, sat. NaHCO3 and brine. The organic layer was dried over MgSO4, filtered, and concentrated to dryness. HPFC Biotage purification using 10% to 55% EtOAc in hexane provided 20 mg of racemic product. Chiral HPLC separation was accomplished using a chiral OD reversed column to 4.3 mg of compound 114 (second eluting fraction).

Compound Examples 115, 116

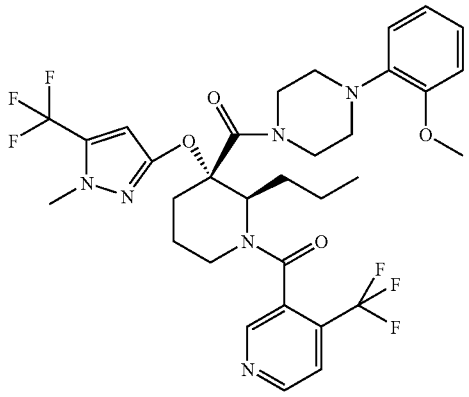

115

-continued

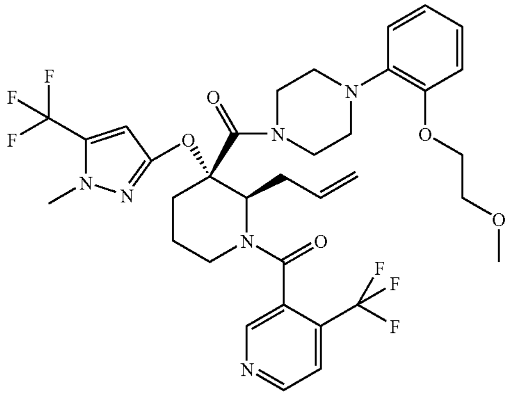

116

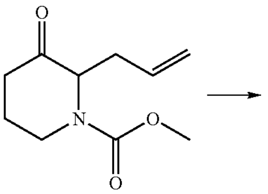

24

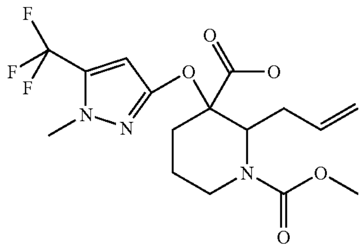

117

To a mixture of NaOH (1.204 g, 30.1 mmol, 5 eq.) in 30 mL of THF was added 1-methyl-5-(trifluoromethyl)-1H-pyrazol-3-ol (1.0 g, 6.02 mmol, 1 eq.). The mixture was stirred at RT for 1.5 hrs under N2. Allyl ketone 24 (1,169 g 6.02 mmol, 1 eq.) in 2 mL of THF was added. After 20 min, the reaction mixture was cooled to 0° C., then CHCl3 (2.2 mL, 27.1 mmol, 4.5 eq.) was added dropwise. The mixture was warmed up to room temperature for 2 h, then heated to 40-42° C. for 18 hours. The mixture was cooled to PT, diluted with 50 mL of 3N NaOH, and stirred for 10 min. The reaction mixture was washed with Et2O (40 mL), then the pH of aqueous layer was adjusted to PH ~5.7 with 3N HCl, and the aqueous layer was extracted with EtOAcx2. The combined EtOAc extracts were dried over MgSO4, filtered, and concentrated to dryness to give 117 (1.36 g, 58%).

Compounds 115 and 116 were prepared from 117 according to similar procedures describe in this invention.

Compound Example 119

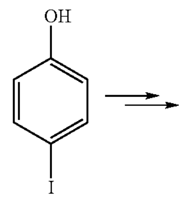

118

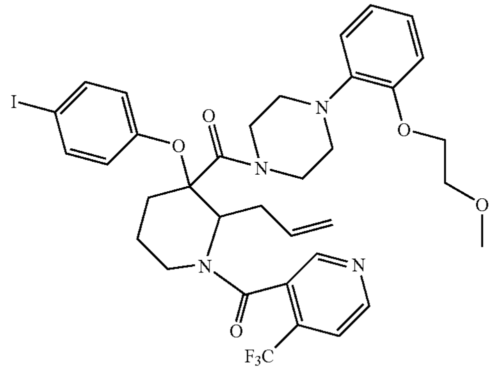

119

Compound 119 was prepared in a similar manner to the previously described procedure using 4-iodophenol 110 as the starting material (LCMS: $M+H^+$: 779.4, retention time: 4.29 min).

Example 8

Compound Example 120

120

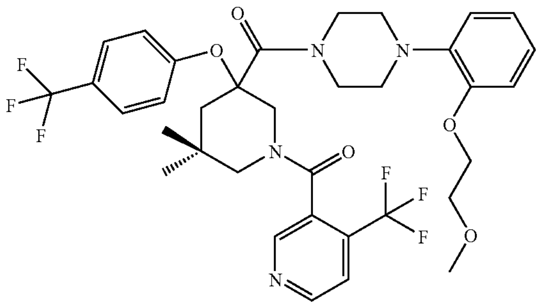

Step 1:

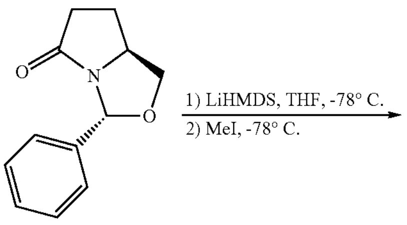

121

-continued

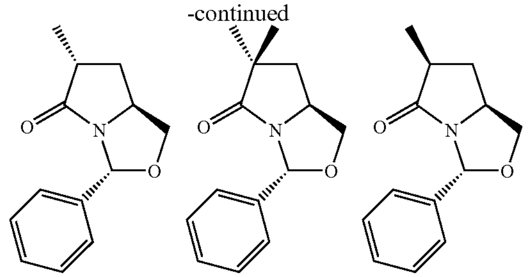

122 123 124

To a −78° C. solution of 121 (prepared according *J. Org. Chem.,* 1986, 51, 3140-3143) (4.06 g, 20 mmol) in THF (80 mL) was added dropwise LiHMDS (1.1 eq, 24 mmol, 24 mL). Reaction turned reddish after first 1 mL of LiHMDS. Reaction was stirred at −78° C. for 30 minutes then MeI (1.05 equiv, 22 mmol, 1.37 mL) was added. Reaction was warmed to −20° C. and diluted with NH4Cl, then the reaction was warmed to RT. The mixture was extracted with EtOAc, washed with NH4Cl and brine, dried over MgSO4, filtered and concentrated in vacuo. Purification by Biotage HPFC 40+M, 5 to 20% EtOAc in Hexane provided 3 fractions referred as compound 122 (2.83 g), compound 123 (400 mg) and compound 1.24 (450 mg) with an overall isolated yield of 56%.

Step 2:

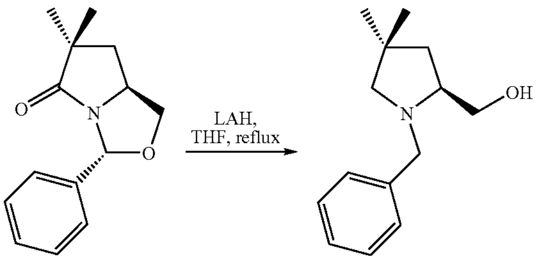

123 125

To a RT solution of 123 (4 g, 17.3 mmol) in THF (100 mL) was added LAH (2.5 equiv, 44 mmol, 1.76 g). The reaction was refluxed (60° C.) overnight. TLC (70/30 Hex/EtOAc) shows reaction completed. Reaction was cooled down to RT and dry work-up was done (Na2SO4/H2O dropwise then MgSO4 and filter). The filtrate was concentrated in vacuo to yield 125 (3.81 g) as a colorless oil.

Step 3:

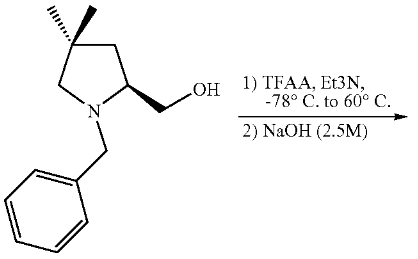

125

-continued

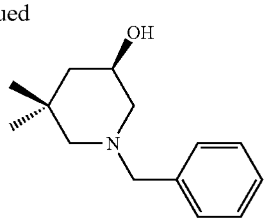

126

To a −78° C. solution of prolinol 125 (17 mmol) in THF (30 mL) was added 1.2 equiv of TFAA (2.82 mL) and the reaction was stirred at −78° C. for 30 minutes, then warmed to RT for 1 hour 30 min. Upon cooling again to −78° C., Et3N (9.7 mL) was added and reaction stirred for 15 min then heated to reflux overnight. After 18 h, 3.3 equiv NaOH (2.5N, 56.1 mmol, 22.5 mL) were added and reaction stirred for 3 h. The reaction mixture was diluted with DCM, washed successively with NH4Cl, NaHCO3, and brine, and organic layer dried over MgSO4 then concentrated in vacuo. Purification by HPFC, 40+M, 5 to 20% EtOAc in Hexane provided 126 in 90% isolated yield.

Step 4:

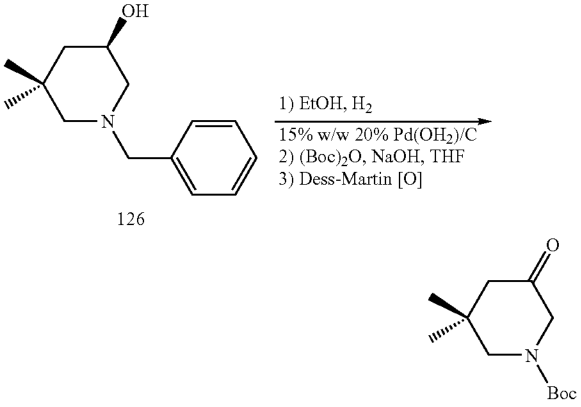

126

127

To a RT solution of 126 (3.3 g, 15 mmol) in EtOH (100 mL) was added under N2 0.5 g of 20% Pd(OH)2/C (15% w/w). The reaction vessel was flushed with H2 and stirred 18 h. The reaction mixture was filtered through celite and concentrated in vacuo to an oil. To a RT solution of this aminoalcohol intermediate (1.39 g, 10.75 mmol) in THF (15 mL) was added NaOH (15 mL) followed by (Boc)2O (1.05 equiv, 11.3 mmol, 2.47 g). The reaction mixture was stirred at RT 18 h, then diluted with EtOAc and washed with water then brine. The organic layer was dried over MgSO4, filtered and concentrate in vacuo. The material crystallized upon standing to provide 1.9 g of the intermediate Boc-protected aminoalcohol. To a RT solution of this alcohol (8.3 mmol) in DCM (50 mL) was added Dess-Martin reagent (2 equiv, 16.6 mmol, 8 g). The reaction mixture was stirred overnight, then diluted with EtOAc and stirred with a 1/1 solution of Na2S2O3-NaHCO3 sat. The organic layer was separated, washed with NaHCO3 then brine, dried over MgSO4, filtered and concentrated in vacuo. Purification HPFC, 40+M, 5 to 20% EtOAc. After purification, 1.53 g of 127 was isolated (62% isolated yield over 3 steps).

Step 5:

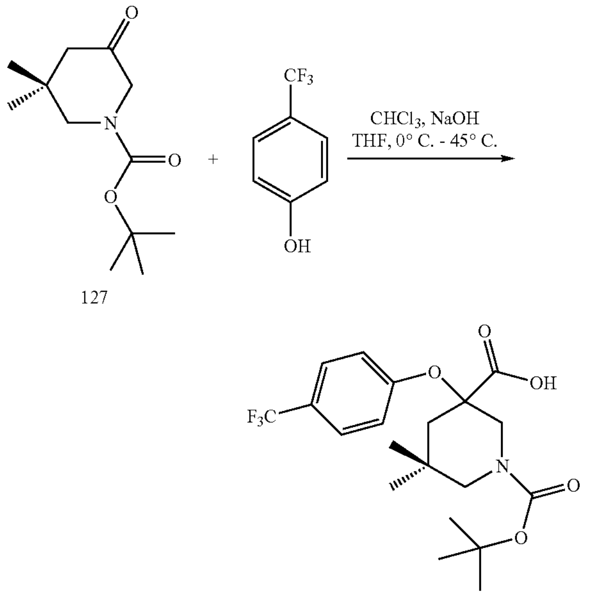

127

128

To a flame-dried 100 mL RB flask was added 4-hydroxy-benzotri-fluoride (1 eq, 2 mmol, 320 mg) in dry THF (5 mL) followed by NaOH (Beads, 20-40 mesh, 5 equiv, 10 mmol, 0.40 g). After 1 h with vigorous stirring, the reaction mixture went from homogeneous to slurry. A solution of the ketone 127 (1 eq, 2 mmol, 0.46 g) in extra dry THF (2 mL+2 mL) was added dropwise at room temperature and stirred for 20 min, then cooled to 0° C. Extra dry CHCl3 (4.5 eq, 9 mmol, 0.7 mL) was then added dropwise. The reaction color turned to dark orange/brown with no rising in temperature. The reaction mixture was warmed to RT and stirred overnight, then diluted with NaOH (2.5N, 25 ml) and stirred for 15 min. The pH was adjusted to 4 using HCl 1.0N, and the reaction was extracted with EtOAc. The combined organic extracts were dried over MgSO4, filtered and concentrated in vacuo to provide 128 (793 mg). Compound 128 was used as described in the invention to yield compound 120.

Similar procedures were used to generate compounds 129 and 130 from intermediates 122 and 124 respectively.

129

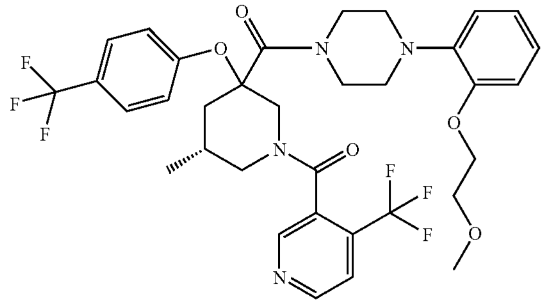

-continued

130

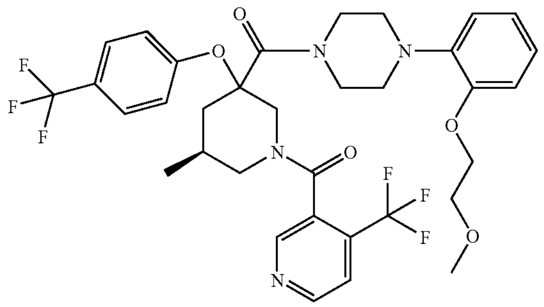

Compound Example 131

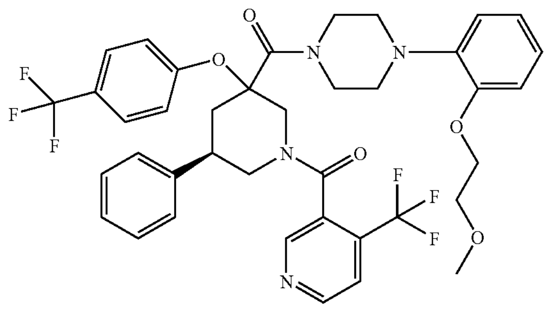

131

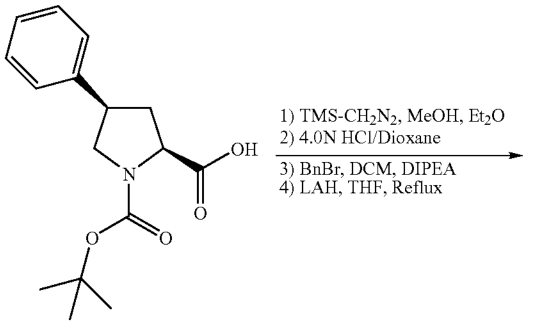

132

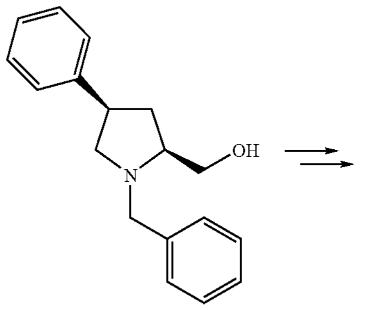

133

-continued

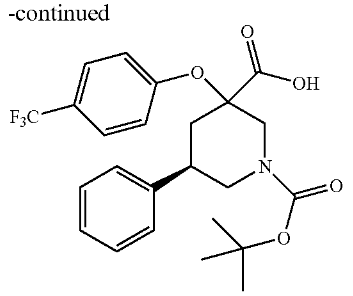

134

To a RT solution of commercially available Boc-(2S,4R)-4-phenylpyrrolidine-2-carboxylic (5 g, 17 mmol) in MeOH/Et2O (100 mL/100 mL) was added slowly TMS-CH2N2: 2.0M in heptane until a persistent yellow color was obtained (after addition of 15 mL, 30 mmol). Reaction was stirred 15 min at RT then concentrated in vacuo to give a light yellow oil, which was then dissolved in 200 mL of 4.0N HCl in dioxane and stirred at RT for 1 h. The reaction mixture was concentrated in vacuo, diluted with 100 mL of DCM, and cooled to 0° C. Benzyl Bromide (1.2 equiv, 20 mmol, 2.4 mL) was added followed by DIPEA (3 equiv, 51 mmol, 8.4 mL) and the reaction stirred for 3 days. After aqueous work-up ($NH_4Cl$, NaHCO3 and brine), the organic layer was dried over MgSO4, filtered and concentrated in vacuo. Purification HPFC 2% to 10% EtOAc in Hexanes provided 5.59 g (100%) of ester precursor of 133. To a 0° C. solution this ester in THF (100 mL) was added LAH (2.5 equiv, 50 mmol, 2 g), and the reaction stirred at 0° C. and gradually warmed up to RT. After dry work up (Na2SO4/H2O dropwise then MgSO4 and filter), the reaction was concentrated in vacuo to give 4.25 g (94% isolated yield over 4 steps) of 133 as white crystalline material.

Intermediate 134, used in the preparation of compound 131, was prepared from 133 using similar protocols as described in the steps 3 to 5 of example 120.

Compound Example 137

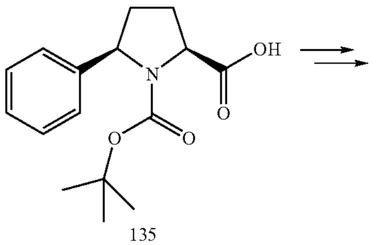

135

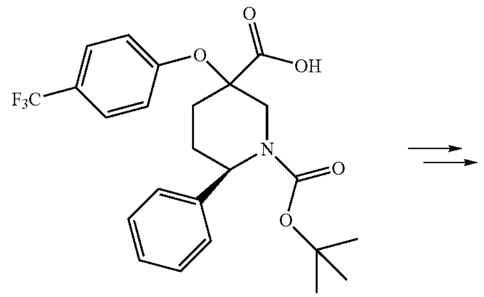

136

-continued

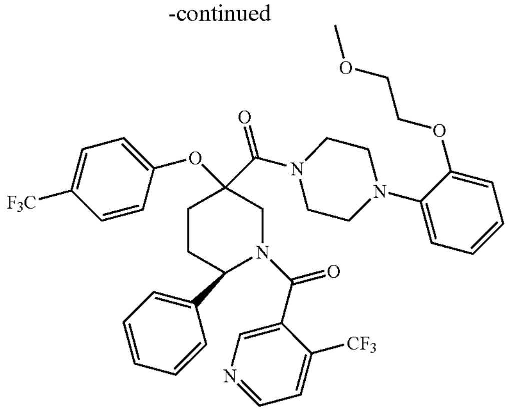

137

Compound 137 was prepared using 135 in a similar manner as described in the preparation of compound 131.

Compound Example 139

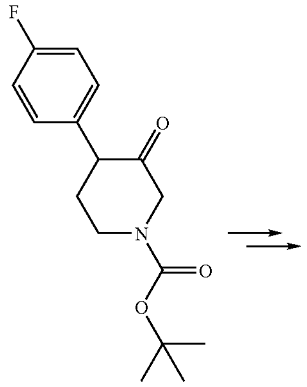

138

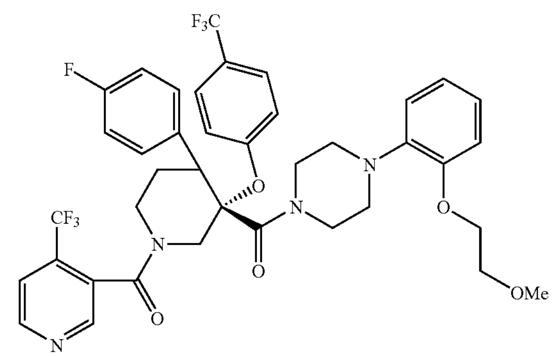

139

Compound 139 was prepared using 138 in a similar manner as described in the preparation of compound 120, where 120 was synthesized from intermediate 127.

Example 9

General Procedures for Olefin Isomerization and Functionalization

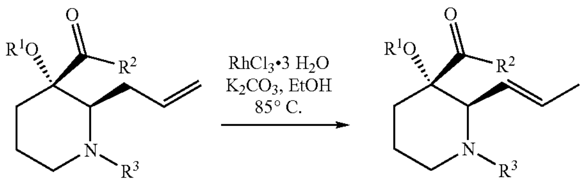

140 141

To $RhCl_3.H_2O$ (0.1 eq) and $K_2CO_3$ (0.18 eq) under argon was added a solution of 140 (1.0 eq) in ethanol (0.1 M) and the reaction mixture heated to 85° C. for 4 h, cooled to room temperature, and poured into ethyl acetate 1 brine (1:1). The mixture was extracted with ethyl acetate (3×), dried ($Na_2SO_4$), filtered through celite, and then concentrated in vacuo to give 141 which was used without further purification.

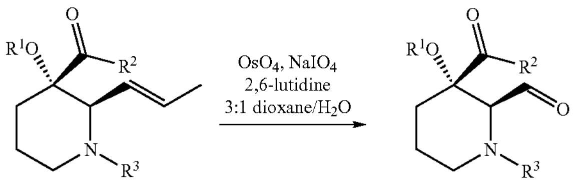

141 142

To a stirring solution of 141 (1.0 eq) in 3:1 dioxane/water (0.1 M) was added 2,6-lutidine (2 eq), $OsO_4$ solution in tert-butanol (0.1 eq), then $NaIO_4$ (5 eq). The reaction mixture was allowed to stir at room temperature 2.5 h then it was diluted with water and extracted with $CH_2Cl_2$ (3×). The crude material was used without further purification.

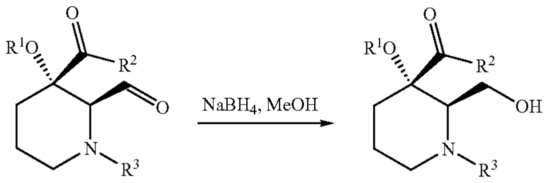

142 143

To a solution of 142 (1.0 eq) in MeOH (0.1 M) was added $NaBH_4$ (0.5 eq) and the reaction mixture was stirred at room temperature 1 h, then concentrated in vacuo. The crude residue was purified by flash silica gel chromatography to give 143.

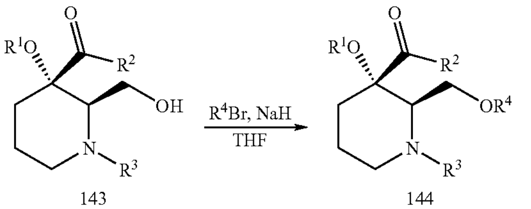

143 144

To a solution of 143 (1.0 eq) and $R^4Br$ (1.2 eq) in THF (0.1 M) was added NaH (1.5 eq) and the reaction mixture stirred at room temperature 2 h. The reaction mixture was quenched with $H_2O$, concentrated in vacuo, and purified by flash silica gel chromatography or HPLC to give 144.
Compounds of Column 2 of Table 1 below were prepared by essentially the same procedures given in the preparative examples above.
TABLE 1
| Compound No. Sch ID | Molstructure | Observed M + H | Retention Time (min) |
|---|---|---|---|
| A | 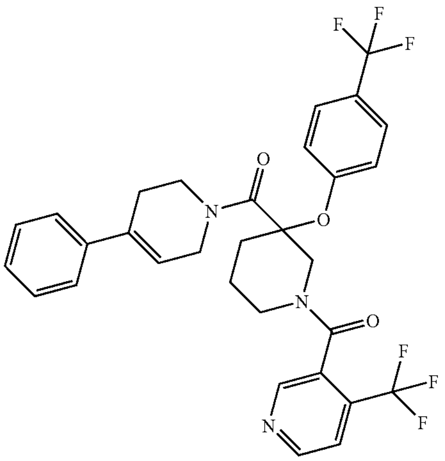 | 604.22 | 6.20 |
| B | 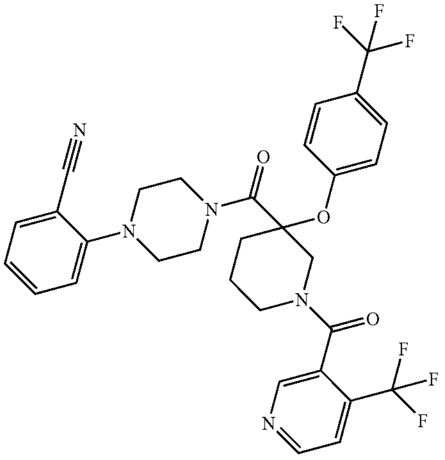 | 632.29 | 5.63 |
| C | 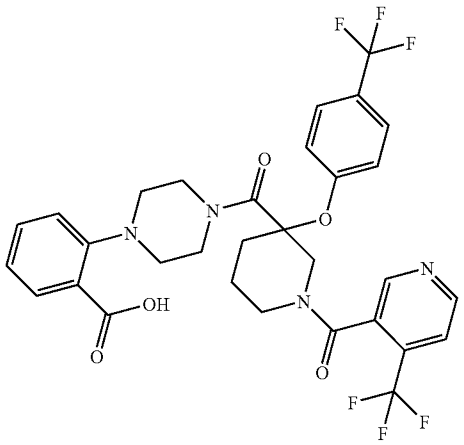 | 651.29 | 4.84 |

TABLE 1-continued
| Compound No. Sch ID | Molstructure | Observed M + H | Retention Time (min) |
|---|---|---|---|
| D | 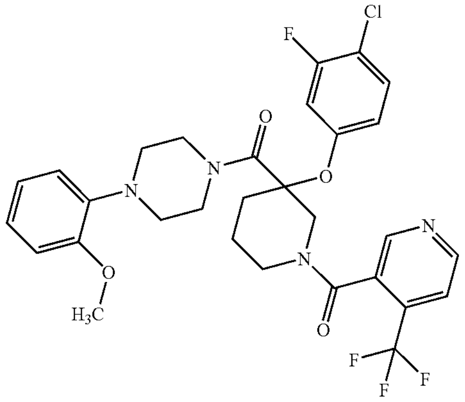 | 621.26 | 5.23 |
| E | 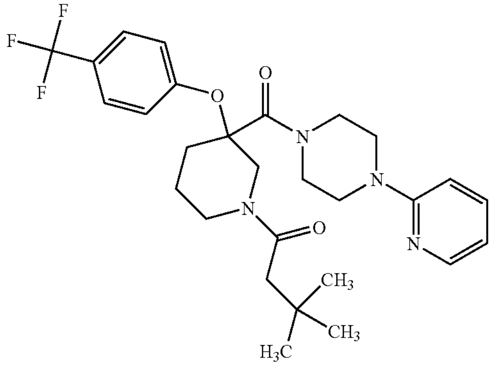 | 533.3 | N/A |
| F | 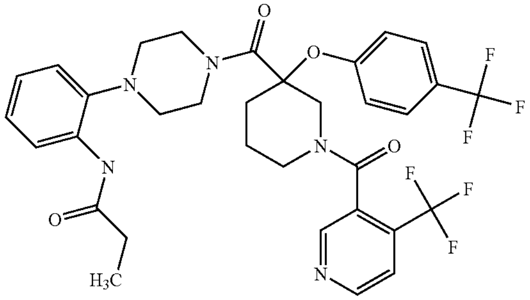 | 678.18 | 5.85 |
| G | 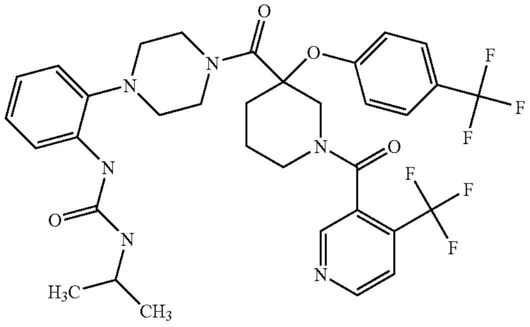 | 707.2 | 2.12 |

TABLE 1-continued
| Compound No. Sch ID | Molstructure | Observed M + H | Retention Time (min) |
|---|---|---|---|
| H | 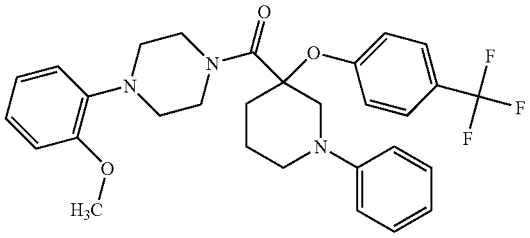 | 540.3 | 6.58 |
| I | 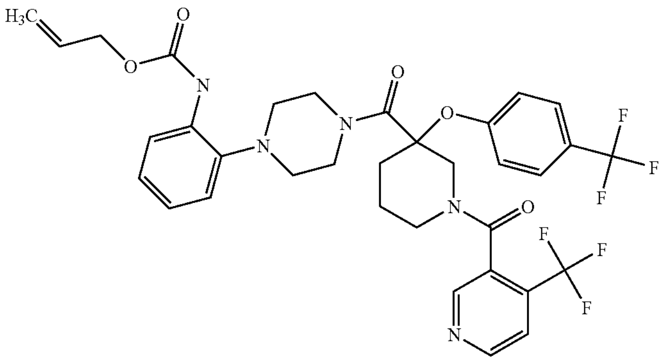 | 706.29 | 6.29 |
| J | 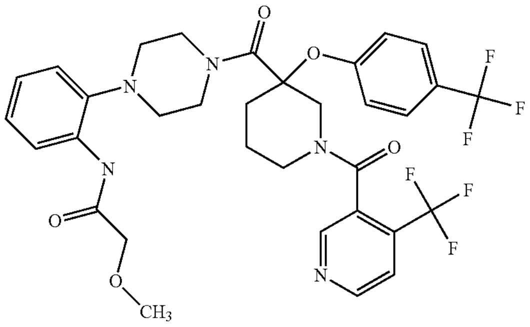 | 694.20 | 5.36 |
| K | 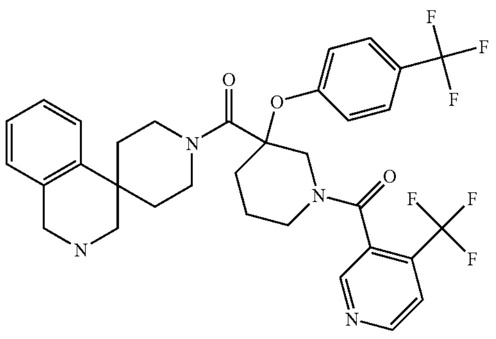 | 647.2 | 4.31 |

TABLE 1-continued
| Compound No. Sch ID | Molstructure | Observed M + H | Retention Time (min) |
|---|---|---|---|
| L | 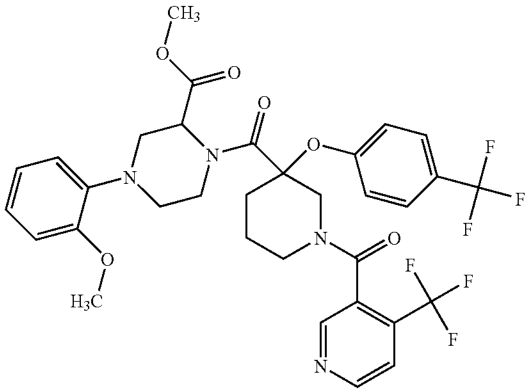 | 695.2 | 5.99 |
| M | 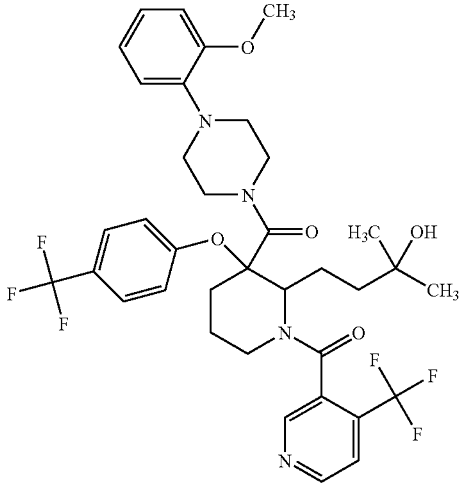 | 723.2 | 2.18 |
| N | 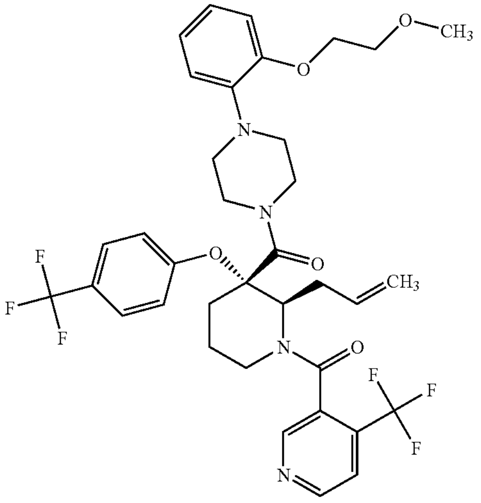 | 721.24 | 5.01 |

TABLE 1-continued
| Compound No. Sch ID | Molstructure | Observed M + H | Retention Time (min) |
|---|---|---|---|
| O | 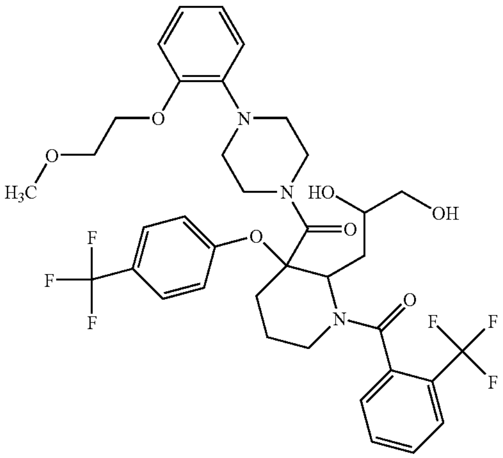 | 754.2 | 2.14 |
| P | 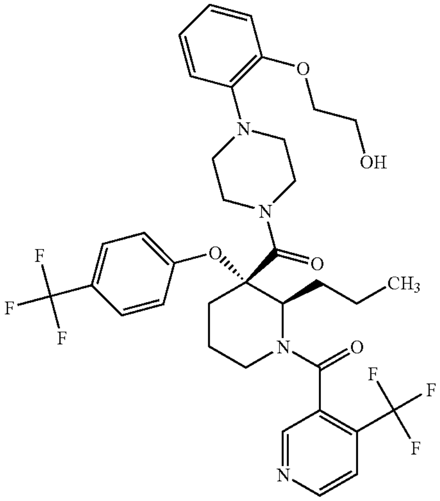 | 709.3 | 4.97 |
| Q | 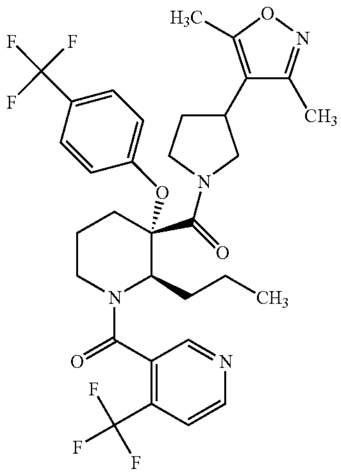 | 653 | 7.37 |

TABLE 1-continued
| Compound No. Sch ID | Molstructure | Observed M + H | Retention Time (min) |
|---|---|---|---|
| R | 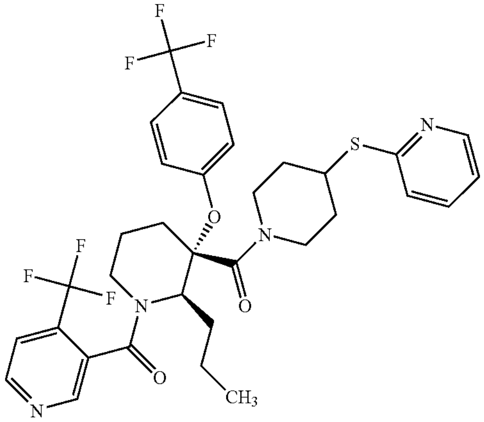 | 681.2 | 5.26 |
| S | 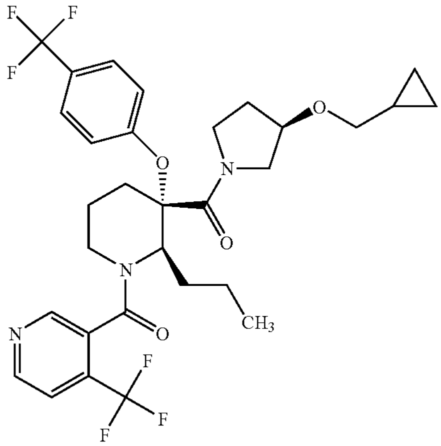 | 628 | 7.81 |
| T | 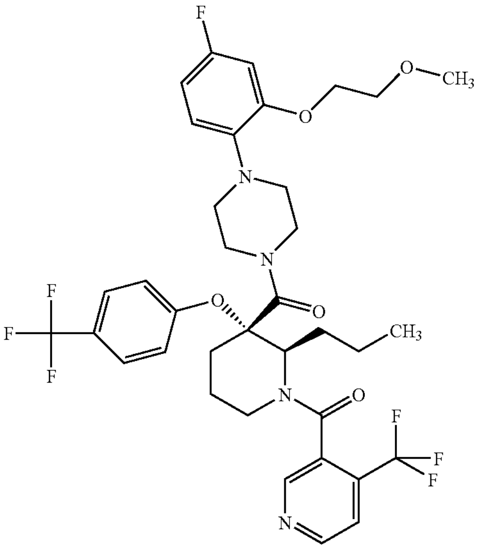 | 741.2 | 5.81 |

TABLE 1-continued
| Compound No. Sch ID | Molstructure | Observed M + H | Retention Time (min) |
|---|---|---|---|
| U | 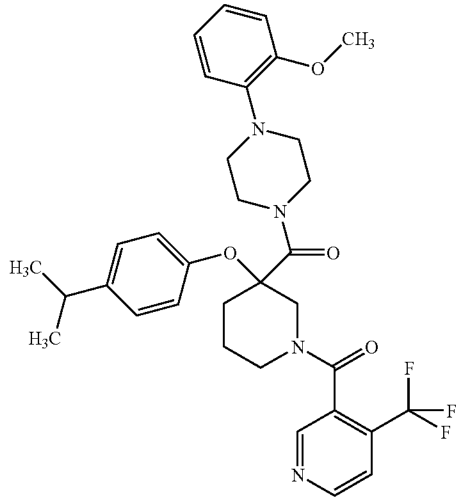 | 611.3 | 4.24 |
| V | 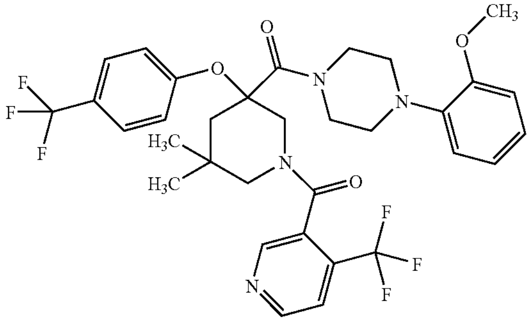 | 665.16 | N/A |
| W | 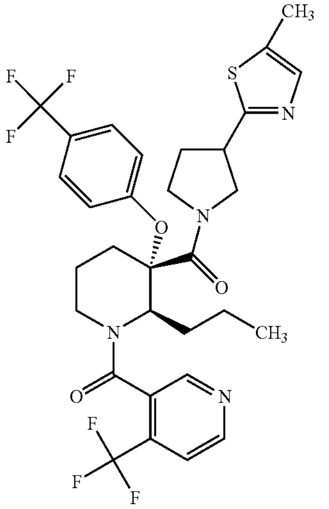 | 655 | 7.32, 7.42 |

TABLE 1-continued
| Compound No. Sch ID | Molstructure | Observed M + H | Retention Time (min) |
|---|---|---|---|
| X | 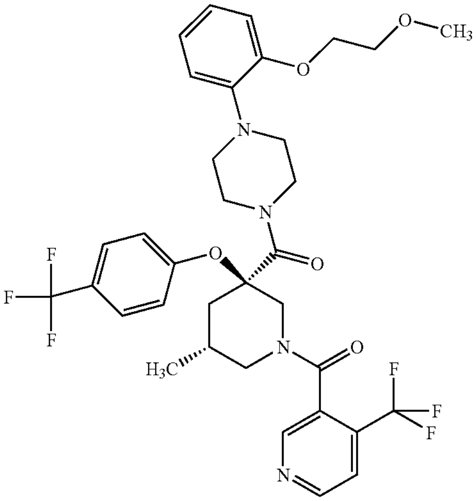 | 695.4 | 4.17 |
| Y | 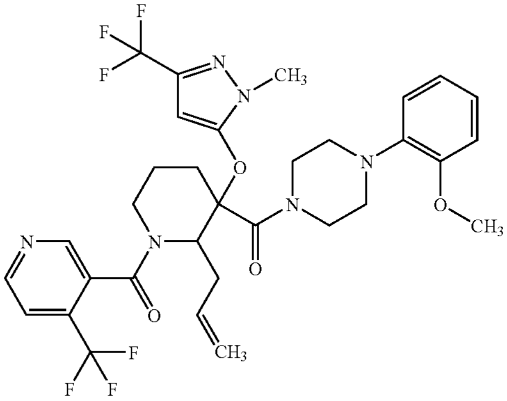 | 681.4 | 3.83 |
| Z | 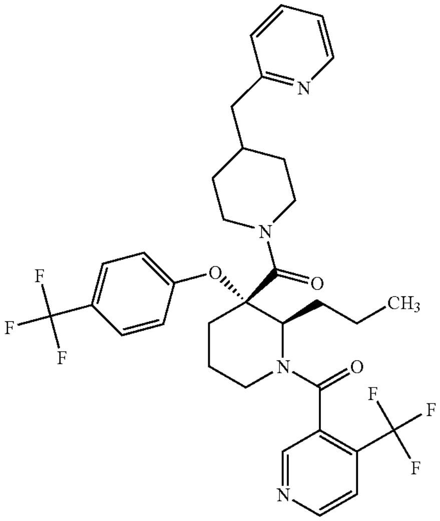 | 663.7 | 3.96 |

TABLE 1-continued
| Compound No. Sch ID | Molstructure | Observed M + H | Retention Time (min) |
|---|---|---|---|
| AA | 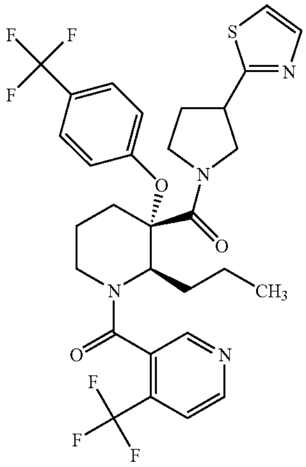 | 641 | 7.13 |
| AB | 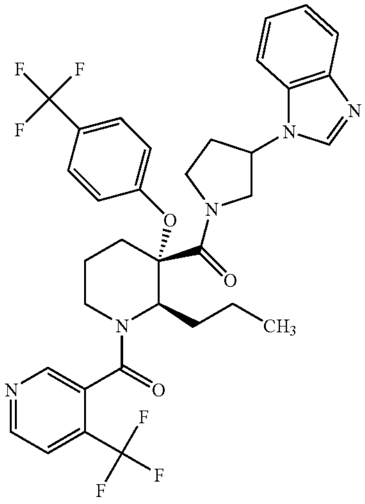 | 674 | 5.67 |
| AC | 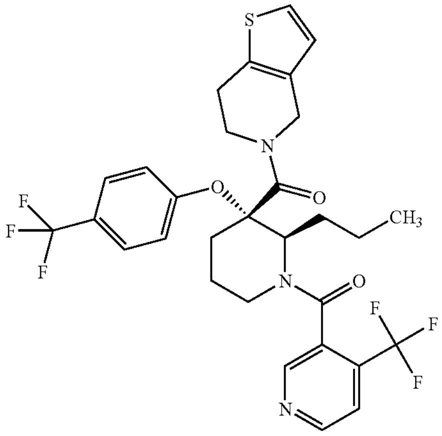 | 626.3 | 5.19 |

TABLE 1-continued
| Compound No. Sch ID | Molstructure | Observed M + H | Retention Time (min) |
|---|---|---|---|
| AD | 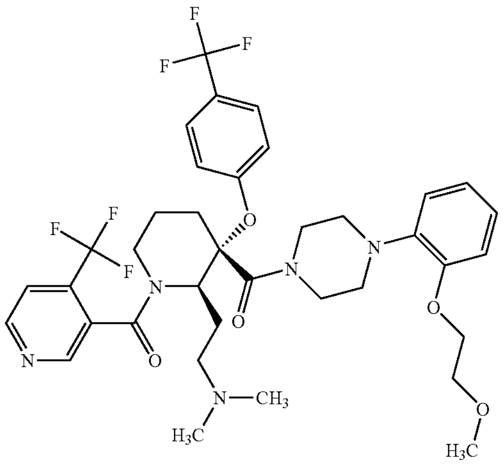 | 752.2 | 4.68 |
| AE | 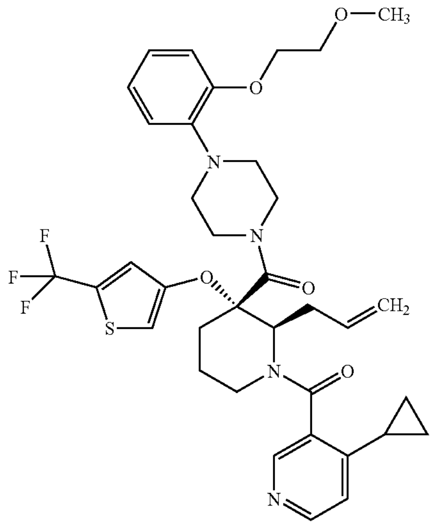 | 699.4 | 3.31 |
| AF | 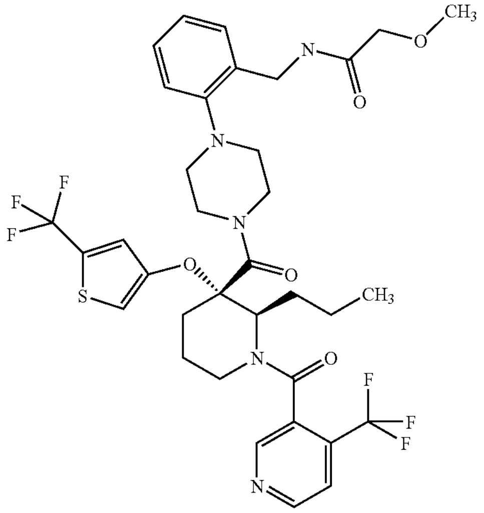 | 756.4 | 4.66 |

TABLE 1-continued
| Compound No. Sch ID | Molstructure | Observed M + H | Retention Time (min) |
|---|---|---|---|
| AG | 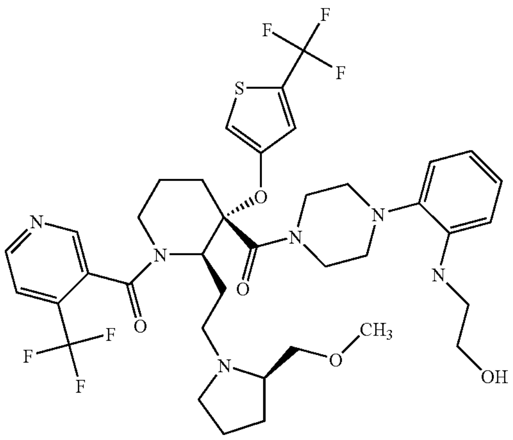 | 814.4 | 4.28 |
| AH | 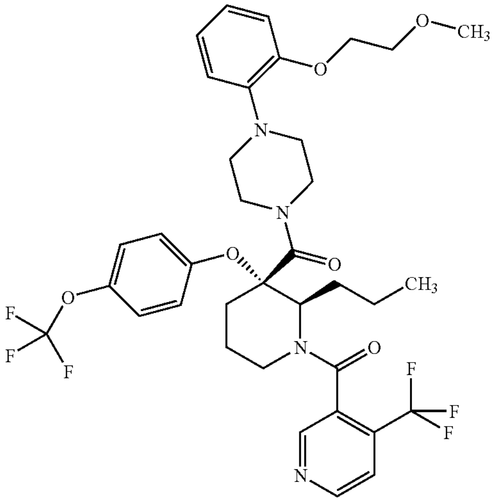 | 739.4 | 4.47 |
| AI | 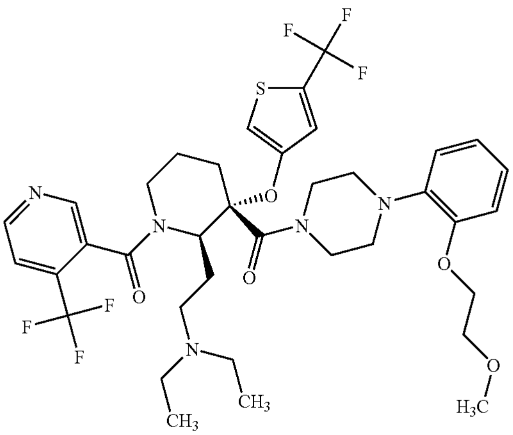 | 786.5 | 4.46 |

TABLE 1-continued
| Compound No. Sch ID | Molstructure | Observed M + H | Retention Time (min) |
|---|---|---|---|
| AJ | 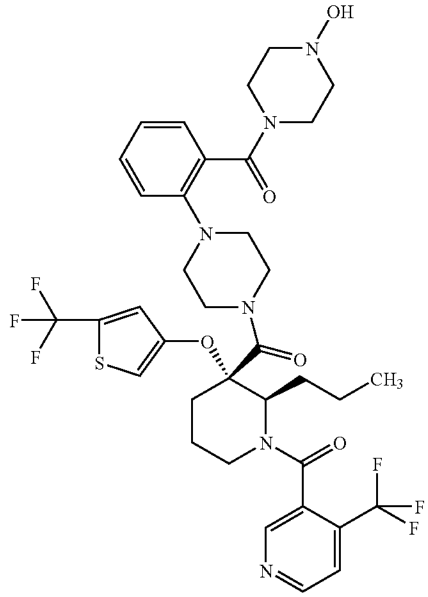 | 781.4 | 3.20 |
| AK | 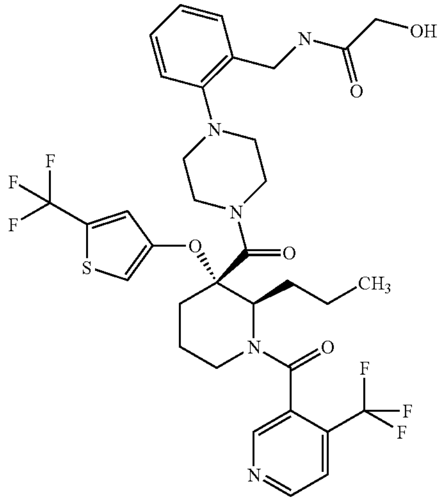 | 742.4 | 4.25 |
| AL | 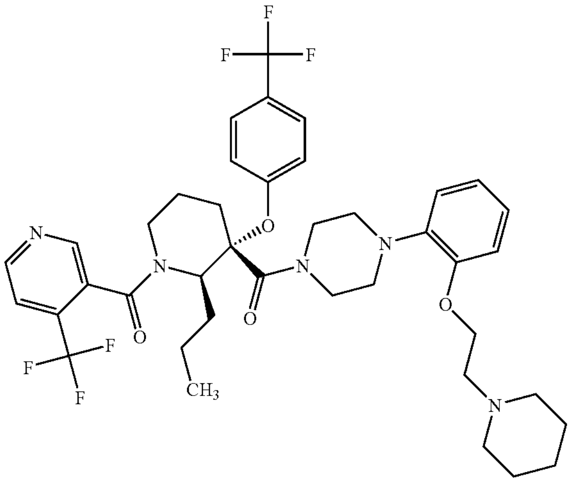 | 776.5 | 4.40 |

TABLE 1-continued
| Compound No. Sch ID | Molstructure | Observed M + H | Retention Time (min) |
|---|---|---|---|
| AM | 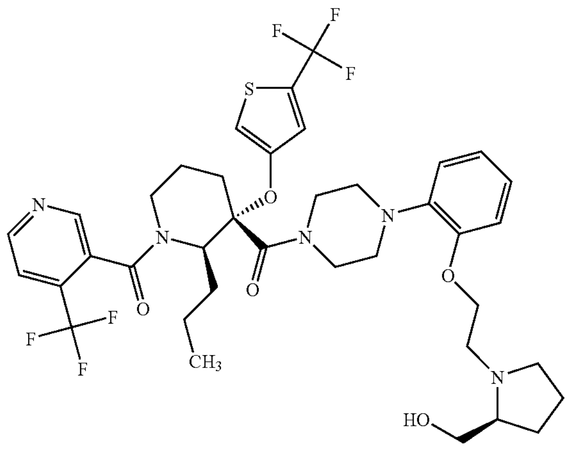 | 798.5 | 4.30 |
| AN | 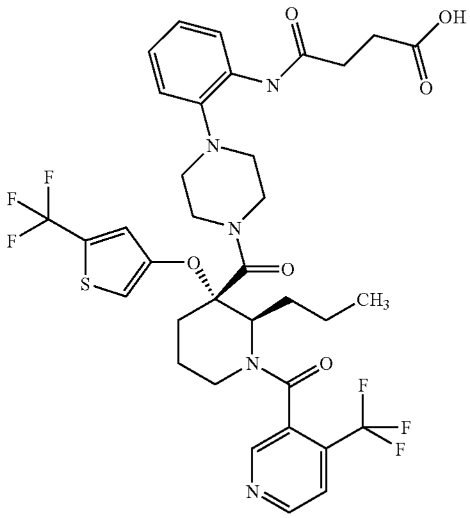 | 770.4 | 4.51 |
| AO | 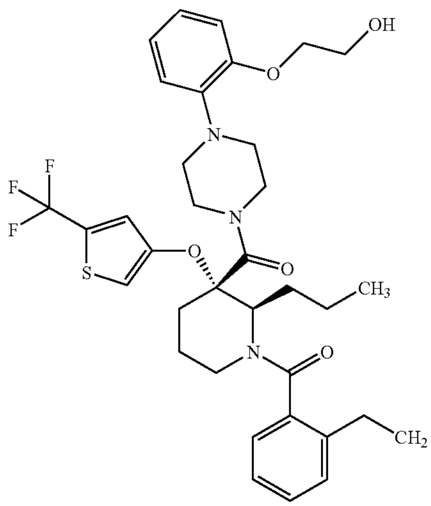 | 674.4 | 4.63 |

TABLE 1-continued
| Compound No. Sch ID | Molstructure | Observed M + H | Retention Time (min) |
|---|---|---|---|
| AP | 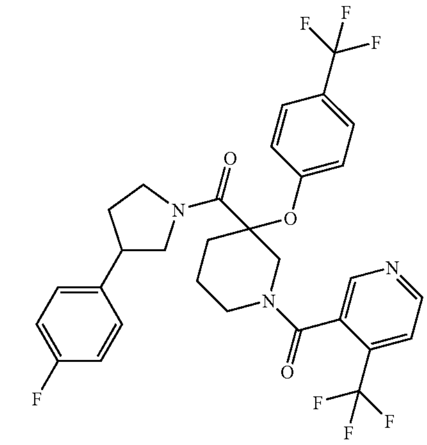 | 610.23 | 5.81 |
| AQ | 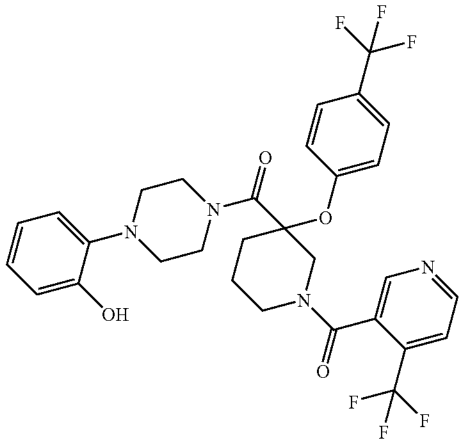 | 623.21 | 5.03 |
| AR | 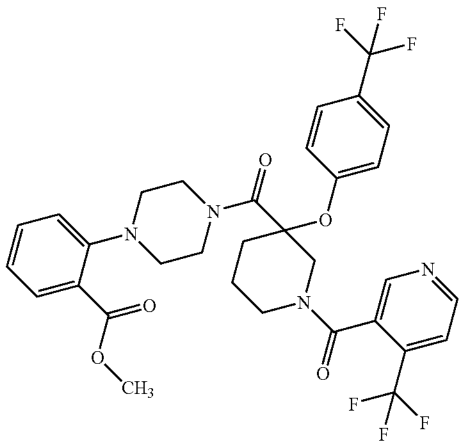 | 665.2 | 5.60 |

TABLE 1-continued
| Compound No. Sch ID | Molstructure | Observed M + H | Retention Time (min) |
|---|---|---|---|
| AS | 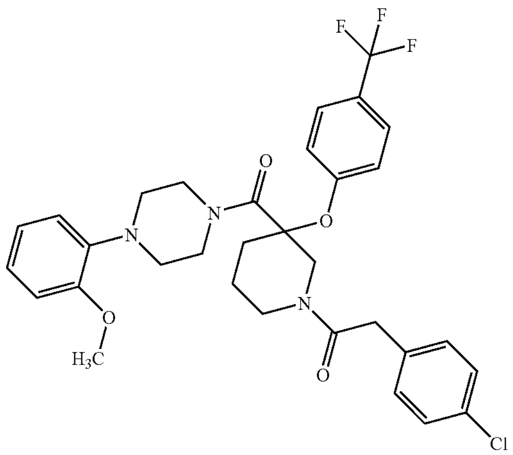 | 616.38 | 6.33 |
| AT | 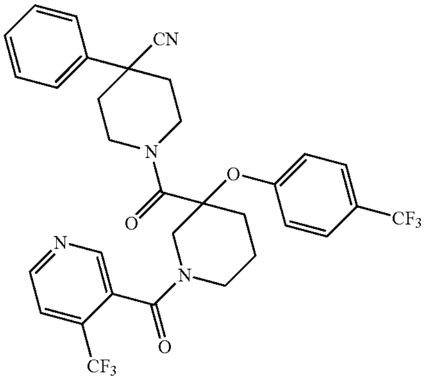 | 631.19 | 6.12 |
| AU | 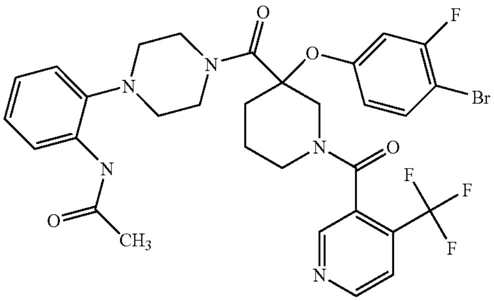 | 692.05 | 5.52 |
| AV | 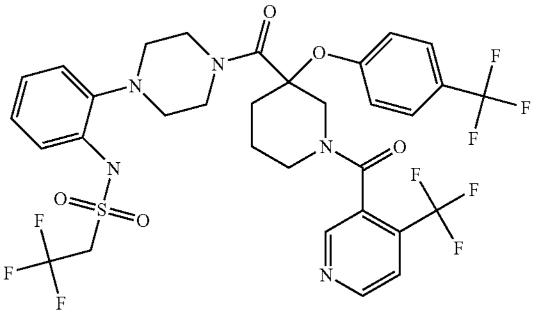 | 768.1 | 2.21 |

TABLE 1-continued
| Compound No. Sch ID | Molstructure | Observed M + H | Retention Time (min) |
|---|---|---|---|
| AW | 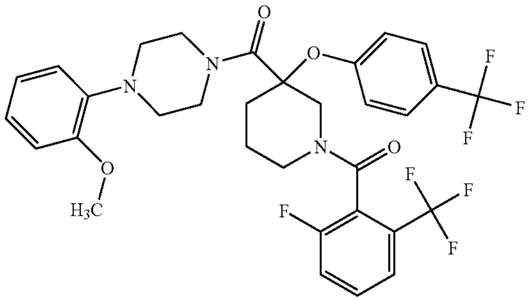 | 654.36 | 6.09 |
| AX | 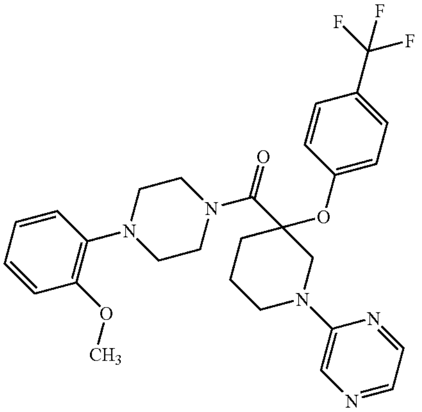 | 542.3 | N/A |
| AY | 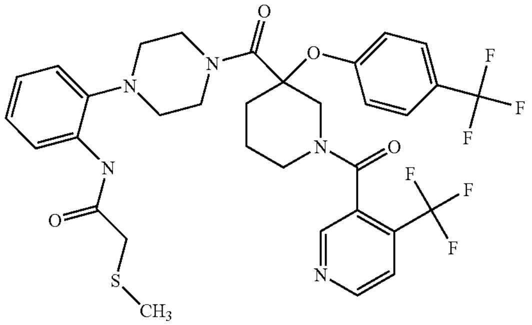 | 710.1 | 5.42 |
| AZ | 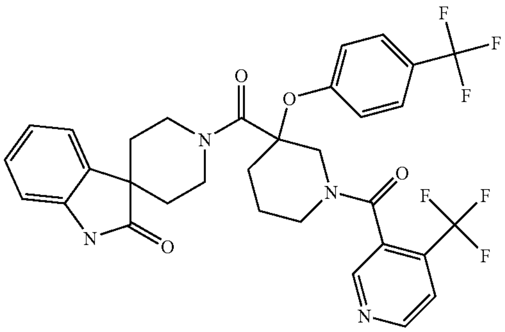 | 647.2 | 5.33 |

TABLE 1-continued
| Compound No. Sch ID | Molstructure | Observed M + H | Retention Time (min) |
|---|---|---|---|
| BA | 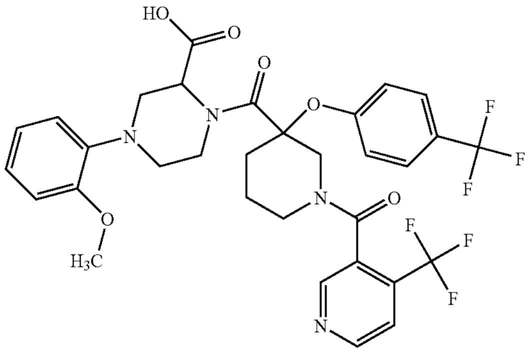 | 681.4 | 5.43 |
| BB | 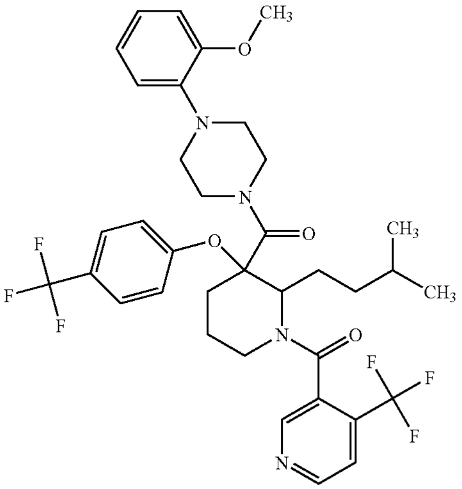 | 707.34 | 6.49 |
| BC | 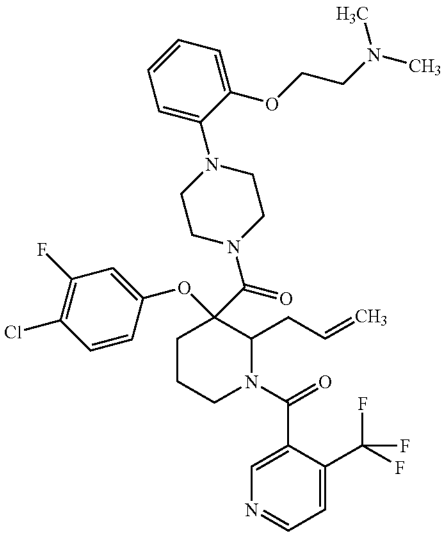 | 718.3 | 5.03 |

TABLE 1-continued
| Compound No. Sch ID | Molstructure | Observed M + H | Retention Time (min) |
|---|---|---|---|
| BD | 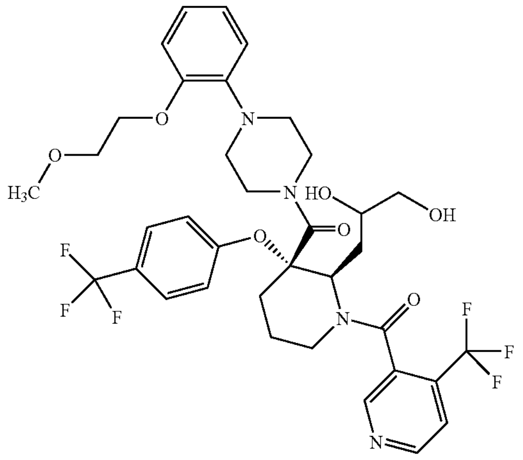 | 755.2 | 1.98 |
| BE | 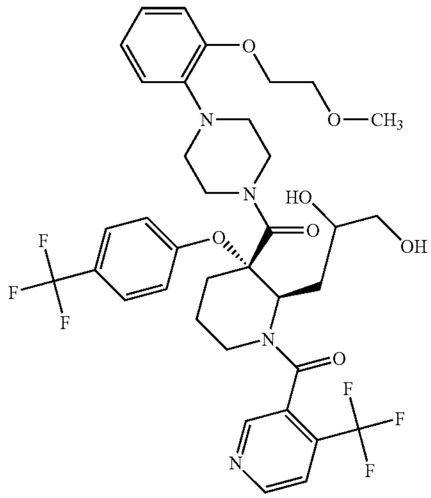 | 755.1 | 4.75 |
| BF | 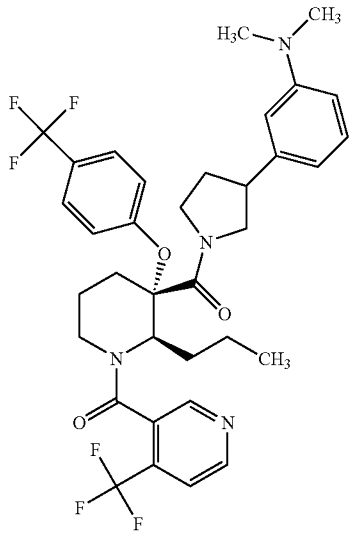 | 677 | 7.47 |

TABLE 1-continued
| Compound No. Sch ID | Molstructure | Observed M + H | Retention Time (min) |
|---|---|---|---|
| BG | 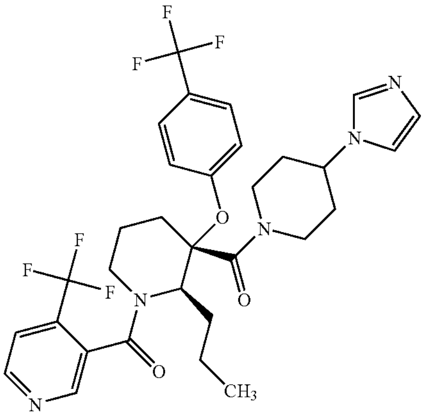 | 638.2 | 4.03 |
| BH | 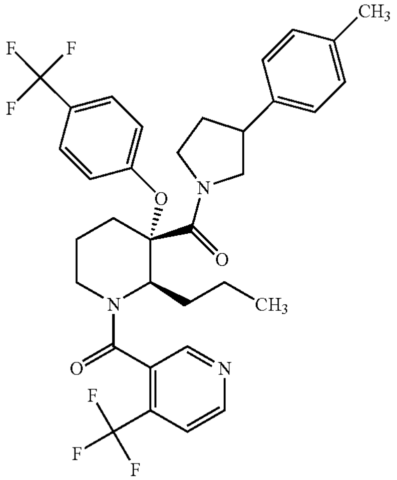 | 668 | 8.52 |
| BI | 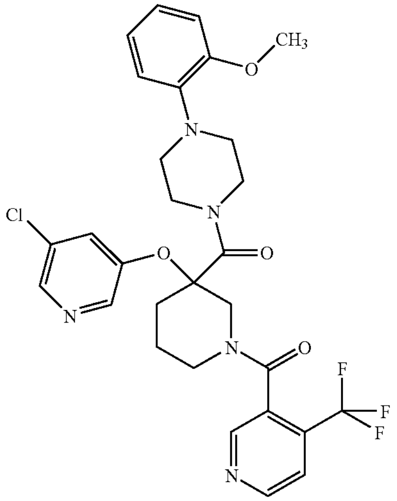 | 604.3 | 6.71 |

TABLE 1-continued
| Compound No. Sch ID | Molstructure | Observed M + H | Retention Time (min) |
|---|---|---|---|
| BJ | 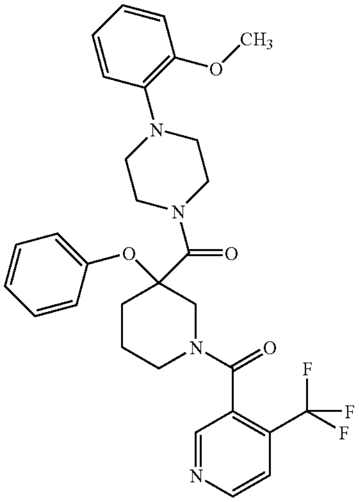 | 569.3 | 3.65 |
| BK | 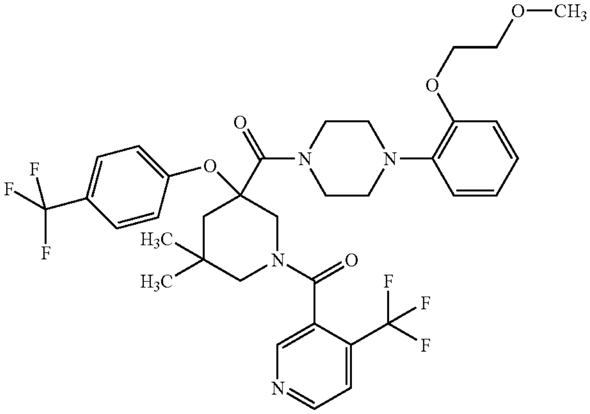 | 709.4 | 4.36 |
| BL | 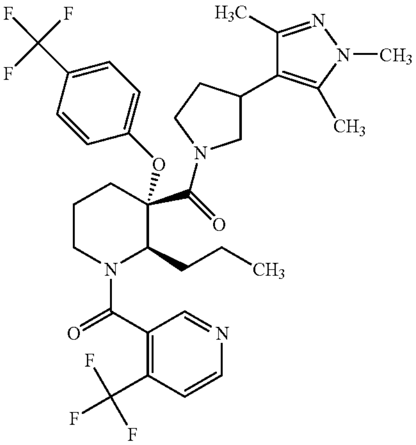 | 666 | 6.07 |

TABLE 1-continued
| Compound No. Sch ID | Molstructure | Observed M + H | Retention Time (min) |
|---|---|---|---|
| BM | 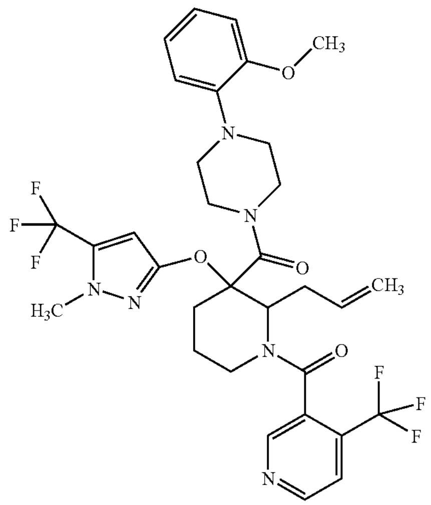 | 681.4 | 4.08 |
| BN | 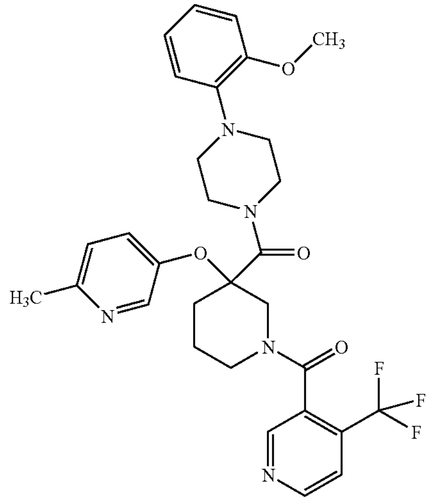 | 584.3 | 2.77 |
| BO | 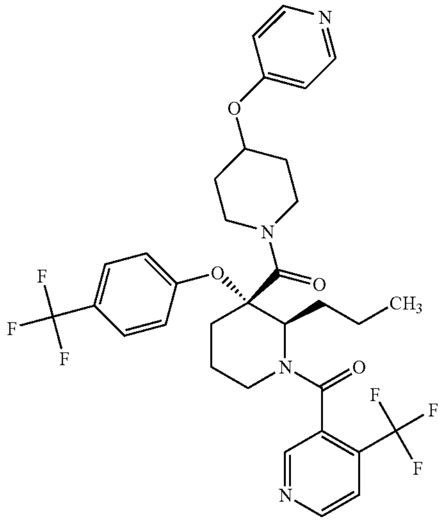 | 665.6 | 4.00 |

TABLE 1-continued
| Compound No. Sch ID | Molstructure | Observed M + H | Retention Time (min) |
|---|---|---|---|
| BP | 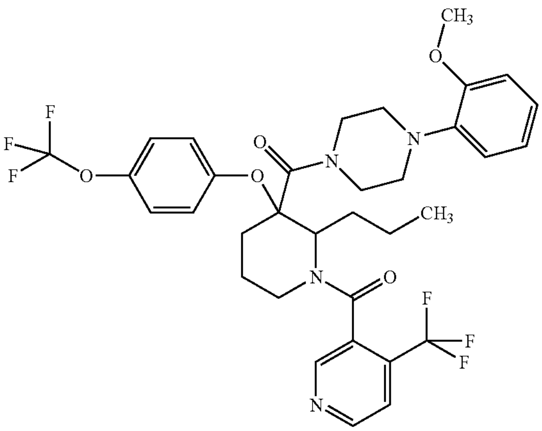 | 695.4 | 4.69 |
| BQ | 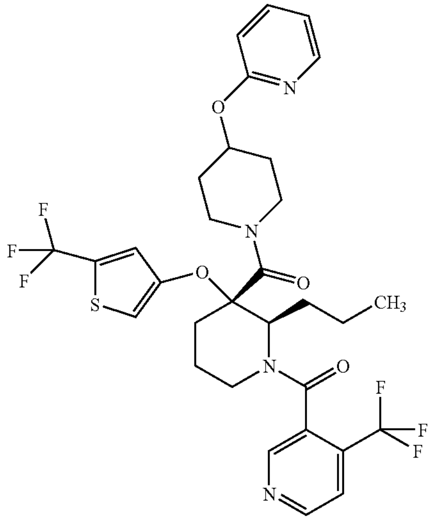 | 671.4 | 4.67 |
| BR | 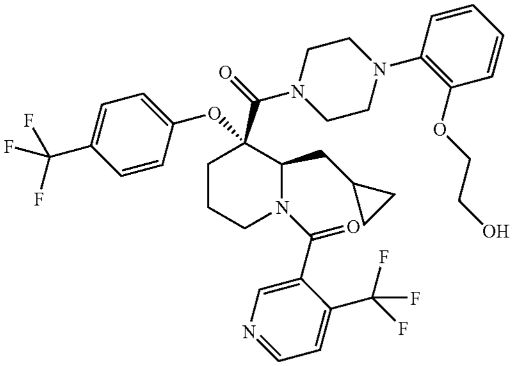 | 721.3 | N/A |

TABLE 1-continued
| Compound No. Sch ID | Molstructure | Observed M + H | Retention Time (min) |
| --- | --- | --- | --- |
| BS | 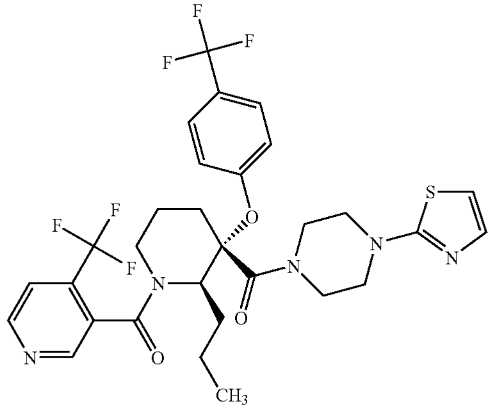 | 656.3 | 4.18 |
| BT | 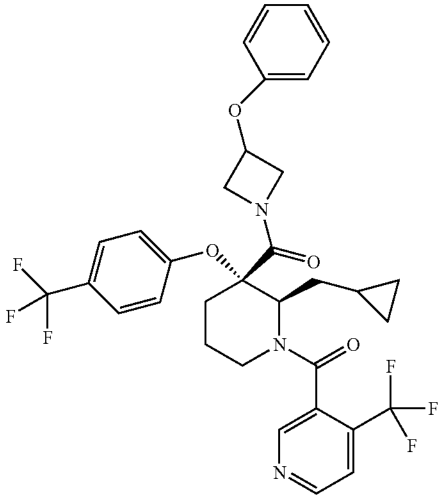 | 648.4 | 5.03 |
| BU | 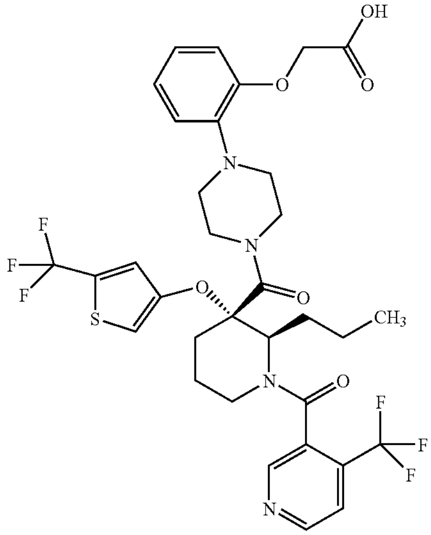 | 729.4 | 4.31 |

TABLE 1-continued
| Compound No. Sch ID | Molstructure | Observed M + H | Retention Time (min) |
|---|---|---|---|
| BV | 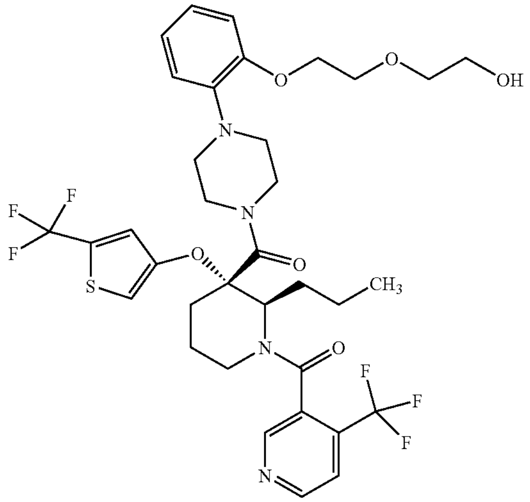 | 759.3 | N/A |
| BW | 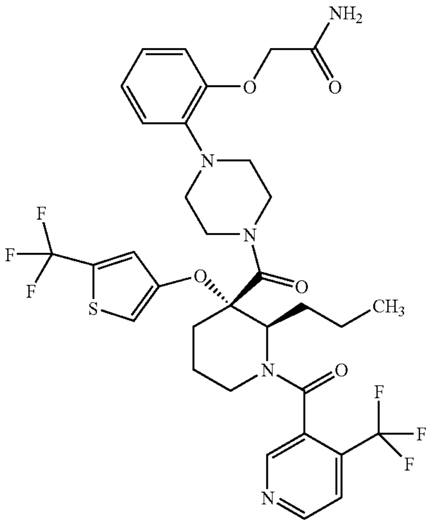 | 728.4 | 4.21 |
| BX | 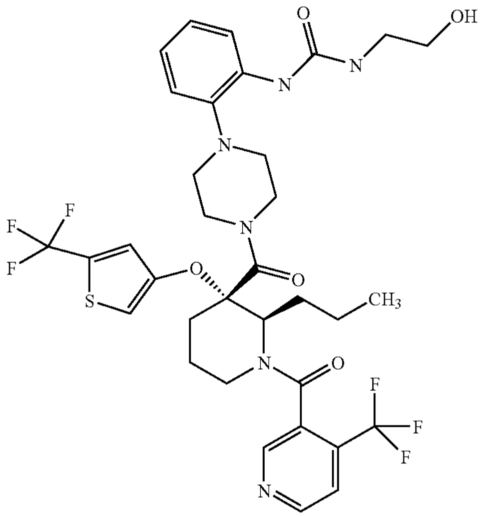 | 757.4 | 4.28 |

TABLE 1-continued
| Compound No. Sch ID | Molstructure | Observed M + H | Retention Time (min) |
|---|---|---|---|
| BY | 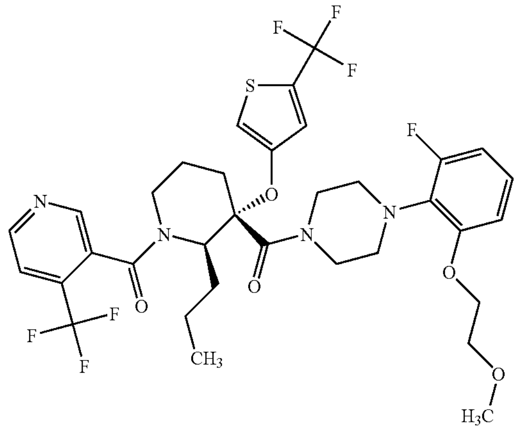 | 747.4 | 5.37 |
| BZ | 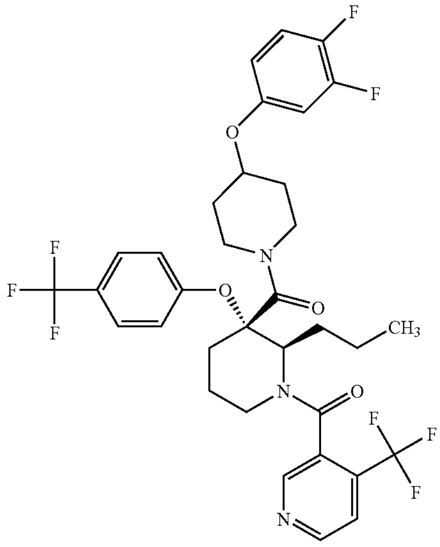 | 700.3 | 7.15 |

TABLE 1-continued
| Compound No. Sch ID | Molstructure | Observed M + H | Retention Time (min) |
|---|---|---|---|
| CA | 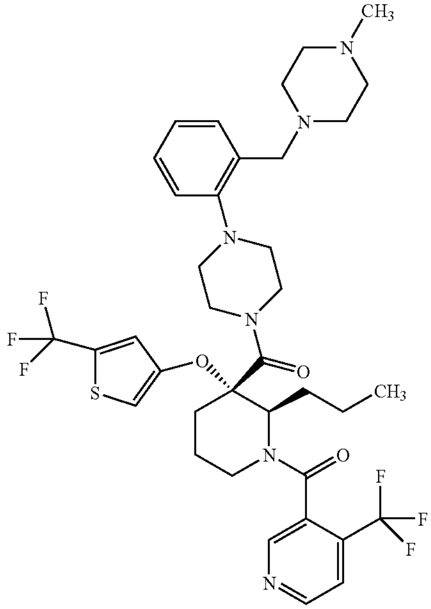 | 767.4 | 2.94 |
| CB | 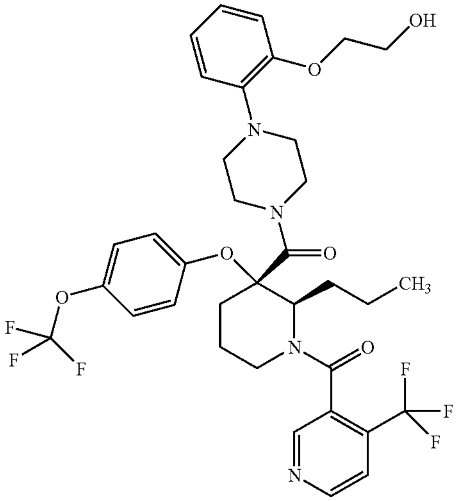 | 725.4 | 4.09 |
| CC | 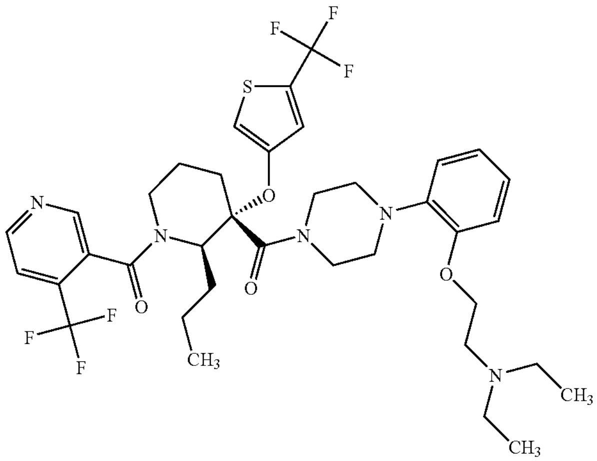 | 770.5 | 4.39 |

TABLE 1-continued
| Compound No. Sch ID | Molstructure | Observed M + H | Retention Time (min) |
|---|---|---|---|
| CD | 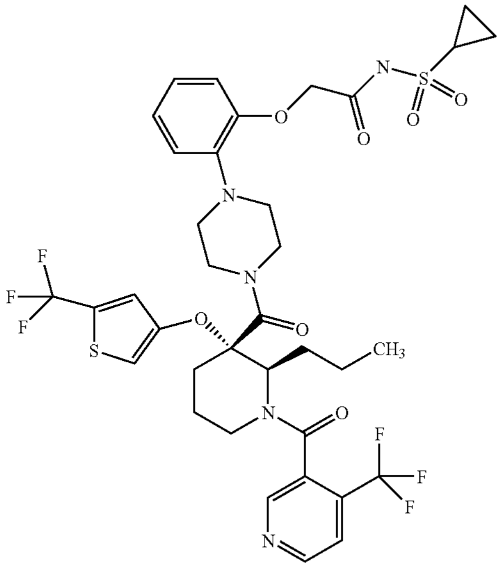 | 832.5 | 4.81 |
| CE | 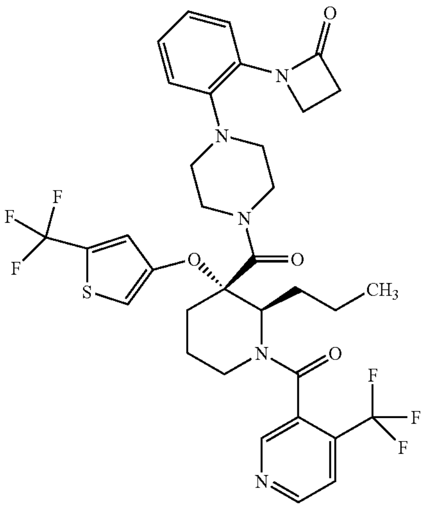 | 724.4 | 5.00 |

TABLE 1-continued
| Compound No. Sch ID | Molstructure | Observed M + H | Retention Time (min) |
|---|---|---|---|
| CF | 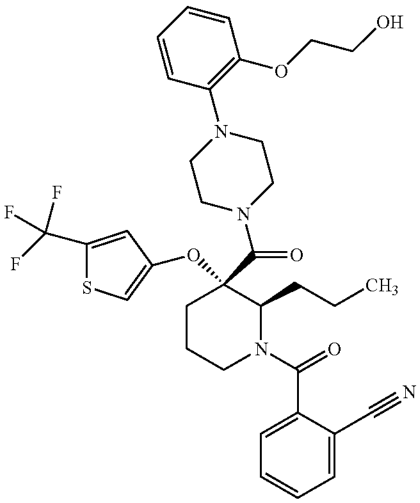 | 671.4 | 4.19 |
| CG | 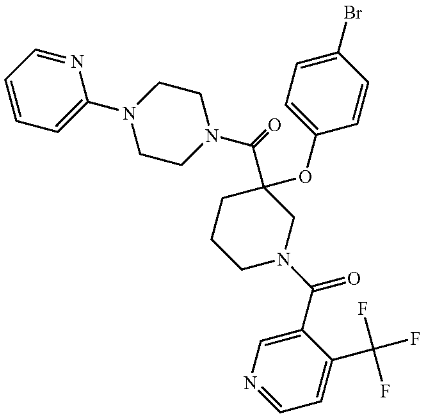 | 618.21 | 4.00 |
| CH | 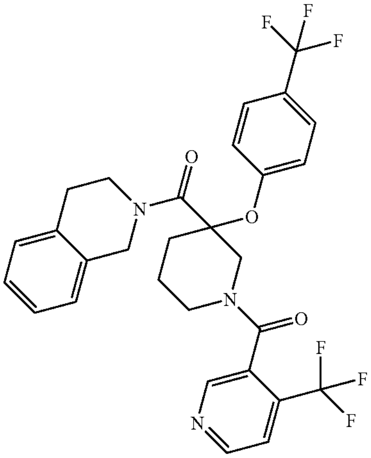 | 578.23 | 5.07 |

TABLE 1-continued
| Compound No. Sch ID | Molstructure | Observed M + H | Retention Time (min) |
|---|---|---|---|
| CI | 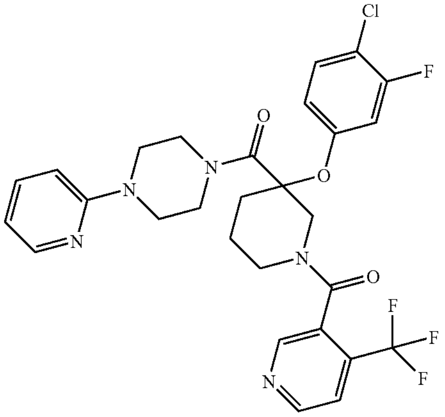 | 592.21 | 3.81 |
| CJ | 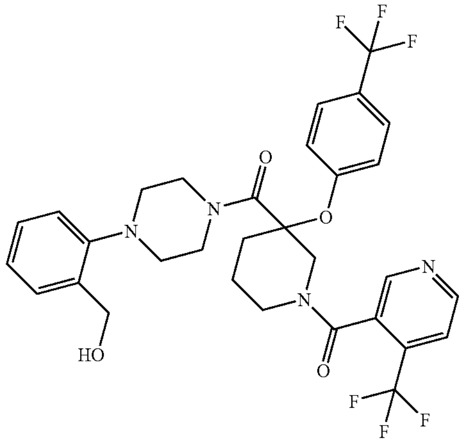 | 637.32 | 5.45 |
| CK | 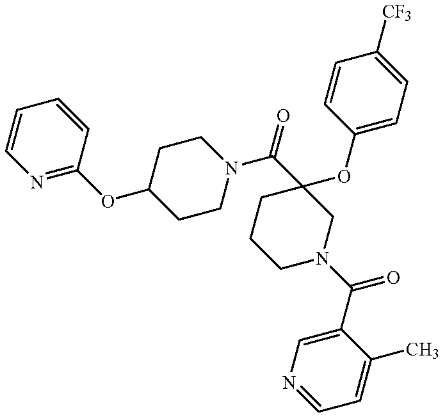 | 623.22 | 6.99 |

TABLE 1-continued
| Compound No. Sch ID | Molstructure | Observed M + H | Retention Time (min) |
|---|---|---|---|
| CL | 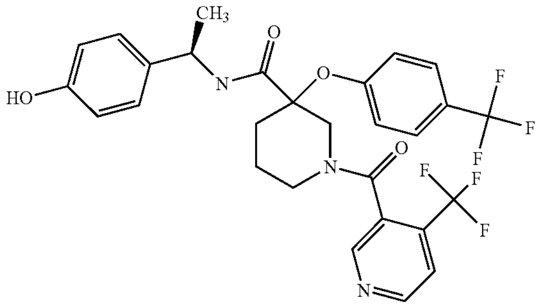 | 582.1 | 1.86 |
| CM | 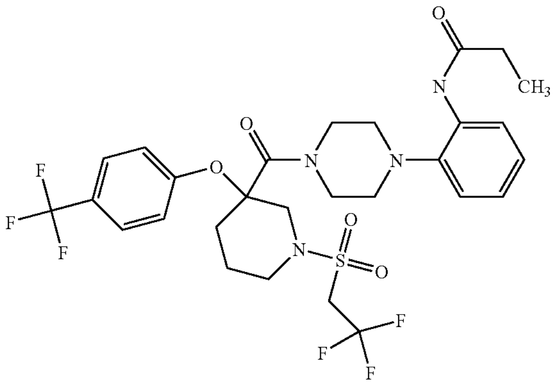 | 651.2 | 2.18 |
| CN | 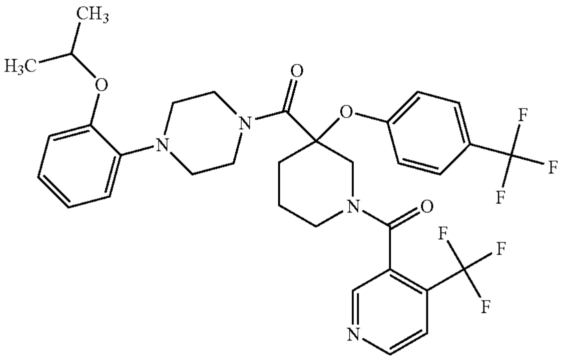 | 665.23 | 6.28 |
| CO | 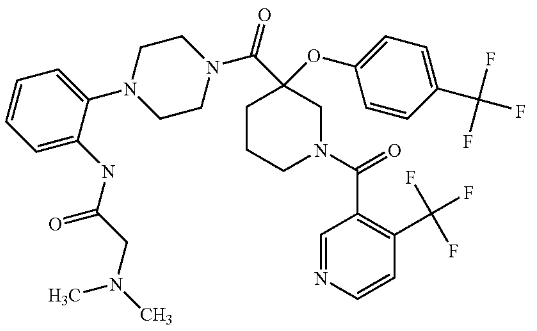 | 707.30 | 4.54 |

TABLE 1-continued
| Compound No. Sch ID | Molstructure | Observed M + H | Retention Time (min) |
|---|---|---|---|
| CP | 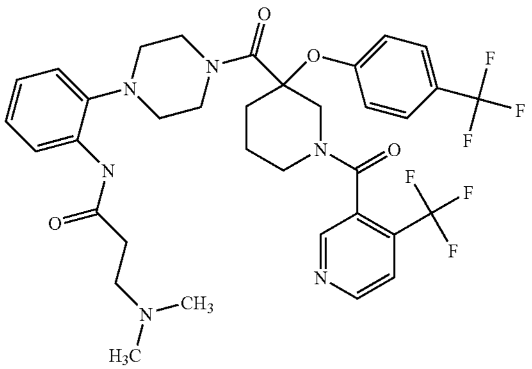 | 721.20 | 4.42 |
| CQ | 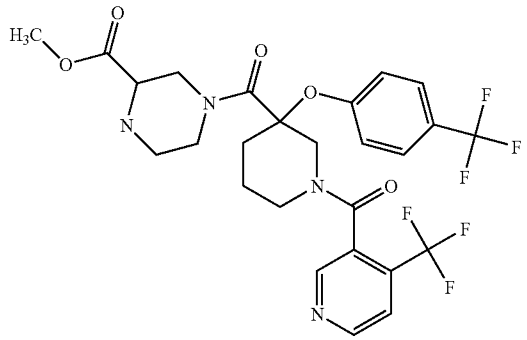 | 589.2 | 3.86 |
| CR | 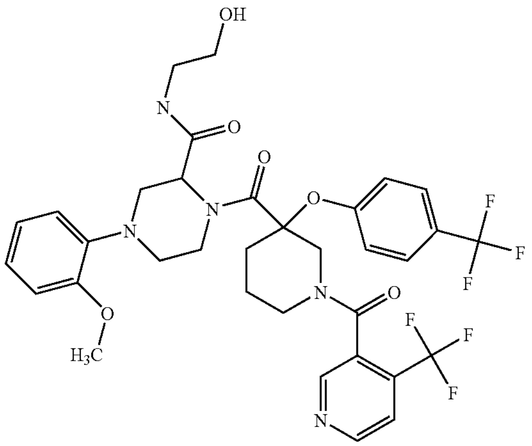 | 724.2 | N/A |

TABLE 1-continued
| Compound No. Sch ID | Molstructure | Observed M + H | Retention Time (min) |
|---|---|---|---|
| CS | 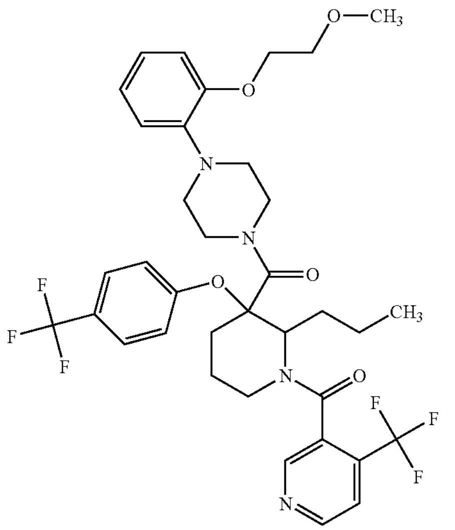 | 723.2 | 5.73 |
| CT | 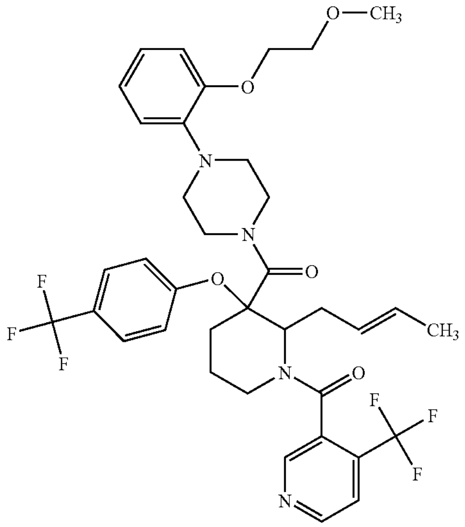 | 735.4 | 5.96 |
| CU | 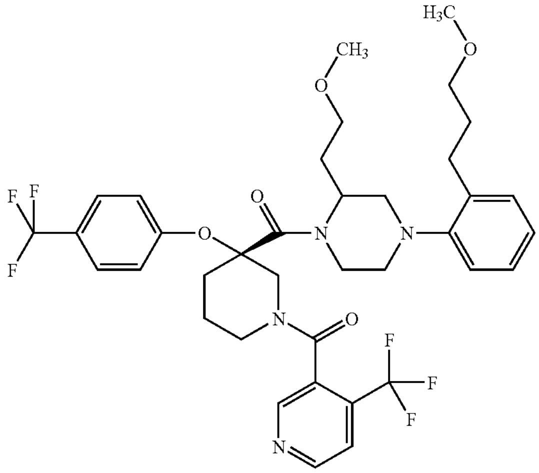 | 739.2 | 5.78 |

TABLE 1-continued
| Compound No. Sch ID | Molstructure | Observed M + H | Retention Time (min) |
|---|---|---|---|
| CV | 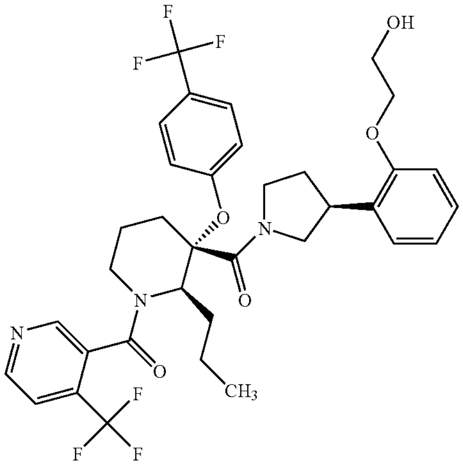 | 694.2 | 5.26 |
| CW | 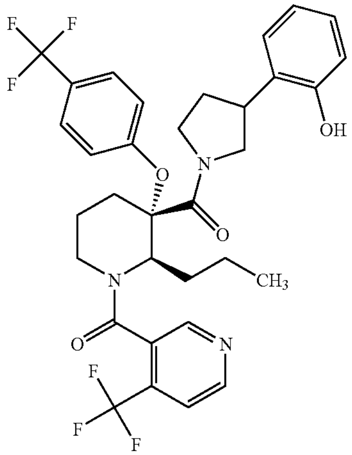 | 650 | 7.47 |
| CX | 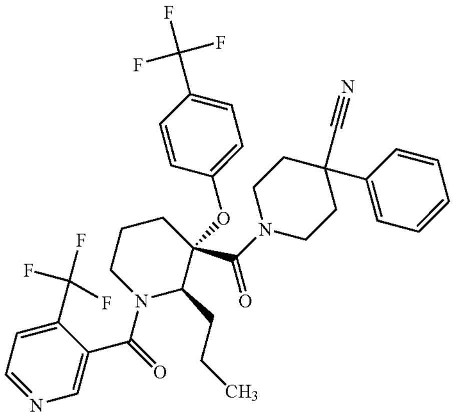 | 673.28 | 5.45 |

TABLE 1-continued
| Compound No. Sch ID | Molstructure | Observed M + H | Retention Time (min) |
| --- | --- | --- | --- |
| CY | 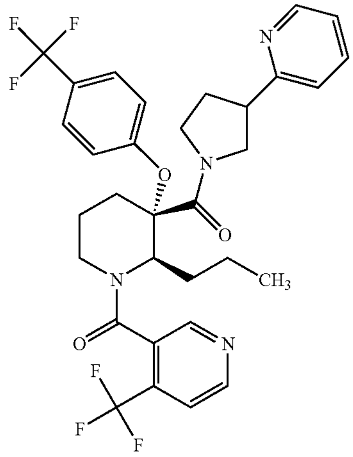 | 635 | 5.56 |
| CZ | 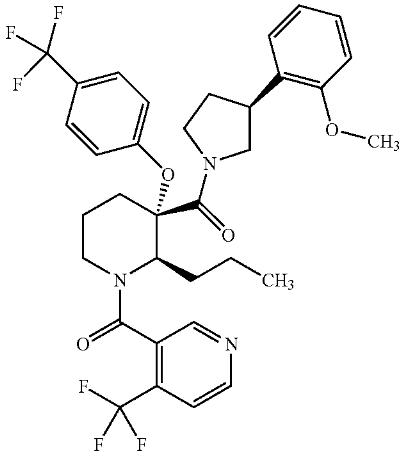 | 664 | 8.28 |
| DA | 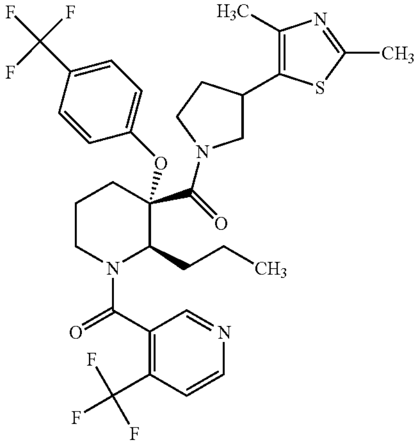 | 669 | 6.09 |

TABLE 1-continued
| Compound No. Sch ID | Molstructure | Observed M + H | Retention Time (min) |
|---|---|---|---|
| DB | 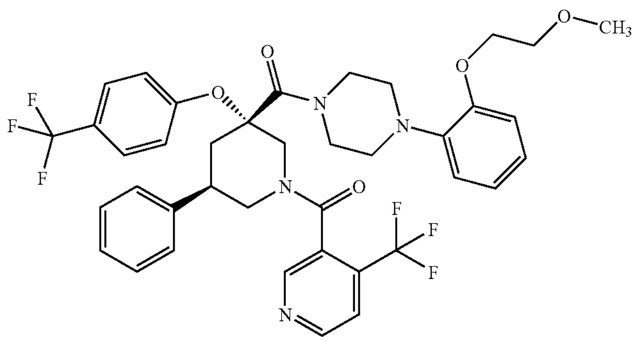 | 757.13 | N/A |
| DC | 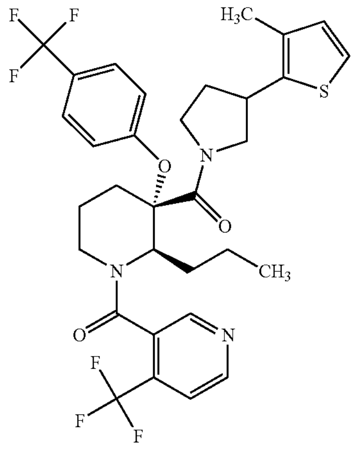 | 654 | 8.44 |
| DD | 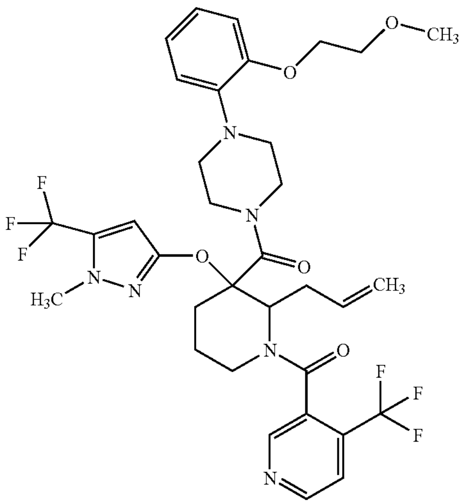 | 725.4 | 3.97 |

TABLE 1-continued
| Compound No. Sch ID | Molstructure | Observed M + H | Retention Time (min) |
|---|---|---|---|
| DE | 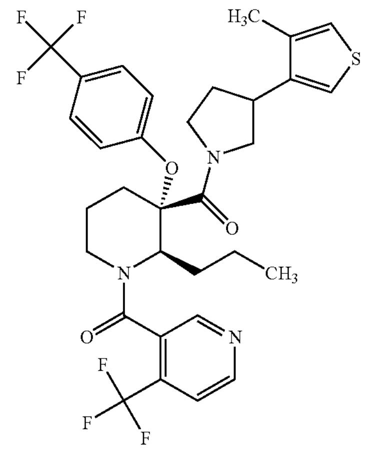 | 654 | 8.22 |
| DF | 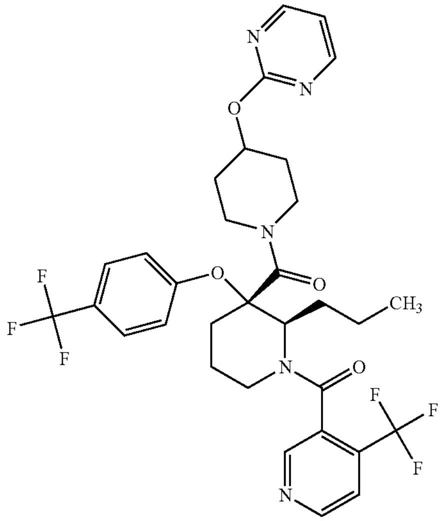 | 666.5 | 4.75 |
| DG | 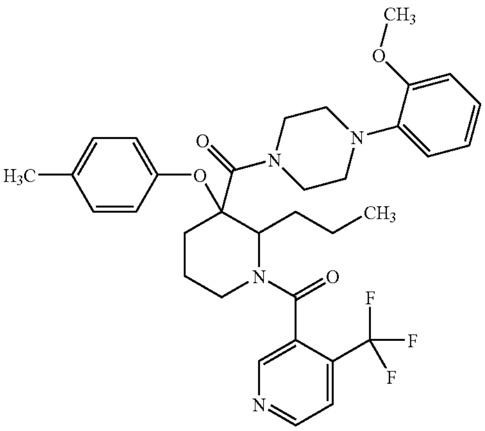 | 625.3 | 4.27 |

TABLE 1-continued
| Compound No. Sch ID | Molstructure | Observed M + H | Retention Time (min) |
|---|---|---|---|
| DH | 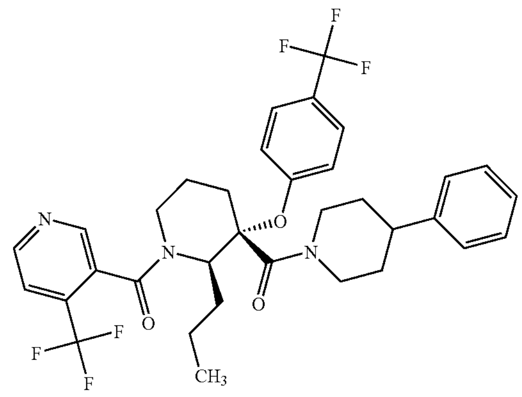 | 648.6 | 5.44 |
| DI | 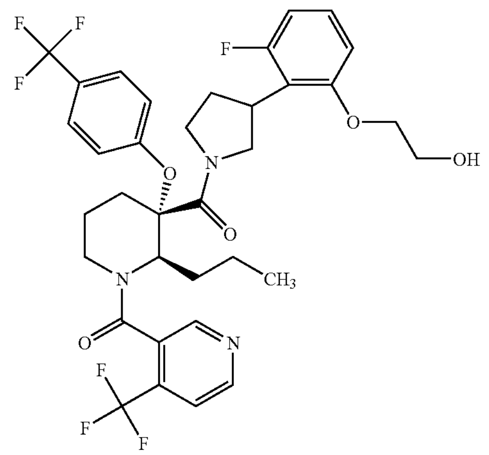 | 712 | 8.35 |
| DJ | 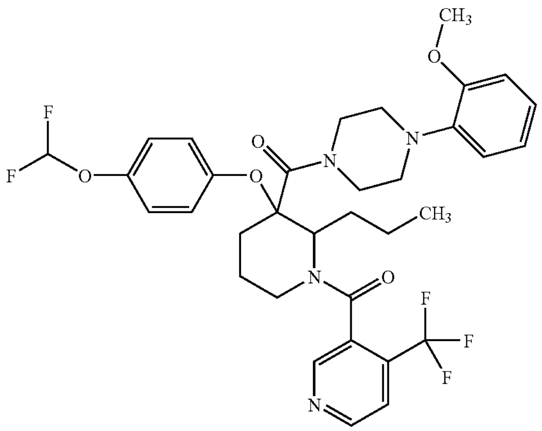 | 677.4 | 4.33 |

TABLE 1-continued
| Compound No. Sch ID | Molstructure | Observed M + H | Retention Time (min) |
| --- | --- | --- | --- |
| DK | 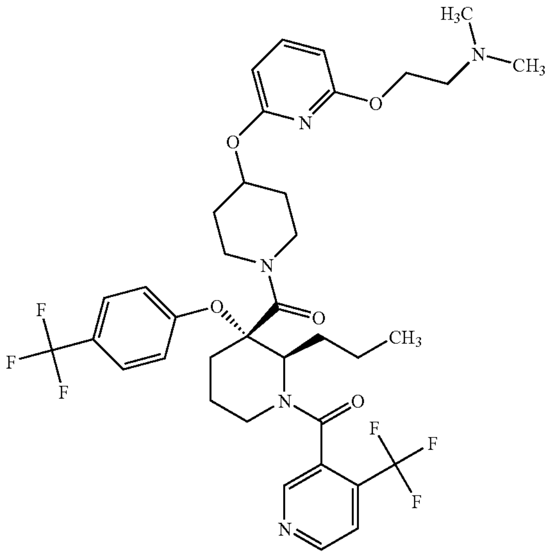 | 752.2 | 4.84 |
| DL | 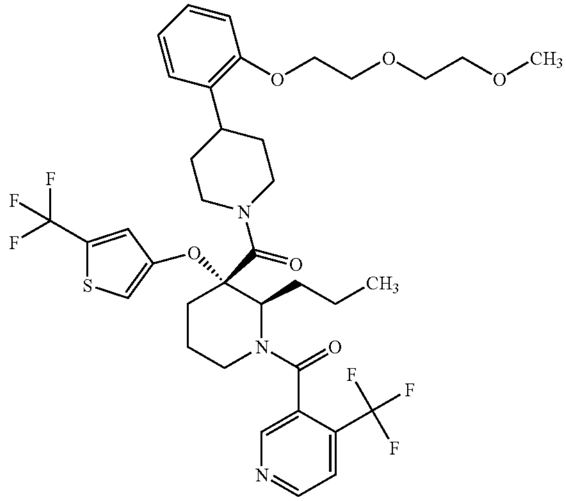 | 773.4 | 4.45 |
| DM | 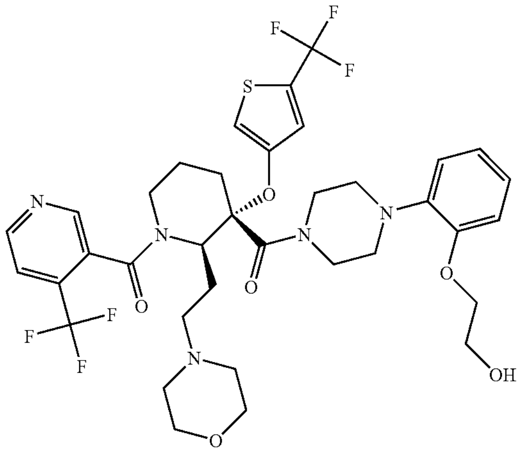 | 786.4 | 4.11 |

TABLE 1-continued
| Compound No. Sch ID | Molstructure | Observed M + H | Retention Time (min) |
|---|---|---|---|
| DN | 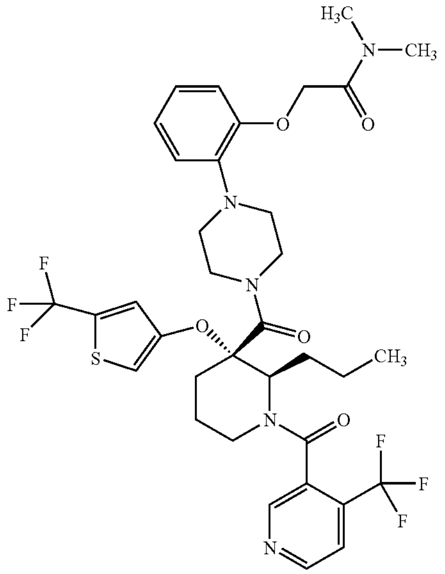 | 756.4 | 3.88 |
| DO | 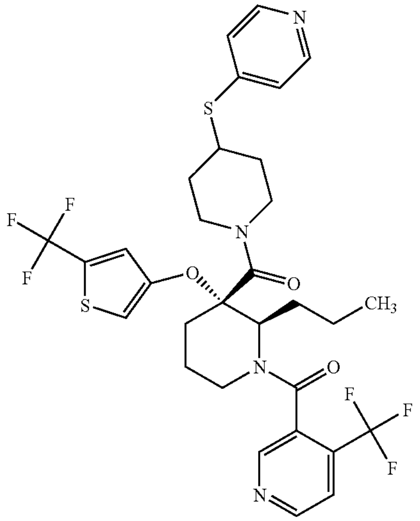 | 687.1 | 4.49 |
| DP | 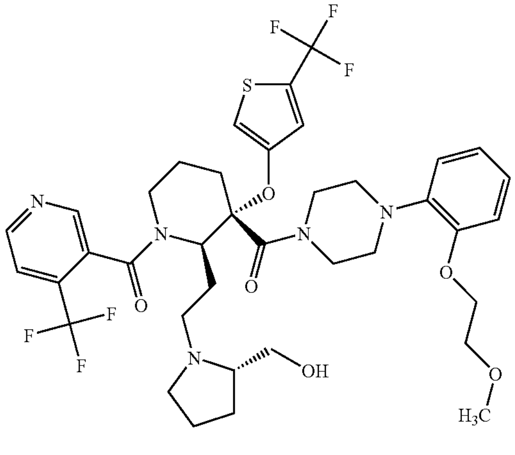 | 814.5 | 4.40 |

TABLE 1-continued
| Compound No. Sch ID | Molstructure | Observed M + H | Retention Time (min) |
|---|---|---|---|
| DQ | 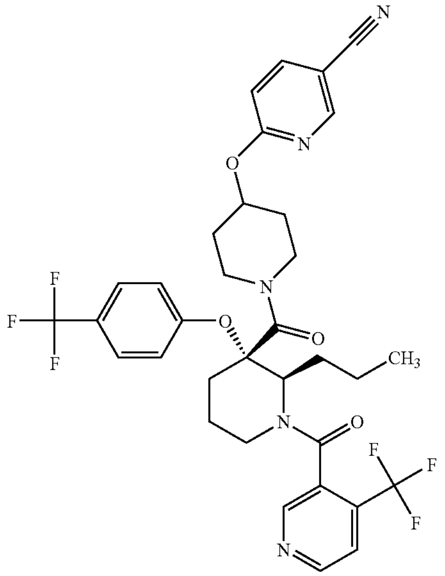 | 690.3 | 6.66 |
| DR | 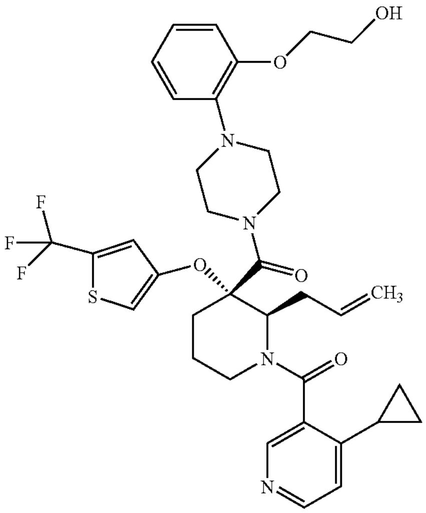 | 685.4 | 3.28 |

TABLE 1-continued
| Compound No. Sch ID | Molstructure | Observed M + H | Retention Time (min) |
|---|---|---|---|
| DS | 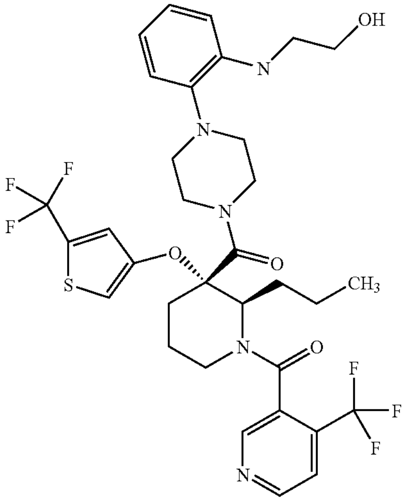 | 714.4 | 3.89 |
| DT | 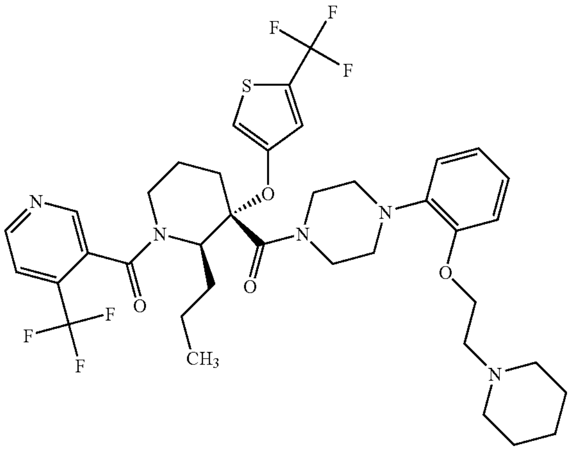 | 782.5 | 4.41 |
| DU | 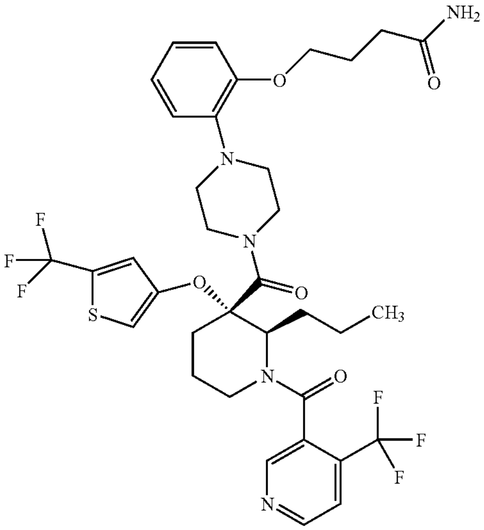 | 756.4 | 4.08 |

TABLE 1-continued
| Compound No. Sch ID | Molstructure | Observed M + H | Retention Time (min) |
|---|---|---|---|
| DV | 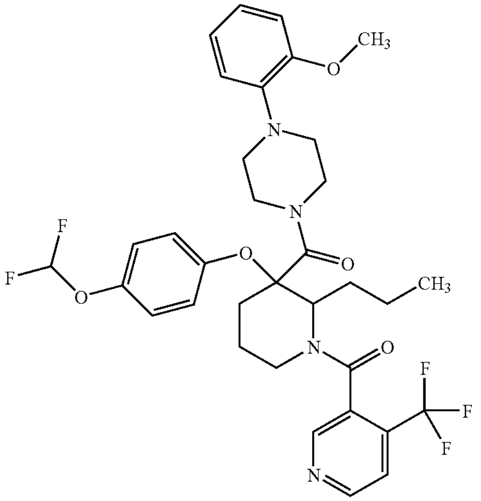 | 677.4 | 4.33 |
| DW | 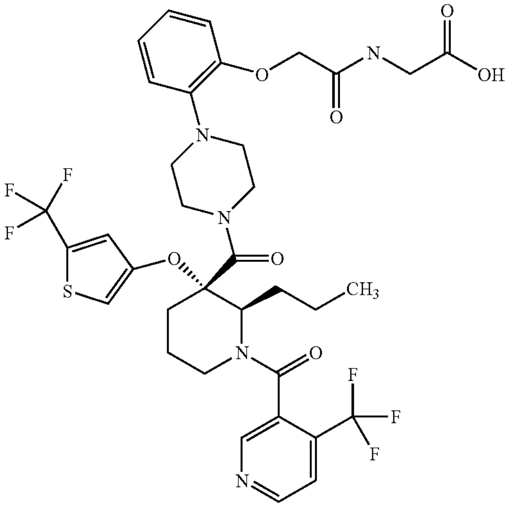 | 786.22 | 4.15 |
| DX | 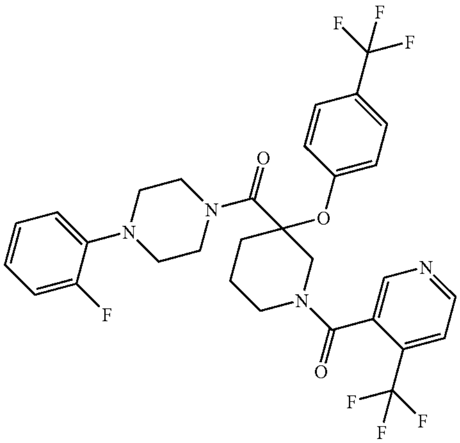 | 625.25 | 5.92 |

TABLE 1-continued
| Compound No. Sch ID | Molstructure | Observed M + H | Retention Time (min) |
|---|---|---|---|
| DY | 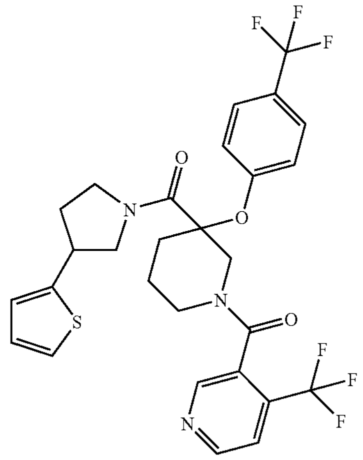 | 598.22 | 5.64 |
| DZ | 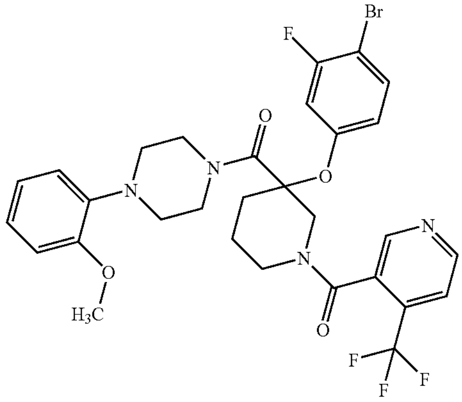 | 665.15 | 5.25 |
| EA | 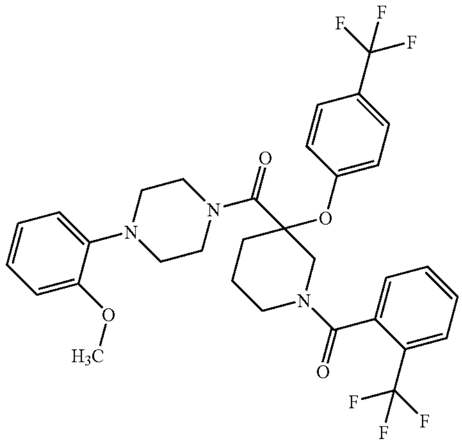 | 636.36 | 6.28 |

TABLE 1-continued
| Compound No. Sch ID | Molstructure | Observed M + H | Retention Time (min) |
|---|---|---|---|
| EB | 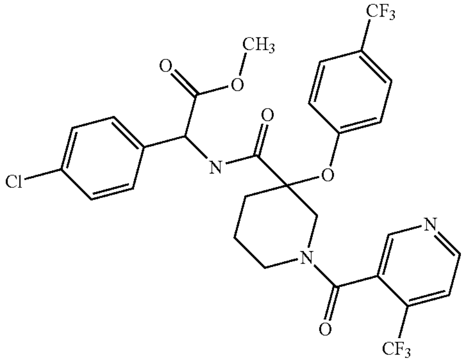 | 644.28 | 6.08, 6.19 |
| EC | 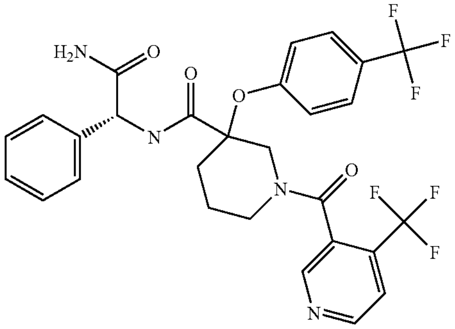 | 595.2 | 1.79 |
| ED | 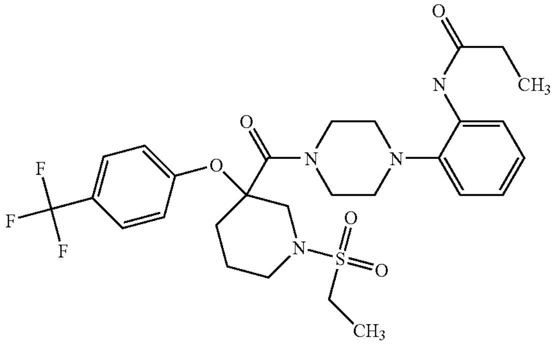 | 597.3 | 2.08 |
| EF | 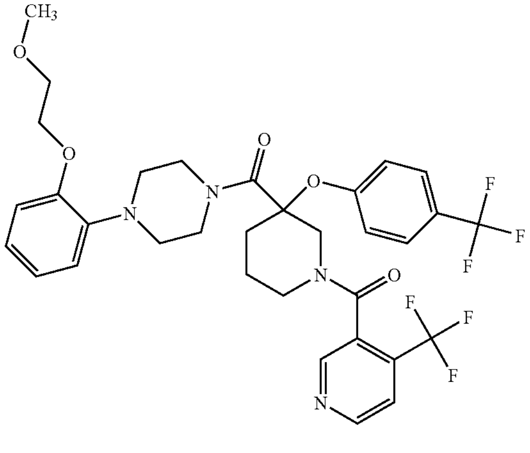 | 681.28 | 5.60 |

TABLE 1-continued
| Compound No. Sch ID | Molstructure | Observed M + H | Retention Time (min) |
|---|---|---|---|
| EG | 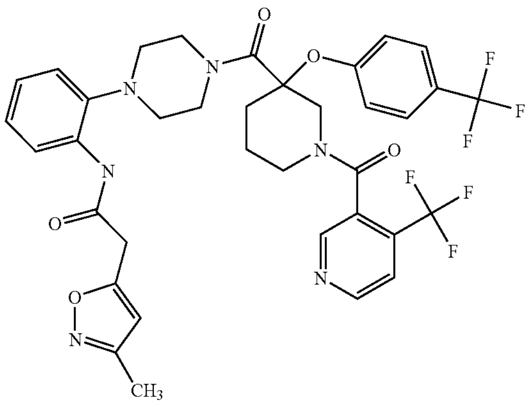 | 745.2 | 5.28 |
| EH | 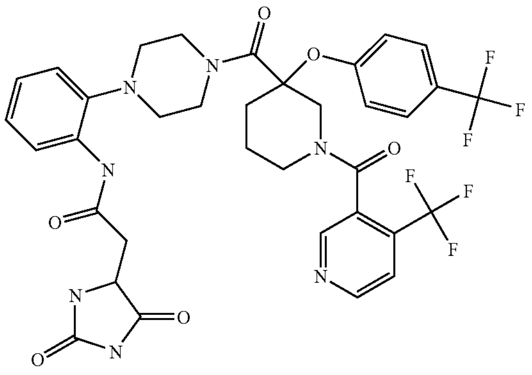 | 762.1 | 4.60 |
| EI | 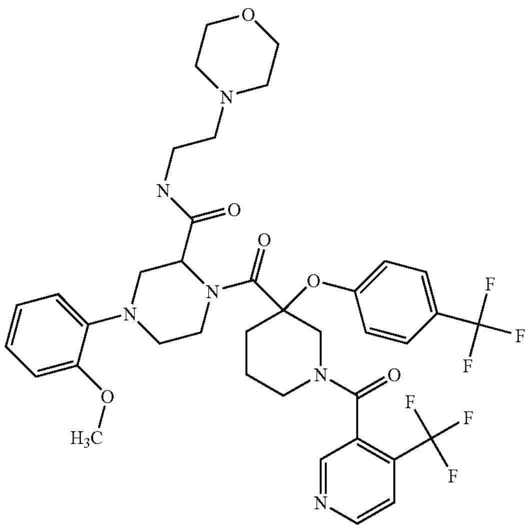 | 793.5 | 4.70 |

TABLE 1-continued
| Compound No. Sch ID | Molstructure | Observed M + H | Retention Time (min) |
|---|---|---|---|
| EJ | 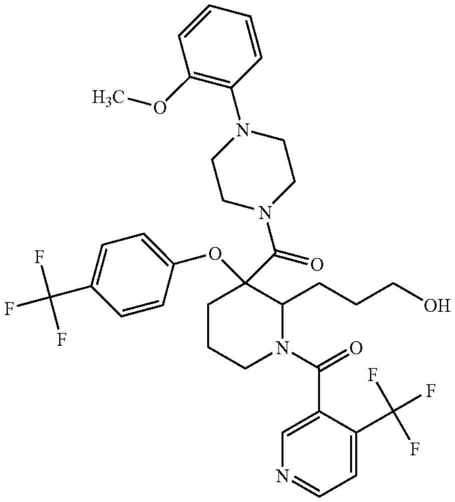 | 695.20 | 2.10 |
| EK | 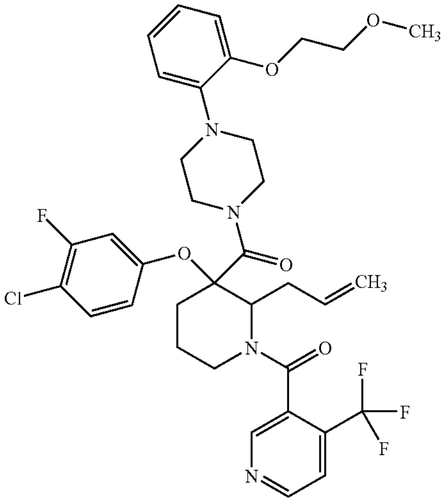 | 705.10 | 2.33 |
| EL | 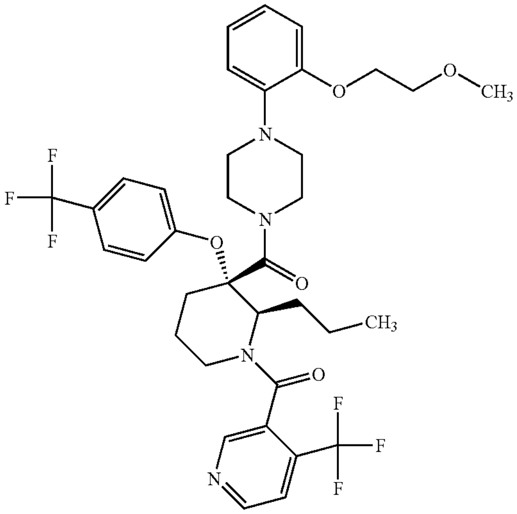 | 723.2 | 2.35 |

TABLE 1-continued
| Compound No. Sch ID | Molstructure | Observed M + H | Retention Time (min) |
|---|---|---|---|
| EM | 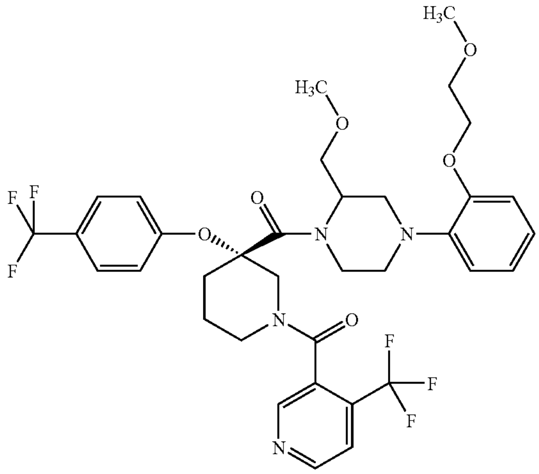 | 725.2 | 5.65 |
| EN | 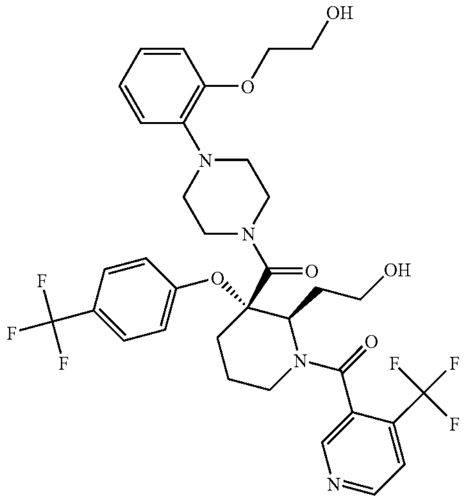 | 711.2 | 1.89 |
| EO | 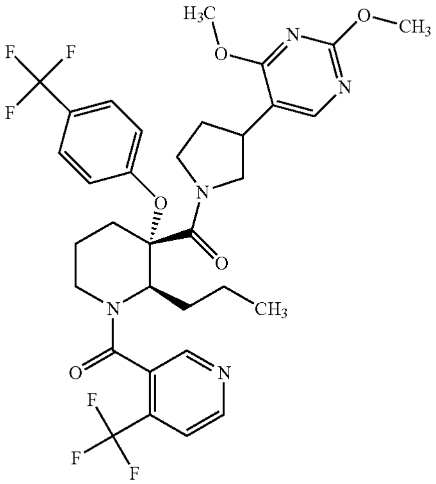 | 696 | 6.78 |

TABLE 1-continued
| Compound No. Sch ID | Molstructure | Observed M + H | Retention Time (min) |
|---|---|---|---|
| EP | 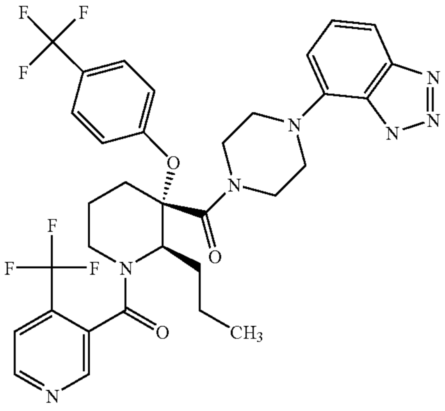 | 690.2 | 5.25 |
| EQ | 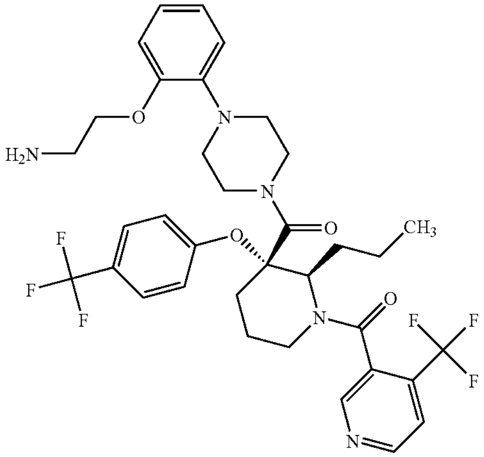 | 708.1 | 4.30 |
| ER | 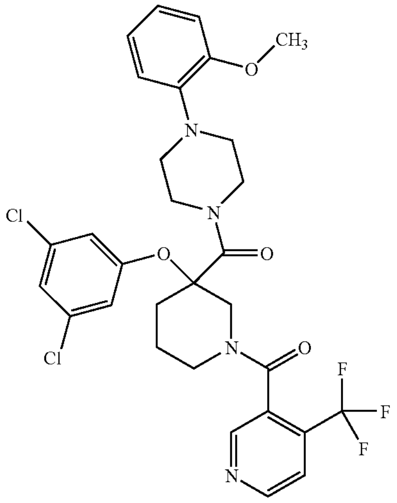 | 637.4 | 4.49 |

TABLE 1-continued
| Compound No. Sch ID | Molstructure | Observed M + H | Retention Time (min) |
|---|---|---|---|
| ES | 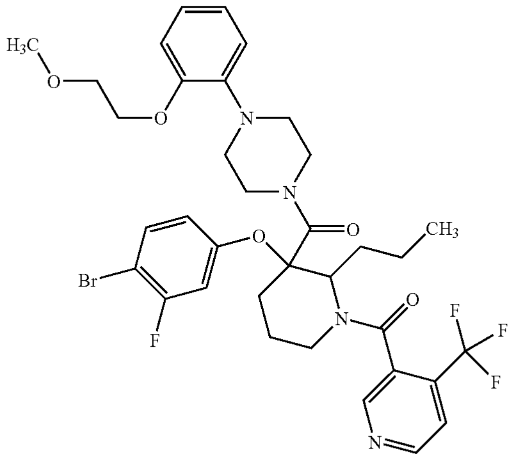 | 751.2 | 2.37 |
| ET | 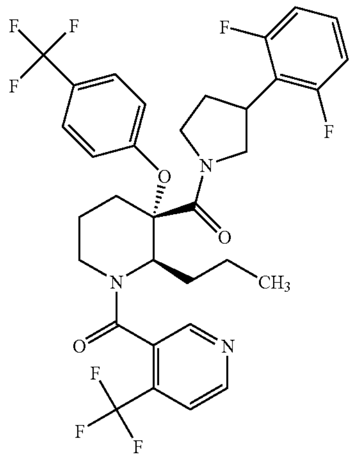 | 670 | 8.18 |
| EU | 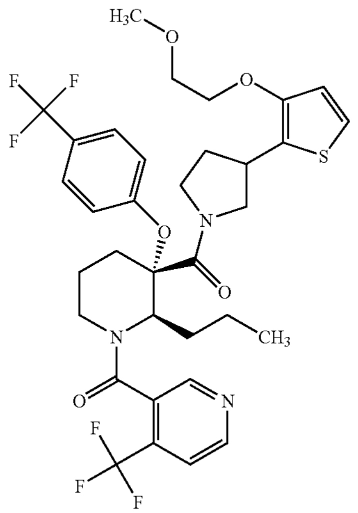 | 714 | 7.91 |

TABLE 1-continued
| Compound No. Sch ID | Molstructure | Observed M + H | Retention Time (min) |
| --- | --- | --- | --- |
| EV | 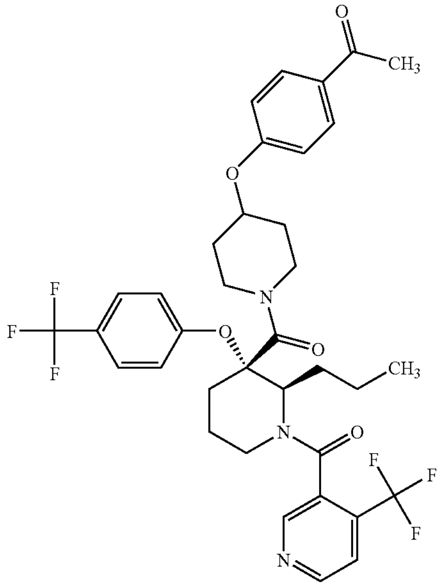 | 707.2 | 5.12 |
| EW | 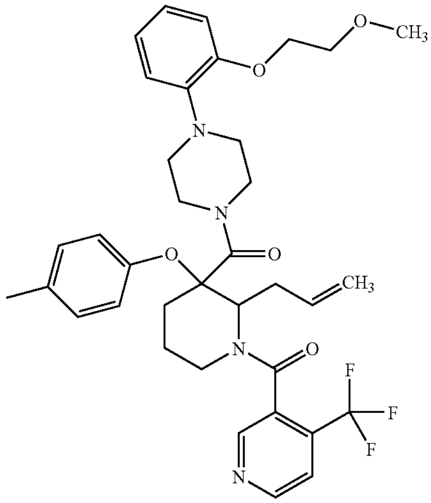 | 779.4 | 4.29 |
| EX | 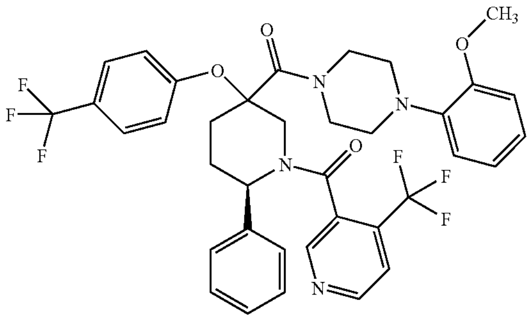 | 713.12 | N/A |

TABLE 1-continued
| Compound No. Sch ID | Molstructure | Observed M + H | Retention Time (min) |
|---|---|---|---|
| EY | 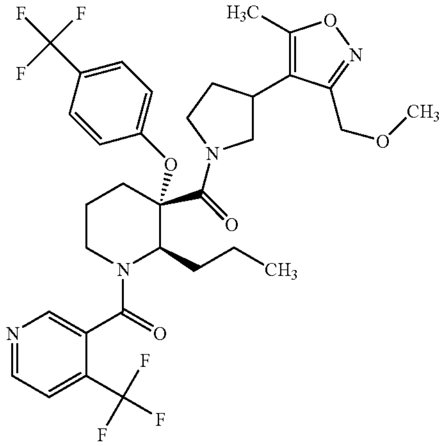 | 683 | 7.41 |
| EZ | 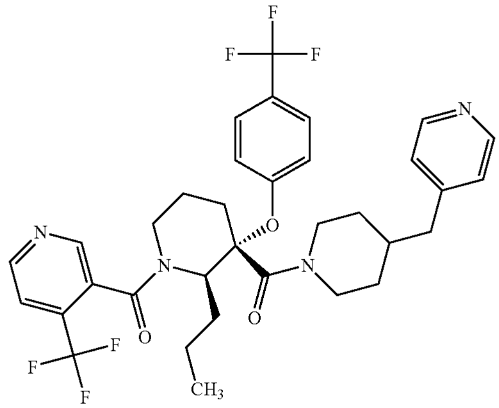 | 663.6 | 4.05 |
| FA | 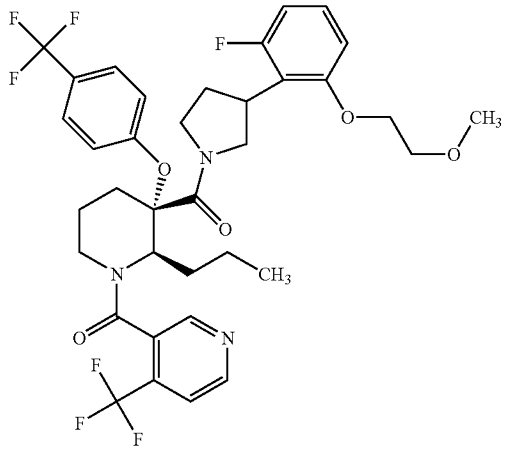 | 726 | 8.19 |

TABLE 1-continued
| Compound No. Sch ID | Molstructure | Observed M + H | Retention Time (min) |
|---|---|---|---|
| FB | 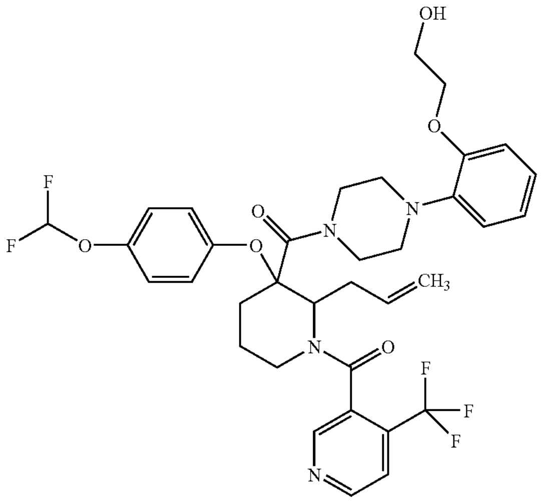 | 705.4 | 3.67 |
| FC | 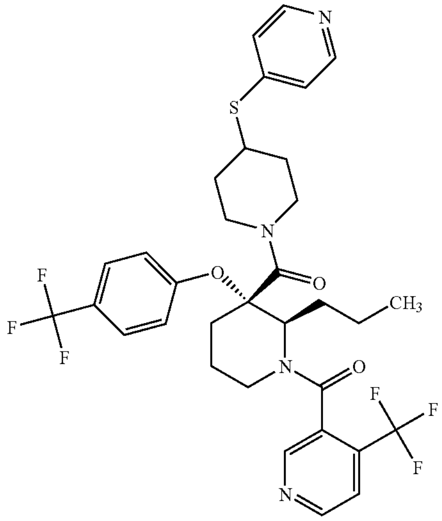 | 681.1 | 4.50 |
| FD | 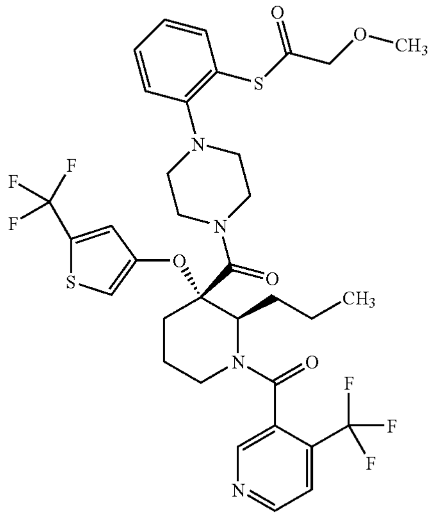 | 742.4 | 5.12 |

TABLE 1-continued
| Compound No. Sch ID | Molstructure | Observed M + H | Retention Time (min) |
|---|---|---|---|
| FE | 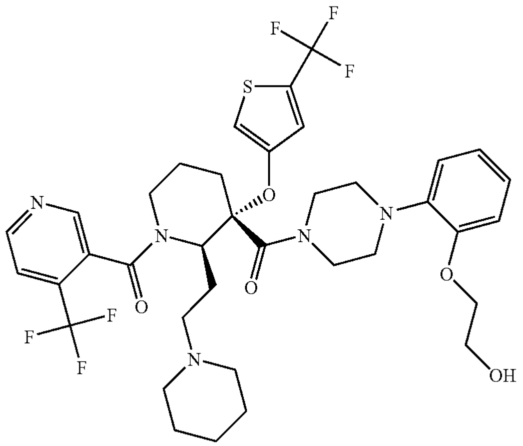 | 784.5 | 4.21 |
| FF | 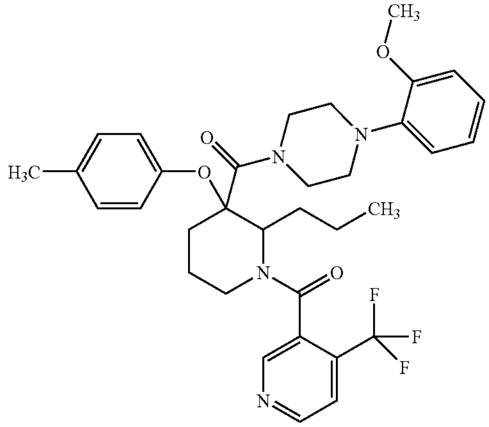 | 625.3 | 4.27 |
| FG | 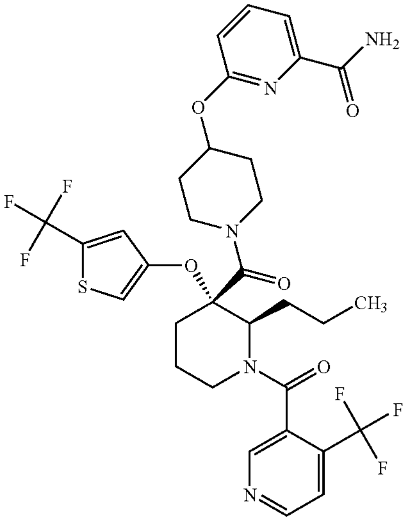 | 714.1 | 5.25 |

TABLE 1-continued
| Compound No. Sch ID | Molstructure | Observed M + H | Retention Time (min) |
|---|---|---|---|
| FH | 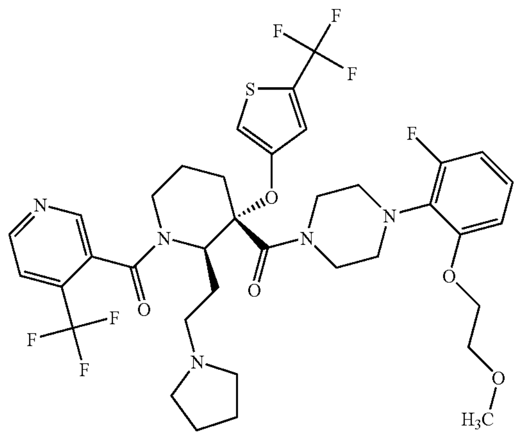 | 802.4 | 4.48 |
| FI | 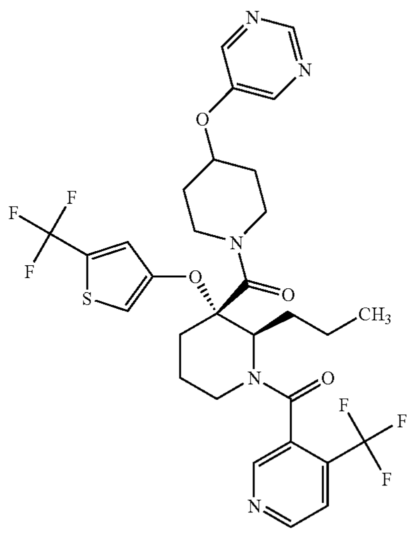 | 672.2 | 5.87 |
| FJ | 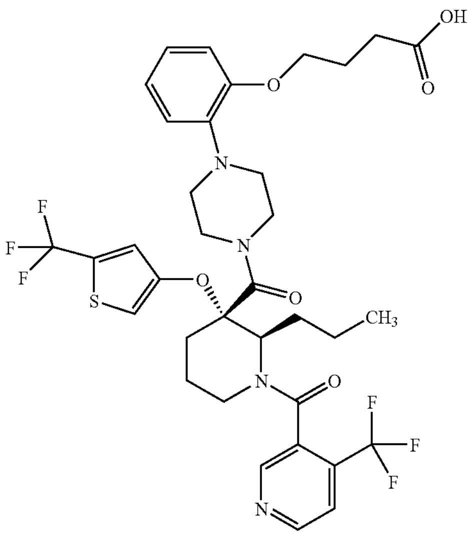 | 757.4 | 4.45 |

TABLE 1-continued
| Compound No. Sch ID | Molstructure | Observed M + H | Retention Time (min) |
|---|---|---|---|
| FK | 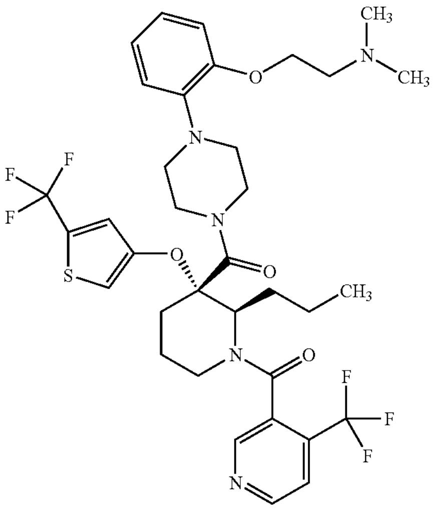 | 742.4 | 3.05 |
| FL | 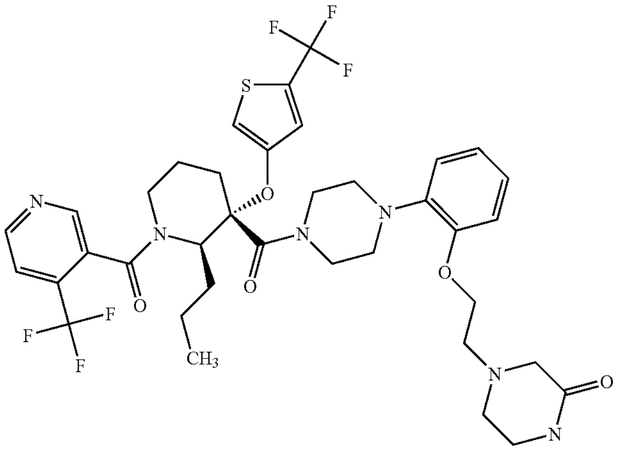 | 797.5 | 4.18 |
| FM | 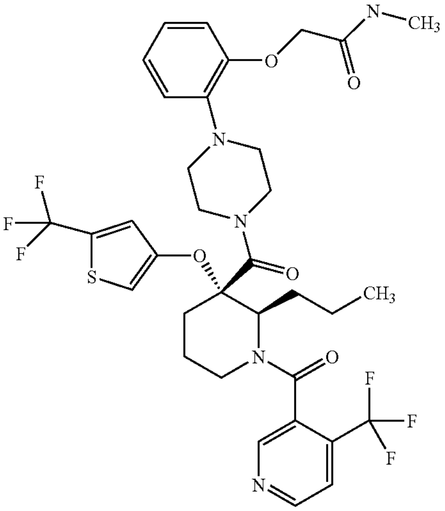 | 742.4 | 4.38 |

TABLE 1-continued
| Compound No. Sch ID | Molstructure | Observed M + H | Retention Time (min) |
|---|---|---|---|
| FN | 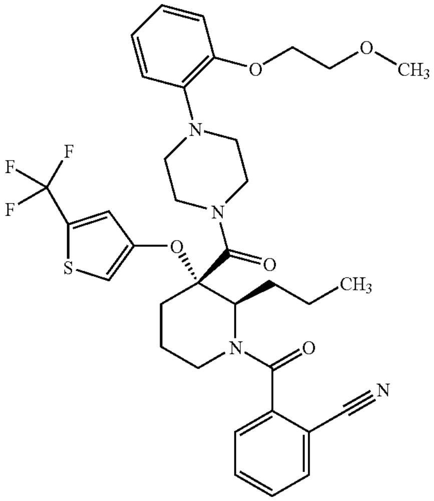 | 685.4 | 4.64, 4.78 |
| FO | 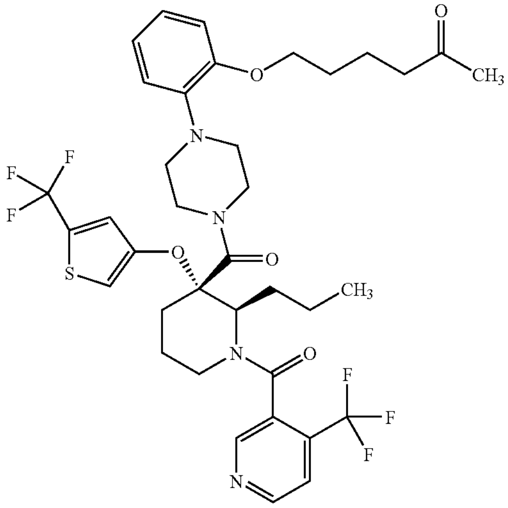 | 771.4 | 4.60 |
| FP | 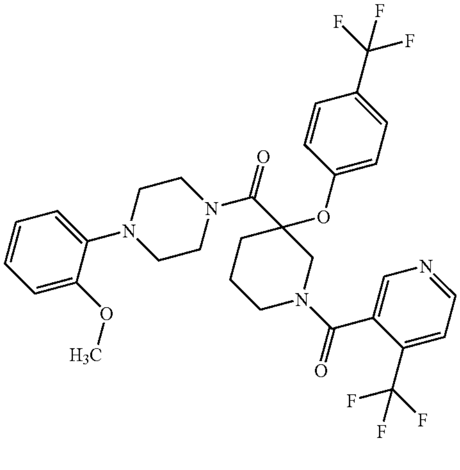 | 637.22 | 5.34 |

TABLE 1-continued
| Compound No. Sch ID | Molstructure | Observed M + H | Retention Time (min) |
|---|---|---|---|
| FQ | 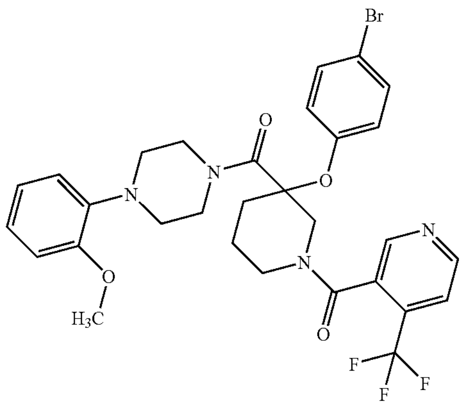 | 647 | 5.38 |
| FR | 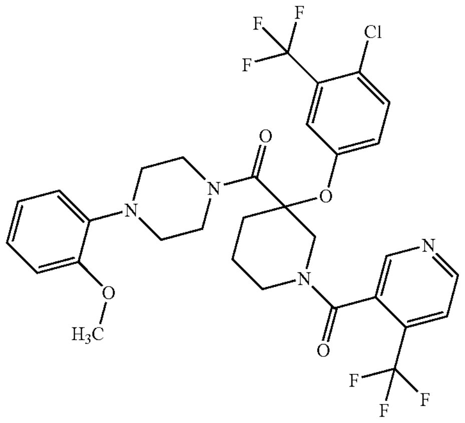 | 671.22 | 5.60 |
| FS | 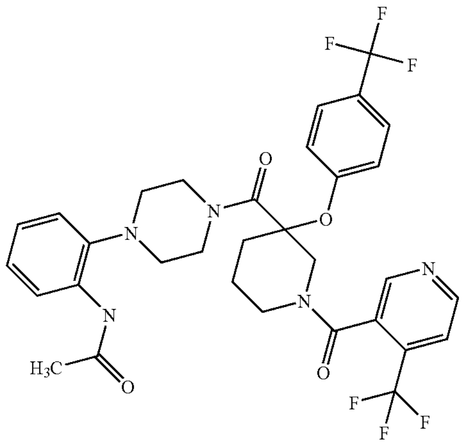 | 664.37 | 5.56 |

TABLE 1-continued
| Compound No. Sch ID | Molstructure | Observed M + H | Retention Time (min) |
|---|---|---|---|
| FT | 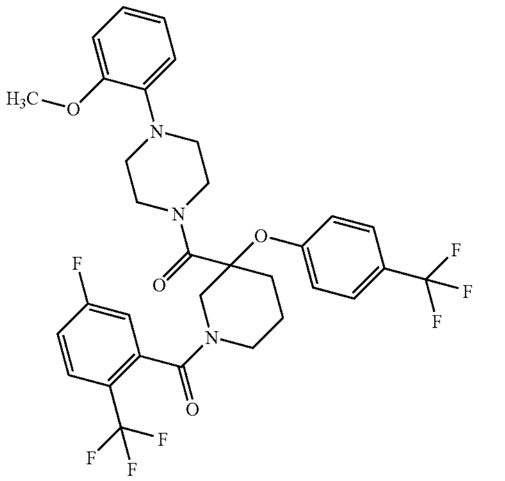 | 654.29 | 6.29 |
| FU | 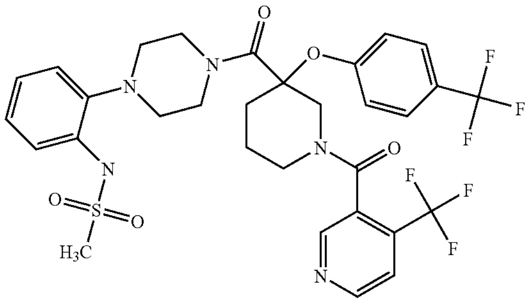 | 700.2 | 2.07 |
| FV | 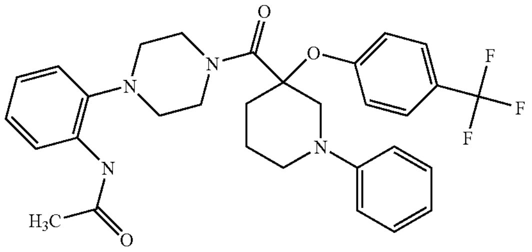 | 567.2 | 6.35 |
| FW | 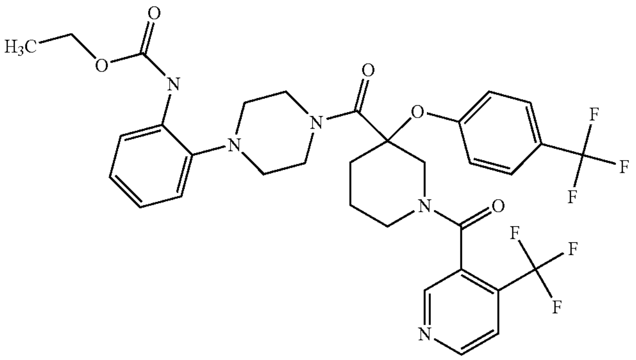 | 694.35 | 6.20 |

TABLE 1-continued
| Compound No. Sch ID | Molstructure | Observed M + H | Retention Time (min) |
|---|---|---|---|
| FX | 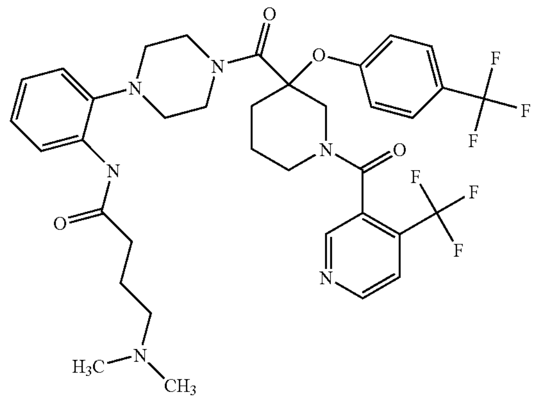 | 735.43 | 4.63 |
| FY | 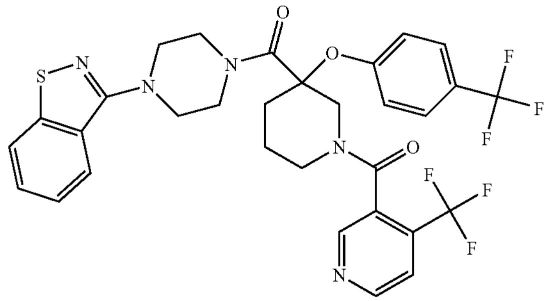 | 664.2 | 6.30 |
| FZ | 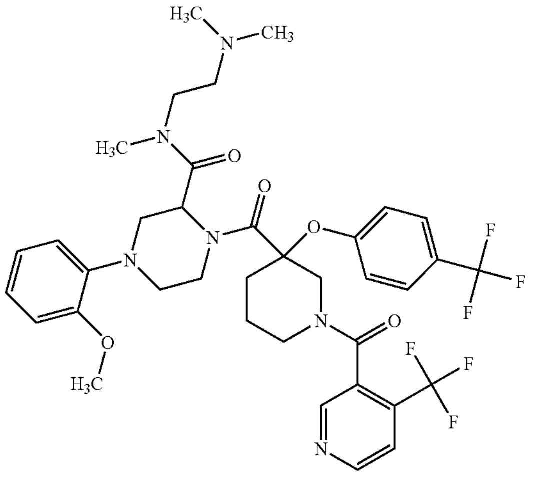 | 765.4 | 4.79 |

TABLE 1-continued
| Compound No. Sch ID | Molstructure | Observed M + H | Retention Time (min) |
|---|---|---|---|
| GA | 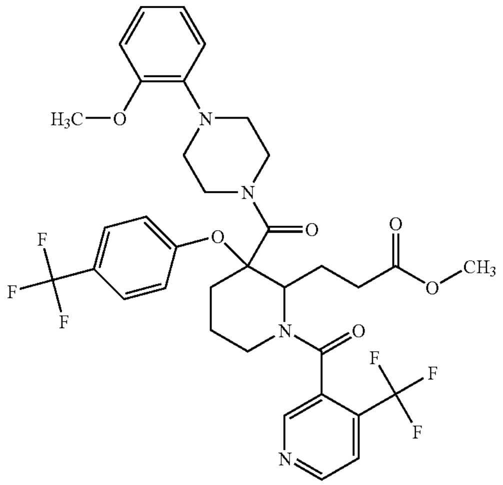 | 723.2 | 2.26, 2.30 |
| GB | 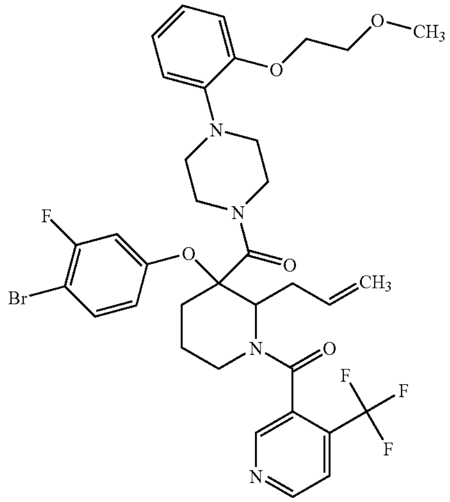 | 749.43 | 5.94 |
| GC | 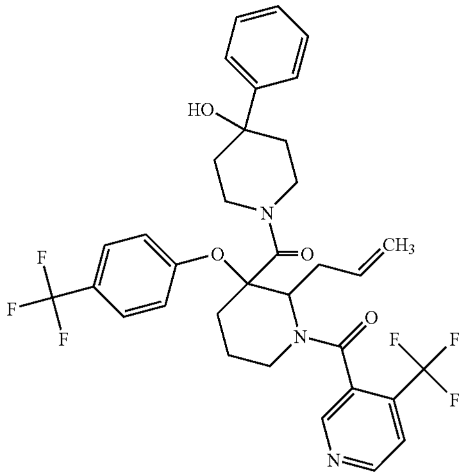 | 662.3 | 5.49 |

TABLE 1-continued
| Compound No. Sch ID | Molstructure | Observed M + H | Retention Time (min) |
|---|---|---|---|
| GD | 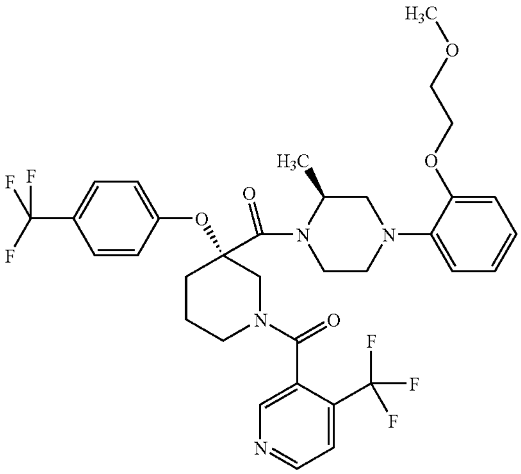 | 695.2 | 5.81 |
| GE | 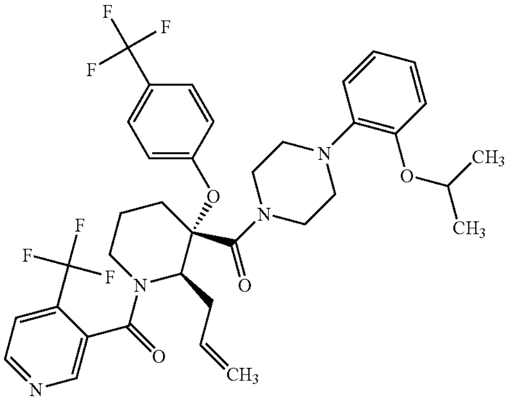 | 705.2 | 6.10 |
| GF | 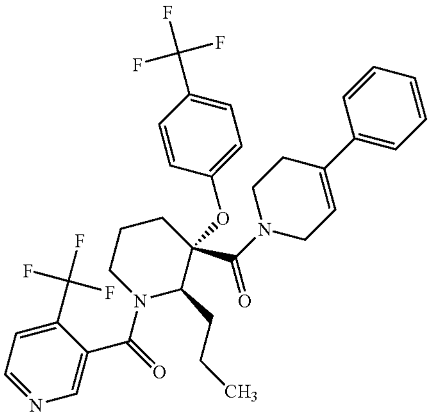 | 646.2 | 5.67 |

TABLE 1-continued
| Compound No. Sch ID | Molstructure | Observed M + H | Retention Time (min) |
|---|---|---|---|
| GG | 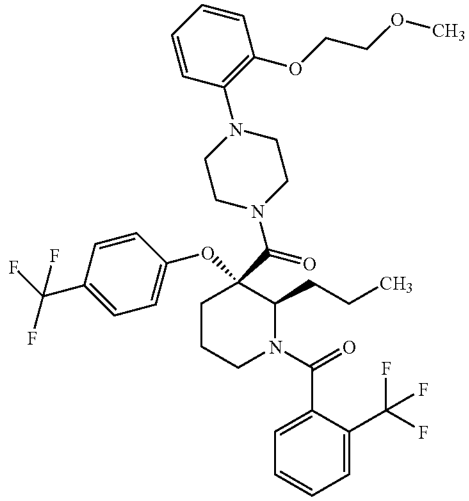 | 723.2 | 1.67 |
| GH | 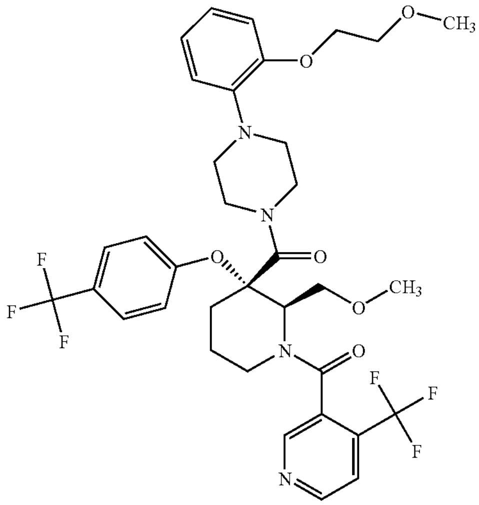 | 725.1 | 4.88 |
| GI | 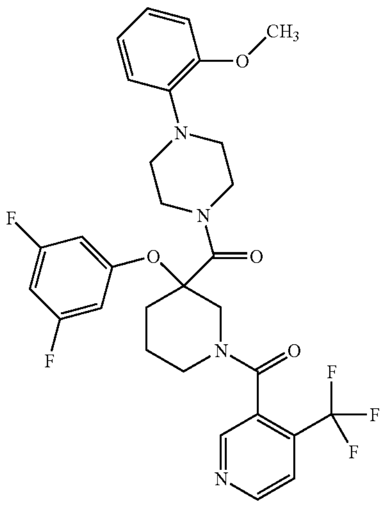 | 605.3 | 4.02 |

TABLE 1-continued
| Compound No. Sch ID | Molstructure | Observed M + H | Retention Time (min) |
|---|---|---|---|
| GJ | 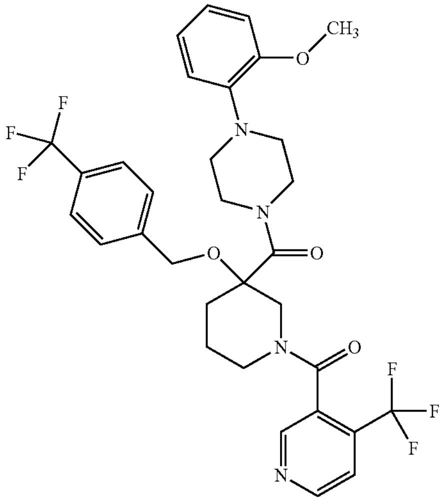 | 651.4 | 4.15 |
| GK | 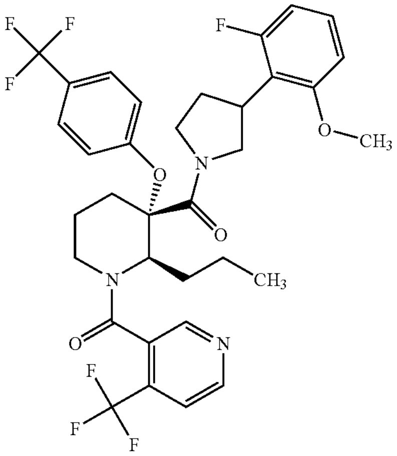 | 682 | 8.31 |
| GL | 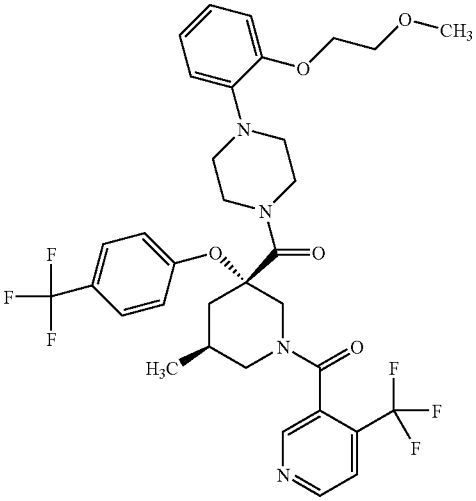 | 695.4 | 4.17 |

TABLE 1-continued
| Compound No. Sch ID | Molstructure | Observed M + H | Retention Time (min) |
|---|---|---|---|
| GM | 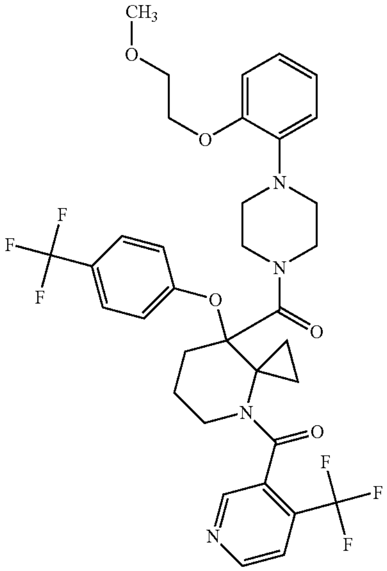 | 707.2 | 4.77 |
| GN | 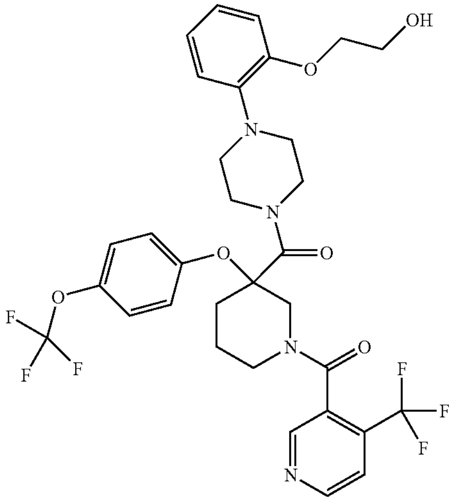 | 683.4 | 4.32 |
| GO | 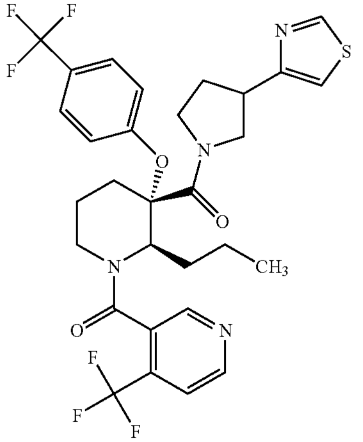 | 641 | 7.08 |

TABLE 1-continued
| Compound No. Sch ID | Molstructure | Observed M + H | Retention Time (min) |
|---|---|---|---|
| GP | 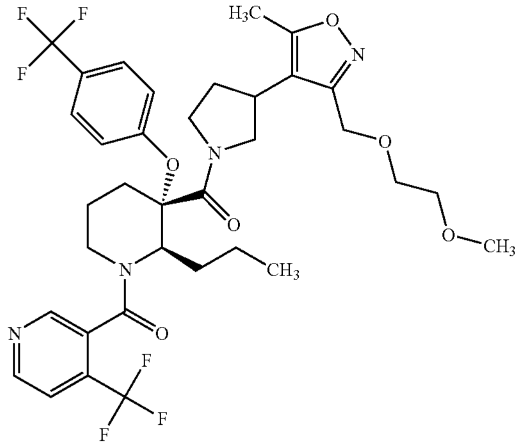 | 727 | 7.34 |
| GQ | 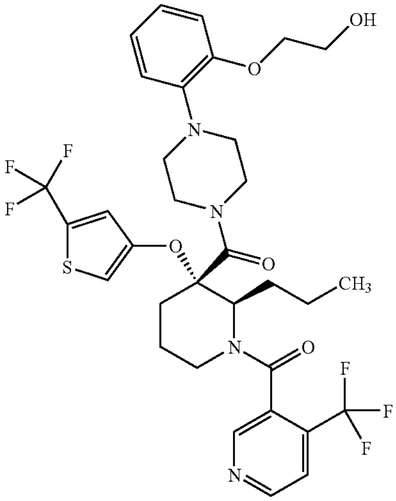 | 715.2 | 5.20 |
| GR | 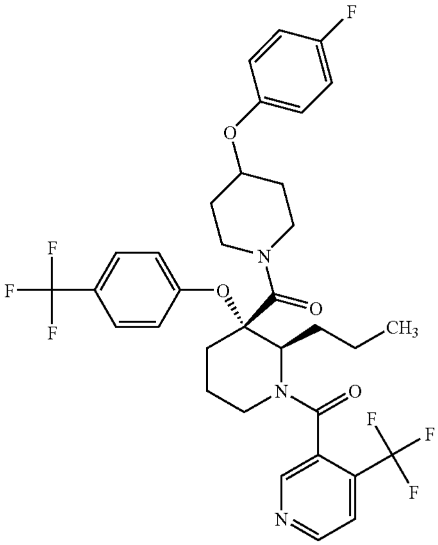 | 682.2 | 6.08 |

TABLE 1-continued
| Compound No. Sch ID | Molstructure | Observed M + H | Retention Time (min) |
|---|---|---|---|
| GS | 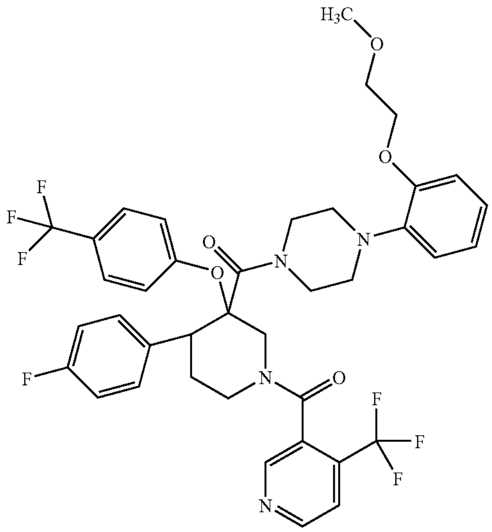 | 775.17 | N/A |
| GT | 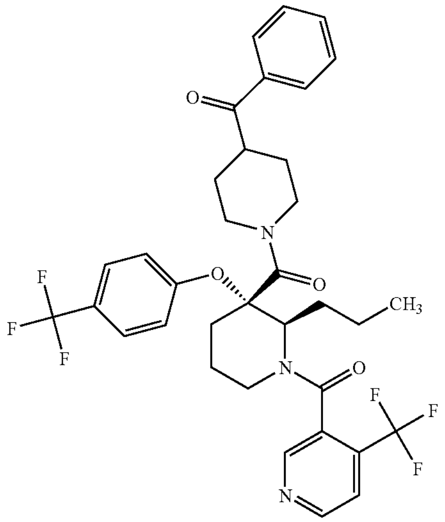 | 676.2 | 5.81 |
| GU | 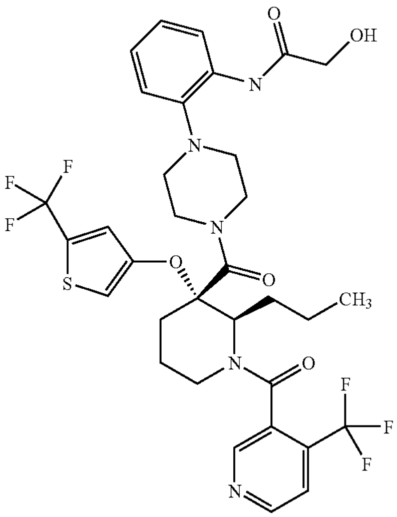 | 728.4 | 4.65 |

TABLE 1-continued
| Compound No. Sch ID | Molstructure | Observed M + H | Retention Time (min) |
|---|---|---|---|
| GV | 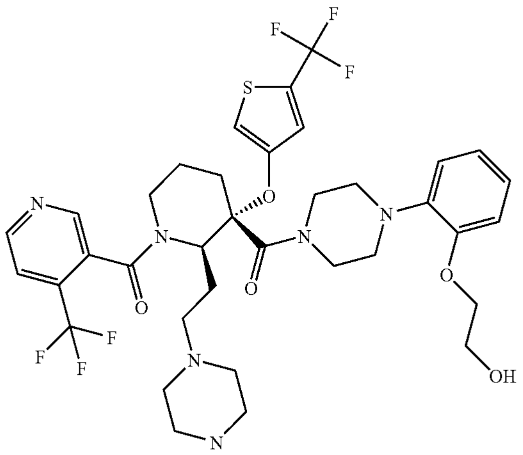 | 785.4 | 3.95 |
| GW | 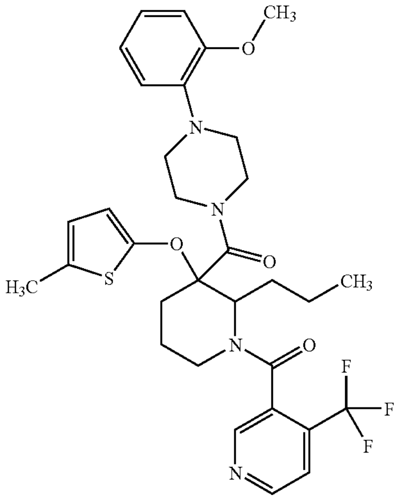 | 631.3 | 4.41 |
| GX | 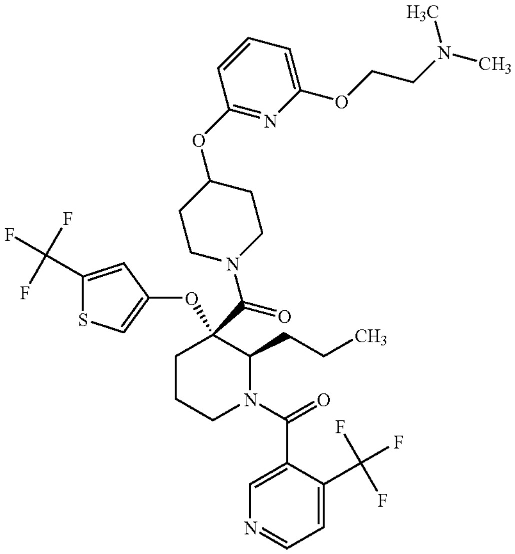 | 758.3 | 4.86 |

TABLE 1-continued
| Compound No. Sch ID | Molstructure | Observed M + H | Retention Time (min) |
|---|---|---|---|
| GY | 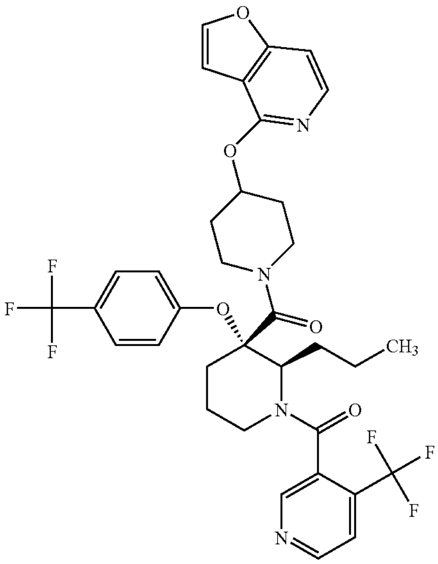 | 705.3 | 6.96 |
| GZ | 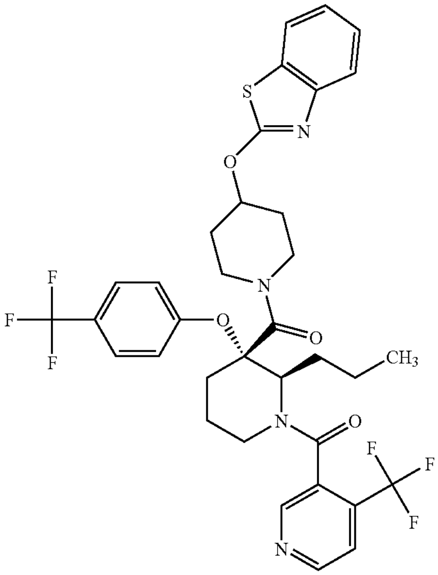 | 721.3 | 7.36 |

TABLE 1-continued
| Compound No. Sch ID | Molstructure | Observed M + H | Retention Time (min) |
|---|---|---|---|
| HA | 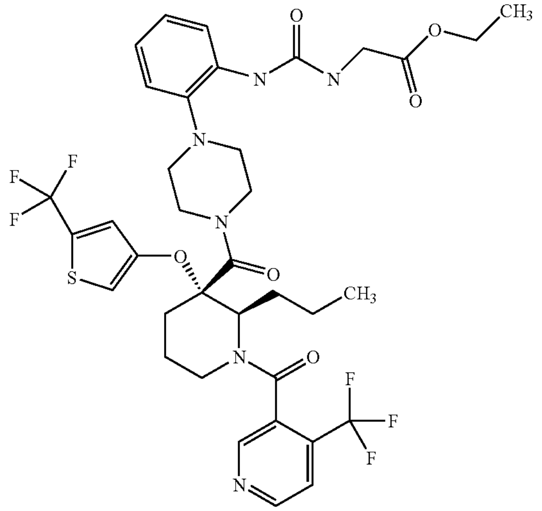 | 799.4 | 4.88 |
| HB | 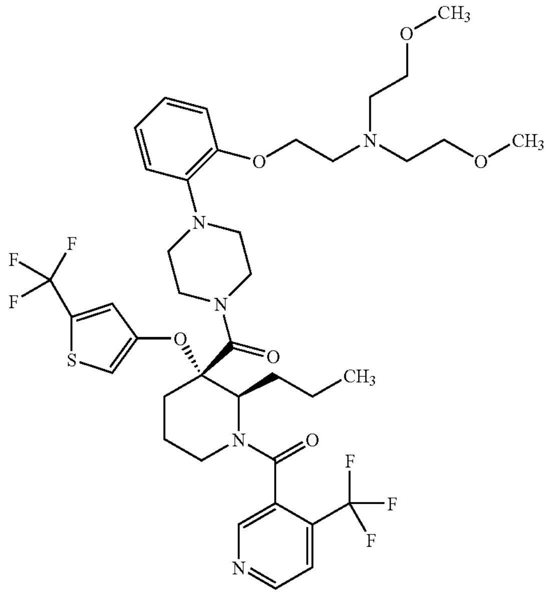 | 830.45 | 3.54 |
| HC | 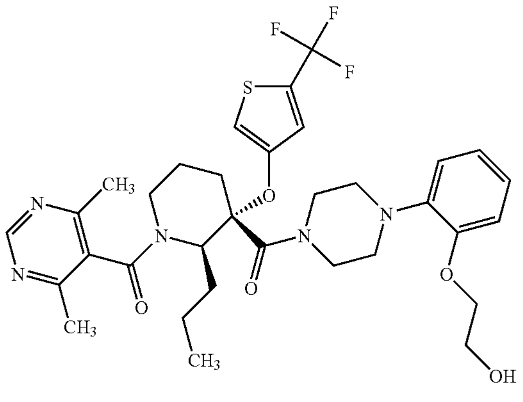 | 676.31 | 4.17 |

TABLE 1-continued

| Compound No. Sch ID | Molstructure | Observed M + H | Retention Time (min) |
|---|---|---|---|
| HD | 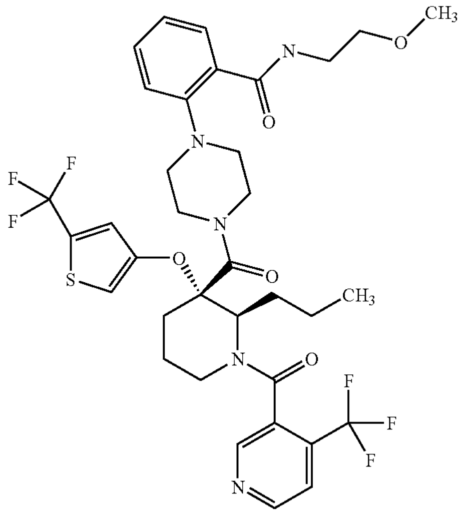 | 756.4 | 4.78 |

The inventive compounds can readily be evaluated to determine activity at the HDM2 protein by known methods such as the fluorescence polarization screening assay that measures the inhibitory concentration that achieves 50% of maximal activity (FP $IC_{50}$) and the dissociation constant for inhibitor binding (FP Ki). [Zhang et al., J. Analytical Biochemistry 331: 138-146 (2004)].

Additionally, compounds are tested for activity at the HDM2 protein using the Cell Viability Assay, which measures the number of viable cells in culture after treatment with the inventive compound for a certain period of time e.g. 72 hours based on quantitation of the ATP present (Cell Viability. $IC_{50}$). [CellTiter-Glo® Luminescent Cell Viability Assay from Promega].

Compounds of the present application exhibit FP $IC_{50}$, FP Ki, and Cell Viability $CO_{50}$ values of less than about 50.0 μM.

The HDM2 inhibitory activities for representative compounds of the invention, are shown in Table 2 below.

TABLE 2

| Compound No. | Compound | FP IC50 (μM) |
|---|---|---|
| AU | 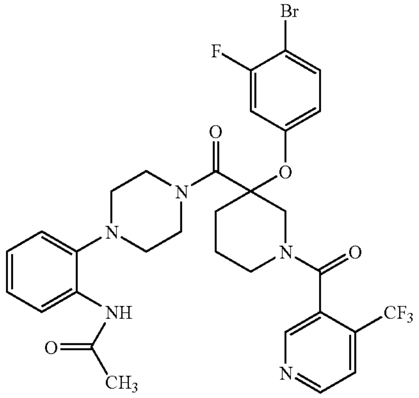 | 0.51 |

TABLE 2-continued

| Compound No. | Compound | FP IC50 (μM) |
|---|---|---|
| CR | 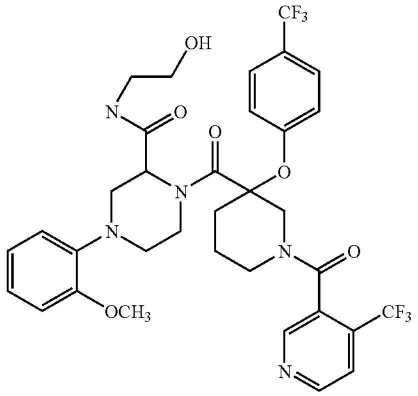 | 0.95 |
| N | 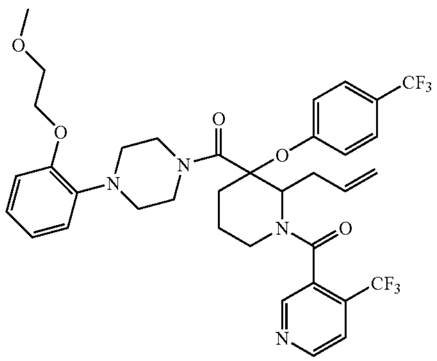 | 0.02 |

TABLE 2-continued

| Compound No. | Compound | FP IC50 (μM) |
| --- | --- | --- |
| EH | 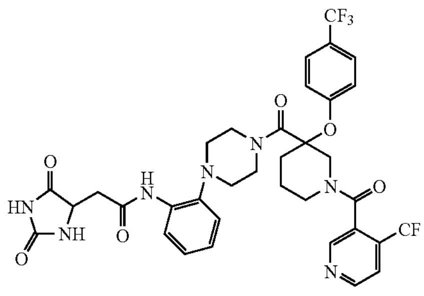 | 0.271 |

From these test results, it would be apparent to the skilled artisan that the compounds of the invention have utility in treating cancer, diseases involving abnormal cell proliferation and diseases caused by inadequate functioning P53.

What is claimed is:

1. A compound of Formula I:

Formula I

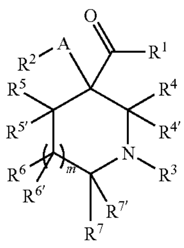

or a pharmaceutically acceptable salt thereof, wherein:

$R^1$ is (a) heterocyclyl selected from the group consisting of piperazinyl, piperidinyl, and pyrrodinyl; each of which can be unsubstituted or independently substituted with at least one moiety, which may be the same or different, selected from the group Z;

(b) heterocyclenyl, that is 1,2,3,6-tetrahydropyridinyl which can be unsubstituted or independently substituted with at least one moiety, which may be the same or different, selected from the group Z; wherein each of said heterocyclyl, or heterocyclenyl is attached by one of its heteroatoms to the carbonyl in Formula I;

(c)

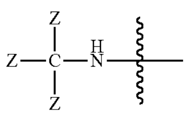

or (d) selected from the group consisting of:

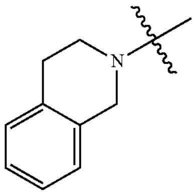

,

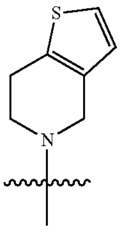

, and

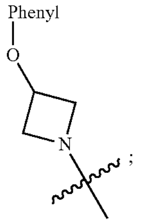

;

wherein each Z, which can be the same or different, is independently selected from the group consisting of H, —$OR^9$, —$CO_2R^9$, alkyl, aryl, heteroaryl, heteroarylalkyl, —O-alkyl, —O-aryl, —O-heterocyclyl, —O-cycloalkyl, —S-heteroaryl, —CO-aryl, and spiroheterocyclyl, wherein each of said alkyl, aryl, heteroaryl, heteroarylalkyl, and spiroheterocyclyl, and the "alkyl", "aryl", and "heteroaryl" portions of each of said —O-alkyl, —O-aryl, —O-heteroaryl, —S-heteroaryl, and —CO-aryl, can be unsubstituted or substituted with one or more moieties, which may be the same or different, each moiety being independently selected from the group consisting of halogen, —CN, hydroxyalkyl, alkyl, —O-alkyl, —S-alkyl, hydroxyl, carboxyl, —$CO_2$-alkyl, —CO—$NR^8R^9$, —$NR^8COR^9$, —$NR^8SO_2R^9$, —$NR^8CONR^8R^9$, —$NR^8CO_2R^9$, —$OR^9$, —$SR^9$, —$SO_2R^9$, —$COR^9$, -alkyl$NR^8R^9$, —$NR^8R^9$, trihaloalkyl, alkoxyalkyl, alkoxyalkoxy, alkoxy$(alkoxy)_b$ alkoxyl, hydroxyalkoxyalkoxyl, hydroxyalkoxy $(alkoxy)_b$alkoxyl, heterocyclyl, heteroaryl, cycloalkyl, aryl, and heterocyclylalkyl;

further wherein, $R^8$ and $R^9$ are independently selected from the group consisting of hydrogen, alkyl-O-alkyl, trifluoroalkyl, difluoroalkyl, monofluoroalkyl, -alkyl-S-alkyl, alkoxyalkyl, alkyl, alkenyl, cycloalkyl, aryl, heterocyclyl, heteroaryl, arylalkyl, heterocyclylalkyl, heteroarylalkyl, -alkyl$N(alkyl)_2$, -alkylNHalkyl, -alkyl-$NH_2$, -alkenyl-$N(alkyl)_2$, -alkyl-$N(alkenyl)_2$, -alkyl-Nalkyl (alkenyl), -alkenyl-$NH_2$, hydroxyalkyl, hydroxyalkenyl, -alkyl-SH, -alkenyl-SH, -alkyl$CO_2H$, -alkyl$CO_2$alkyl, -alkylCONHalkyl, -alkyl$CONH_2$, -alkyl$CON(alkyl)_2$, -alkyl$CON(alkenyl)_2$, wherein each of said cycloalkyl, aryl, heterocyclyl, heteroaryl arylalkyl, heterocyclylalkyl, and heteroarylalkyl, can be unsubstituted or substituted with one or more moieties, which can be the same or different, independently selected from the group consisting of alkyl, heteroalkyl, heteroalkenyl, alkenyl, alkynyl, alkoxyalkoxy, —S-alkyl-S-alkyl, hydroxyalkyl, -alkylSH, hydroxyalkenyl, -alkyl-$NH_2$, -alkyl-$N(alkyl)_2$, and -alkylN-Halkyl;

b is 0-3;

$R^{10}$ and $R^{11}$, which can be the same or different, are independently selected from the group consisting of hydrogen, alkyl, cycloalkyl, and alkoxyalkyl;

further wherein, in any —$NR^{10}R^{11}$ in Formula I, said $R^{10}$ and $R^{11}$ can optionally be joined together with the N of said —$NR^{10}R^{11}$ to form a cyclic ring;

A is O;

m is 0-2;

$R^2$ is aryl, or heteroaryl, wherein each of said aryl, and heteroaryl, can be unsubstituted or substituted with one or more moieties, which may be the same or different, each moiety being independently selected from the group consisting of trihaloalkyl, halogen, alkyl, and trifluoroalkoxy;

$R^3$ is

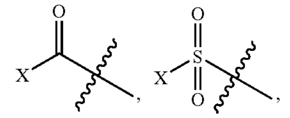

aryl, or heteroaryl, wherein X is selected from the group consisting of aryl, heteroaryl, arylalkyl, alkyl, and trihaloalkyl;

further wherein, each of said X, aryl, and heteroaryl can be unsubstituted or substituted with one or more moieties, which can be the same or different, each moiety being independently selected from the group consisting of trihaloalkyl, halogen, CN, hydroxyl, alkoxy, aryloxy, alkyl, and cycloalkyl;

$R^4$ or $R^{4'}$, which may be the same or different, are independently selected from the group consisting of hydrogen, alkyl, alkenyl, hydroxyalkyl, -alkyl$CO_2R^9$, alkoxyalkyl, aminoalkyl, alkyl$NR^{10}R^{11}$, cycloalkylalkyl, and heterocyclylalkyl wherein each of said alkyl, alkenyl, hydroxyalkyl, -alkyl$CO_2R^9$, alkoxyalkyl, aminoalkyl, alkyl$NR^{10}R^{11}$, cycloalkylalkyl, and heterocyclylalkyl can be unsubstituted or substituted with one or more moieties, which can be the same or different, independently selected from the group consisting of trihaloalkyl, dihaloalkyl, monohaloalkyl, trihaloalkenyl, dihaloalkenyl, monohaloalkenyl, halogen, CN, hydroxyl, thiohydroxyl, amine, alkoxy, alkenoxy, aryloxy, cyclenyloxy, cycloalkyloxy, heteroaryloxy, heterocyclenyloxy, heterocyclyloxy, alkyl, alkenyl, trifluoroalkoxy, difluoroalkoxy, monofluoroalkoxy, heteroalkyl, heteroalkenyl, carboxyl, —$CONR^{10}R^{11}$, —$COOR^9$, —$OCOR^9$, —$NR^{10}COR^9$, cycloalkyl, heterocyclyl, —$NR^{10}R^{11}$, —S-alkyl, —S-alkenyl, —S-cycloalkyl, —S-cyclenyl, —S-aryl, —S-heterocyclyl, —S-heterocyclenyl, —S-heteroaryl, —S-trifluoroalkyl, —S-difluoroalkyl, —S-monofluoroalkyl, cyclenyl, heterocyclenyl, aryl, heteroaryl, and alkynyl;

or wherein $R^4$ and $R^{4'}$ together with the carbon to which each is attached, form a spirocyclic group, wherein said spirocyclic group can be unsubstituted or substituted with one or more moieties, which can be the same or different, independently selected from the group consisting of trihaloalkyl, dihaloalkyl, monohaloalkyl, trihaloalkenyl, dihaloalkenyl, monohaloalkenyl, halogen, CN, hydroxyl, thiohydroxyl, amine, alkoxy, alkyl, alkenyl, trifluoroalkoxy, difluoroalkoxy, monofluoroalkoxy, heteroalkyl, heteroalkenyl, carboxyl, —$CONR^{10}R^{11}$, —$COOR^9$, —$OCOR^9$, —$NR^{10}COR^9$, cycloalkyl, heterocyclyl, —$NR^{10}R^{11}$, alkylthio, trifluoroalkylthio, difluoroalkylthio, monofluoroalkylthio, cyclenyl, heterocyclenyl, aryl, heteroaryl, and alkynyl;

$R^5$, $R^{5'}$, $R^7$ or $R^{7'}$, which may be the same or different, are independently selected from the group consisting of hydrogen, and alkyl;

$R^6$ or $R^{6'}$, which may be the same or different, are independently selected from the group consisting of hydrogen, and alkyl;

provided that the following compounds, which are identified as Group A Compounds herein, are excluded from Formula I:

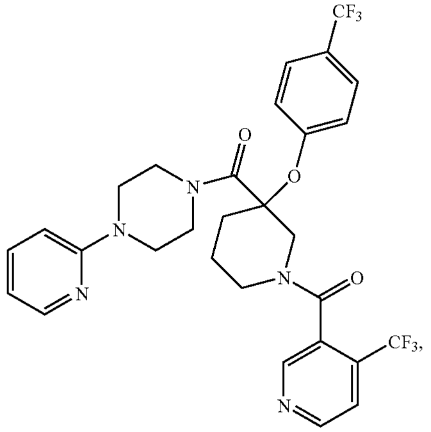

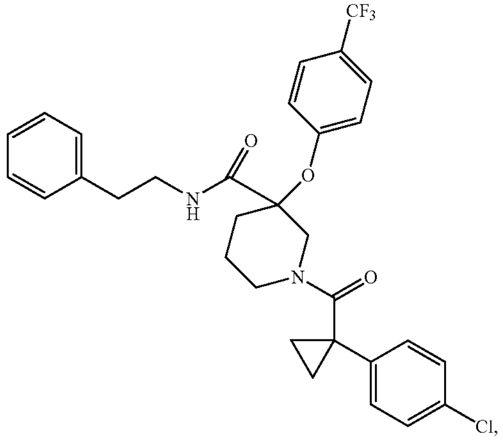

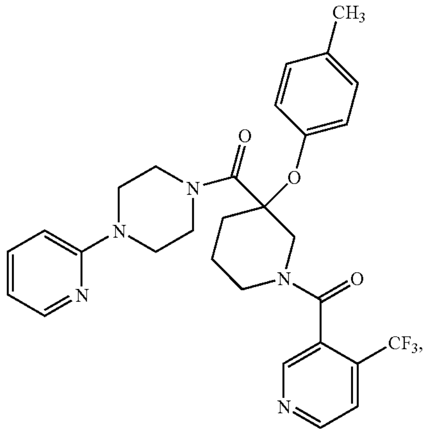

-continued
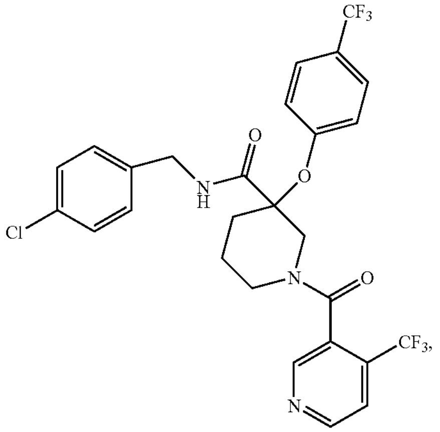
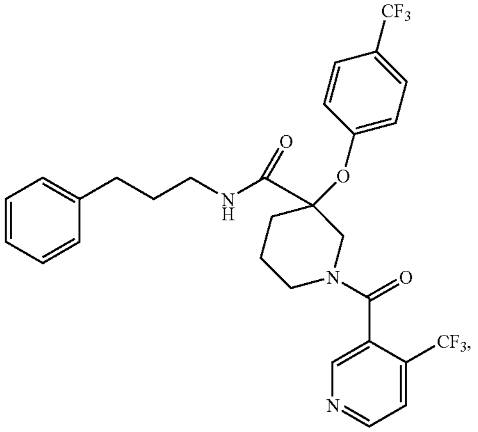
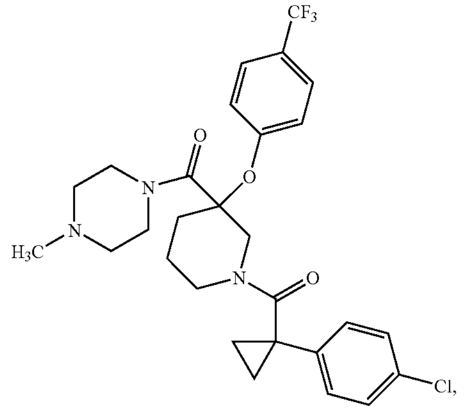
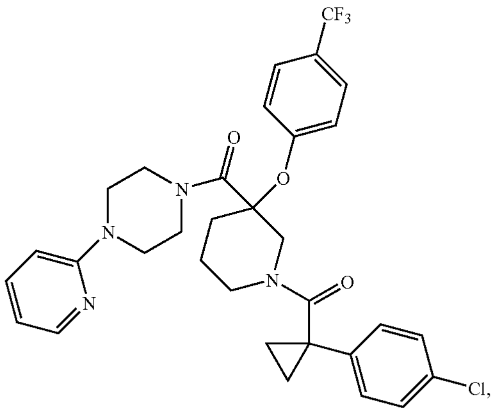
-continued
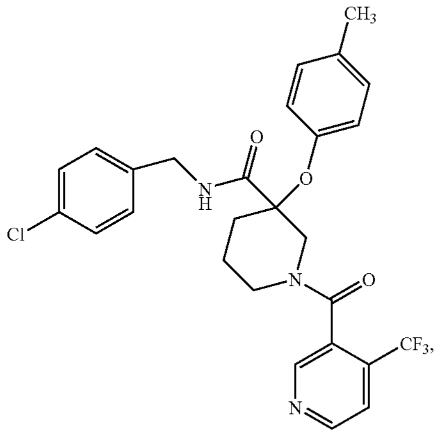
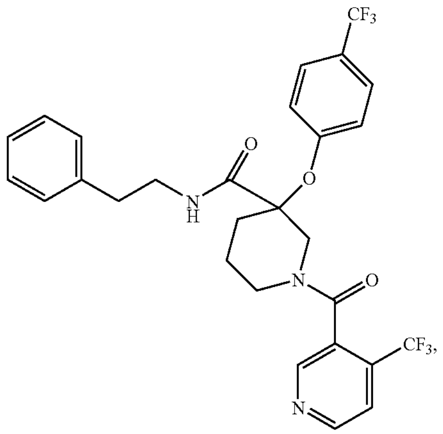
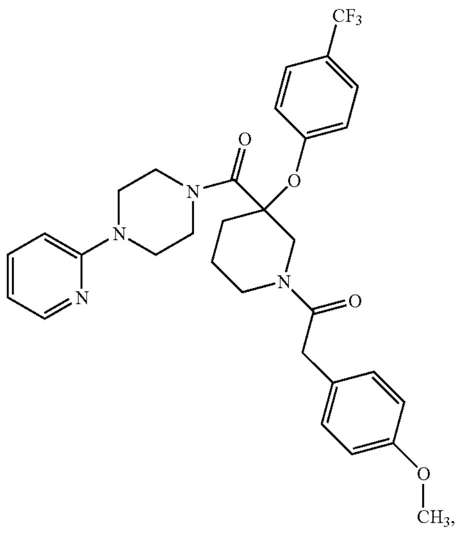

-continued
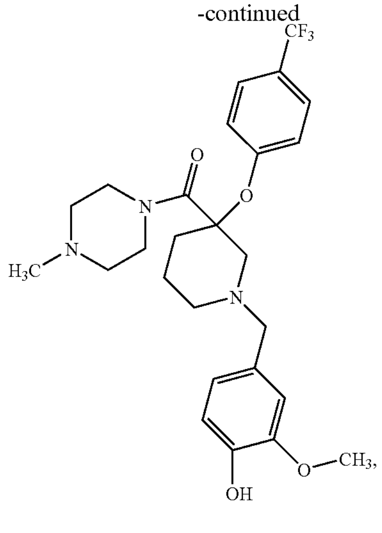
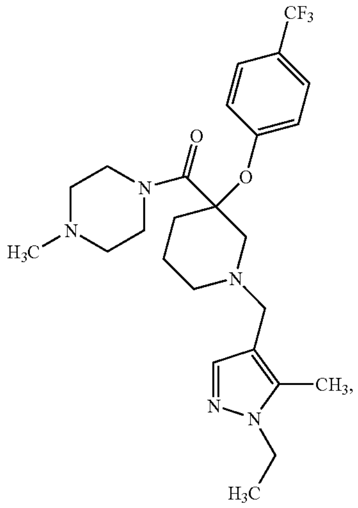
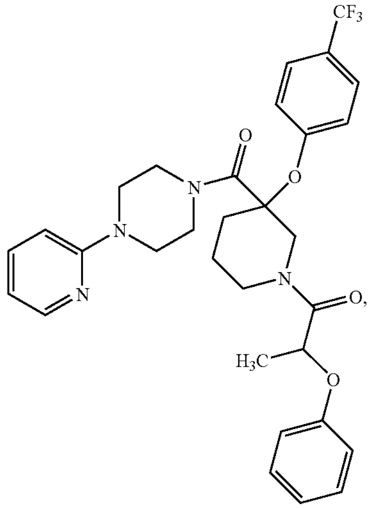
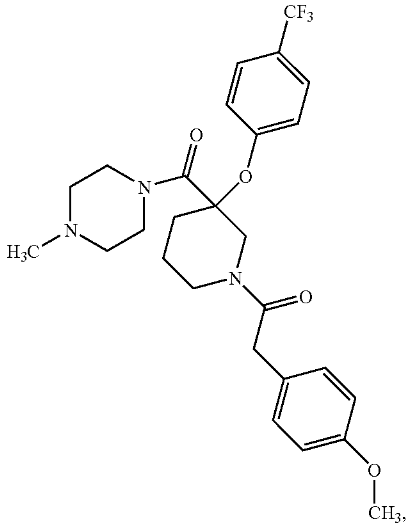
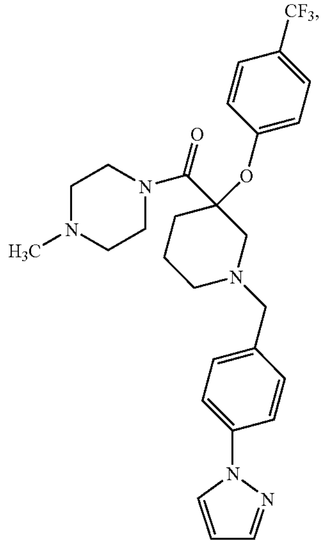
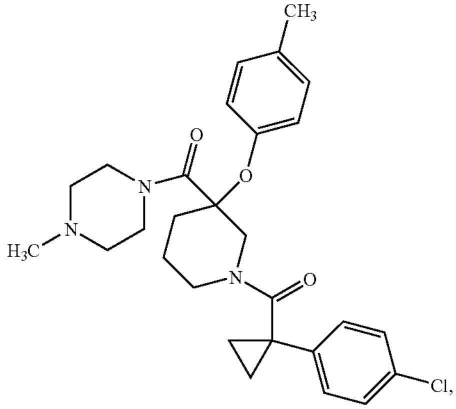

-continued
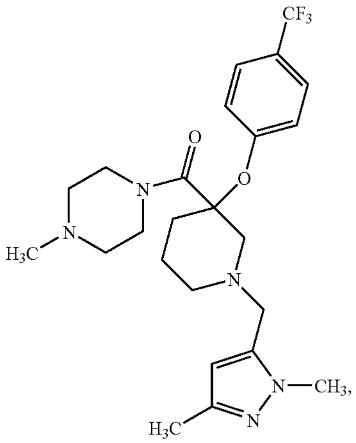
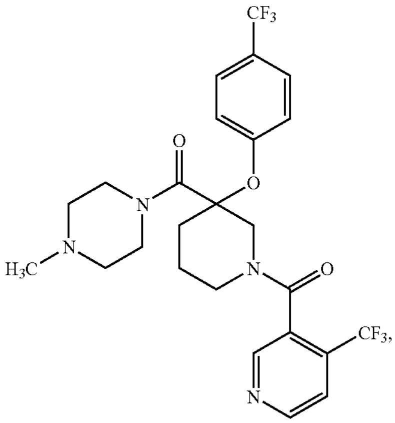
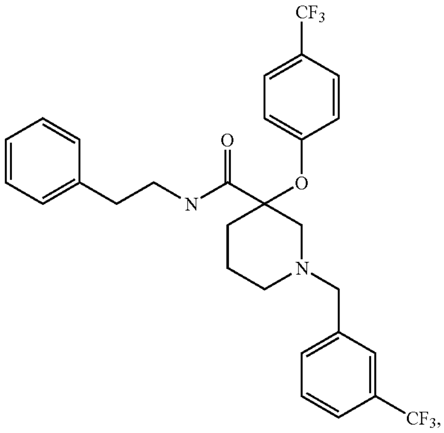
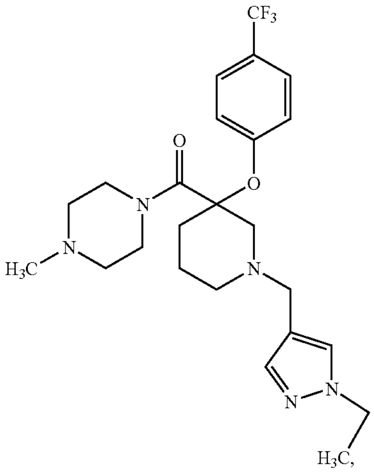
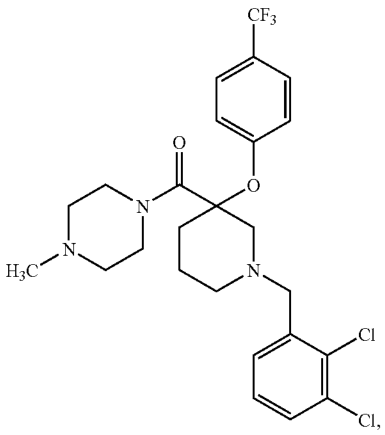
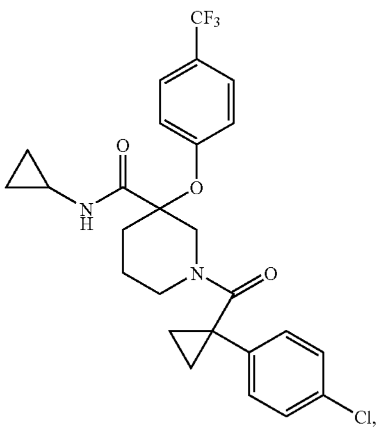
-continued -continued

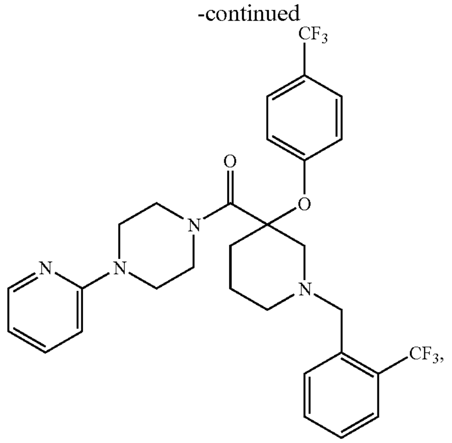

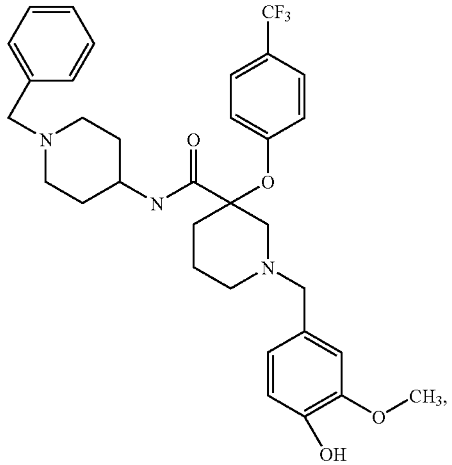 and

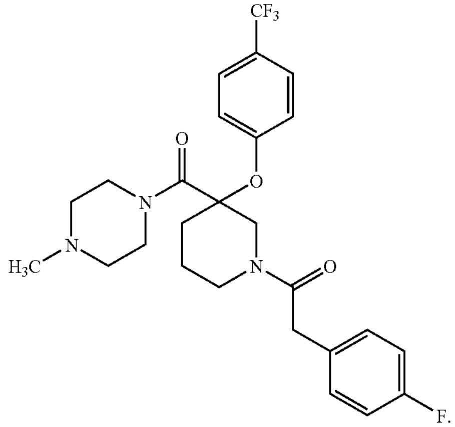

2. The compound of claim 1, wherein, $R^1$ is heterocyclenyl, wherein said heterocyclenyl is unsubstituted or substituted with aryl.

3. The compound of claim 1, wherein, $R^1$ is

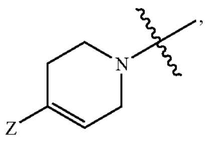

wherein Z is phenyl.

4. The compound of claim 1, wherein, $R^1$ is piperazinyl, piperidinyl, or pyrrolidinyl substituted with Z, wherein Z is phenyl, wherein said phenyl can be unsubstituted or substituted with at least one moiety, which may be the same or different, independently selected from the group consisting of halogen, heterocyclyl, —O-heterocyclyl, alkoxyalkoxyl, hydroxyalkoxyl, alkoxy(alkoxy)$_b$alkoxyl, hydroxyalkoxyalkoxyl, heterocyclylalkyl, —NHCONHalkylCOOalkyl, —O-alkylCONR$^{10}$R$^{11}$, —O-alkylNR$^{10}$R$^{11}$, —NHCOalkylcarboxyl, —CONHalkyl-O-alkyl, —O-heterocyclylalkyl, wherein said heterocyclylalkyl is unsubstituted or substituted with hydroxyalkyl, further wherein $R^{10}$ and $R^{11}$ are independently selected from the group consisting of hydrogen, alkyl, alkoxyalkyl, and cycloalkyl, and still further wherein b is 1.

5. The compound of claim 1, wherein $R^1$ is heterocyclyl substituted with Z, wherein Z is,

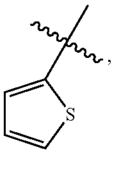, 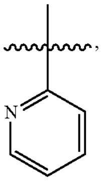, 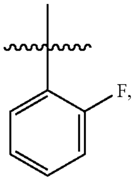

or —O-pyridinyl, wherein said —O-pyridinyl can be unsubstituted or substituted with —$CONH_2$.

6. The compound of claim 1, wherein, $R^1$ is

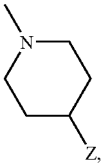

wherein Z is

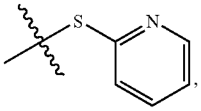, 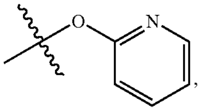,

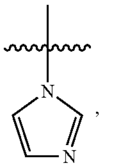, 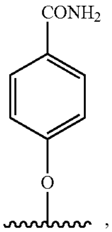, 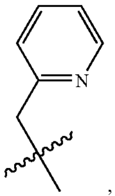,

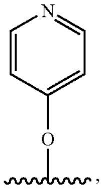, 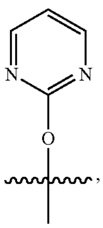, 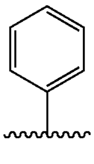,

-continued
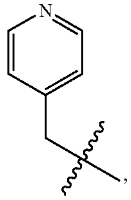,
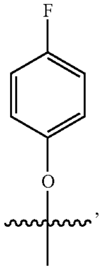,
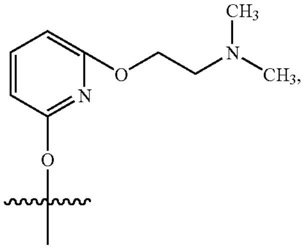,
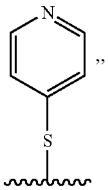,
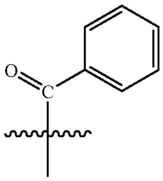,
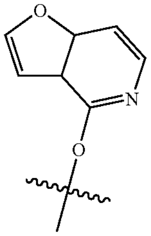,
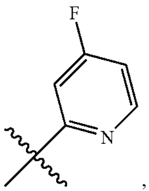,
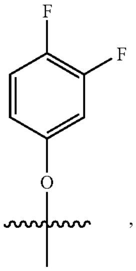,
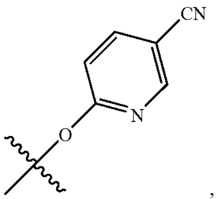,
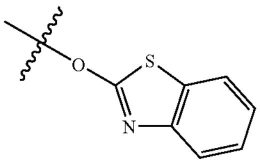, or
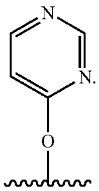.
7. The compound of claim 1, wherein, $R^1$ is
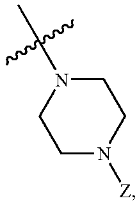
wherein Z is
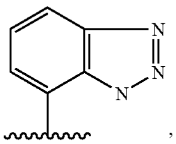,
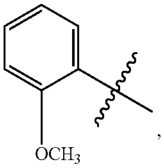,
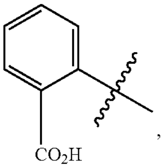,
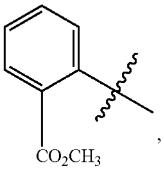,
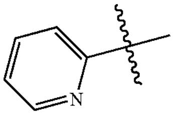,
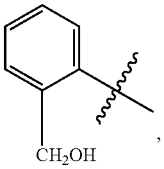,
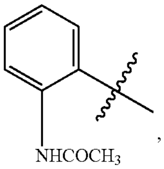,
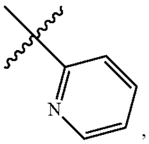,
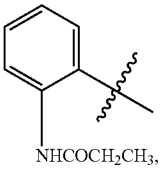
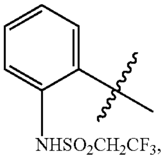
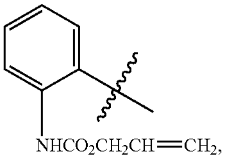
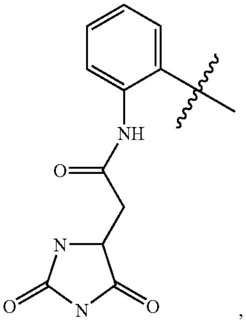,
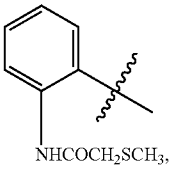
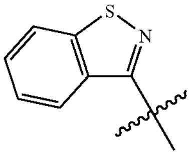,
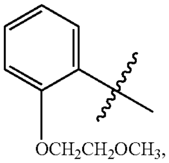
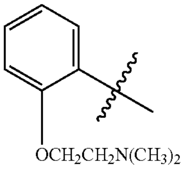 or
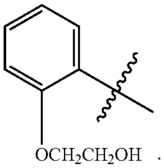.

8. The compound of claim 1, wherein, $R^1$ is
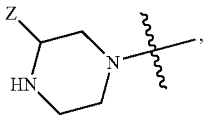
wherein Z is $—CO_2CH_3$.
9. The compound of claim 1, wherein, $R^1$ is
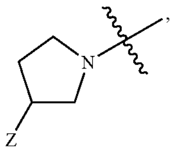
wherein Z is
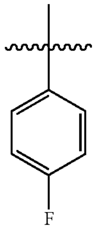 or 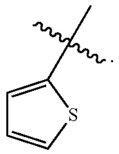
10. The compound of claim 1, wherein, $R^1$ is
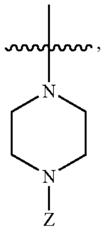
wherein Z is
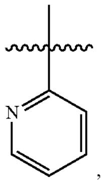, 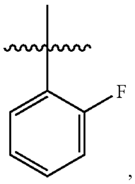, 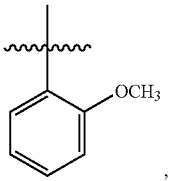,
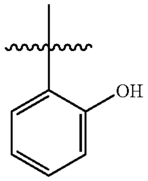, 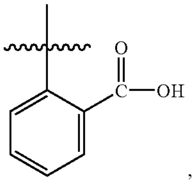,
-continued
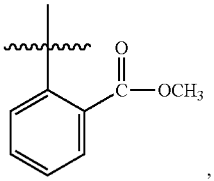, 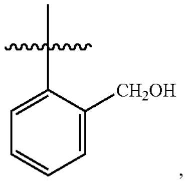,
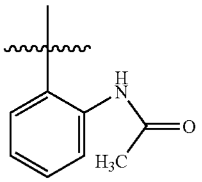, 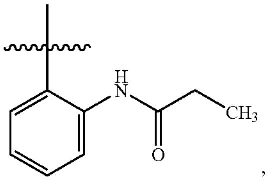,
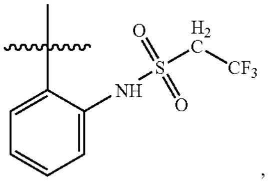, 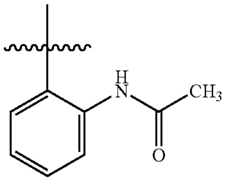,
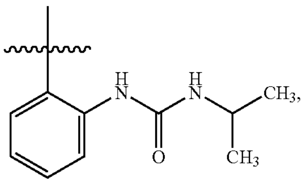
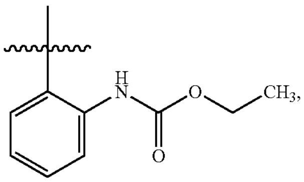
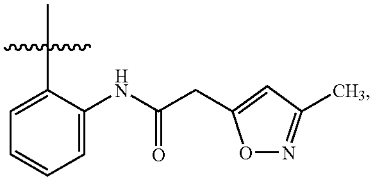
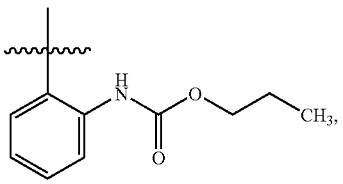
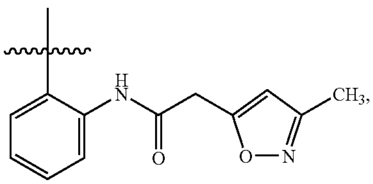
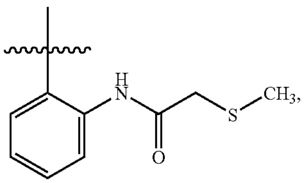

-continued

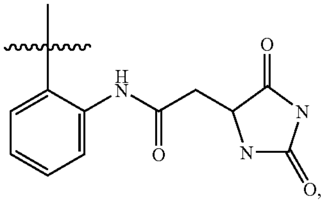

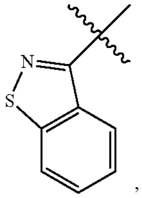

,

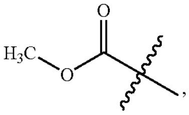

,

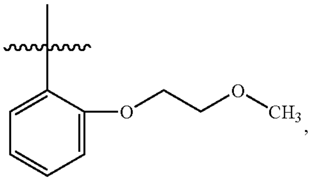

, or

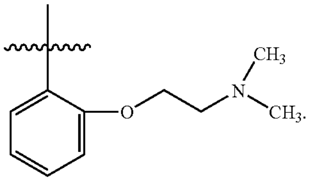

11. The compound of claim 1, wherein, $R^1$ is

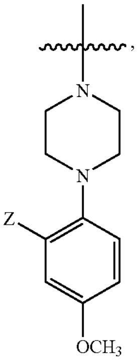

wherein Z is

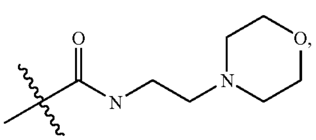

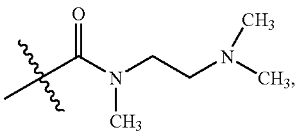

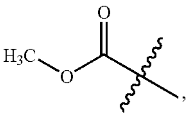

,

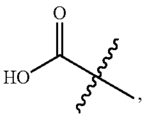

, or

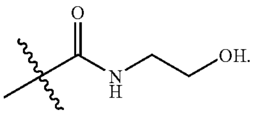

12. The compound of claim 1, wherein, $R^1$ is

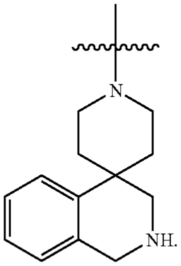

13. The compound of claim 1, wherein, $R^1$ is

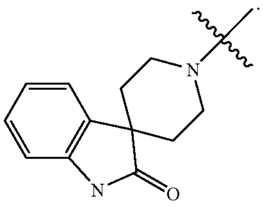

14. The compound of claim 1, wherein, $R^1$ is

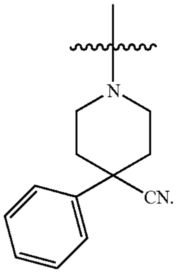

15. The compound of claim 1, wherein, $R^1$ is

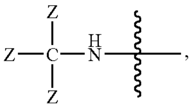

wherein each Z is different and independently selected from the group consisting of hydrogen, —C(=O)$OCH_3$, and phenyl substituted in its para position with chloro.

16. The compound of claim 1, wherein, $R^1$ is

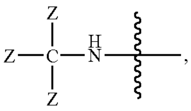

wherein each Z is different and independently selected from the group consisting of hydrogen, alkyl, and phenyl substituted in its para position with hydroxyl.

17. The compound of claim 1, wherein, $R^1$ is

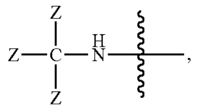

wherein each Z is different and independently selected from the group consisting of hydrogen, methyl, and phenyl substituted in its para position with hydroxyl.

18. The compound of claim 1, wherein, $R^1$ is

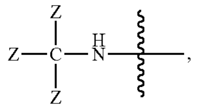

wherein each Z is different and independently selected from the group consisting of hydrogen, and unsubstituted aryl.

19. The compound of claim 1, wherein, $R^1$ is

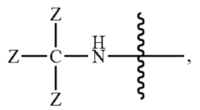

wherein each Z is different and independently selected from the group consisting of hydrogen,

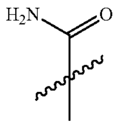

and phenyl.

20. The compound of claim 1, wherein, $R^2$ is heteroaryl or aryl, wherein said heteroaryl or aryl, can be unsubstituted or substituted with at least one moiety, which can be the same or different, independently selected from the group consisting of trifluoroalkyl, difluoroalkyl, —O-trifluoroalkyl, —S-trifluoroalkyl, —O-difluoroalkyl, alkyl, and halogen.

21. The compound of claim 1, wherein, $R^2$ is thiophene, phenyl, or 4-H-pyrazole wherein said thiophene, 4-H-pyrazole, or phenyl can be unsubstituted or substituted with at least one moiety, which can be the same or different, independently selected from the group consisting of trifluoromethyl, difluoromethyl, —O-trifluoromethyl, —S-trifluoromethyl, —O-difluoromethyl, methyl, R, Br, Cl, and I.

22. The compound of claim 1, wherein, $R^3$ is —CO—X or —$SO_2$—X wherein X is heteroaryl, arylalkyl, aryl, alkyl, or trifluoroalkyl, wherein said heteroaryl or arylalkyl, can be unsubstituted or substituted, with at least one moiety, independently selected from the group consisting of trifluoroalkyl, halogen and cycloalkyl.

23. The compound of claim 1, wherein, $R^3$ is —CO—X or —$SO_2$—X, wherein X is pyridinyl, oxazolyl, thiophene, pyrimidinyl, phenylmethyl, phenyl, 2,2-dimethylpropyl, ethyl, or trifluoroethyl, wherein each of said pyridinyl, oxazolyl, thiophene, pyrimidinyl or phenylmethyl can be unsubstituted or substituted, with at least one moiety, independently selected from the group consisting of trifluoromethyl, methyl, chloro and cyclopropyl.

24. The compound of claim 1, wherein, $R^3$ is —CO—X, wherein X is

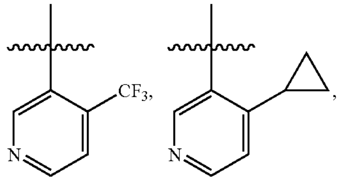

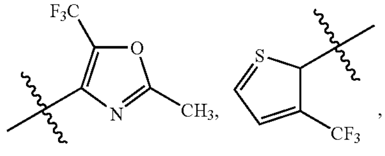

, or

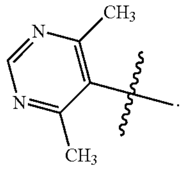

25. The compound of claim 1, wherein, $R^3$ is —$SO_2$—X, wherein X is ethyl or trifluoroethyl.

26. The compound of claim 1, wherein, $R^3$ is

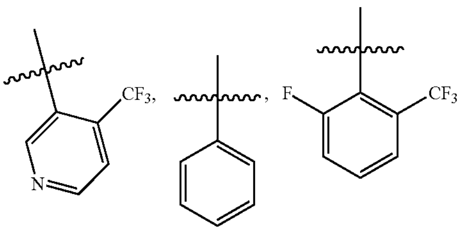

or

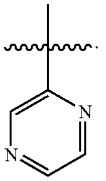

27. The compound of claim 1, wherein, $R^4$ or $R^{4'}$ are independently selected from the group consisting of hydrogen, alkyl, alkenyl, heterocyclylalkyl, -alkyl$NR^8R^9$, hydroxyalkyl, cycloalkylalkyl, -alkyl$CO_2R^9$, and alkoxyalkyl, wherein each of said heterocyclylalkyl, hydroxyalkyl or alkyl can be unsubstituted or substituted with a moiety selected from the group consisting of alkoxyl, alkoxyalkyl, hydroxyalkyl, and hydroxyl.

28. The compound of claim 1, wherein, $R^4$ and $R^{4'}$, together with the carbon to which they are attached, form a spirocyclopropyl.

29. The compound of claim 1, wherein, $R^4$ or $R^{4'}$ are independently selected from the group consisting of hydrogen, propyl, propenyl, butenyl, aminoalkyl, cycloalkylalkyl, methylesterethyl,

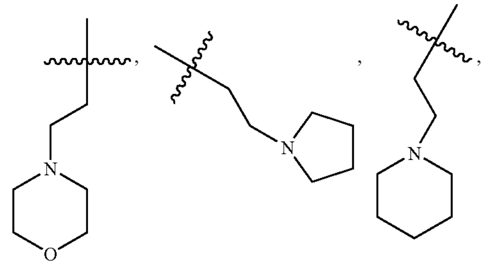
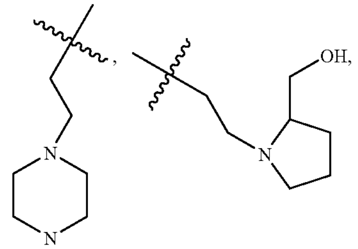
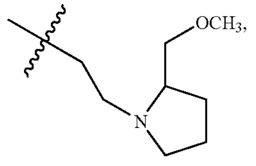
$-CH_2CH_2N(ethyl)_2$, $-CH_2CH_2N(methyl)_2$, $-CH_2CH_2-OH$,
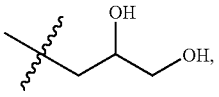
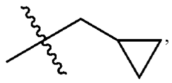
and $-CH_2OCH_3$.
30. The compound of claim 1, wherein, $R^5$, $R^{5'}$, $R^6$, $R^{6'}$, $R^7$, and $R^{7'}$ are each independently hydrogen.
31. The compound of claim 1, wherein, m is 1.
32. A compound of the formula:
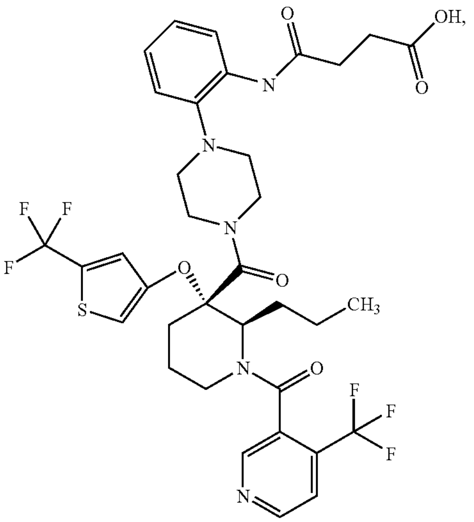
-continued
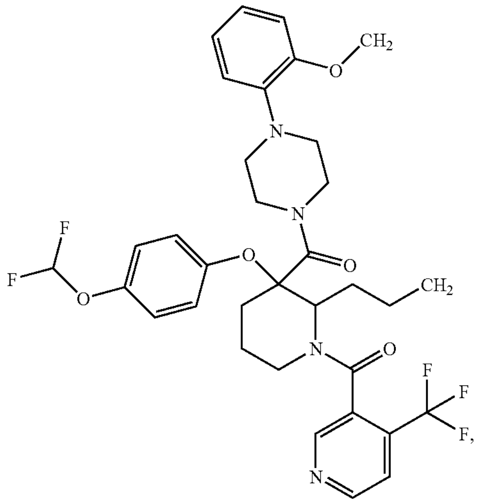
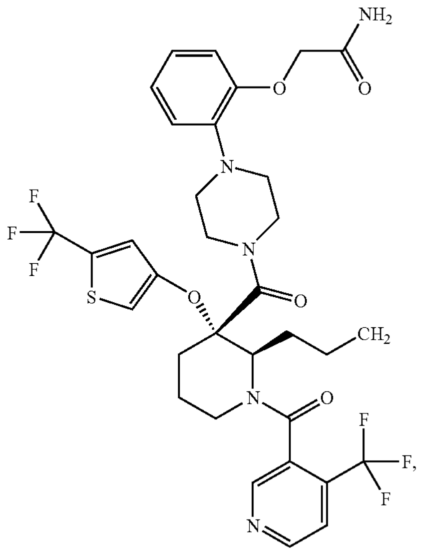
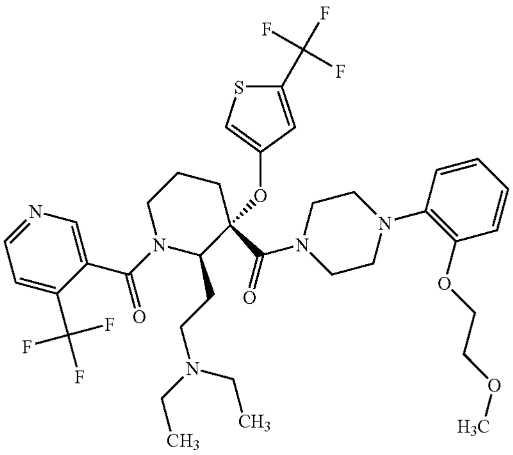

-continued
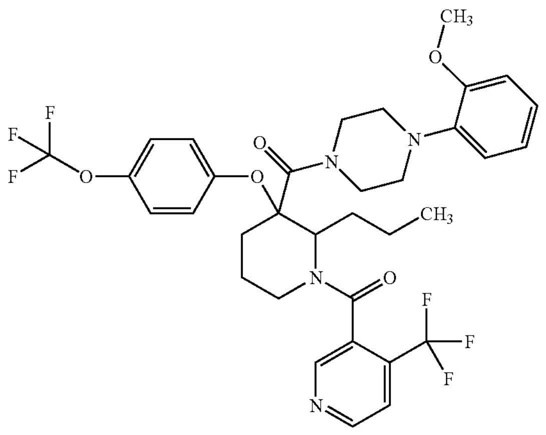
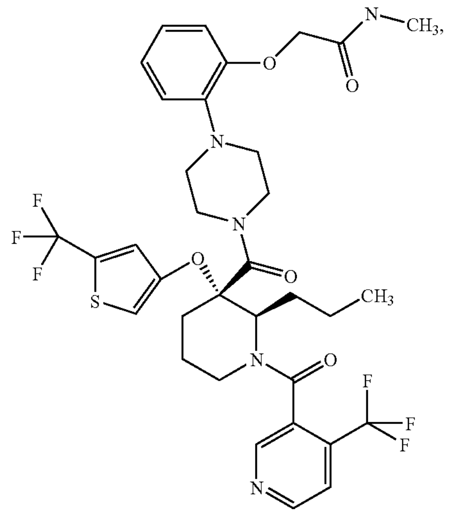
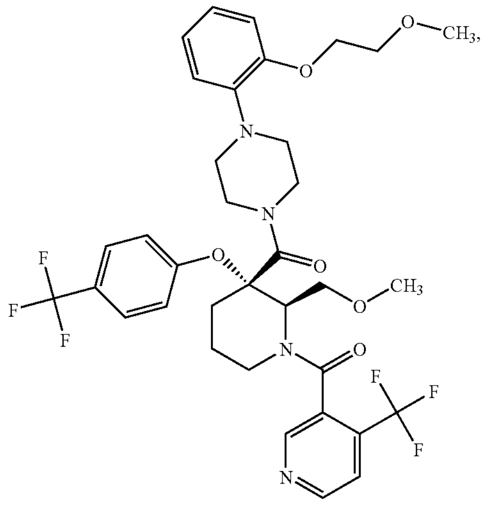
-continued
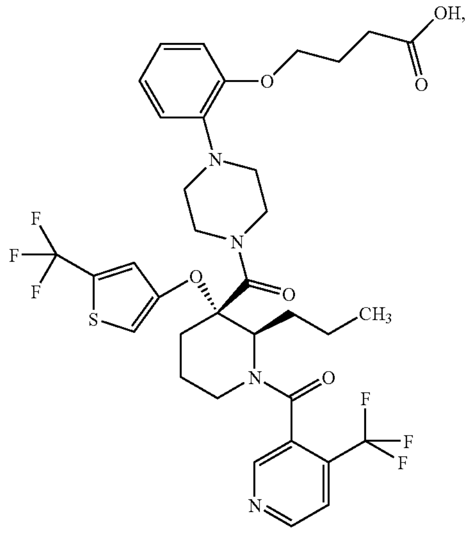
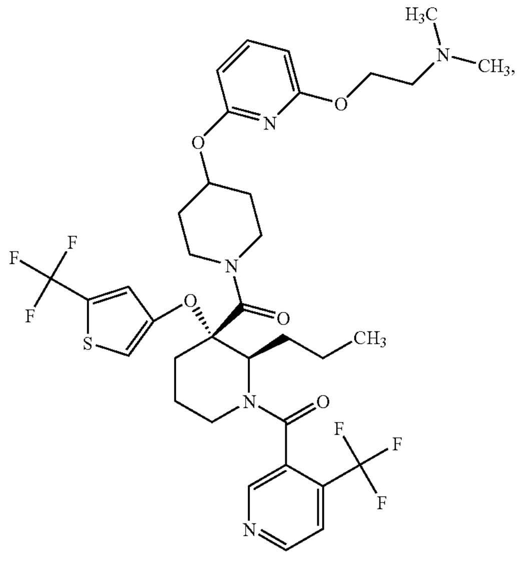
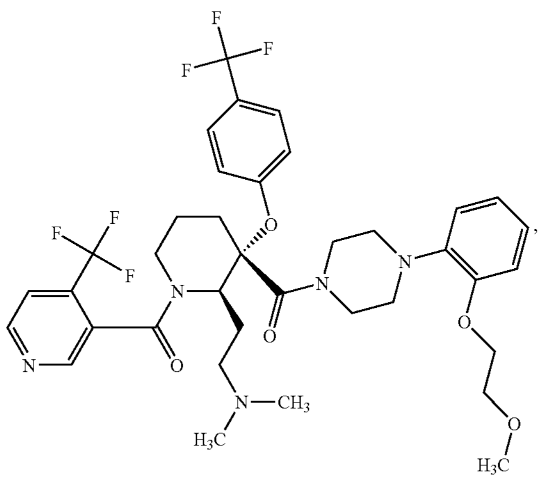

-continued
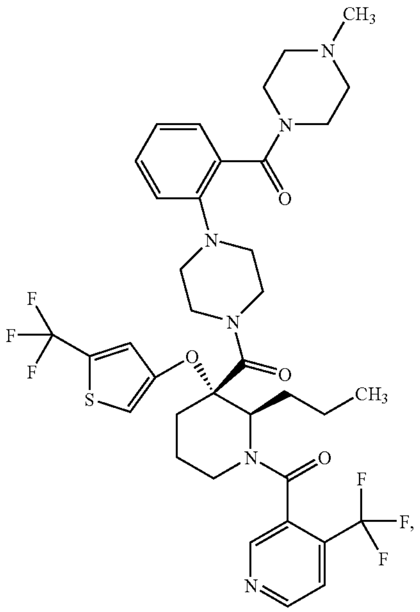
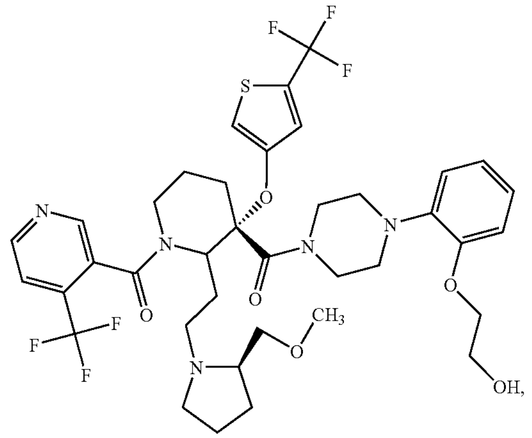
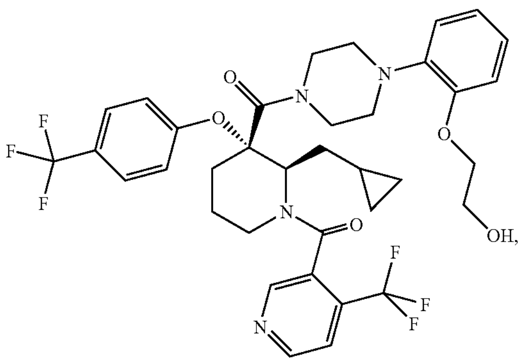
-continued
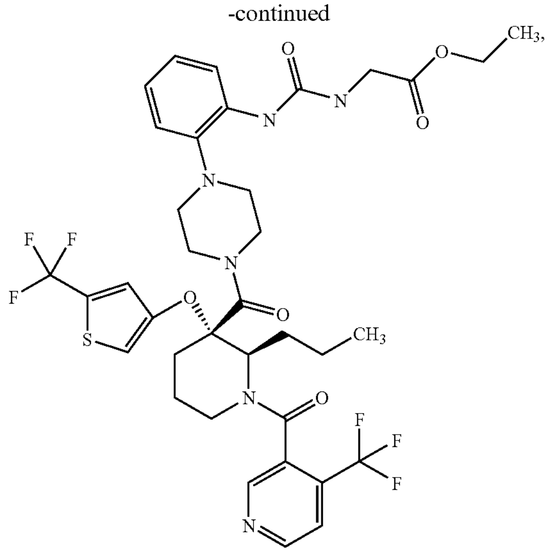
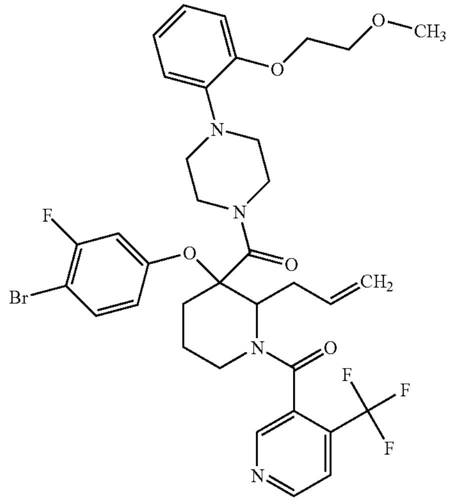
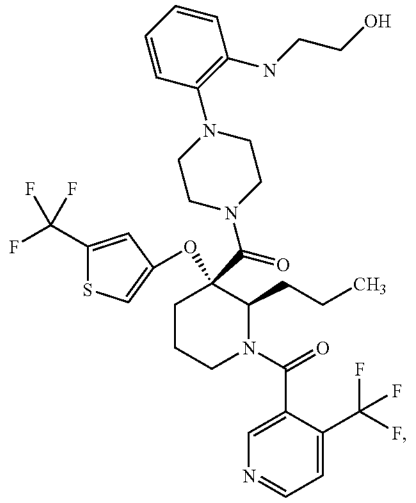

-continued
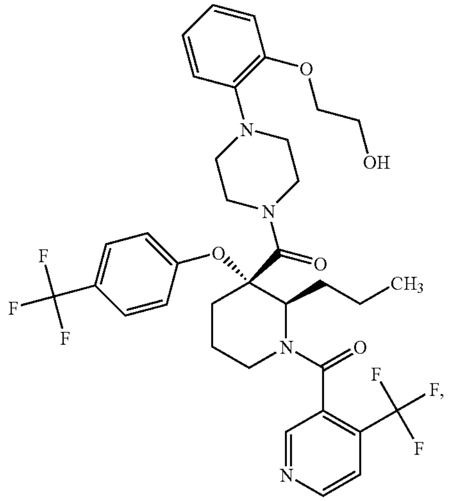
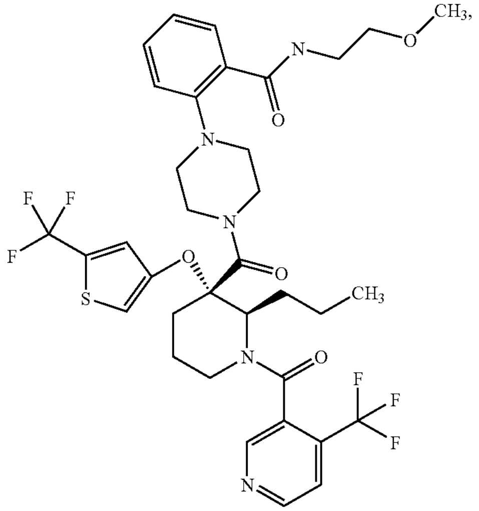
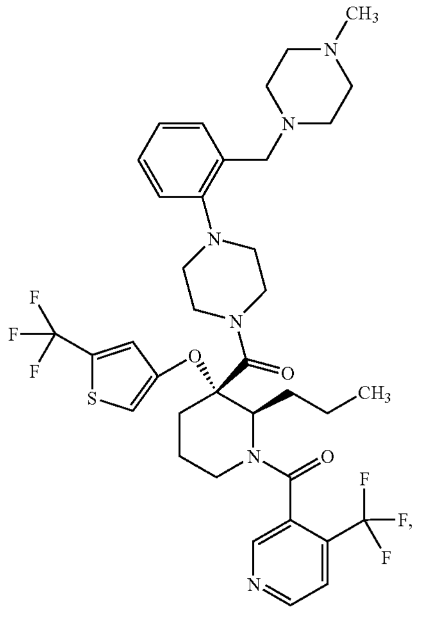
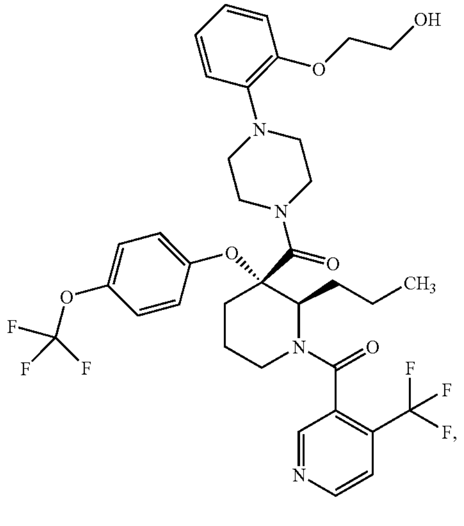
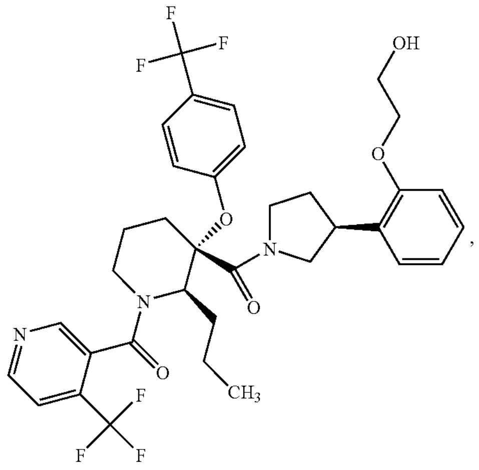
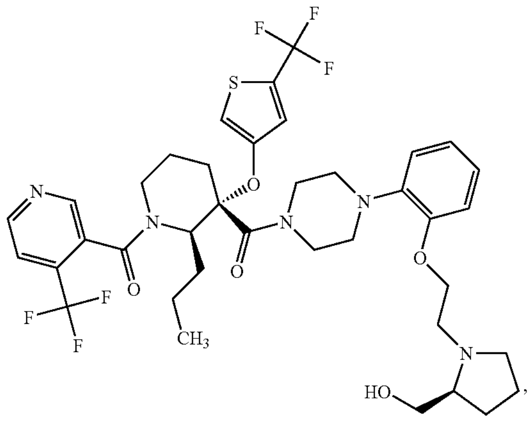

-continued
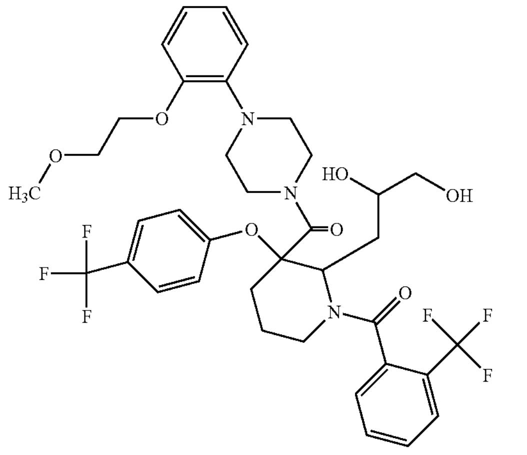
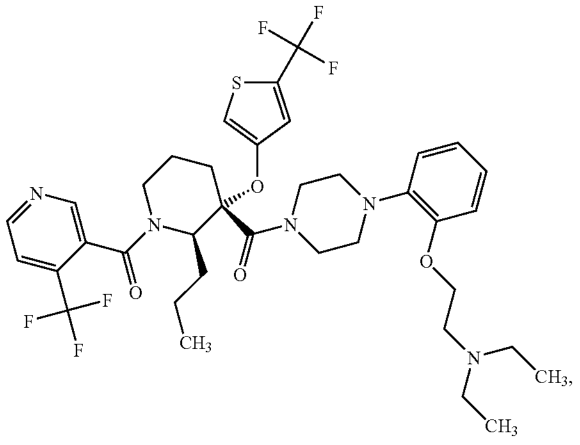
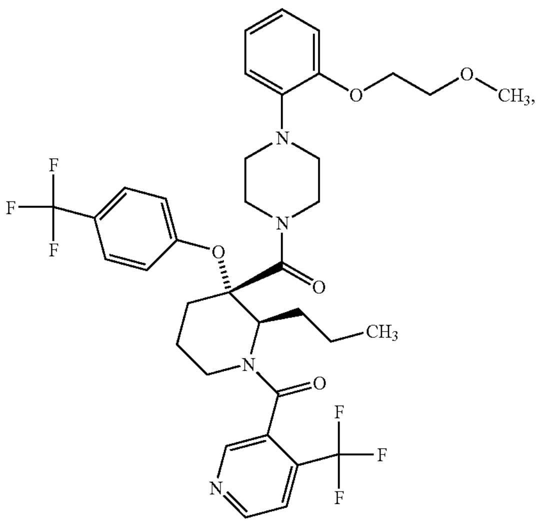
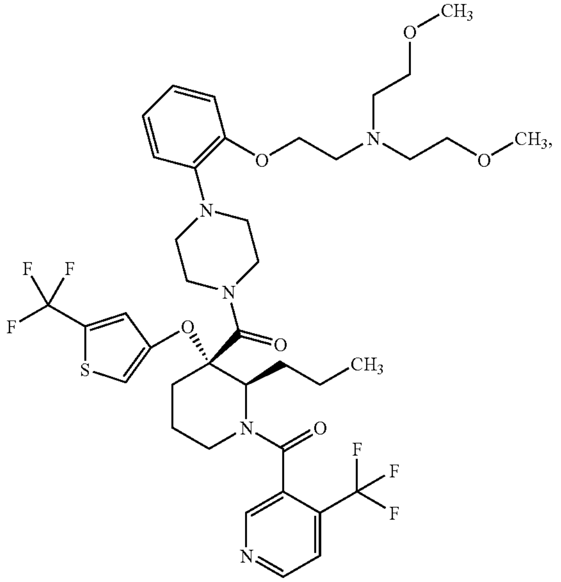
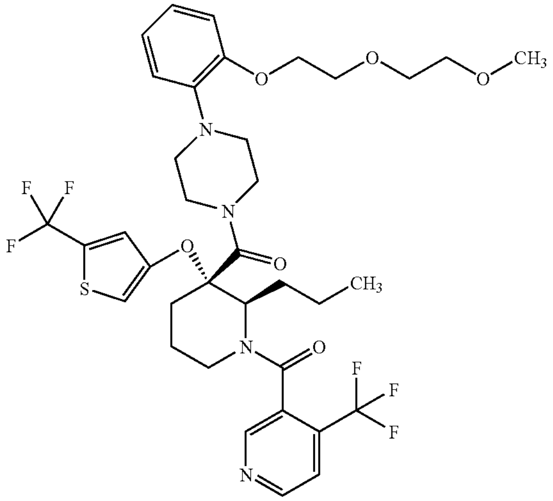
-continued
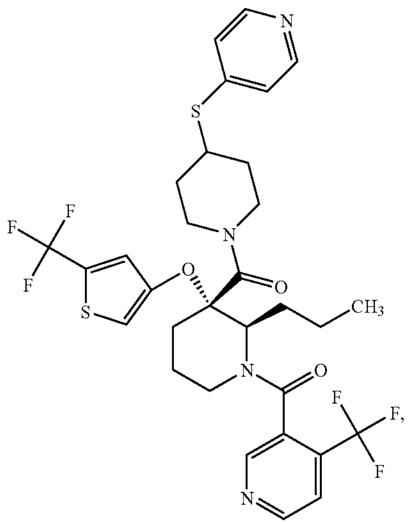

-continued
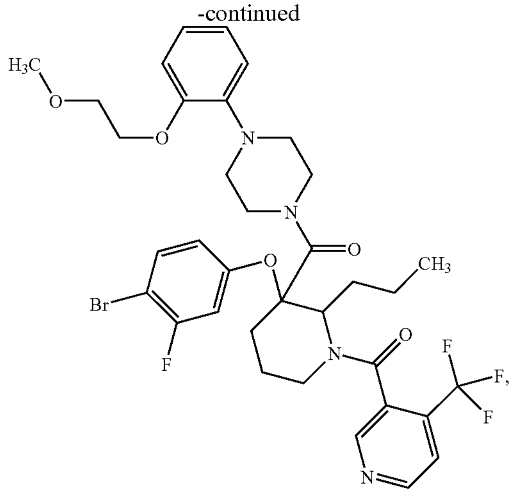
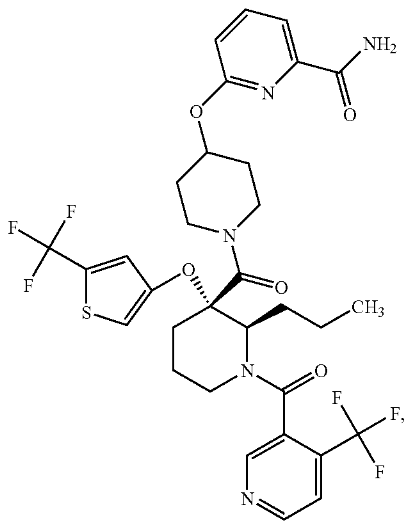
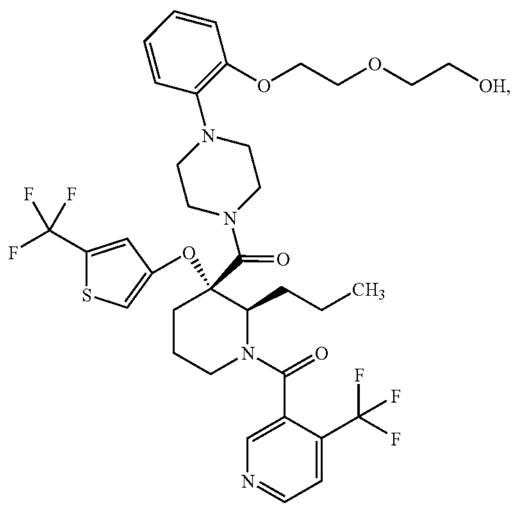
-continued
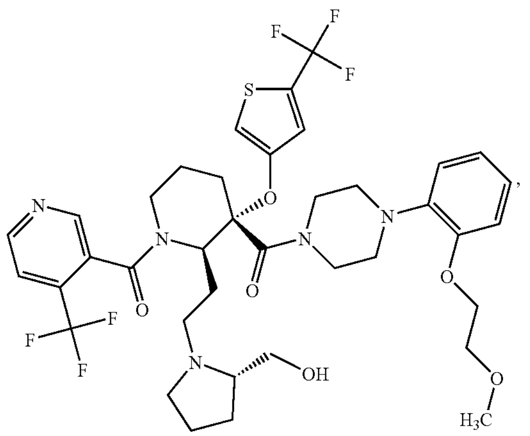
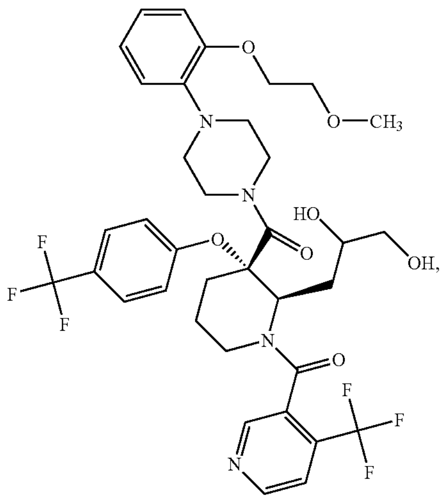
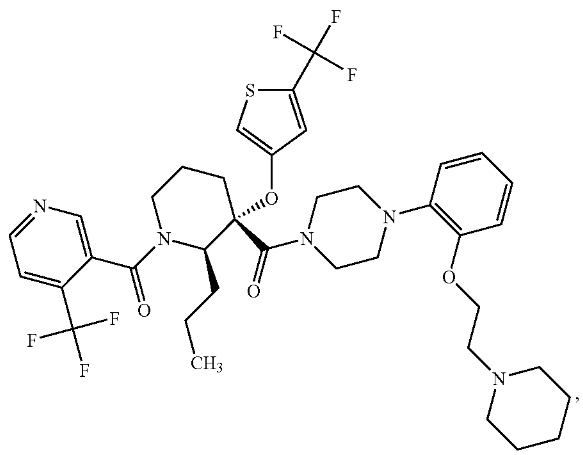

-continued
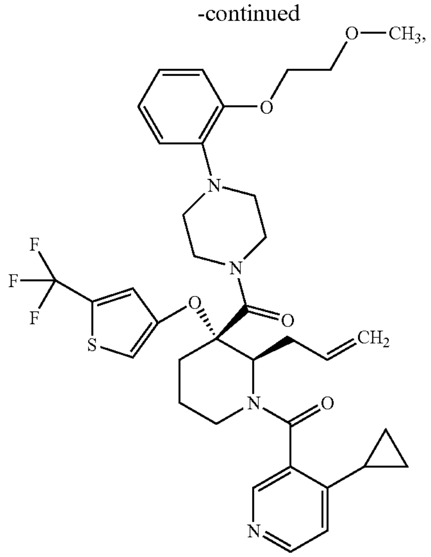
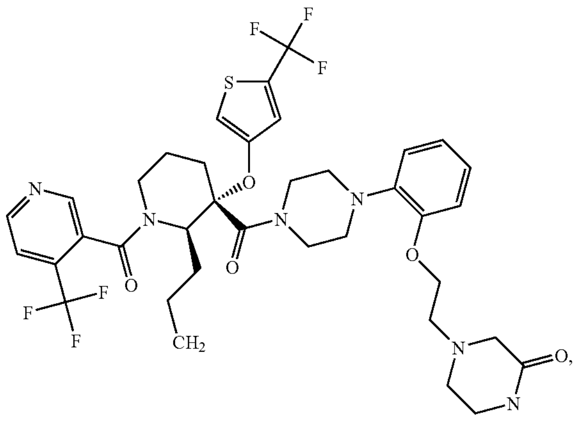
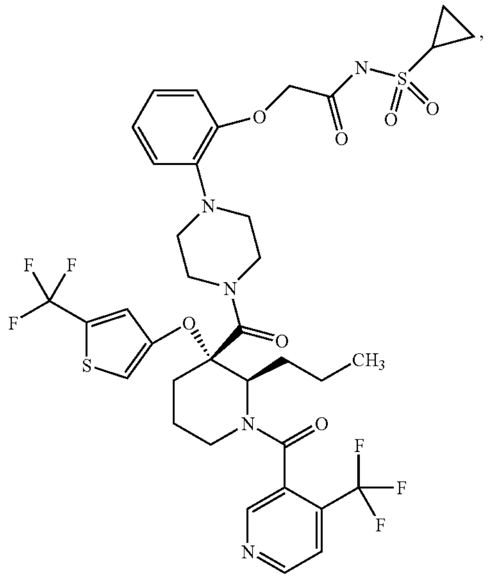
-continued
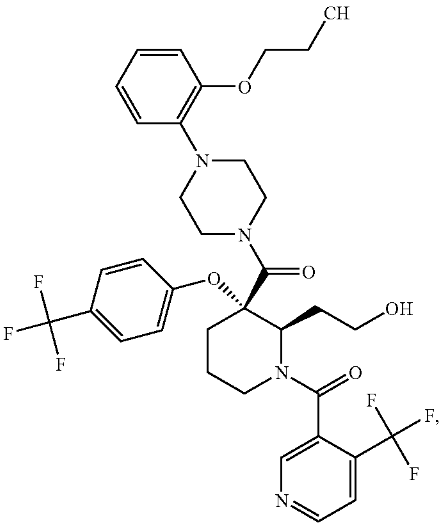
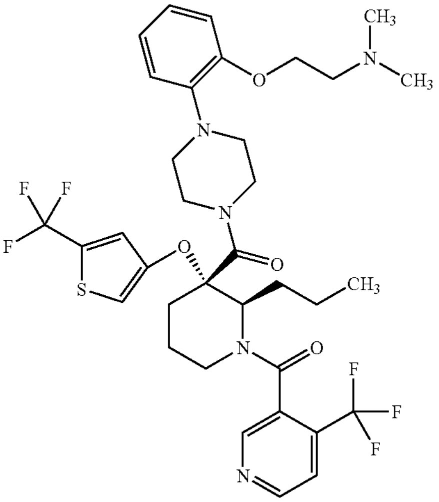
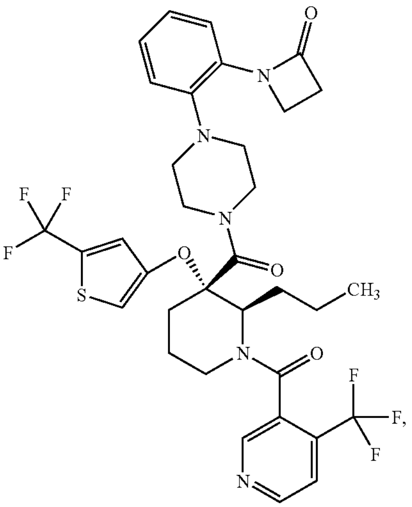

-continued
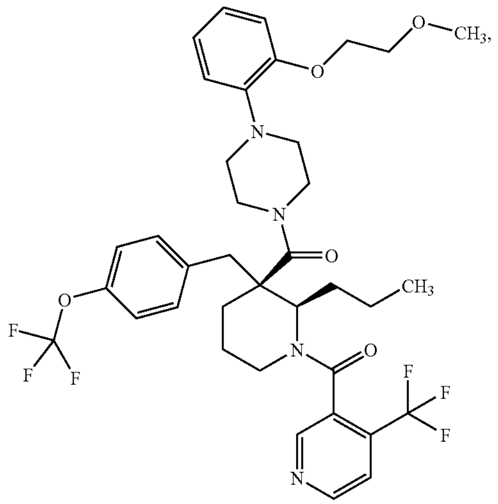
-continued
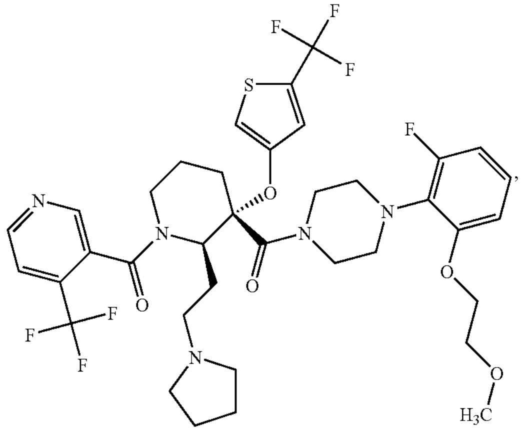
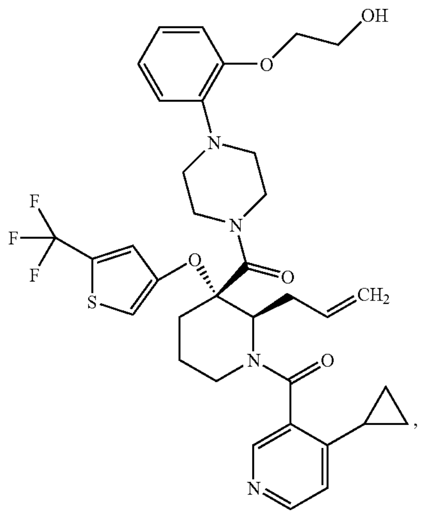
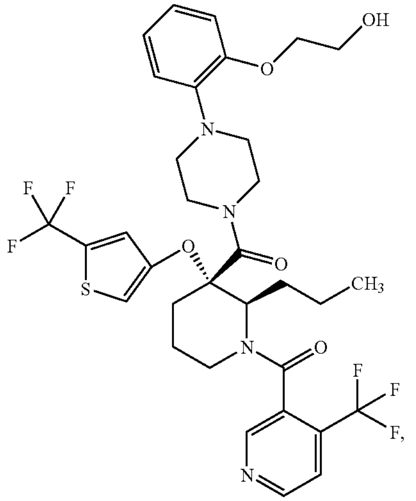
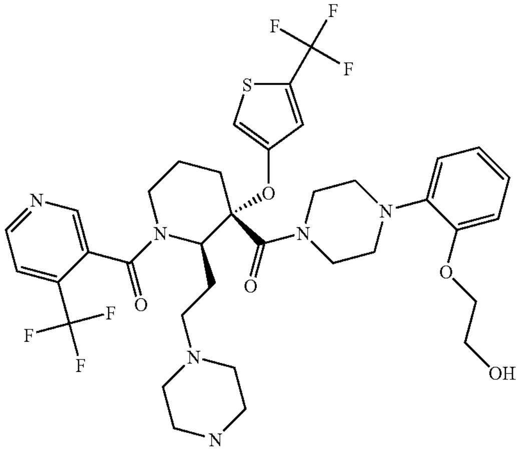
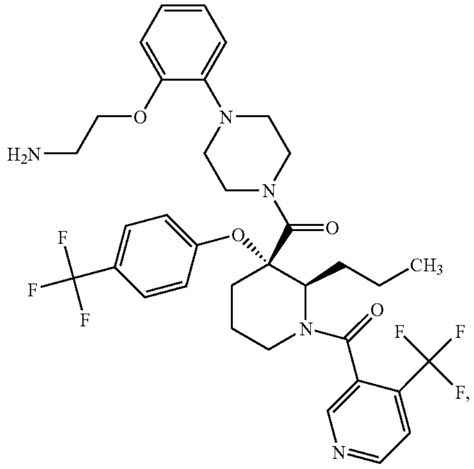

-continued

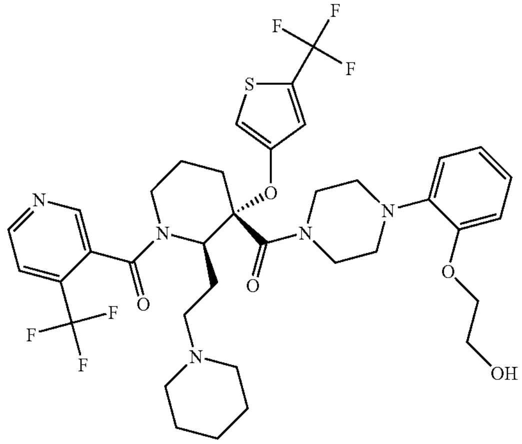

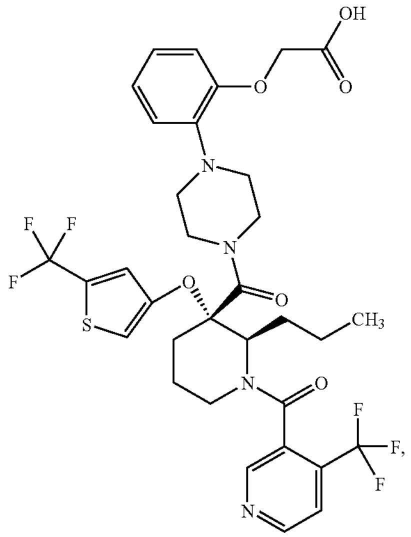

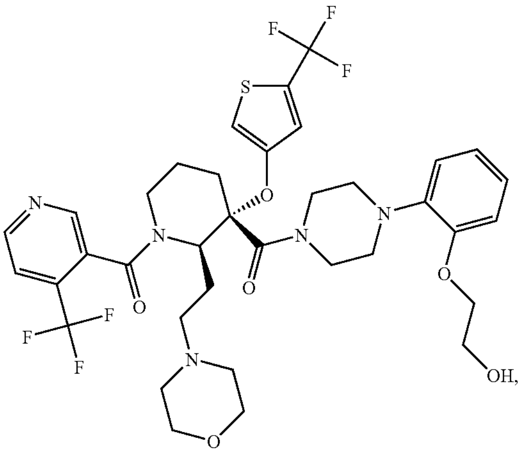

or

-continued

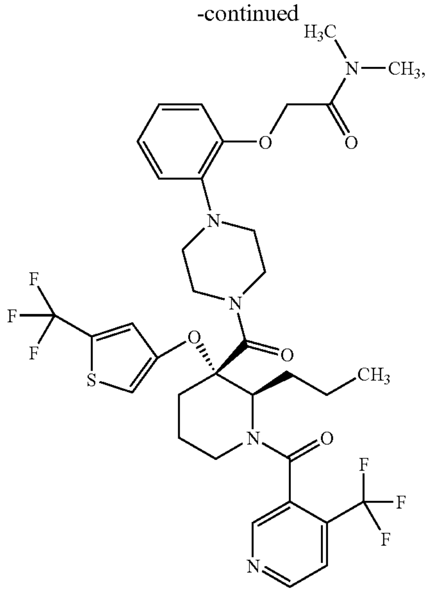

or a pharmaceutically acceptable salt thereof.

33. A pharmaceutical composition comprising a therapeutically effective amount of at least one compound of claim 1 or a pharmaceutically acceptable salt thereof, in combination with at least one pharmaceutically acceptable carrier.

34. A pharmaceutical composition comprising a therapeutically effective amount of at least one compound of claim 32 or a pharmaceutically acceptable salt thereof, in combination with at least one pharmaceutically acceptable carrier.

35. A compound selected from the group consisting of:

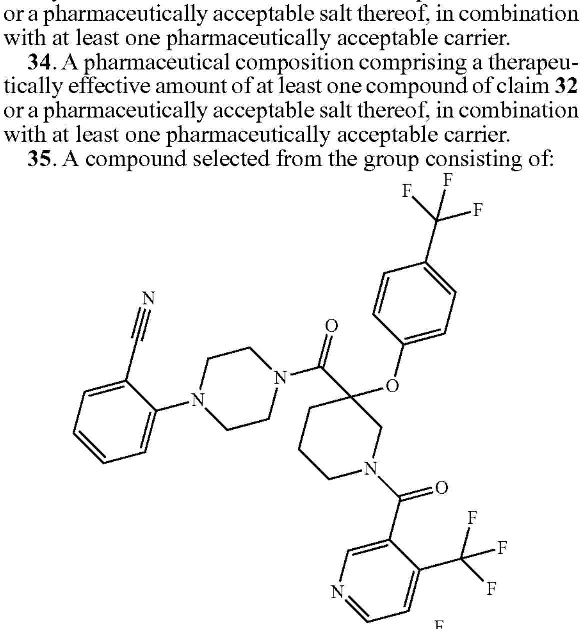

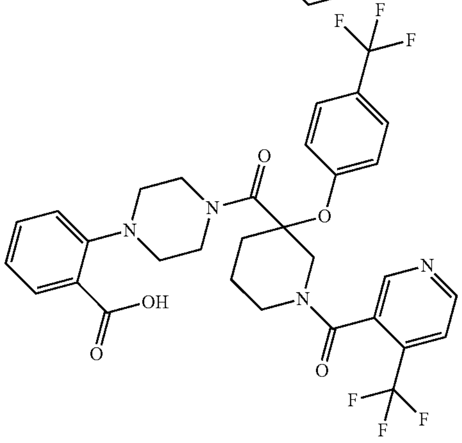

-continued
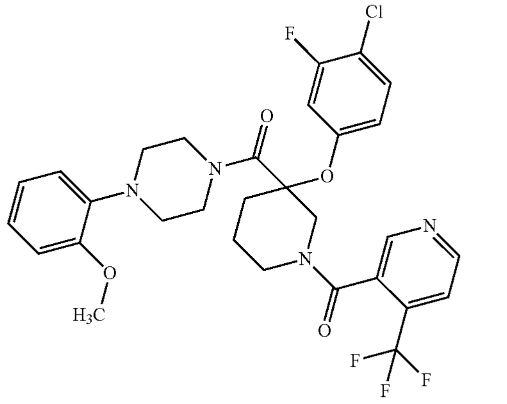
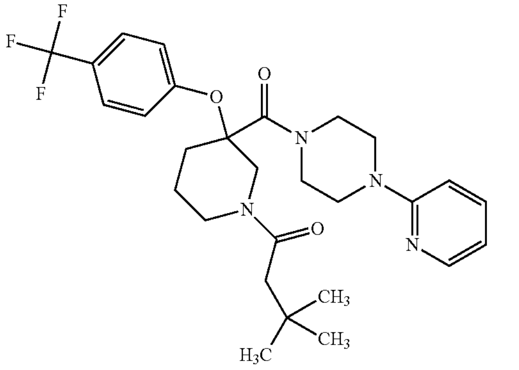
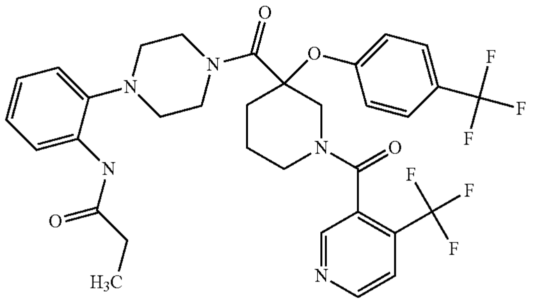
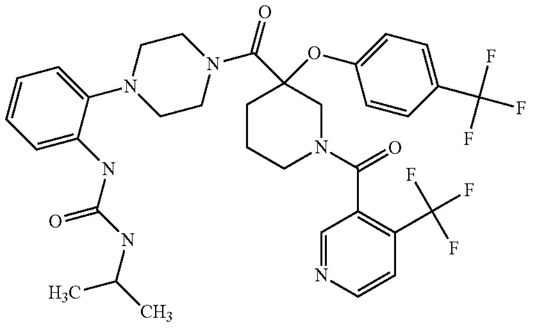
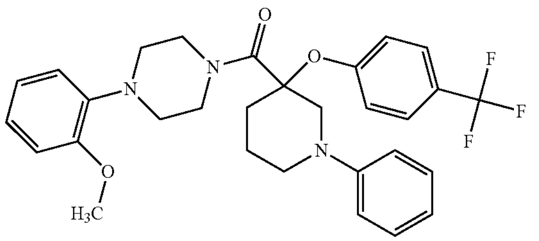
-continued
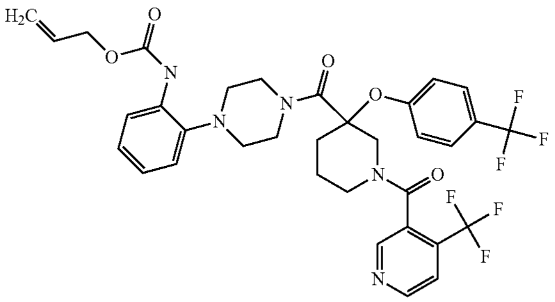
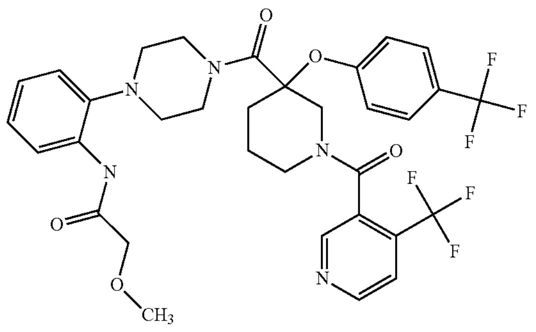
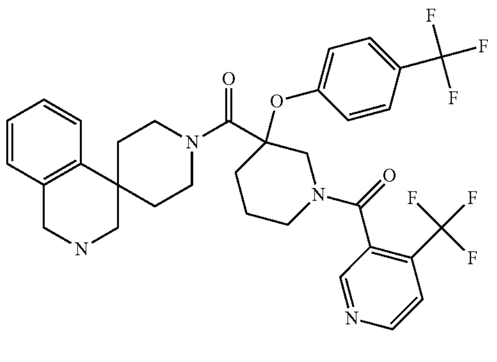
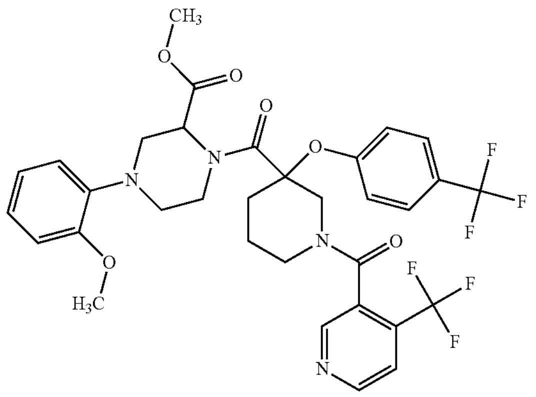

-continued
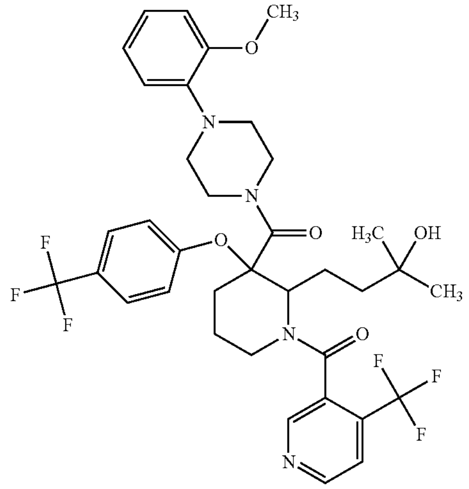
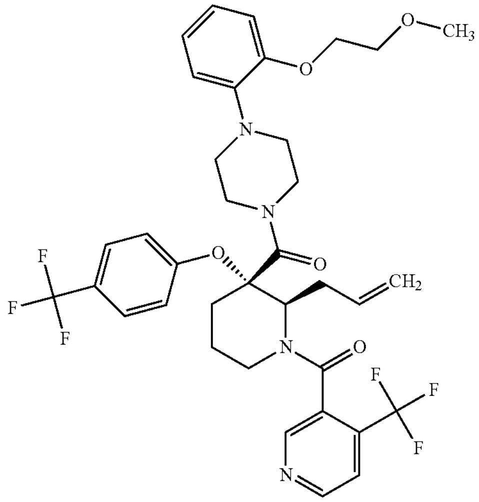
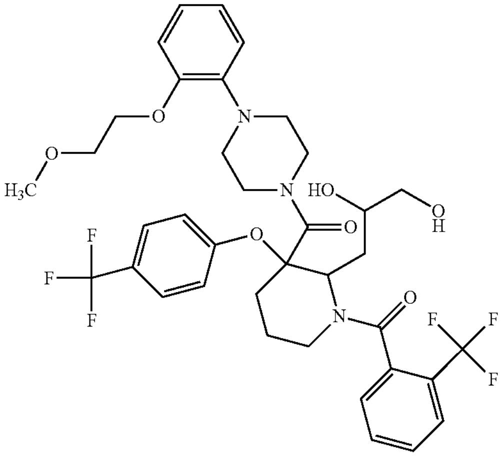
-continued
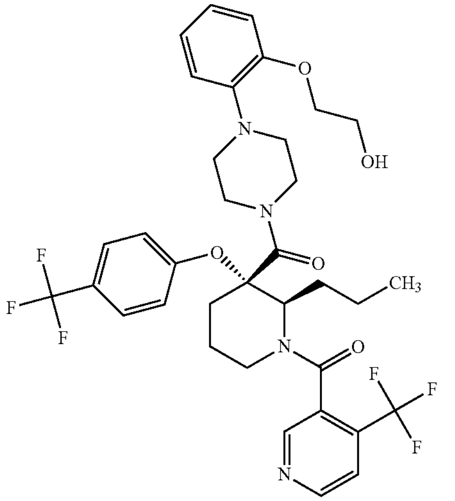
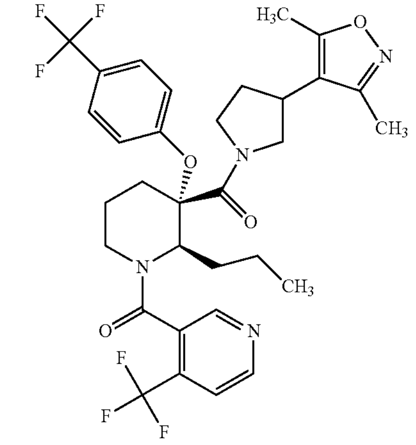
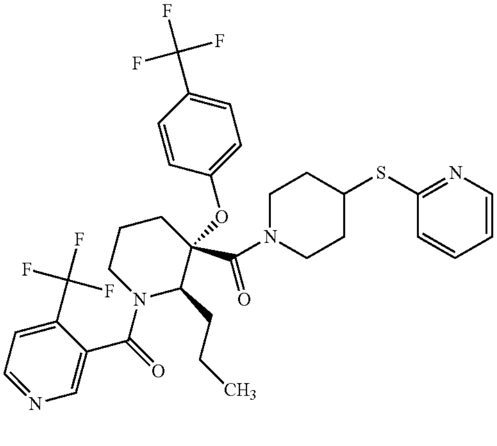

-continued
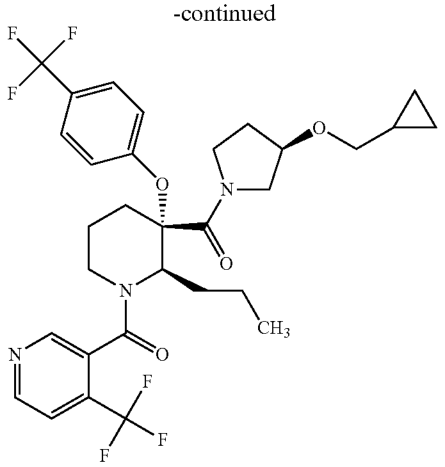
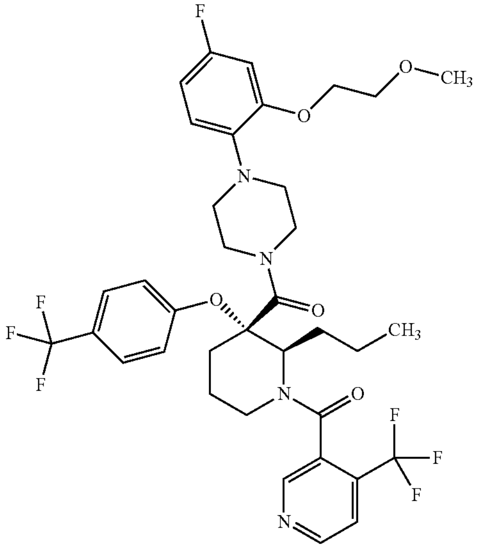
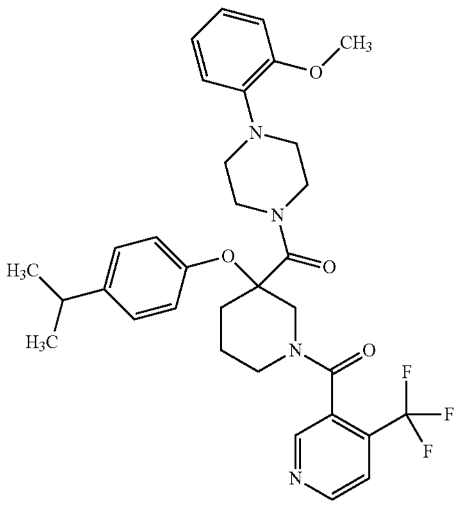
-continued
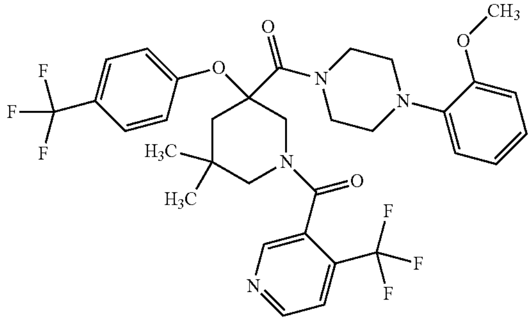
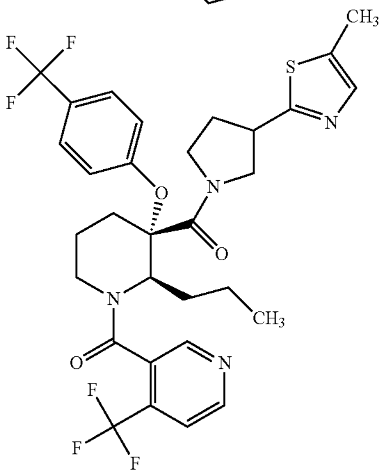
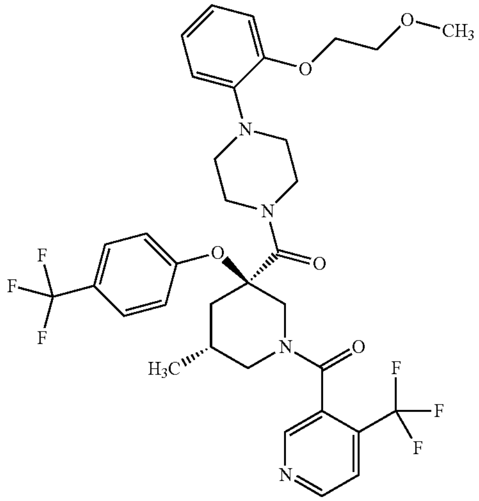
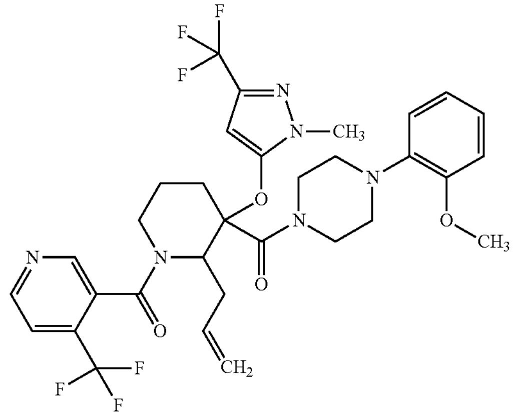

-continued
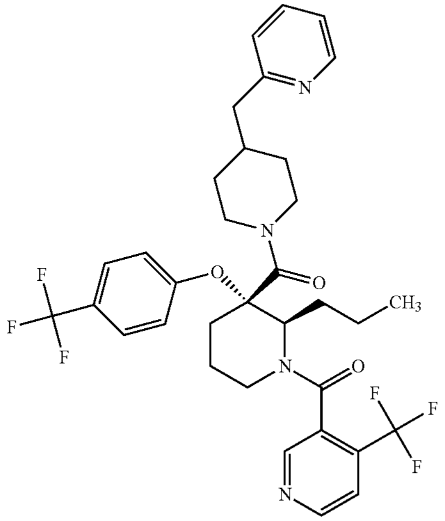
-continued
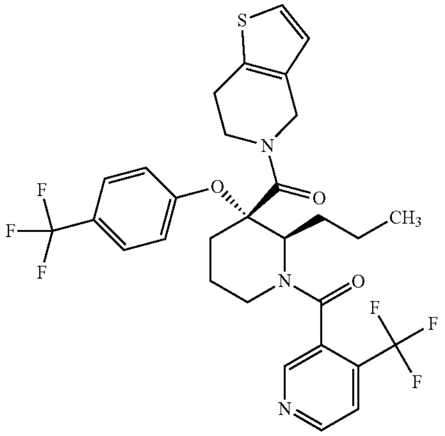
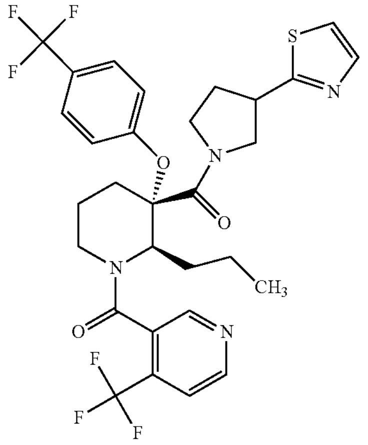
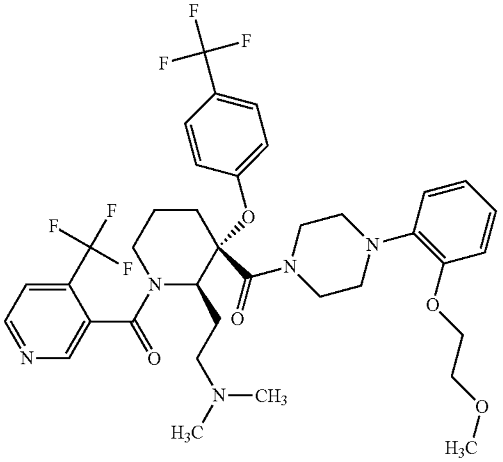
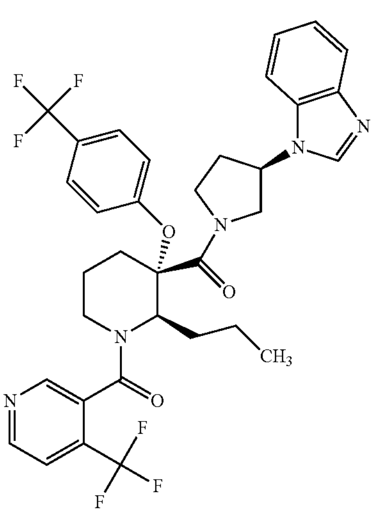
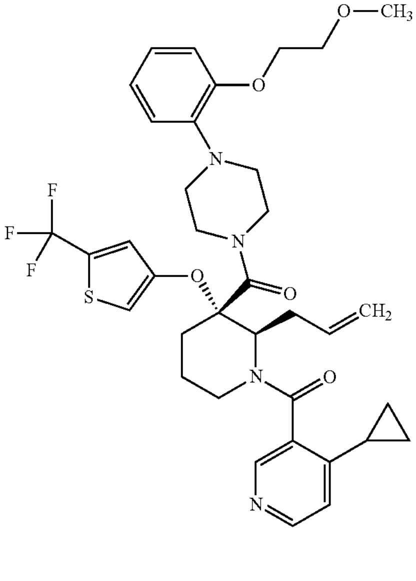

-continued
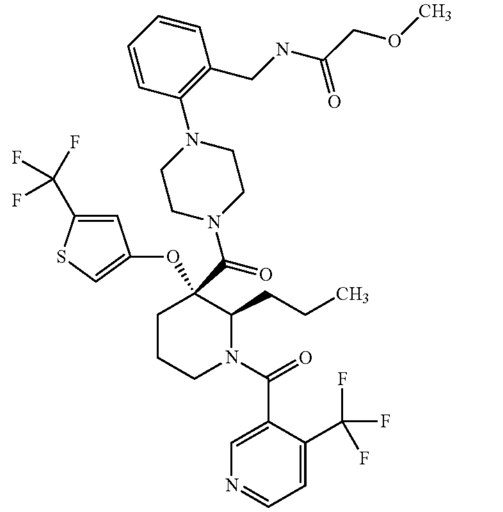
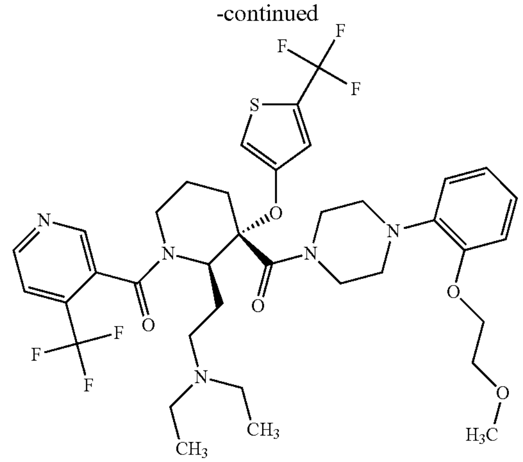
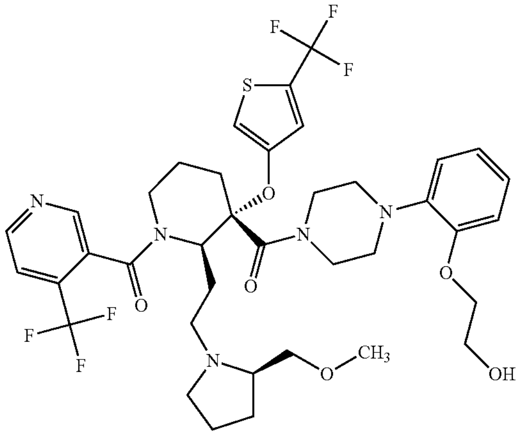
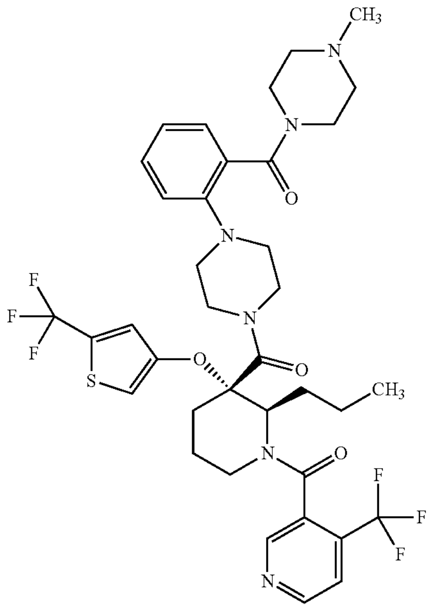
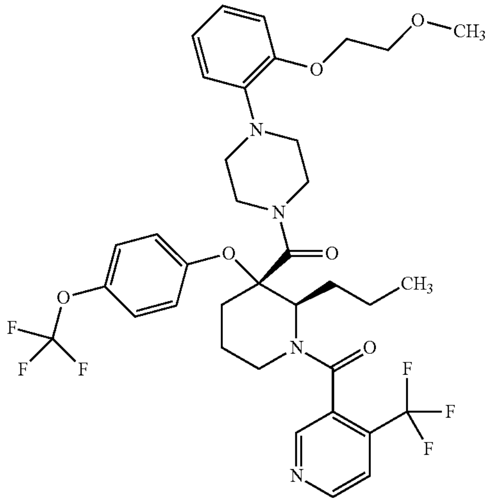
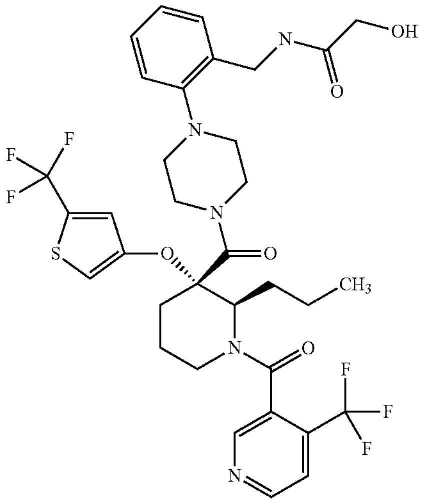
-continued -continued
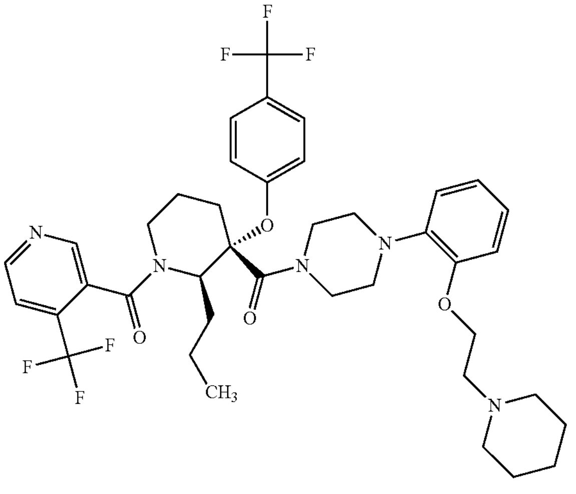
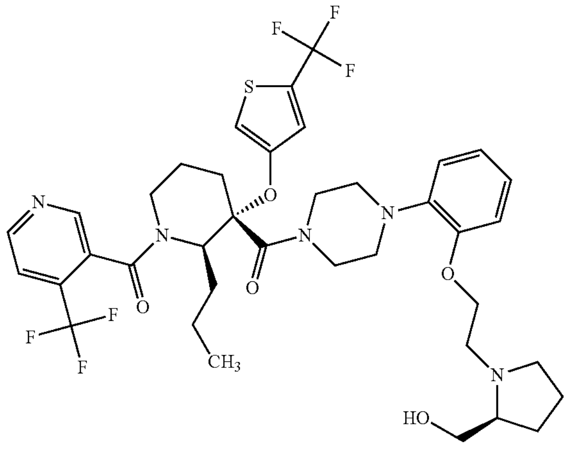
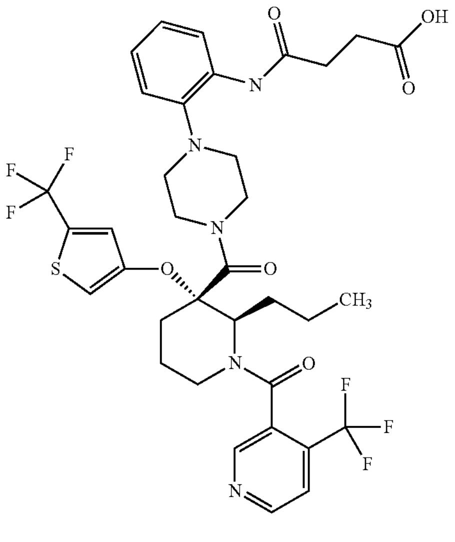
-continued
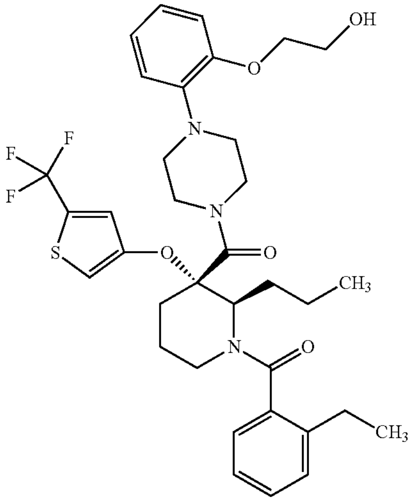
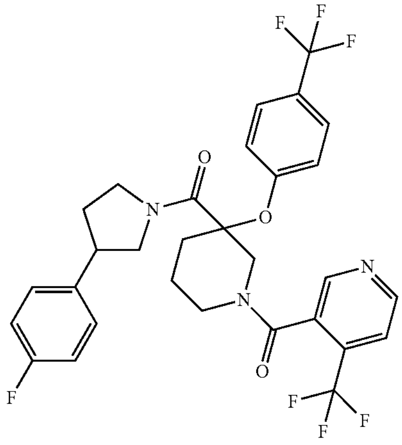
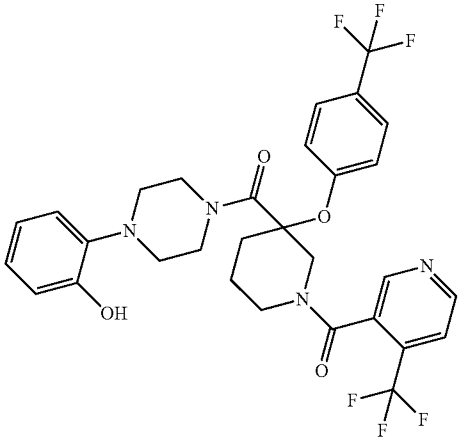

-continued
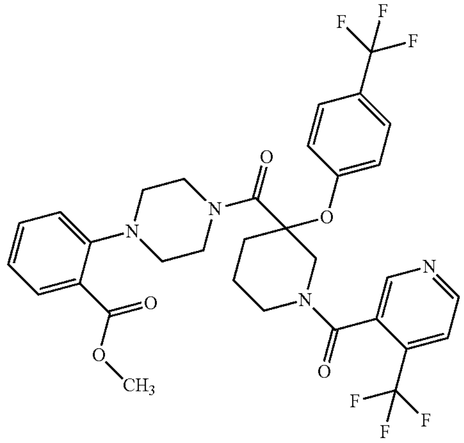
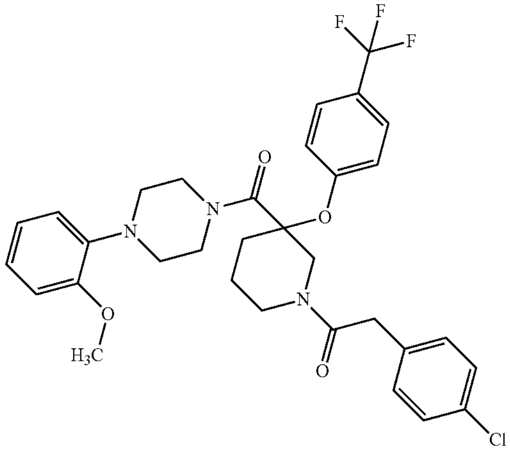
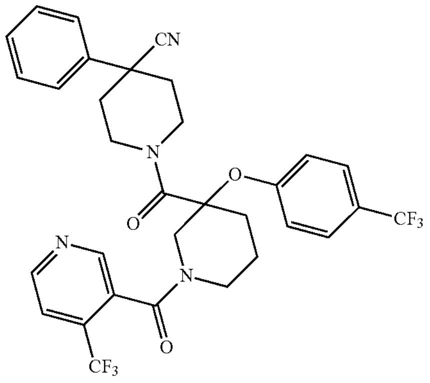
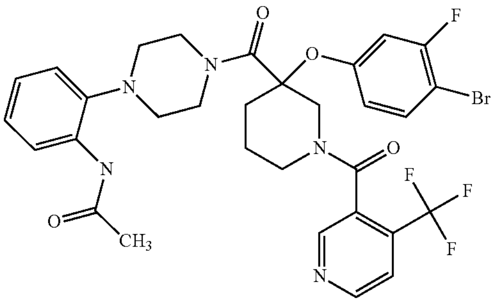
-continued
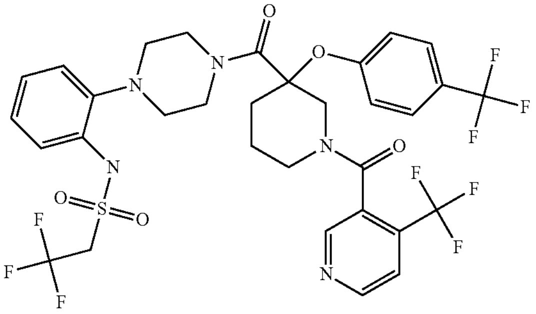
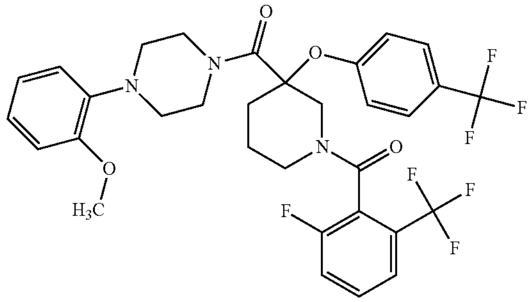
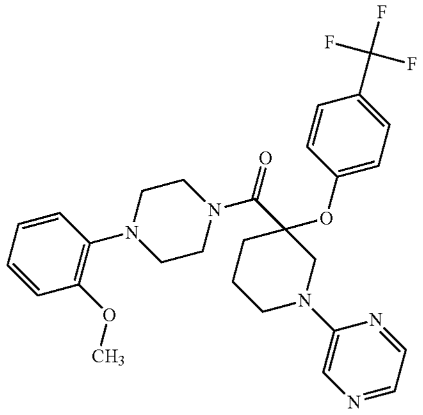
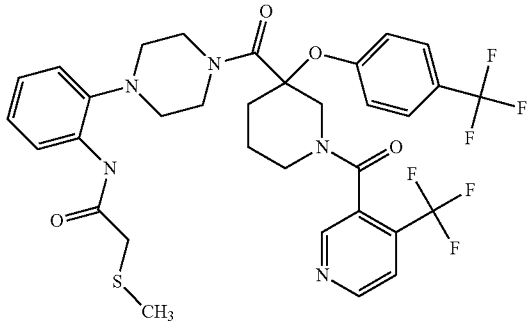
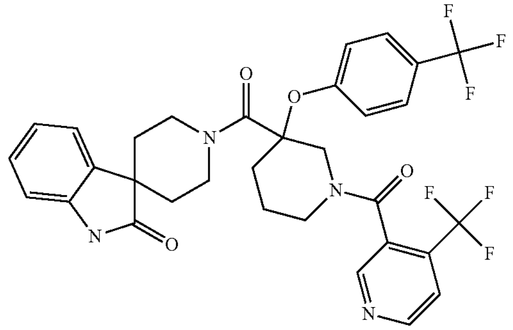

-continued
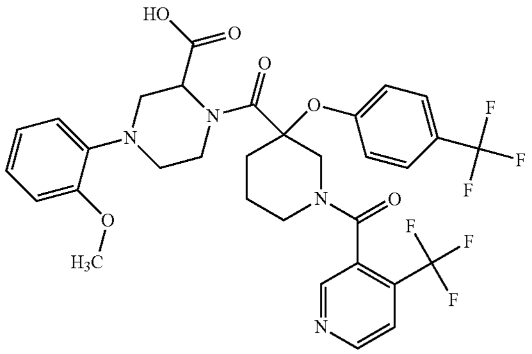
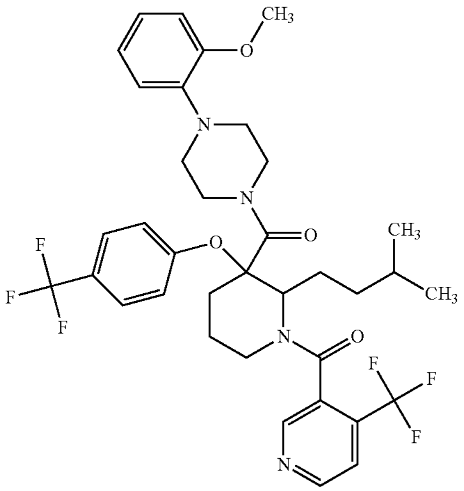
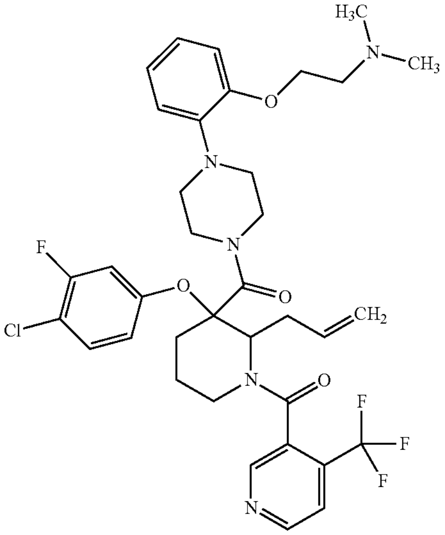
-continued
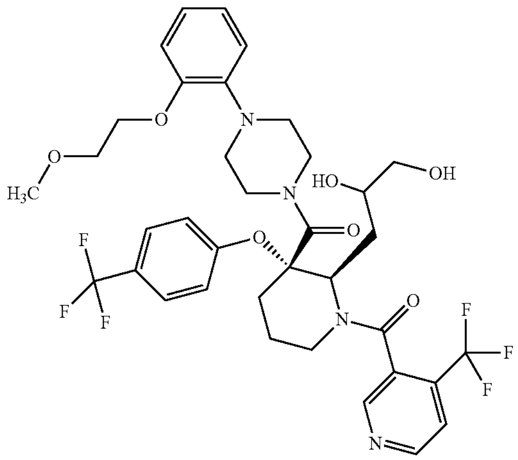
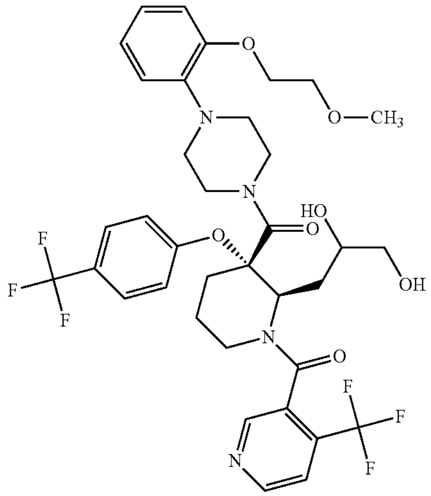
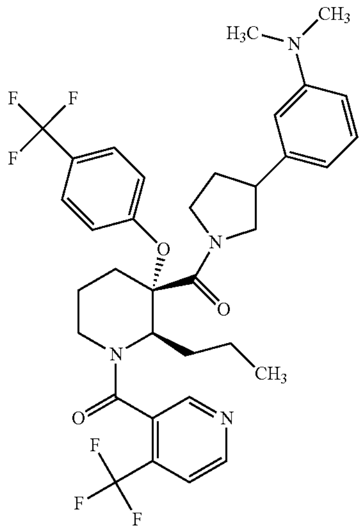

-continued
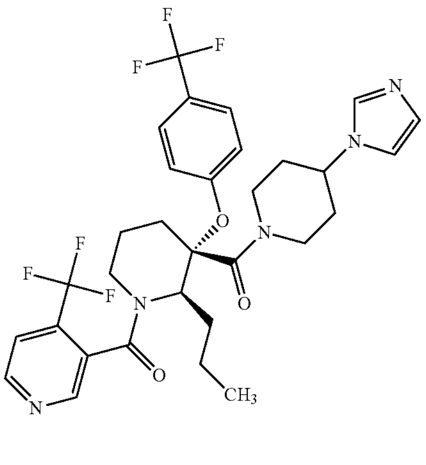
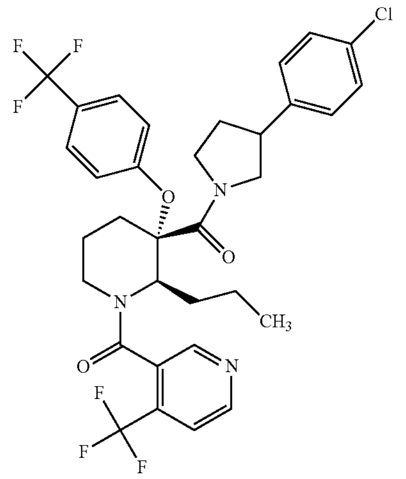
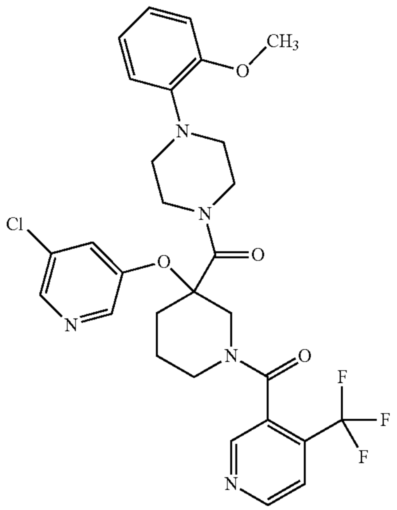
-continued
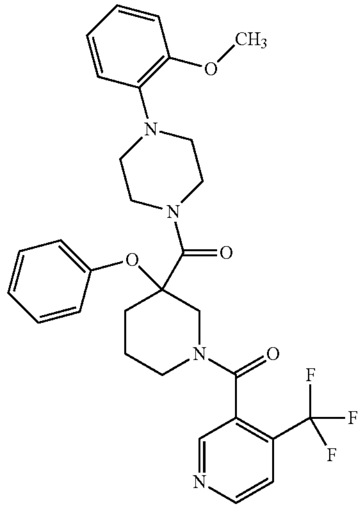
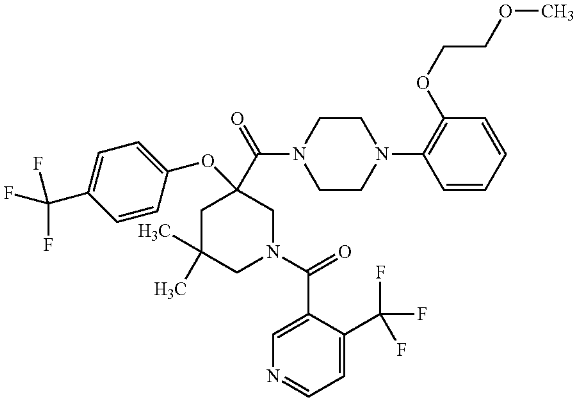
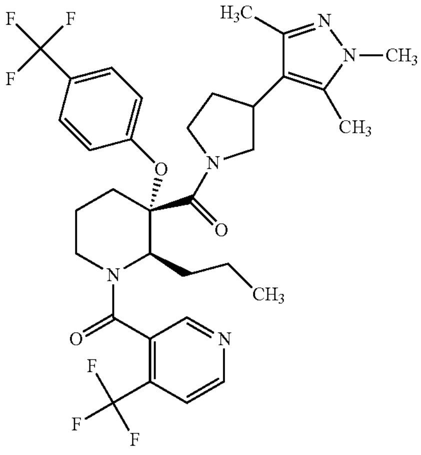

-continued
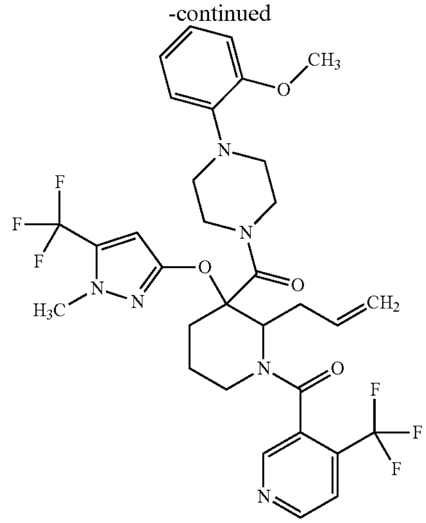
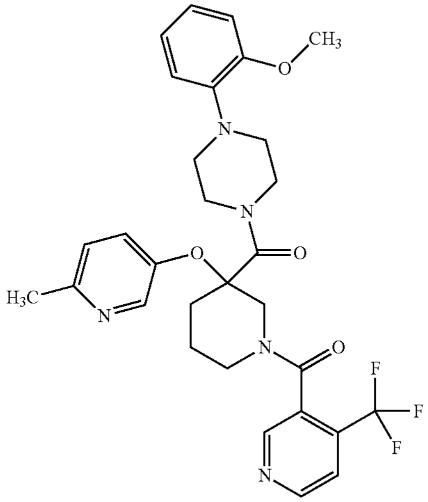
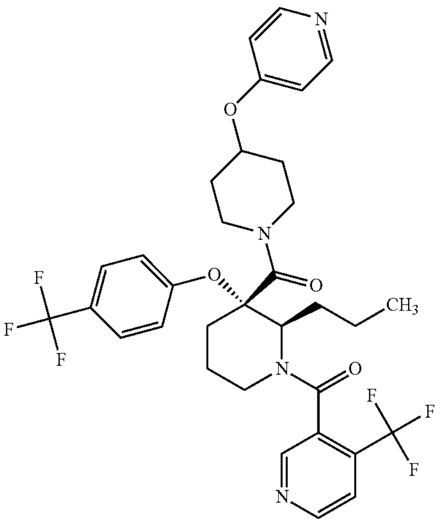
-continued
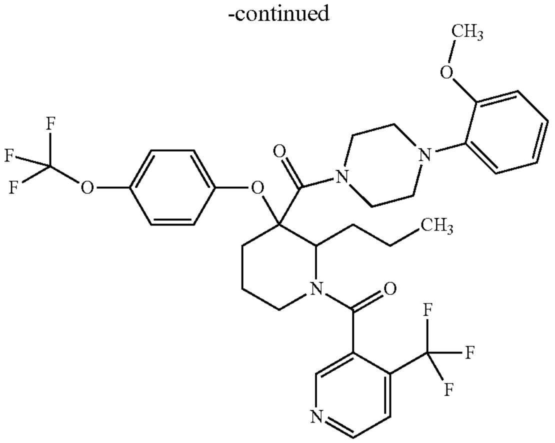
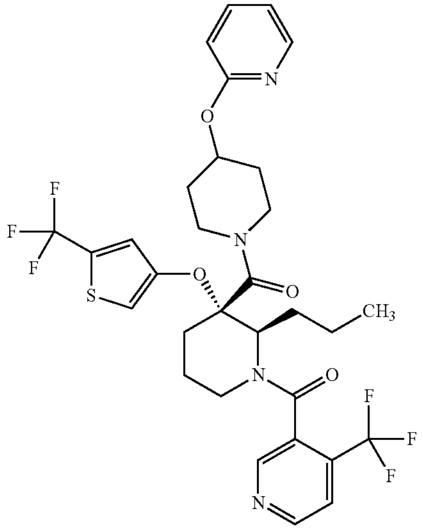
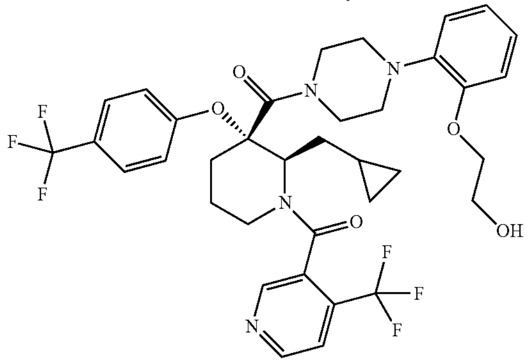
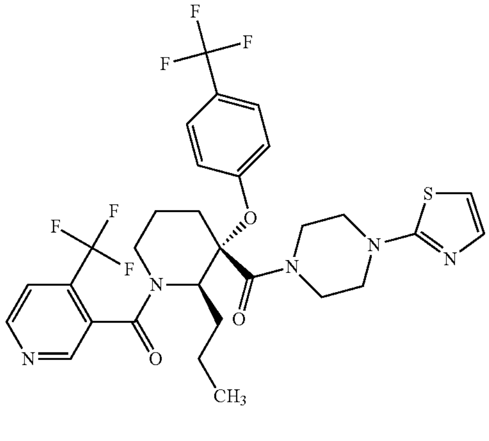

-continued
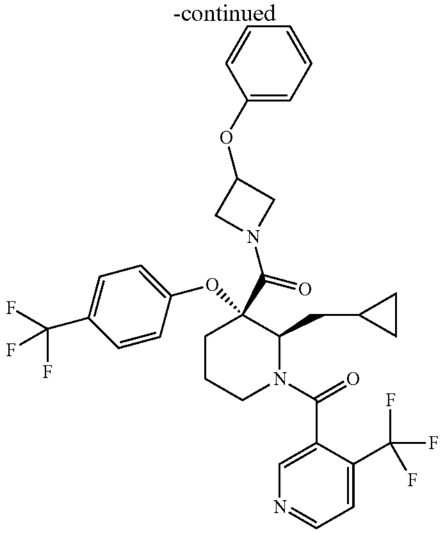
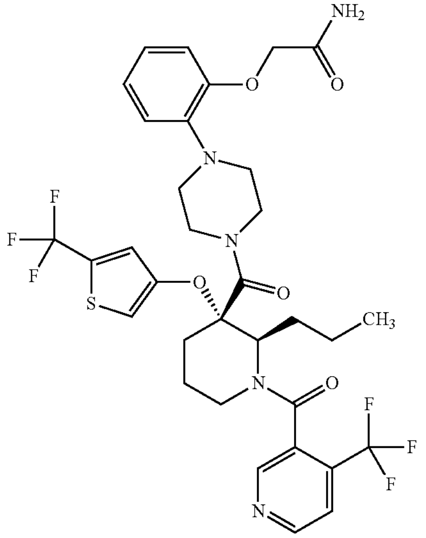
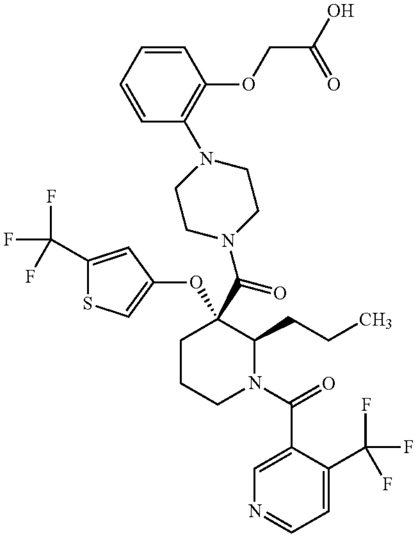
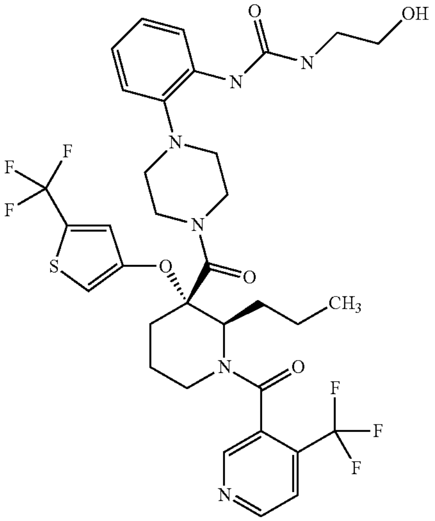
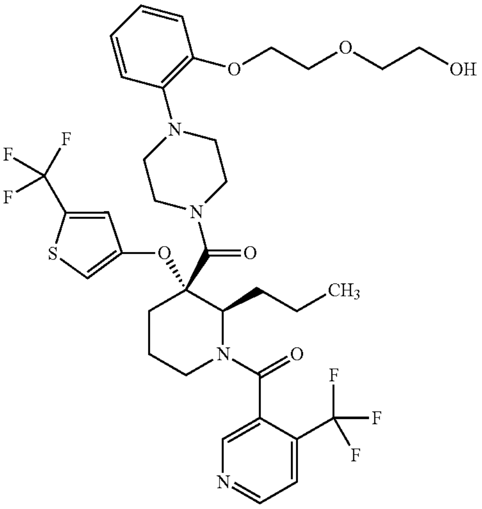
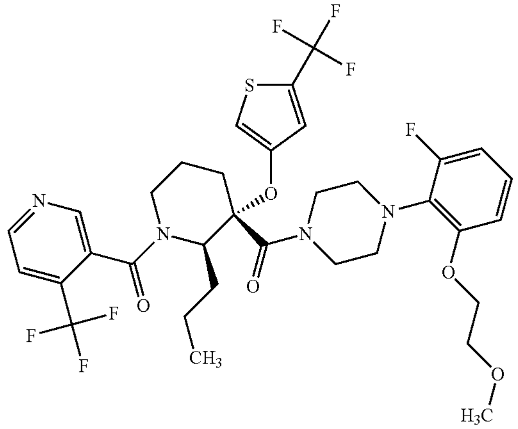
-continued -continued
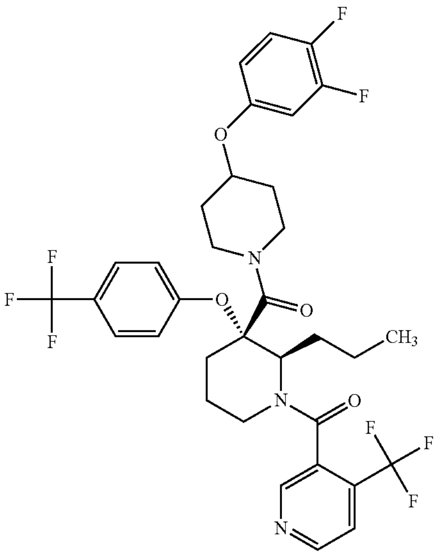
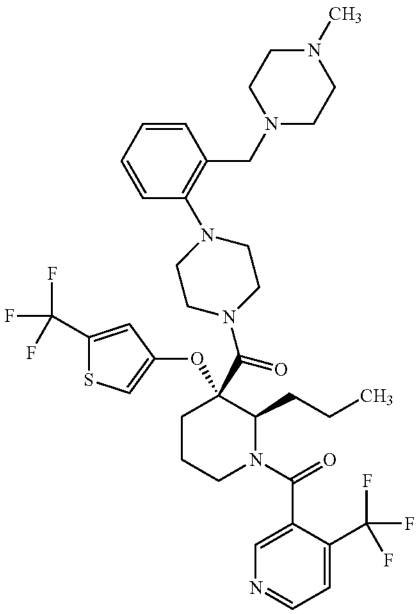
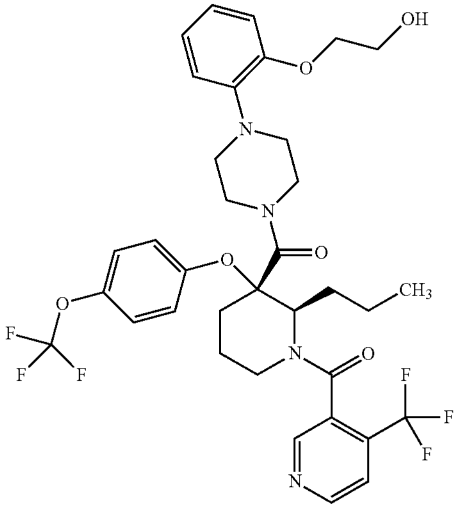
-continued
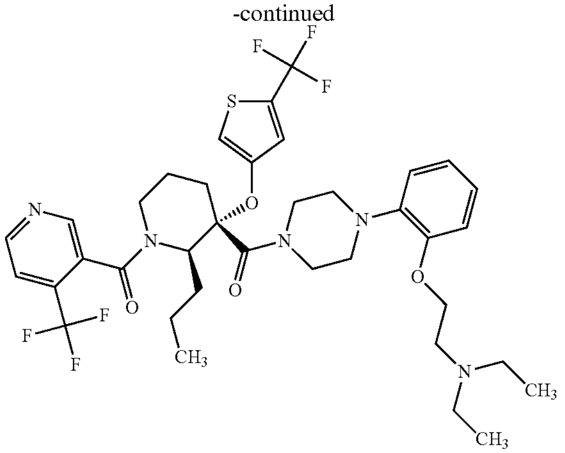
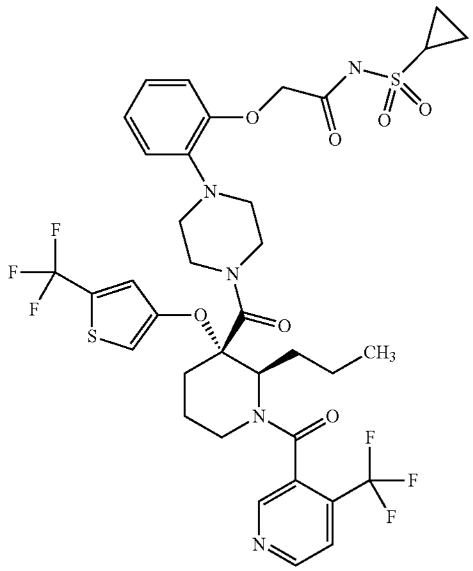
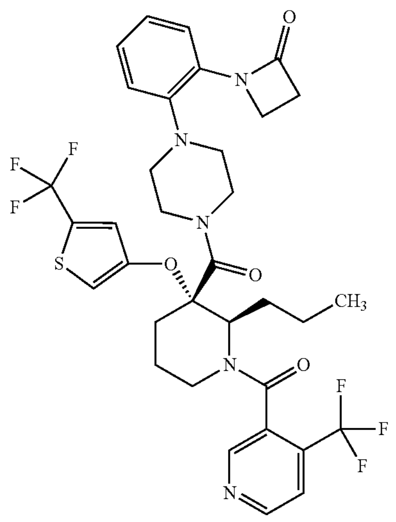

-continued
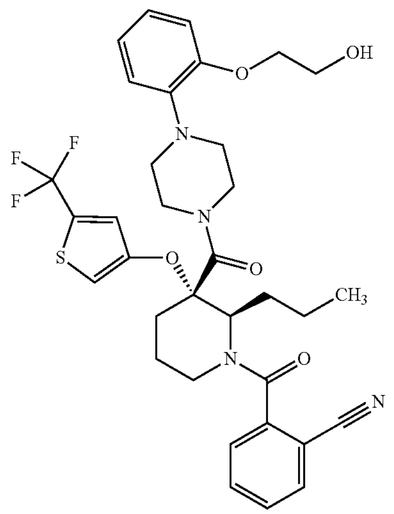
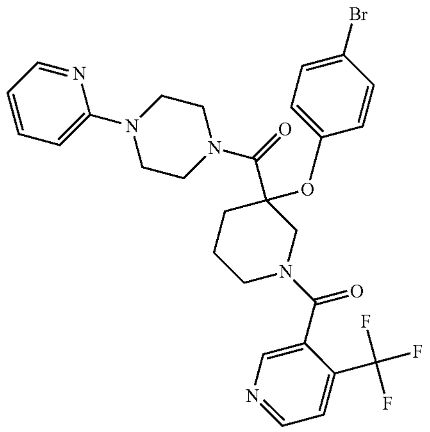
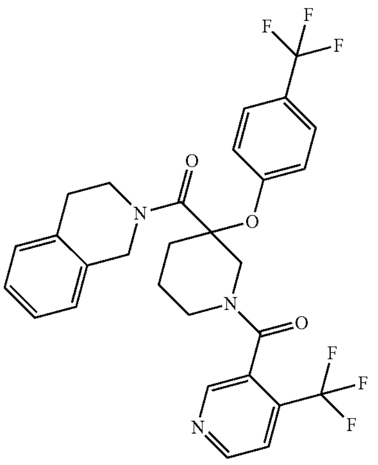
-continued
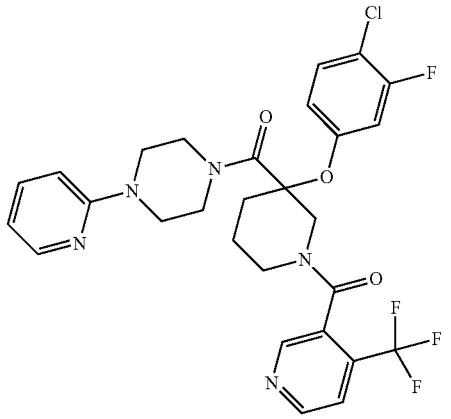
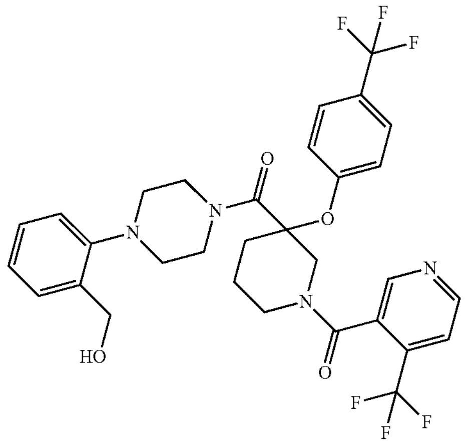
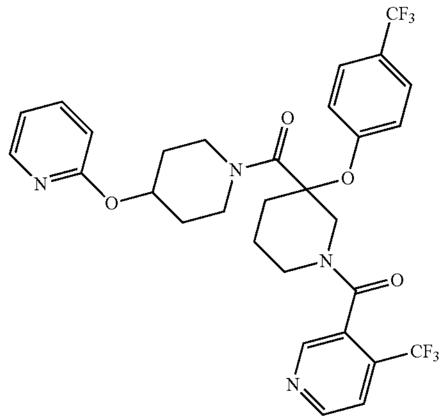
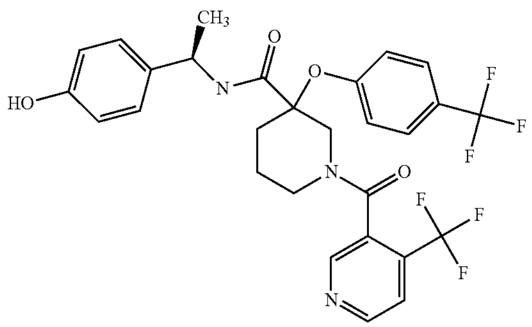

-continued
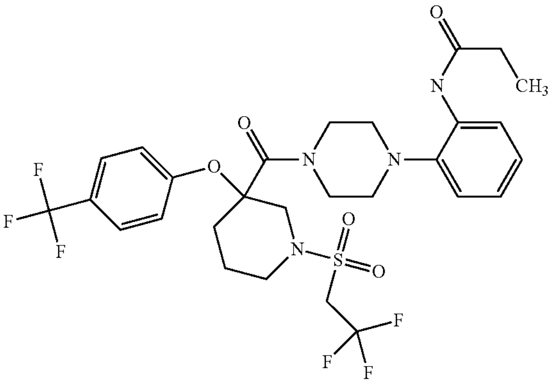
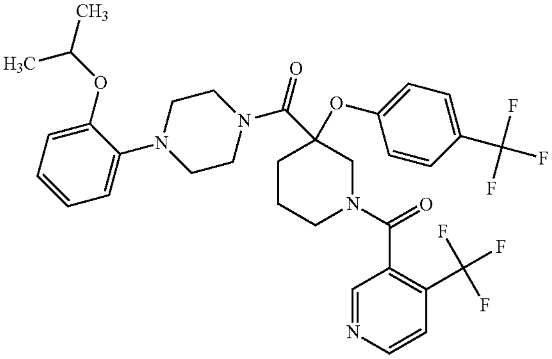
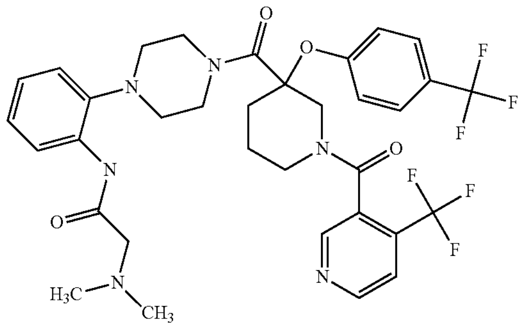
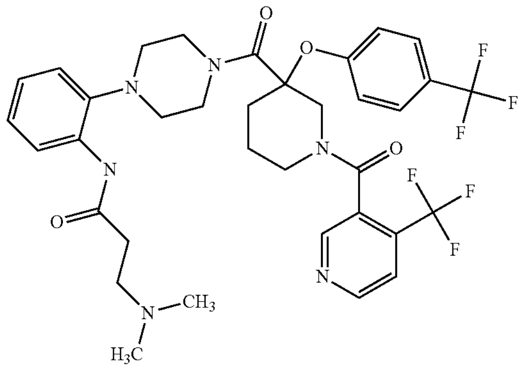
-continued
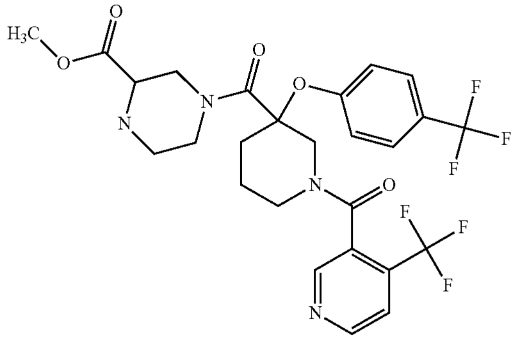
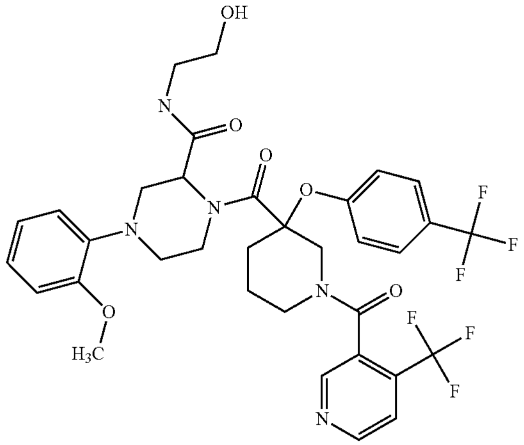
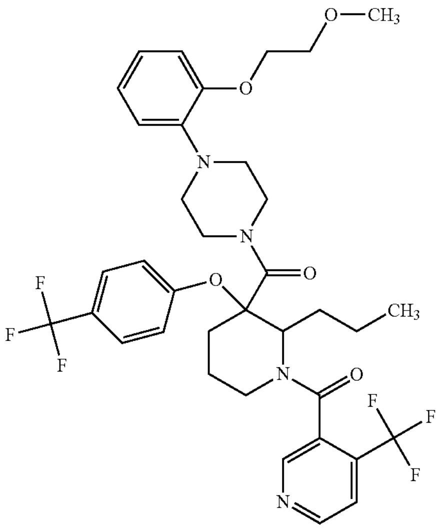

-continued
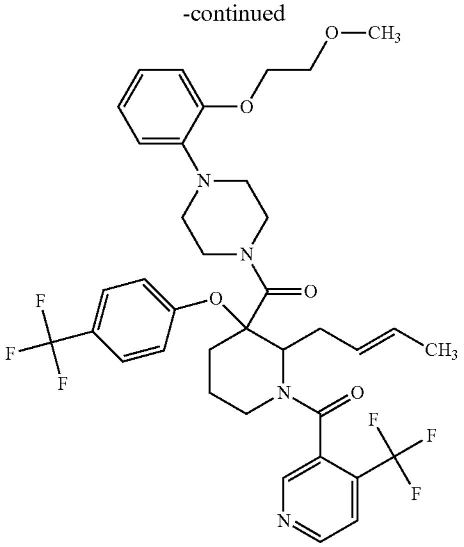
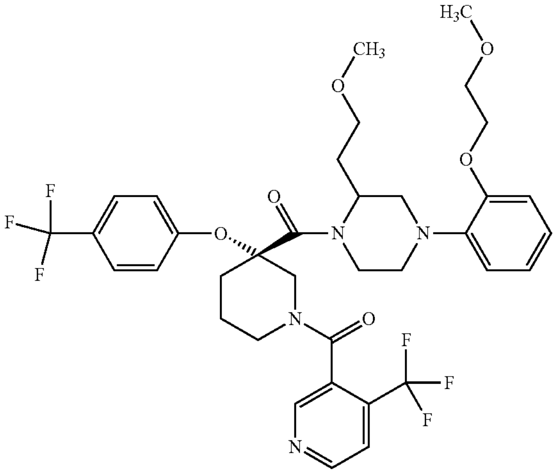
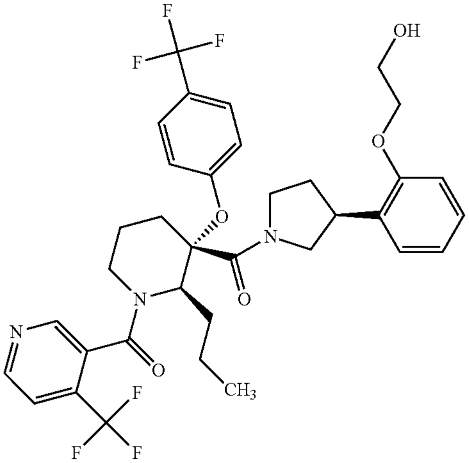
-continued
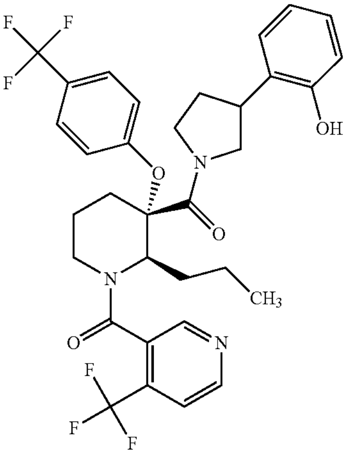
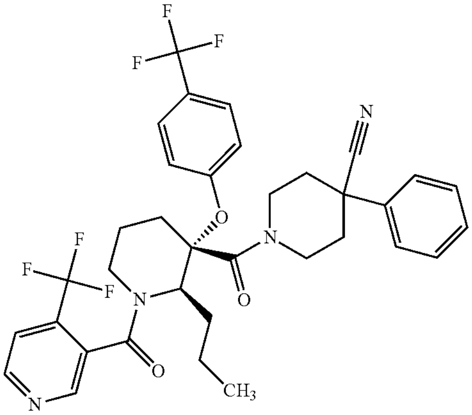
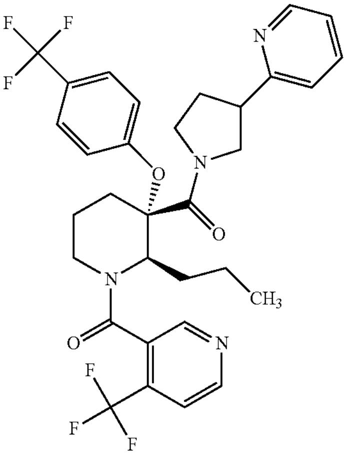

-continued
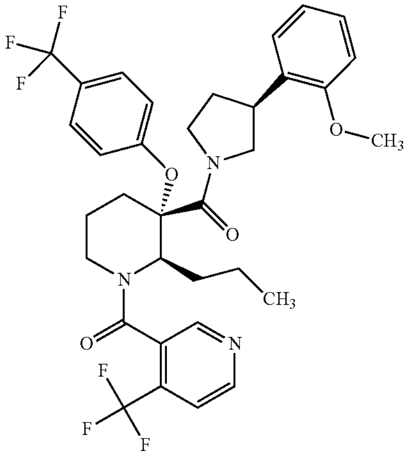
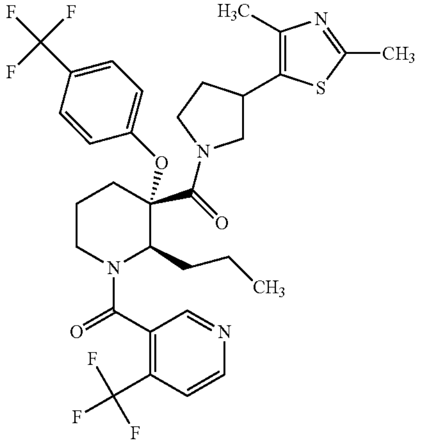
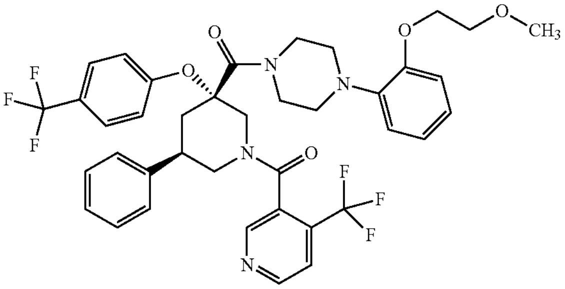
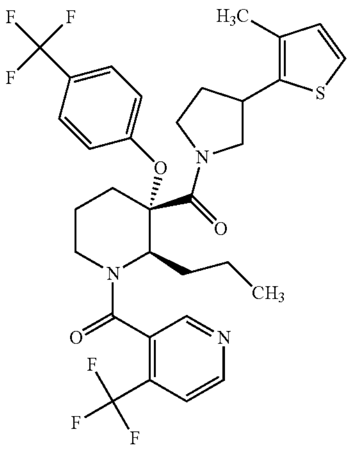
-continued
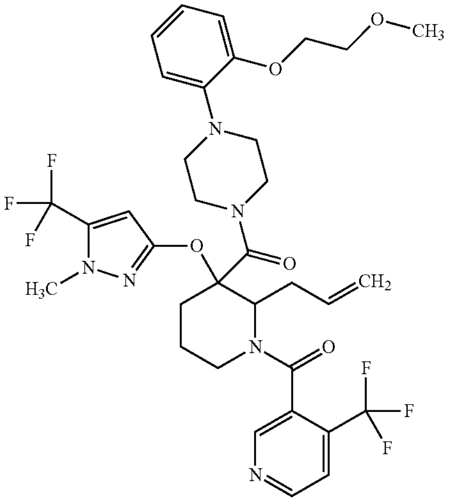
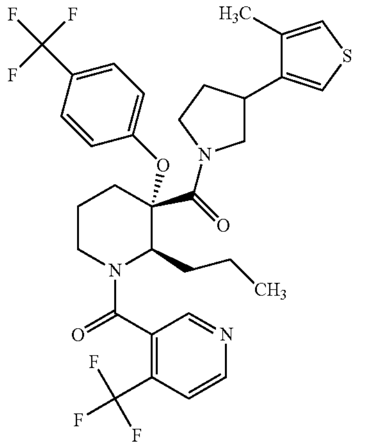
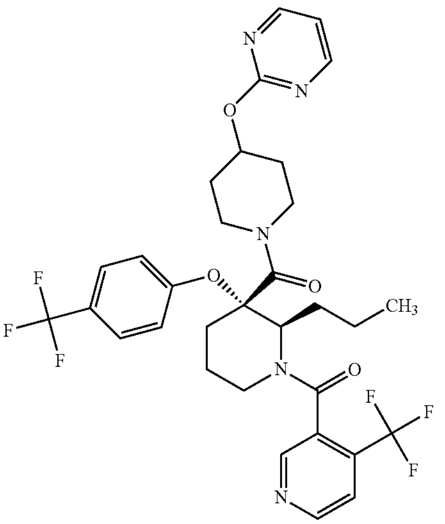

-continued
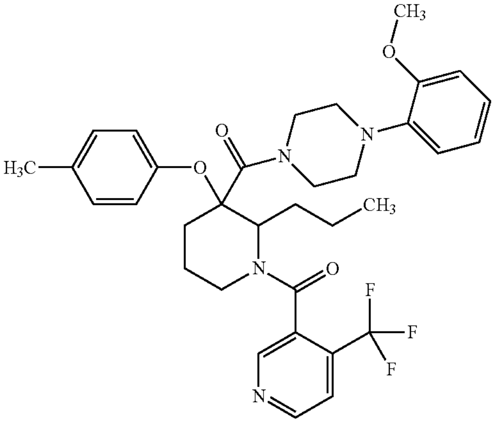
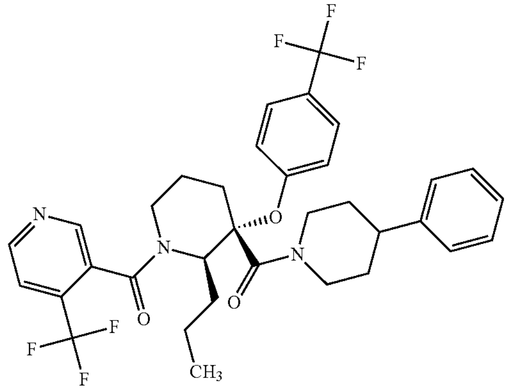
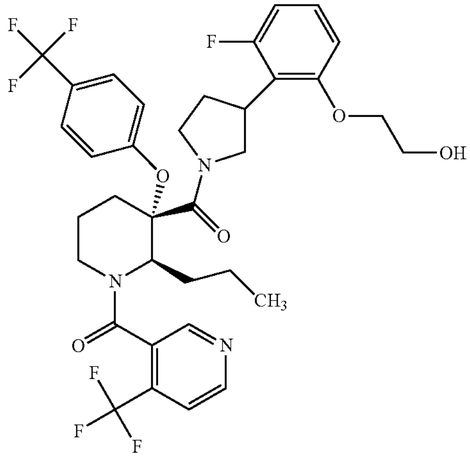
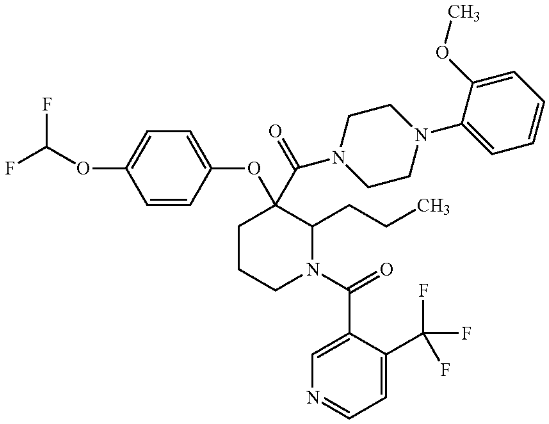
-continued
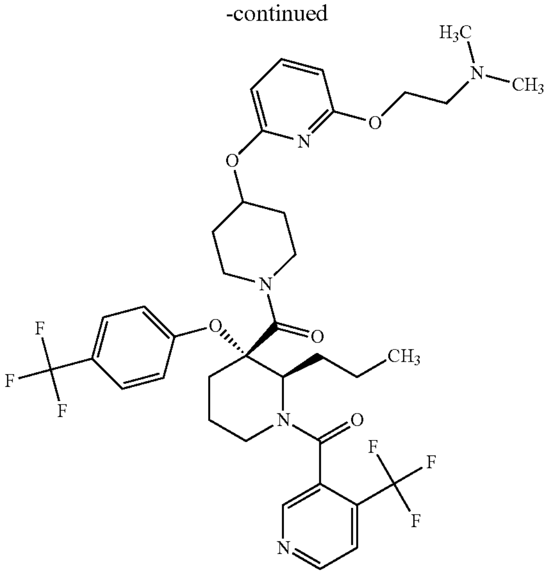
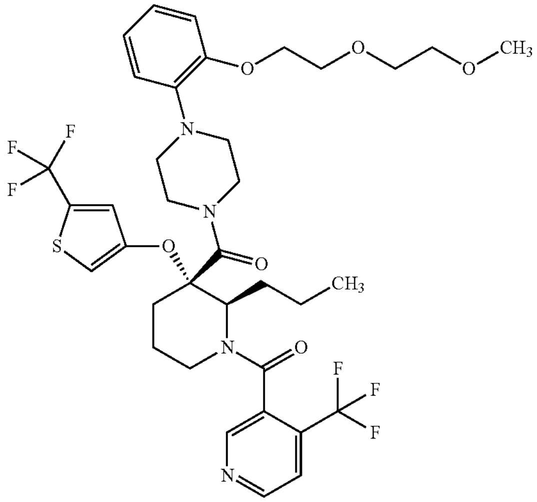
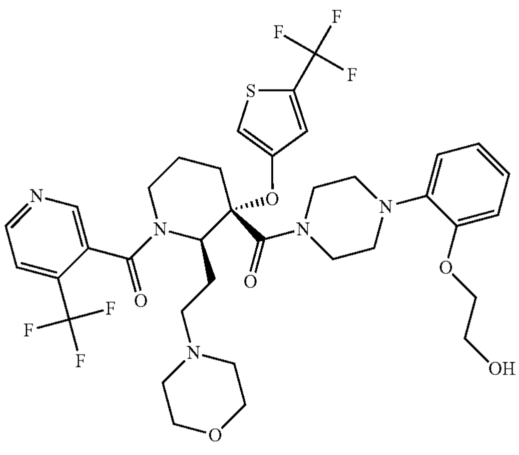

-continued
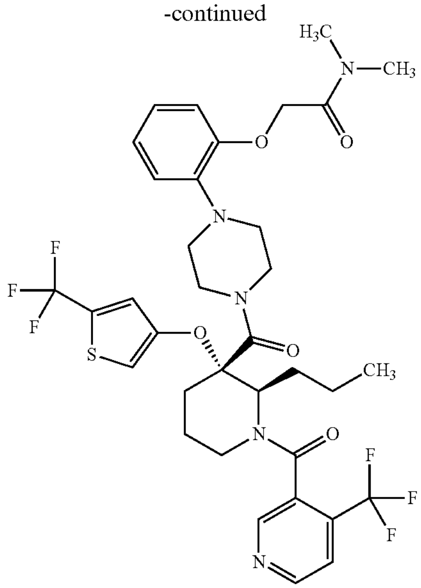
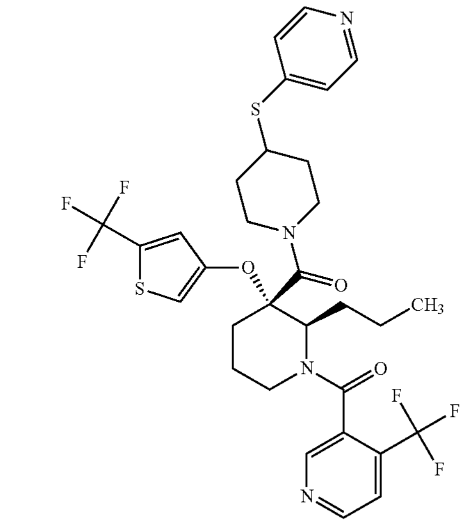
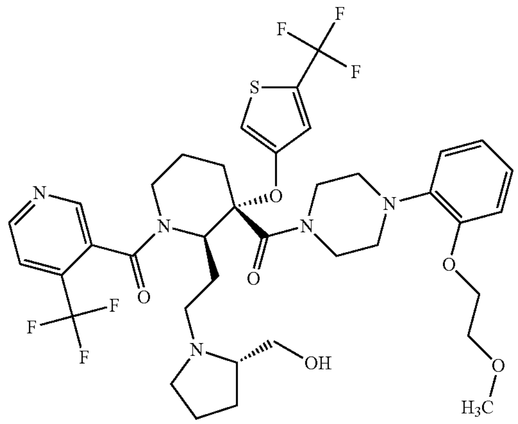
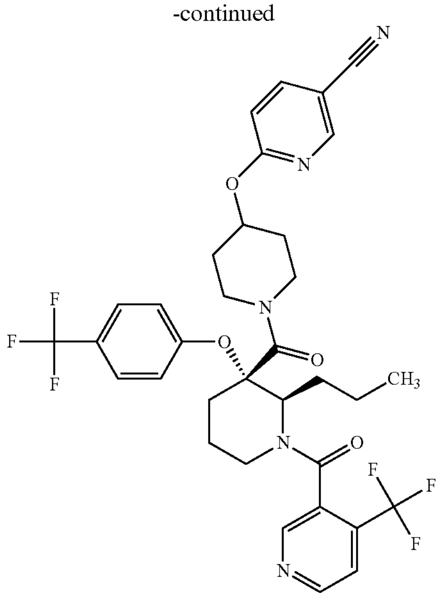
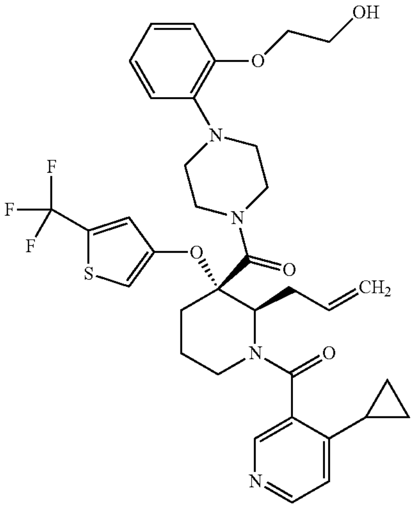
-continued
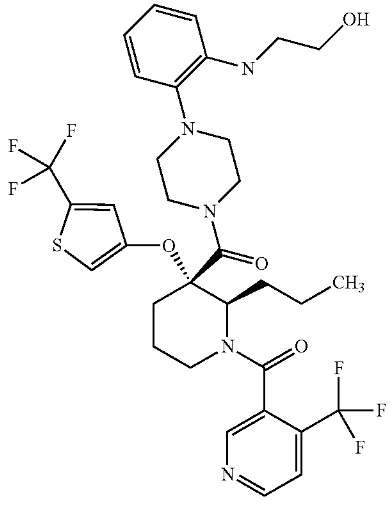

-continued
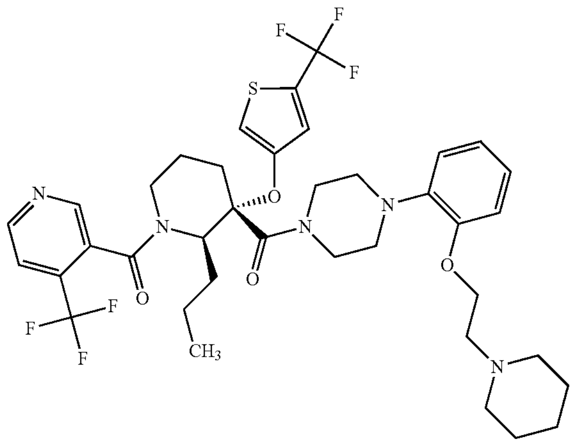
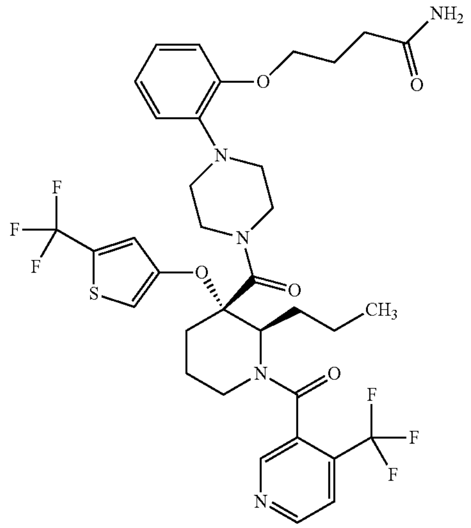
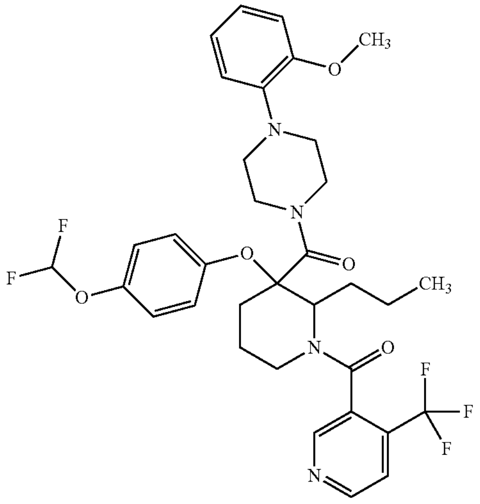
-continued
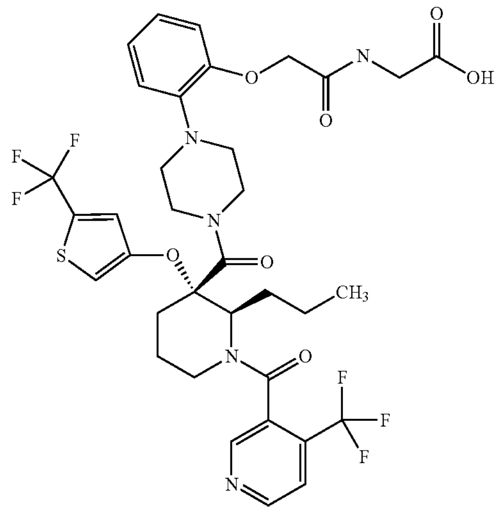
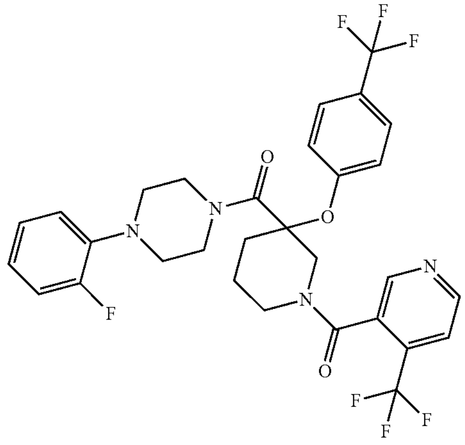
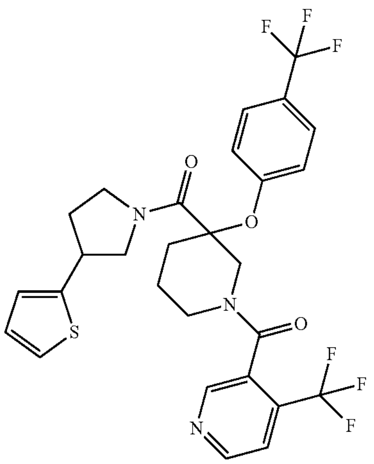

-continued
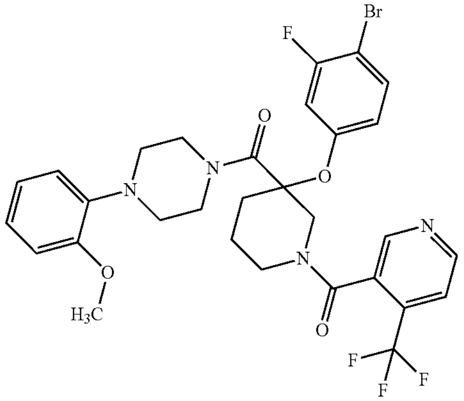
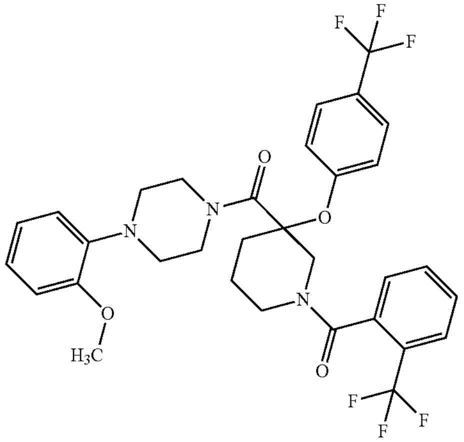
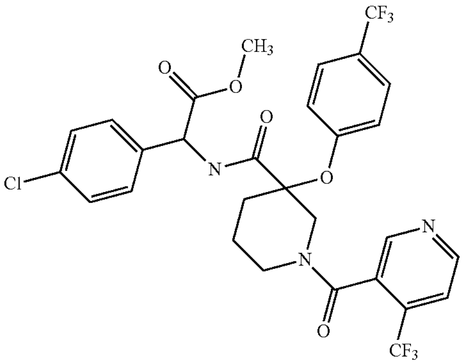
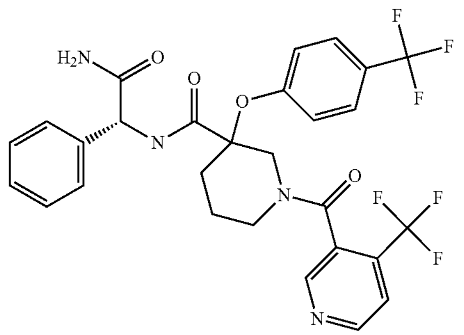
-continued
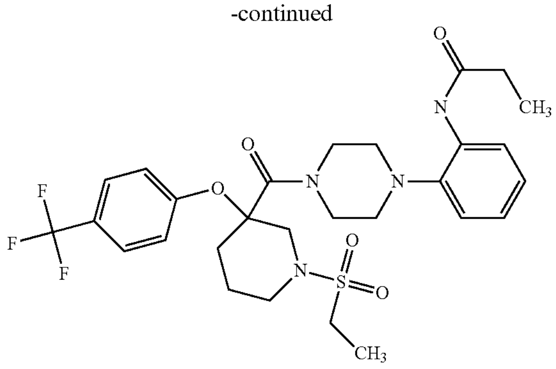
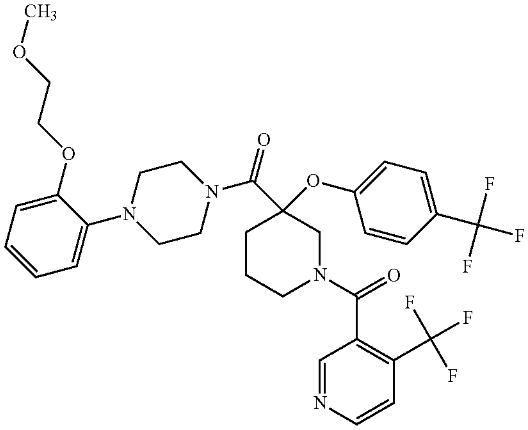
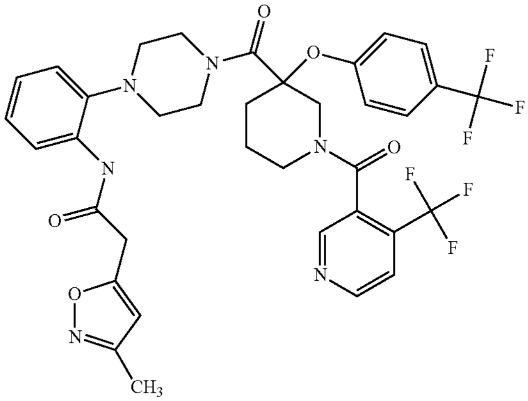
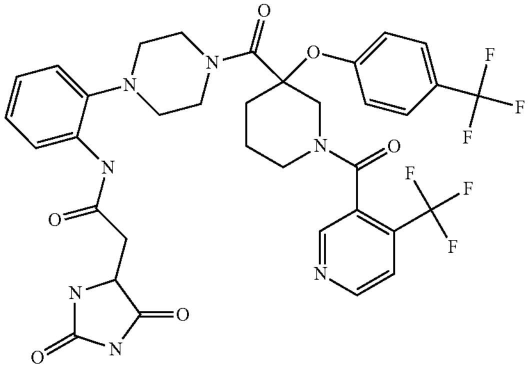

-continued
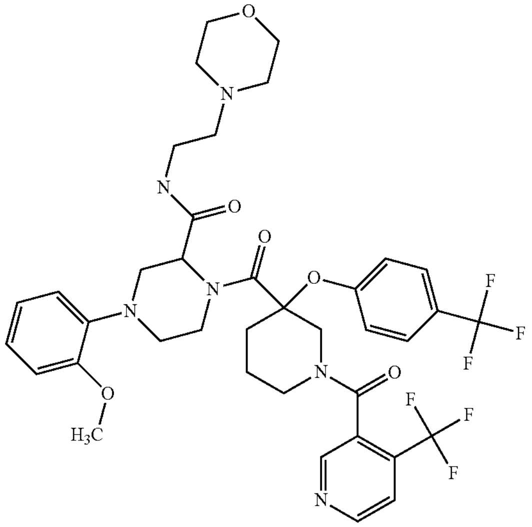
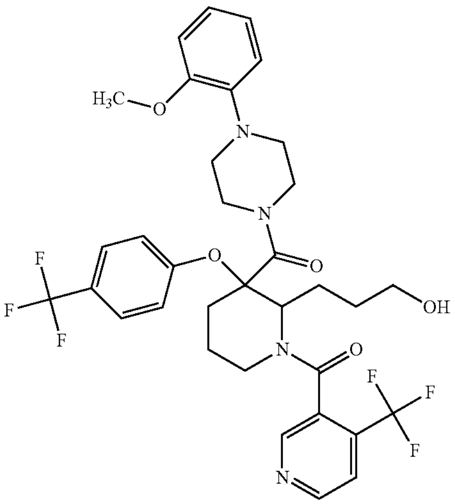
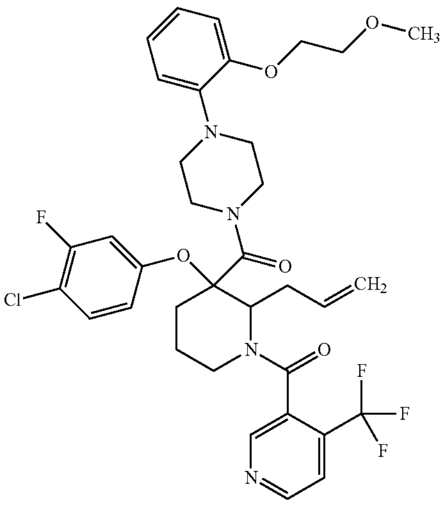
-continued
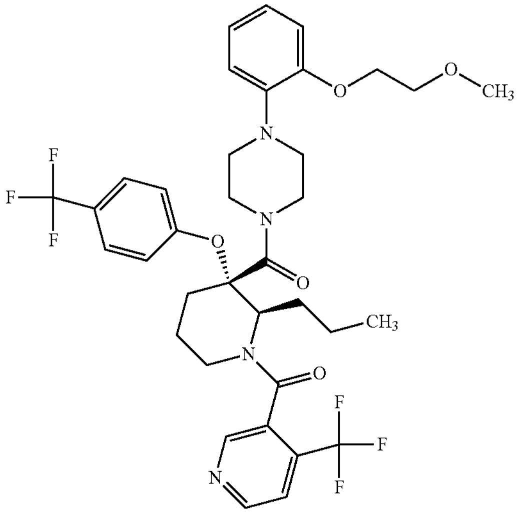
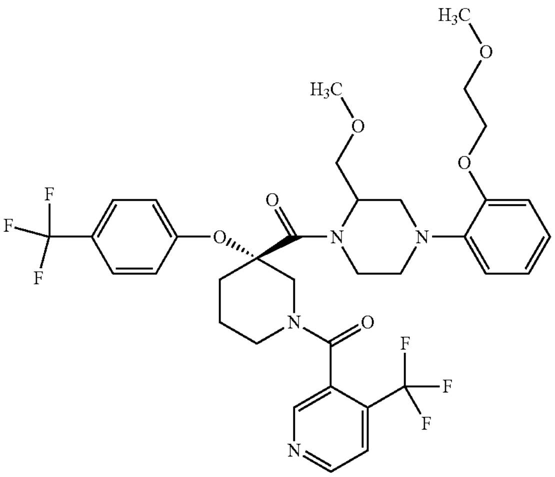
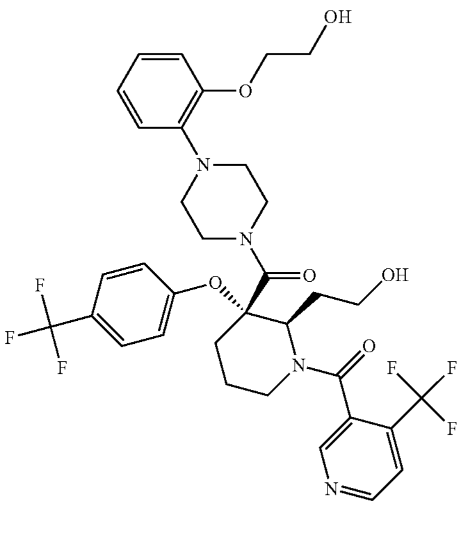

-continued
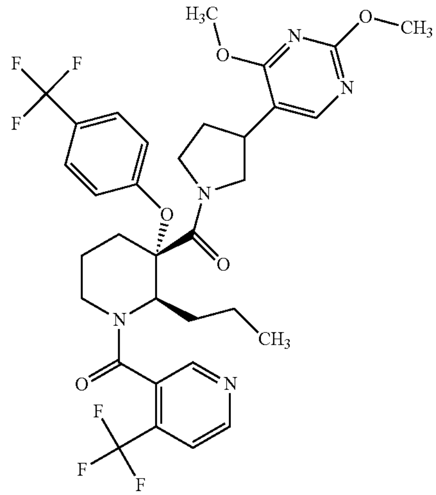
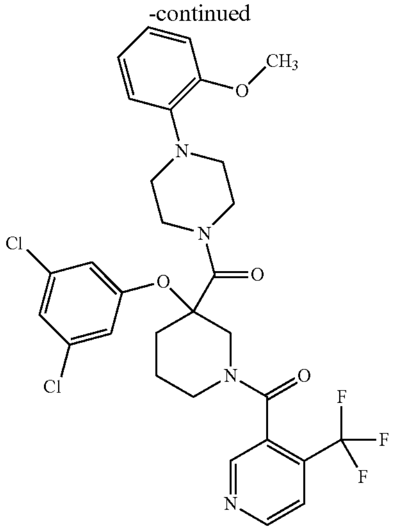
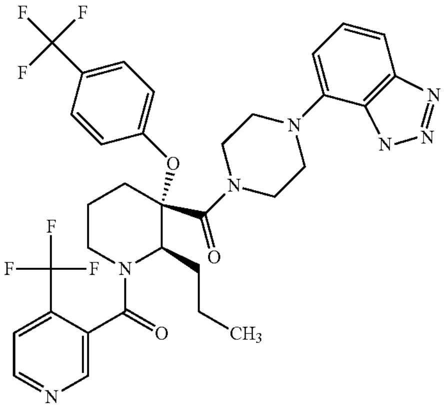
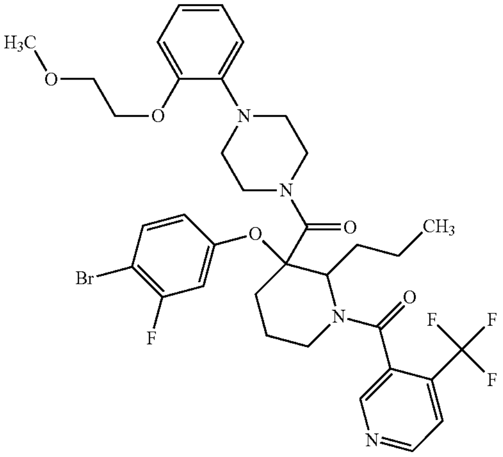
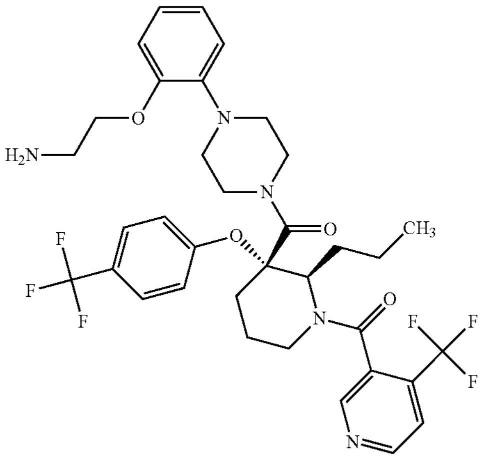
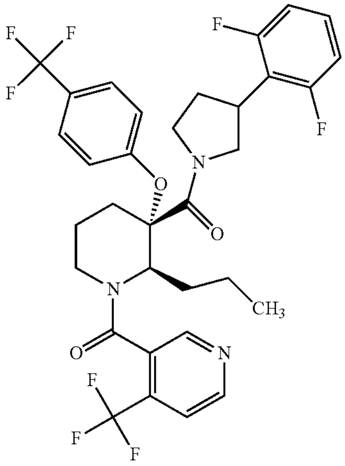

-continued
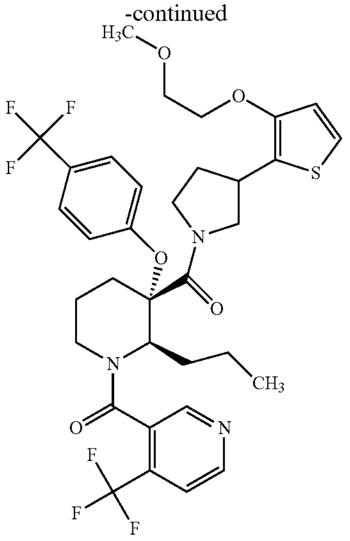
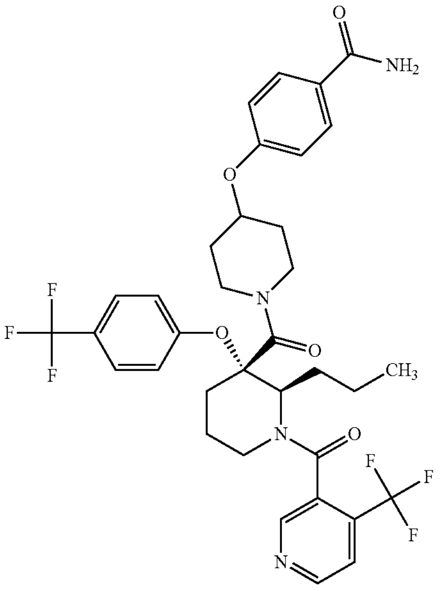
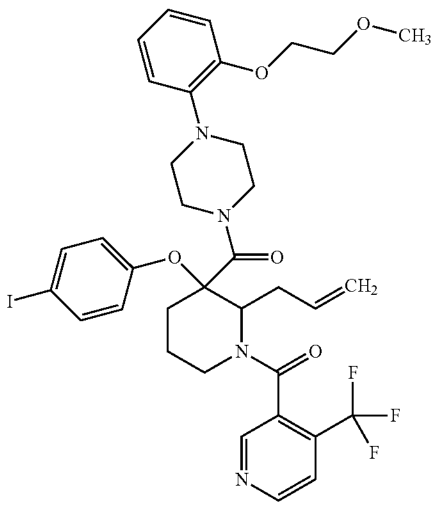
-continued
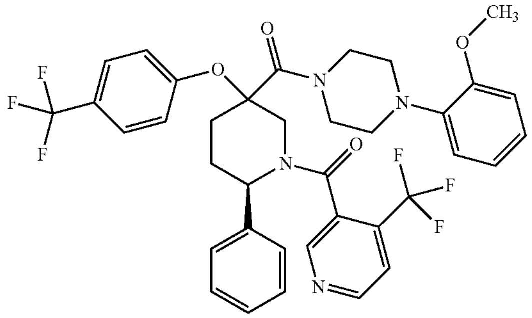
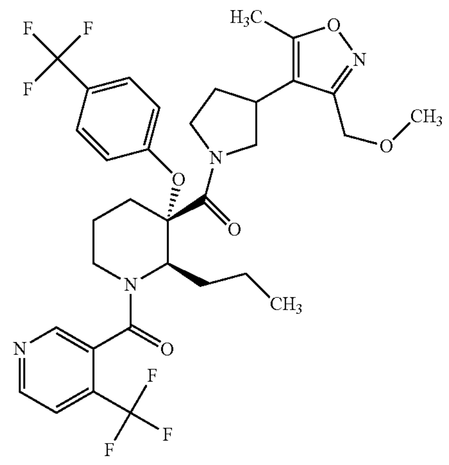
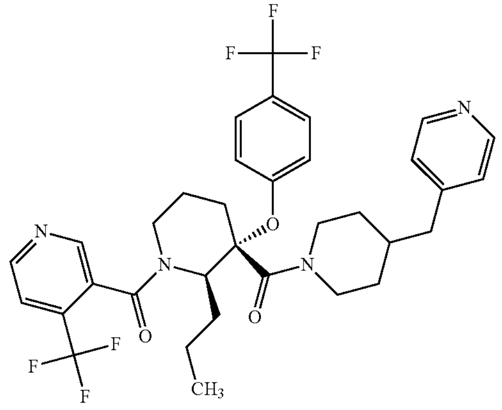
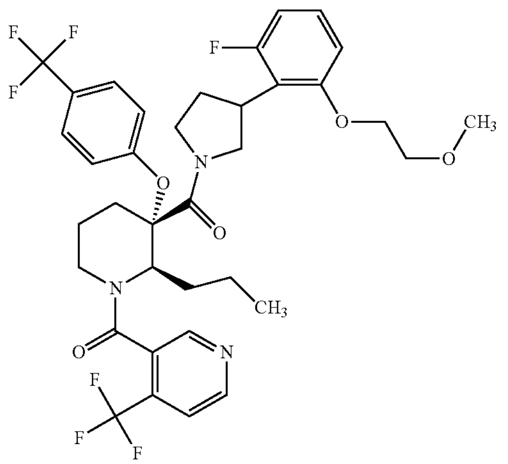

-continued
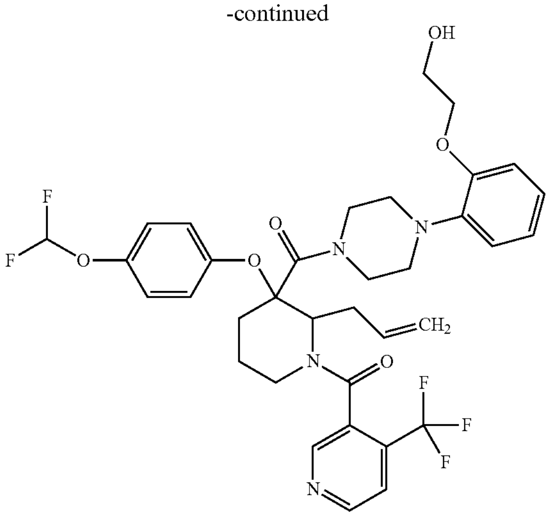
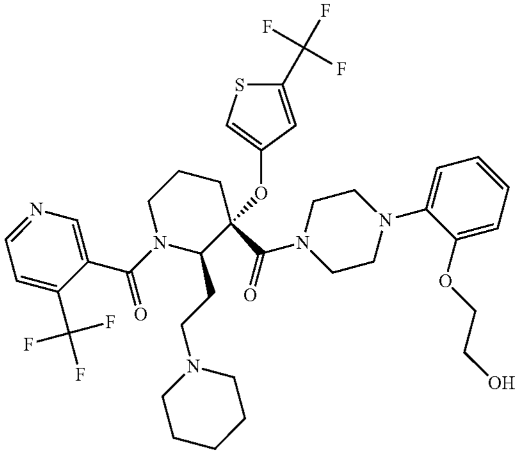
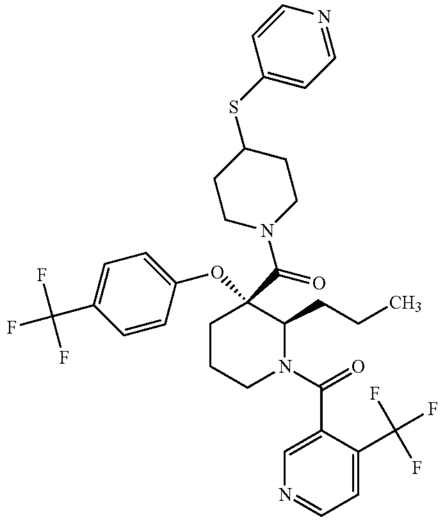
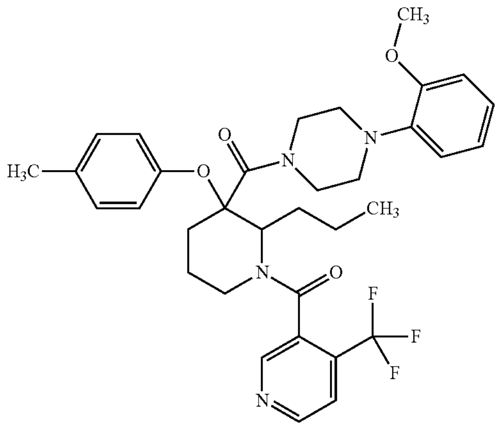
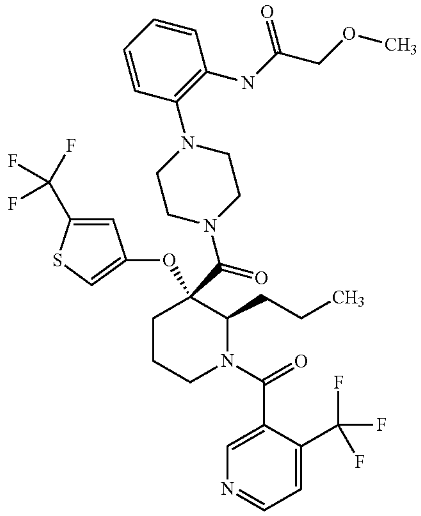
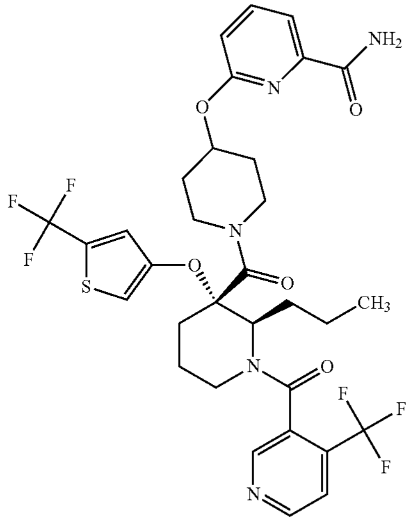
-continued -continued
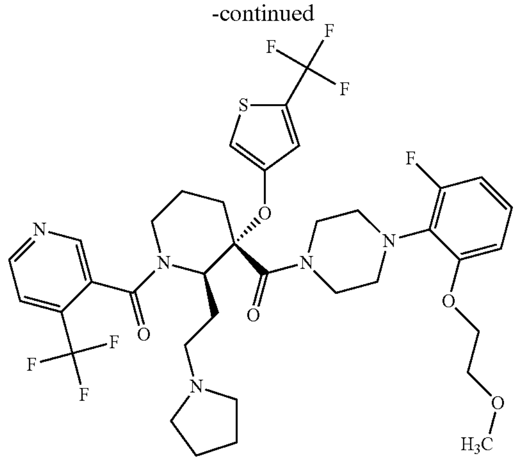
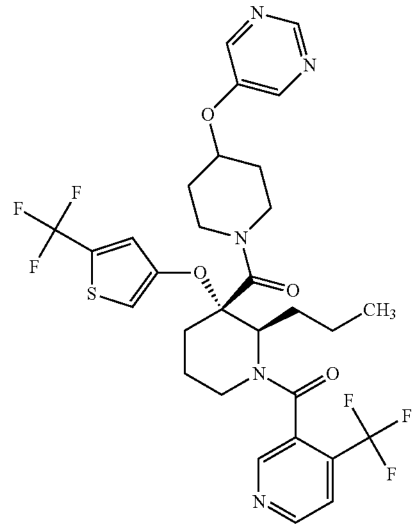
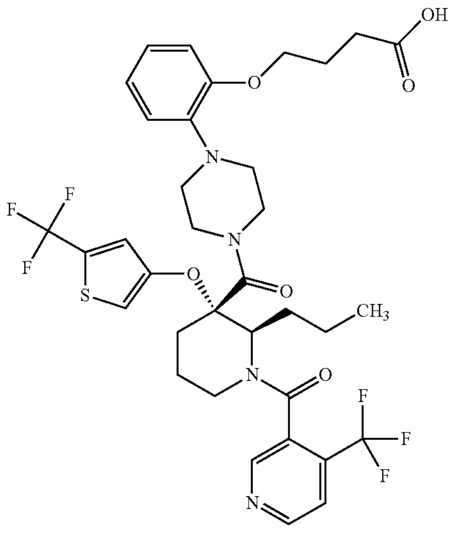
-continued
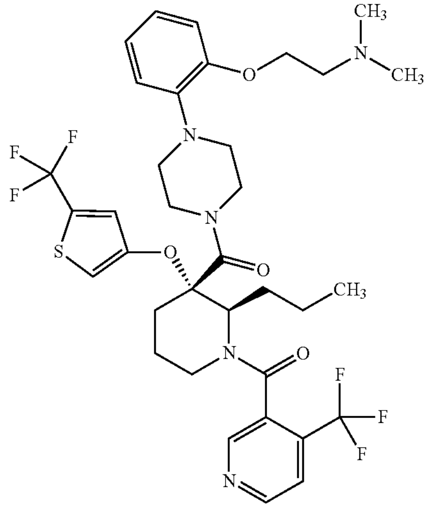
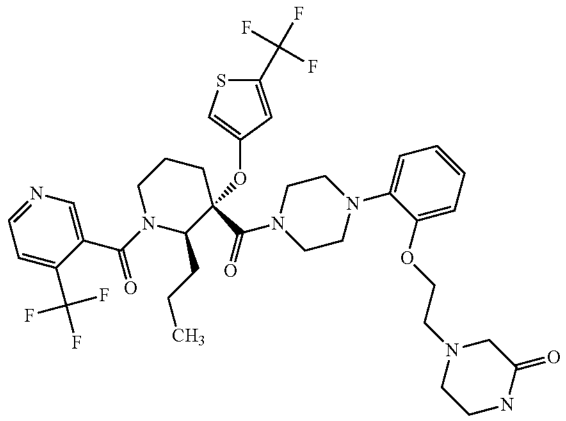
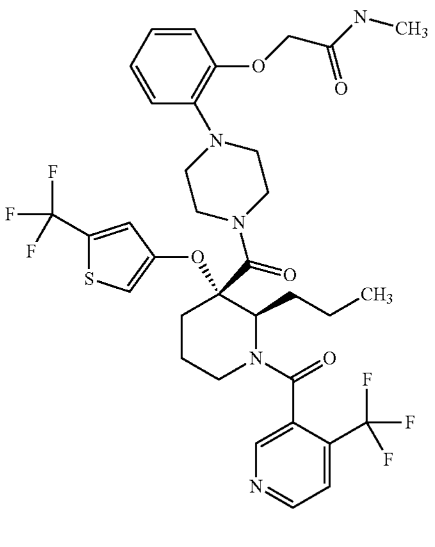

-continued
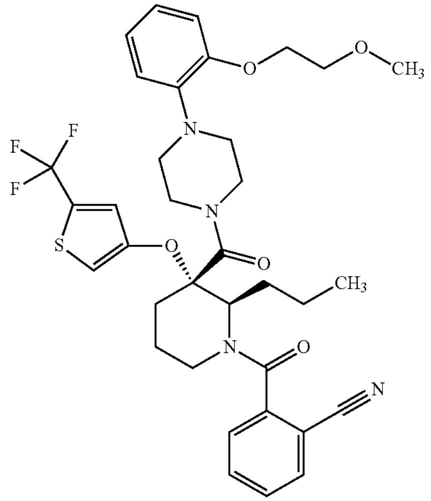
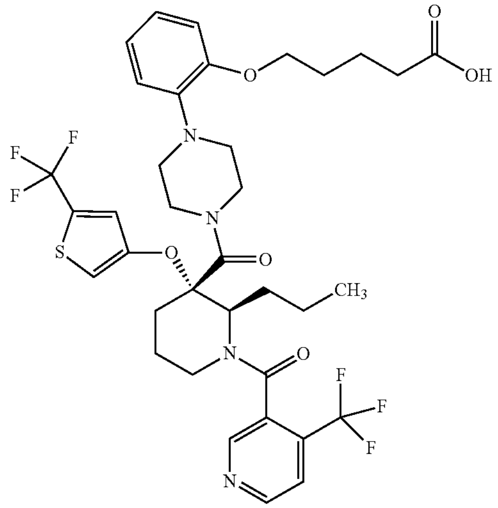
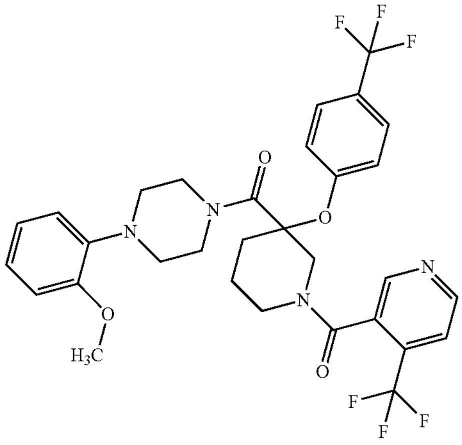
-continued
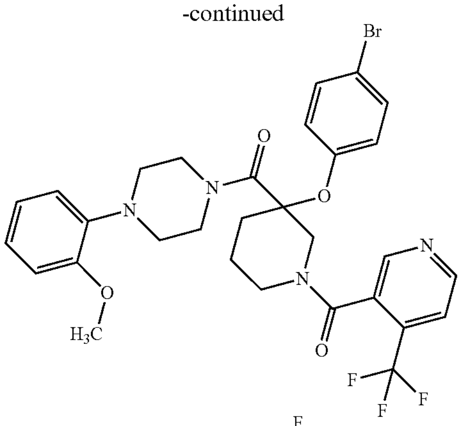
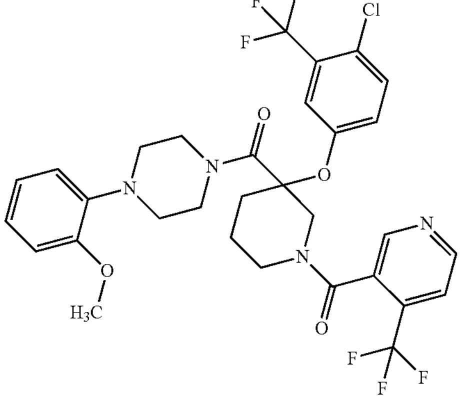
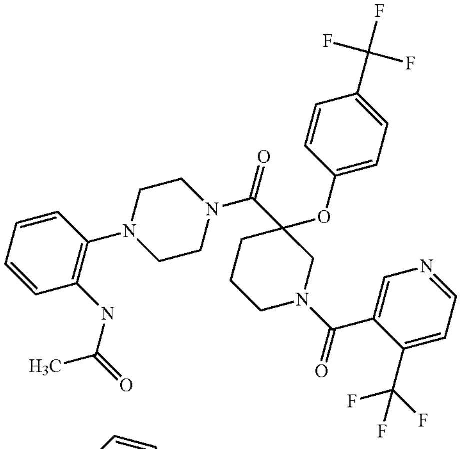
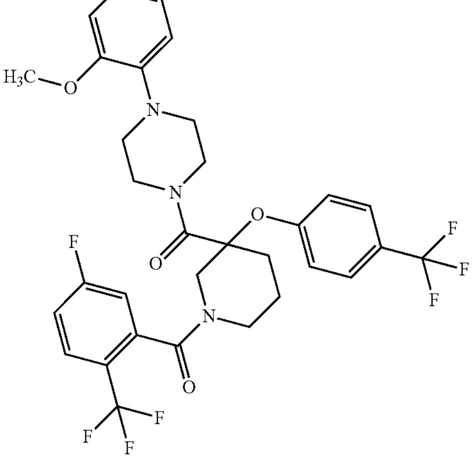

-continued
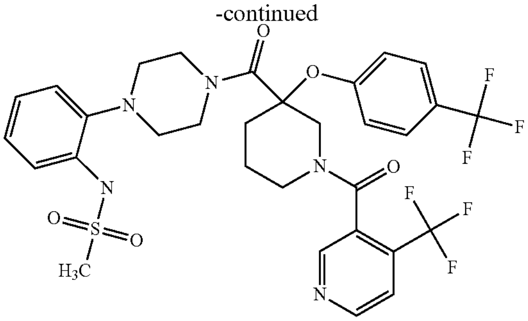
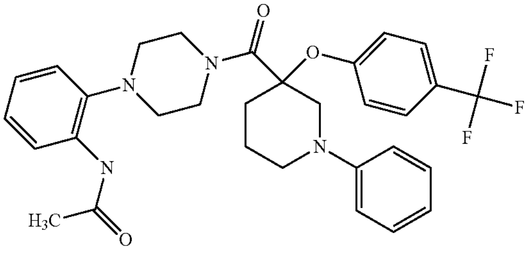
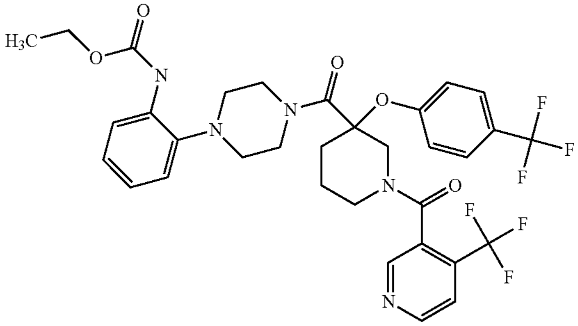
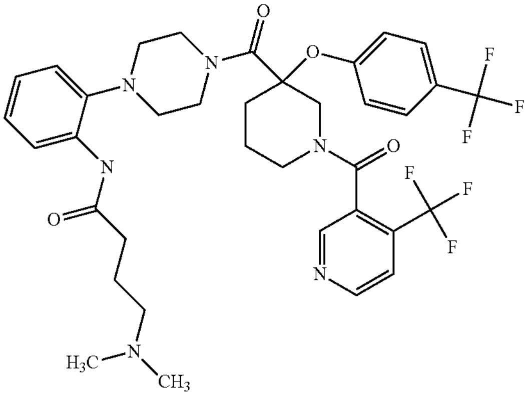
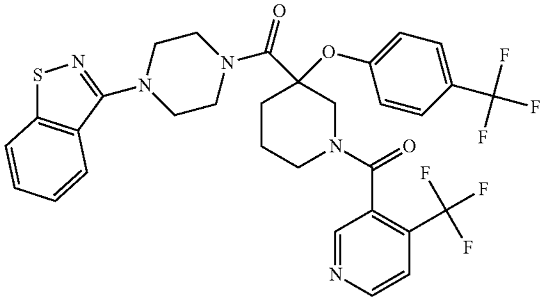
-continued
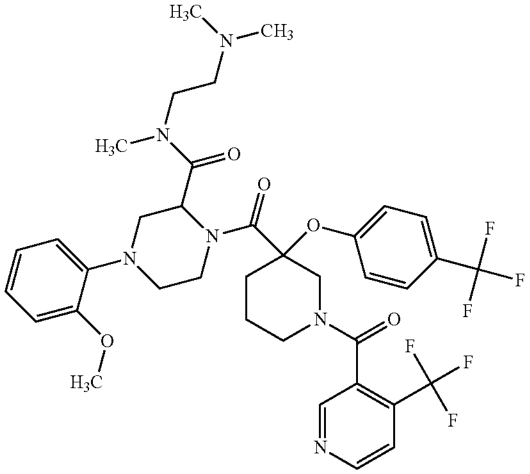
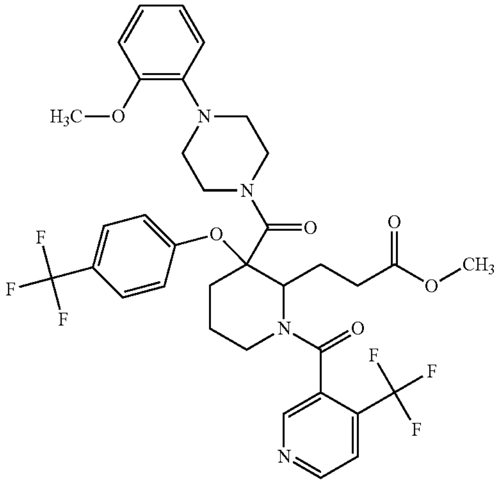
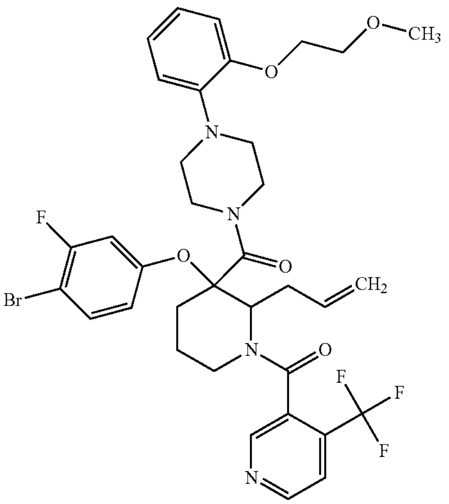

-continued
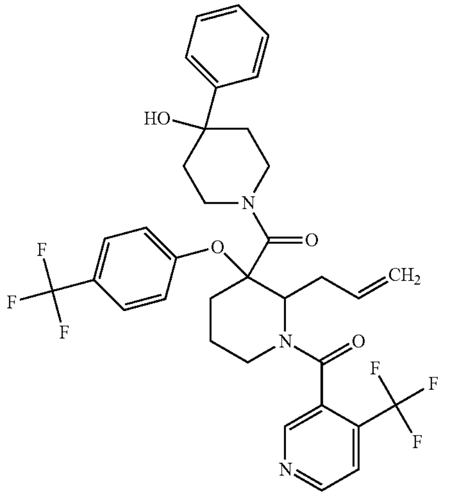
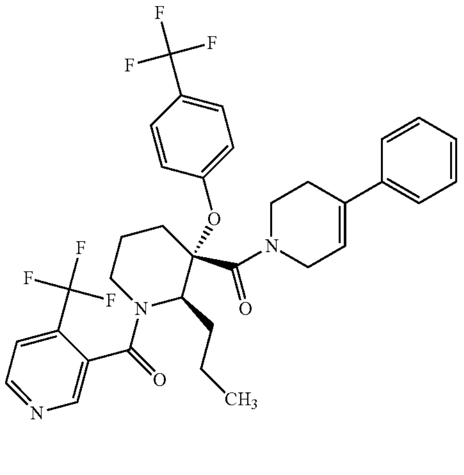
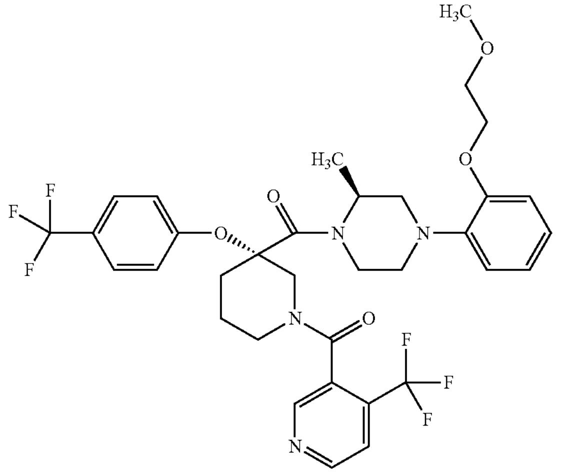
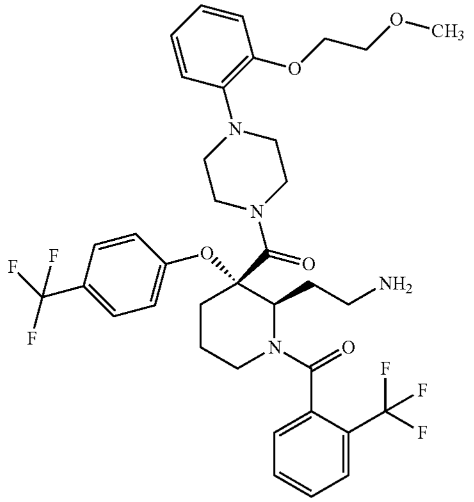
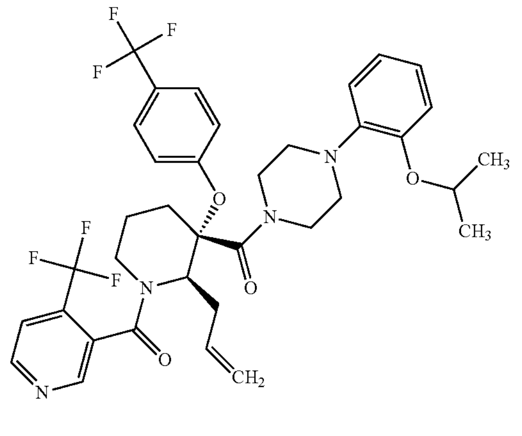
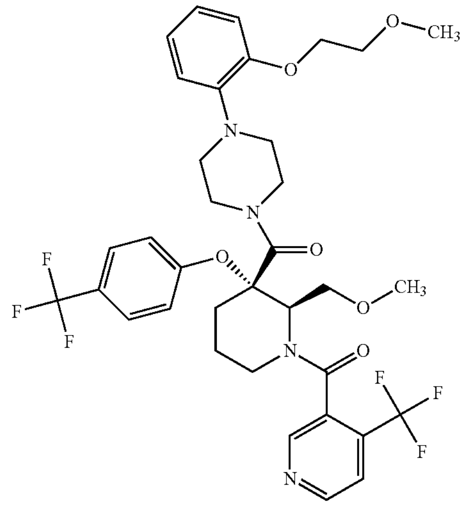
-continued -continued
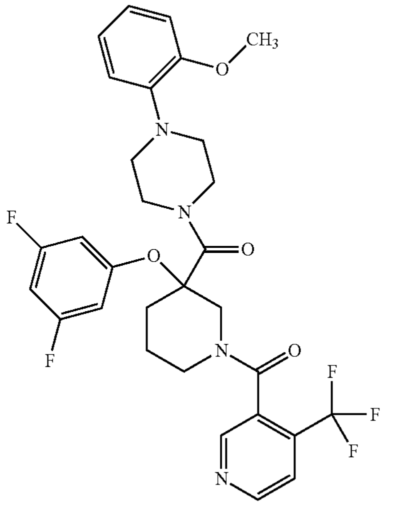
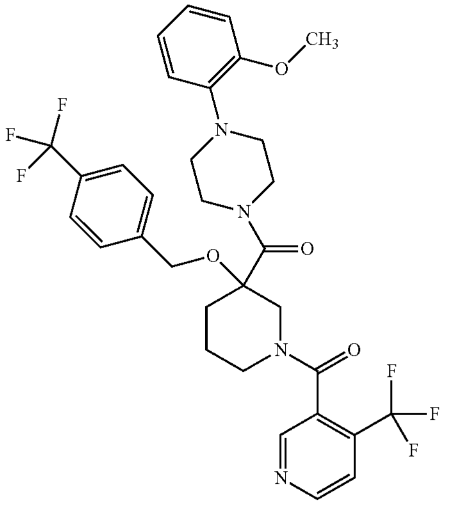
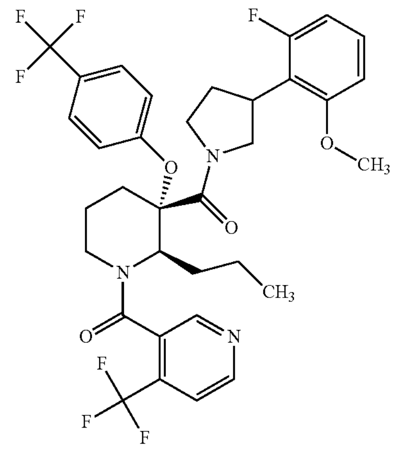
-continued
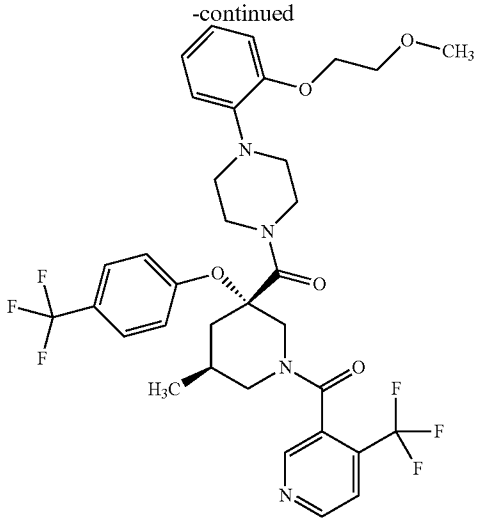
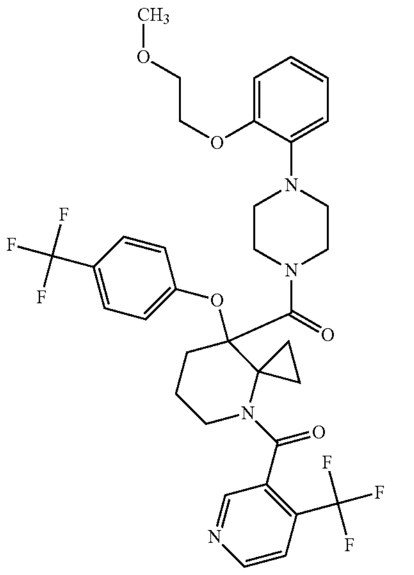
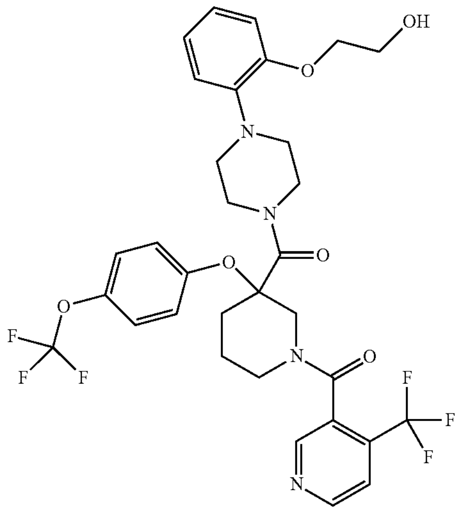

-continued
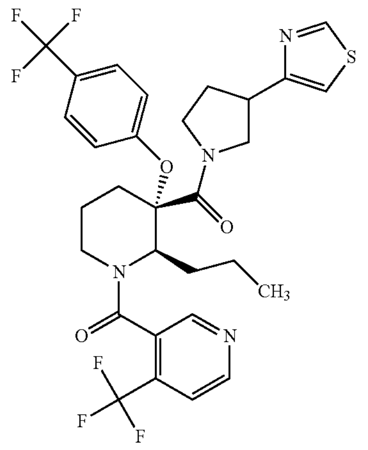
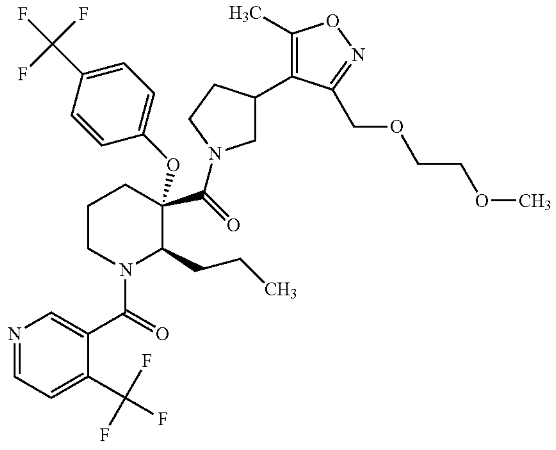
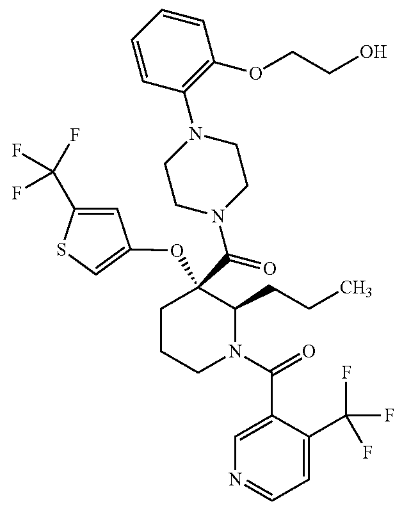
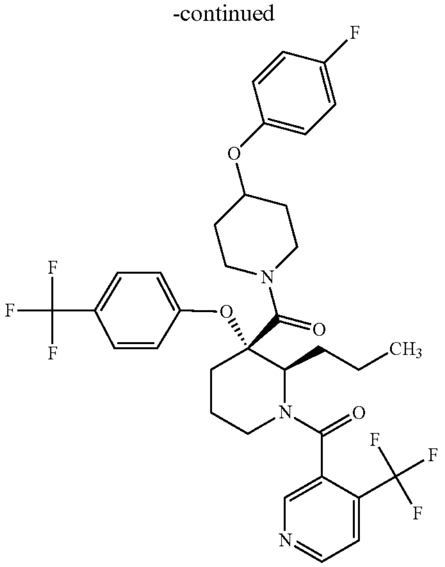
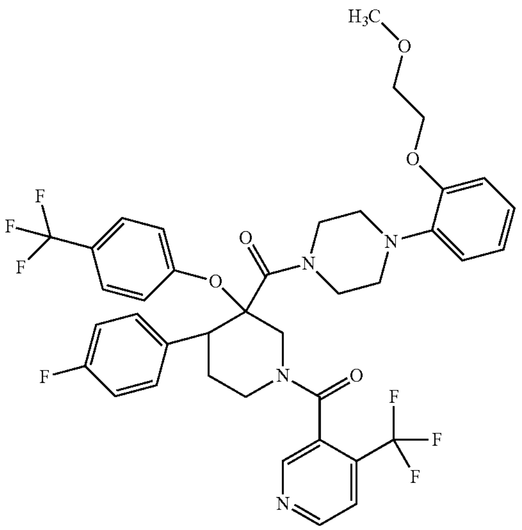
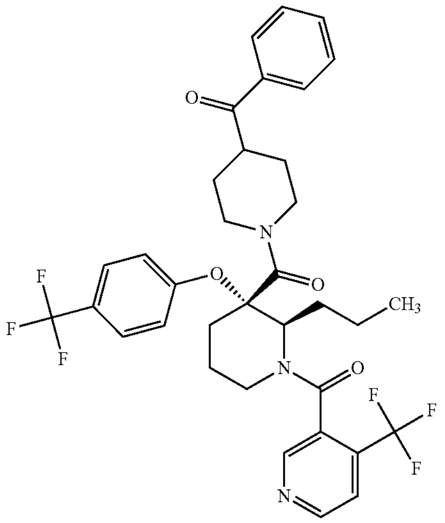
-continued -continued
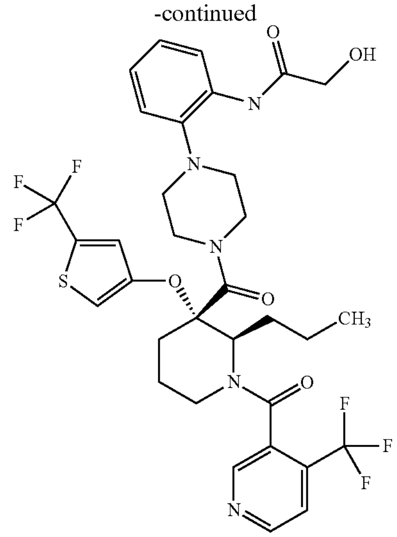
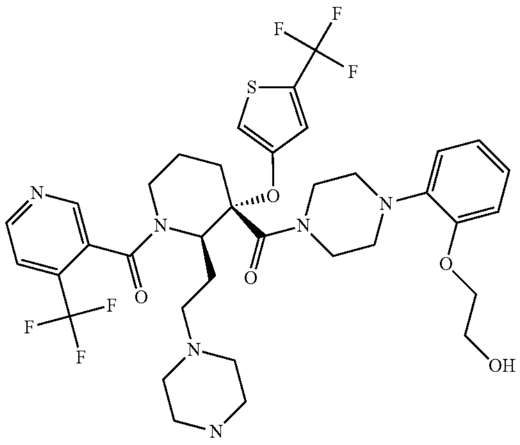
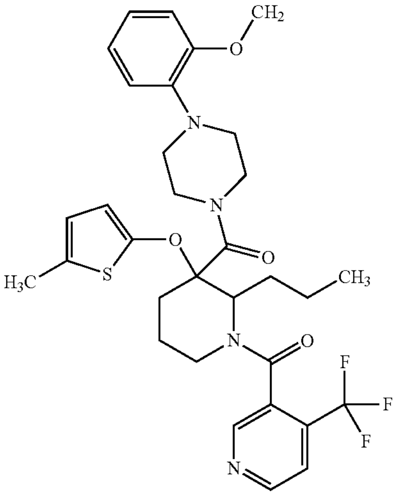
-continued
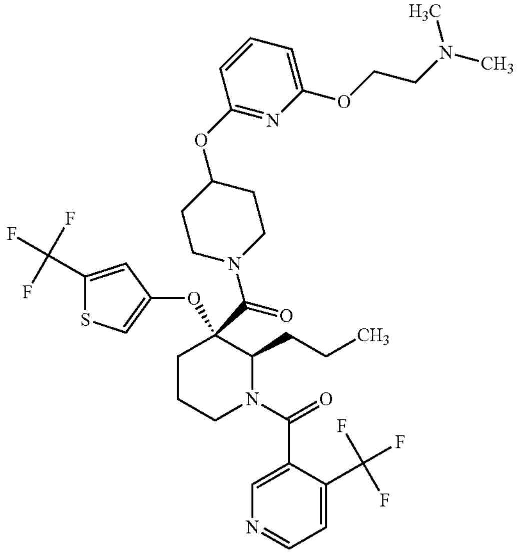
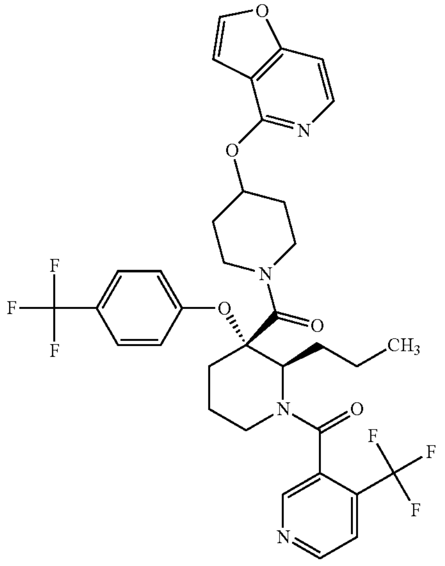
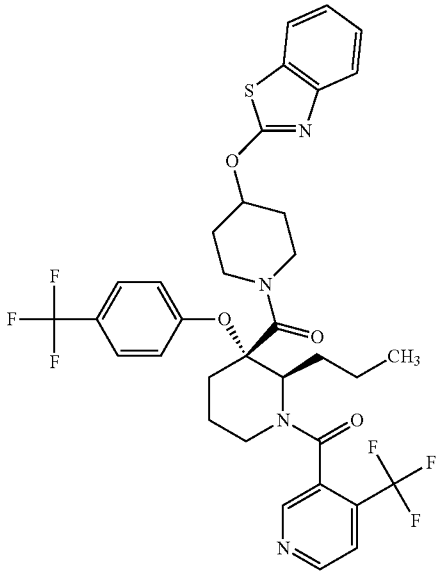

-continued
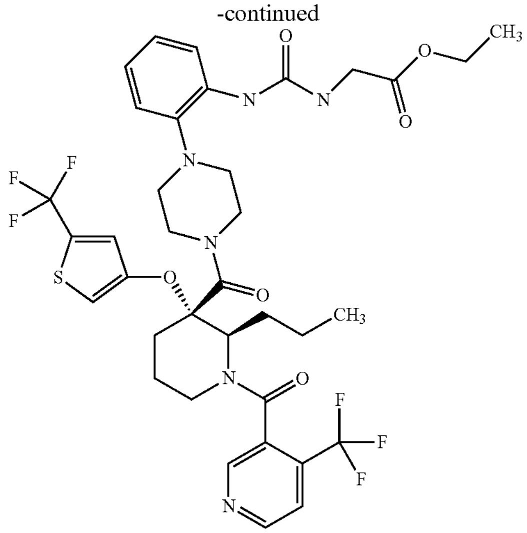
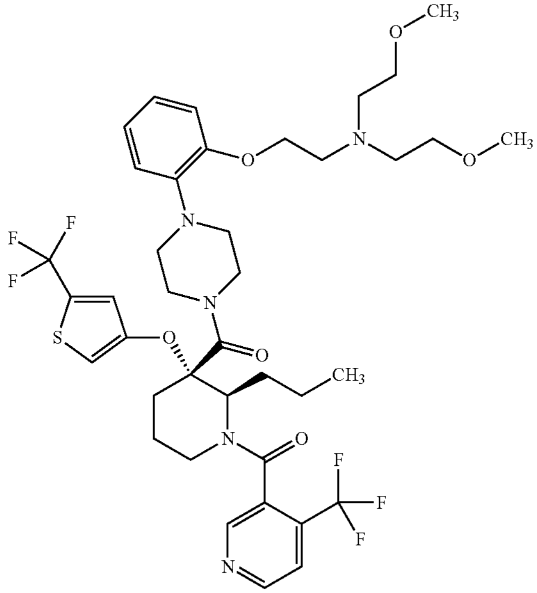
-continued
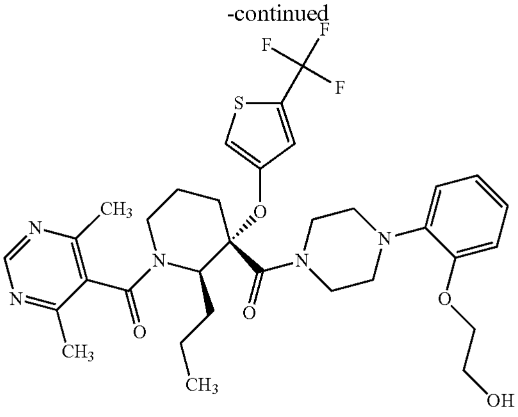
and
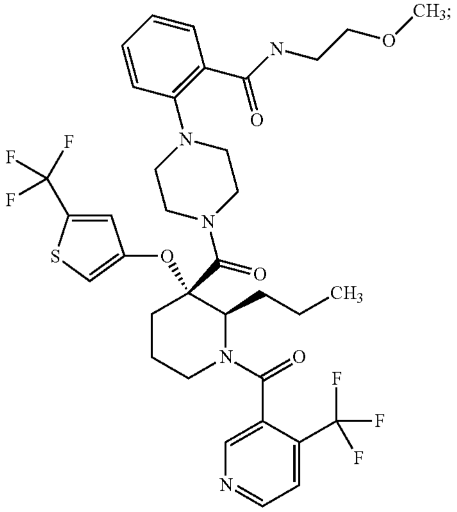
or a pharmaceutically acceptable salt thereof.
36. A pharmaceutical composition comprising a therapeutically effective amount of at least one compound of claim 35 or a pharmaceutically acceptable salt thereof, in combination with at least one pharmaceutically acceptable carrier.
* * * * *